(12) United States Patent
Maguire et al.

(10) Patent No.: US 11,981,915 B2
(45) Date of Patent: May 14, 2024

(54) VECTOR-FREE INTRACELLULAR DELIVERY BY REVERSIBLE PERMEABILIZATION

(71) Applicant: Avectas Limited, County Kildare (IE)

(72) Inventors: Michael Maguire, Dublin (IE); Shirley O'Dea, Maynooth (IE)

(73) Assignee: Avectas Limited, Kildare (IE)

( * ) Notice: Subject to any disclaimer, the term of this patent is extended or adjusted under 35 U.S.C. 154(b) by 411 days.

(21) Appl. No.: 16/471,466

(22) PCT Filed: Dec. 21, 2017

(86) PCT No.: PCT/IB2017/001713
§ 371 (c)(1),
(2) Date: Jun. 19, 2019

(87) PCT Pub. No.: WO2018/115973
PCT Pub. Date: Jun. 28, 2018

(65) Prior Publication Data
US 2020/0063162 A1 Feb. 27, 2020

Related U.S. Application Data

(60) Provisional application No. 62/536,831, filed on Jul. 25, 2017, provisional application No. 62/528,963, (Continued)

(51) Int. Cl.
*C12N 15/87* (2006.01)
*B01J 19/00* (2006.01)
(Continued)

(52) U.S. Cl.
CPC ............ *C12N 15/87* (2013.01); *B01L 3/5027* (2013.01); *C07K 14/7051* (2013.01);
(Continued)

(58) Field of Classification Search
CPC ...... C12N 15/87; C12N 5/0636; C12N 13/00; C12N 15/113; B01L 3/5027;
(Continued)

(56) References Cited

U.S. PATENT DOCUMENTS 5,411,208 A 5/1995 Burgener
6,634,572 B1 10/2003 Burgener
(Continued)

FOREIGN PATENT DOCUMENTS

CA 2112093 C 2/1995
CA 2384201 A1 9/2002
(Continued)

OTHER PUBLICATIONS

Shu et al., "CRISPR-Cas9 Mediated Efficient PD-1 Disruption on Human Primary T Cells from Cancer Patients", Scientific Reports, vol. 6:20070, 2016.
(Continued)

*Primary Examiner* — William H. Beisner
*Assistant Examiner* — Danielle B Henkel
(74) *Attorney, Agent, or Firm* — Mintz Levin Cohn Ferris Glovsky and Popeo, P.C.

(57) ABSTRACT

The invention provides a solution to the problem of transfecting non-adherent cells. Devices and delivery compositions containing ethanol and an isotonic salt solution are used for delivery of compounds and compositions to non-adherent cells.

38 Claims, 136 Drawing Sheets

Specification includes a Sequence Listing.

Related U.S. Application Data filed on Jul. 5, 2017, provisional application No. 62/438,298, filed on Dec. 22, 2016.

(51) Int. Cl.

| | |
|---|---|
| B01L 3/00 | (2006.01) |
| C07K 14/725 | (2006.01) |
| C12M 1/00 | (2006.01) |
| C12M 1/32 | (2006.01) |
| C12M 1/42 | (2006.01) |
| C12M 3/00 | (2006.01) |
| C12M 3/02 | (2006.01) |
| C12N 5/0783 | (2010.01) |
| C12N 13/00 | (2006.01) |
| C12N 15/113 | (2010.01) |

(52) U.S. Cl.
CPC .............. *C12M 3/006* (2013.01); *C12M 3/02* (2013.01); *C12M 35/00* (2013.01); *C12M 35/04* (2013.01); *C12N 5/0636* (2013.01); *C12N 13/00* (2013.01); *C12N 15/113* (2013.01); *B01J 19/0026* (2013.01); *C07K 2319/03* (2013.01); *C12M 23/12* (2013.01); *C12M 29/06* (2013.01); *C12M 41/14* (2013.01)

(58) Field of Classification Search
CPC .. C07K 14/705; C07K 2319/03; C12M 3/006; C12M 3/02; C12M 35/04; C12M 23/12; C12M 29/06; C12M 41/14; C12M 35/00; B01J 19/0026
See application file for complete search history.

(56) References Cited

U.S. PATENT DOCUMENTS

| | | | |
|---|---|---|---|
| 7,667,004 | B2 | 2/2010 | Zhong et al. |
| 8,697,359 | B1 | 4/2014 | Zhang |
| 8,932,814 | B2 | 1/2015 | Cong et al. |
| 9,023,649 | B2 | 5/2015 | Mali et al. |
| 9,074,199 | B1 | 7/2015 | Chavez et al. |
| 9,616,084 | B2 * | 4/2017 | Mutzke .............. A61K 39/0011 |
| 10,087,442 | B2 * | 10/2018 | Shen .................... A61K 31/713 |
| 2002/0129813 | A1 * | 9/2002 | Litherland .......... B05B 17/0646 128/200.16 |
| 2002/0151004 | A1 | 10/2002 | Craig |
| 2004/0219676 | A1 | 11/2004 | Held et al. |
| 2005/0014259 | A1 * | 1/2005 | Conroy ................. C12N 15/86 514/44 A |
| 2012/0258046 | A1 * | 10/2012 | Mutzke .................. A61K 48/00 424/9.1 |
| 2014/0342445 | A1 * | 11/2014 | Ingber ............... B01L 3/502761 435/294.1 |
| 2015/0079670 | A1 * | 3/2015 | Domansky .......... B05B 11/3028 435/305.1 |
| 2015/0141498 | A1 * | 5/2015 | Mutzke .............. A61K 31/7088 514/44 R |
| 2021/0054413 | A1 | 2/2021 | Maguire et al. |
| 2021/0261901 | A1 | 8/2021 | Maguire |
| 2021/0284945 | A1 | 9/2021 | Maguire |
| 2021/0363544 | A1 | 11/2021 | Maguire et al. |

FOREIGN PATENT DOCUMENTS

| | | |
|---|---|---|
| WO | 03000174 A1 | 1/2003 |
| WO | 2012106536 A2 | 8/2012 |
| WO | 2015036764 A1 | 3/2015 |
| WO | 2015071474 A2 | 5/2015 |
| WO | 2016065341 A1 | 4/2016 |
| WO | 2016070136 A1 | 5/2016 |
| WO | 2017115128 A2 | 7/2017 |
| WO | 2018115973 A2 | 6/2018 |

OTHER PUBLICATIONS

O'Dea et al., "Vector-Free Intracellular Delivery by Reversible Permeabilization", PLOS ONE, 12:3, pp. 1-23, 2017.
International Search Report and the Written Opinion from corresponding PCT International Application No. PCT/IB2017/001713 dated Nov. 29, 2018.
Besser , et al., "Modifying Interleukin-2 Concentrations During Culture Improves Function of T Cells for Adoptive Immunotherapy", Cytotherapy, 2009, 11(2):206-217.
Brocard , et al., "Peroxisome Targeting Signal 1: Is it Really a Simple Tripeptide?", Biochimica et Biophysica Acta (BBA)—Molecular Cell Research, Dec. 2006, 1763(12):1565-1573.
Cho , et al., "Targeted Genome Engineering in Human Cells with the Cas9 RNA-Guided Endonuclease", Nature Biotechnology, Mar. 2013, 31(3):230-232.
Cui , et al., "Transmembrane Routes of Cationic Liposome-Mediated Gene Delivery Using Human Throat Epidermis Cancer Cells", Biotechnology Letters, 2014, 36(1):1-7.
D'Astolfo , et al., "Efficient Intracellular Delivery of Native Proteins", Cell, Apr. 23, 2015, 161(3):674-690.
Dingwall , et al., "Nuclear Targeting Sequences—A Consensus?", Trends in Biochemical Sciences, Dec. 1991, 16(12):478-481.
Jinek , et al., "A Programmable Dual-RNA-Guided DNA Endonuclease in Adaptive Bacterial Immunity", Science, Aug. 17, 2012, 337(6069):816-821.
Kalderon , "A Short Amino Acid Sequence Able to Specify Nuclear Location", Cell, Dec. 1984, 3( Pt 2):499-509.
Makkerh , et al., "Comparative Mutagenesis of Nuclear Localization Signals Reveals the Importance of Neutral and Acidic Amino Acids", Current Biology, Aug. 1996, 6(8):1025-1027.
Nakamura , et al., "Codon Usage Tabulated from International DNA Sequence Database: Status for the Year 2000", Nucleic Acid Research, 2000, 28(1):292.
Niedzinski , et al., "Zinc Enhancement of Nonviral Salivary Gland Transfection", Molecular Therapy, Mar. 2003, 7(3):396-400.
Omura, Tsuneo , "Mitochondria-Targeting Sequence, a Multi-Role Sorting Sequence Recognized at All Steps of Protein Import into Mitochondria", The Journal of Biochemistry, 1998, 123(6):1010-1016.
Park , et al., "Engineering Mesenchymal Stem Cells for Regenerative Medicine and Drug Delivery", Methods, Aug. 2015, 84:3-16.
Ran , et al., "Genome engineering using the CRISPR-Cas9 system", Nature Protocols, Nov. 2013, 8(11):2281-2308.
Rapaport, Doron , "Finding the Right Organelle. Targeting Signals in Mitochondrial Outer-Membrane Proteins", EMBO Reports, Nov. 2003, 4(10):948-952.
Scott , et al., "NoD: A Nucleolar Localization Sequence Detector for Eukaryotic and Viral Proteins", BMC Bioinformatics, Aug. 3, 2011, 12:317.
Tumeh , et al., "The Impact of Ex Vivo Clinical Grade Activation Protocols on Human T cell Phenotype and Function for the Generation of Genetically Modified Cells for Adoptive Cell Transfer Therapy", Journal of Immunotherapy, Oct. 2010, 33(6):759-768.
Uniprot , "CRISPR Associated Protein [*Streptococcus pyogenes*]", Accession No. CDJ55032.1, Feb. 4, 2016, 1 page.
Uniprot , "CRISPR-Associated Endonuclease Cas9", UniProtKB Accession No. Q03JI6.1, Oct. 10, 2018, 3 pages.
Uniprot , "CRISPR-associated endonuclease Cas9/Csn1", UniProtKB Accession No. Q99ZW2, 12 pages.
Yu , et al., "Regulation of T Cell Receptor Signaling by Activation-Induced Zinc Influx", The Journal of Experimental Medicine, 2011, 208(4):775-785.
Rupp et al. (Apr. 2017) "CRISPR/Cas9-Mediated PD-1 Disruption Enhances Anti-Tumor Efficacy of Human Chimeric Antigen Receptor T Cells", Scientific Reports, 7(737):1-10.

\* cited by examiner

CD4+ enriched T cells

PBMC-initiated T cells

Ultrasonic nozzle, 180 kHz
U2OS cells, 48 well plate
Payload: Alexa 488 10000 dextran

| | %Positive cells | MFI |
|---|---|---|
| Current method, 1.5 bar | 46 | $5.2 \times 10^6$ |
| Ultrasonic, 1.5 bar | 61 | $9.7 \times 10^6$ |
| Ultrasonic, 1.0 bar | 64 | $6.7 \times 10^6$ |

FIG. 23

| Test Rig - Spray Rig ||||
|---|---|---|---|
| # | Description | Supplier | Product I.D |
| 1 | Delivery Solution Nebulizer | Burgerier Reseach | AirMist |
| 2 | Pinch Value | Clippard | NPV1-1C-D1-24 |
| 3 | Delivery Solution Reservoir | Elveflovy | 1.Sml Eppendorf |

Fig. 35A
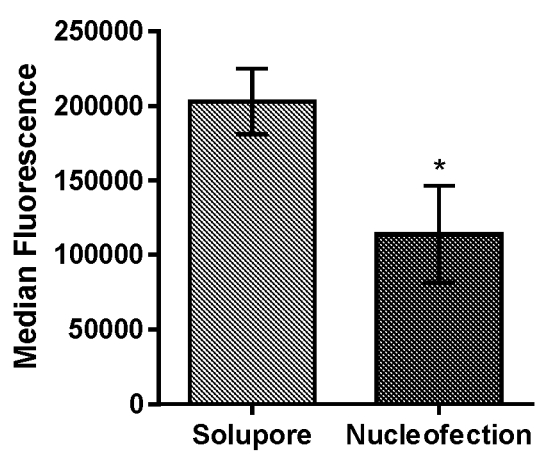
Fig. 35B
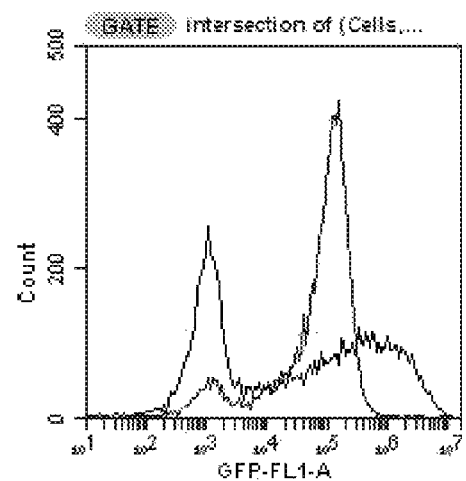
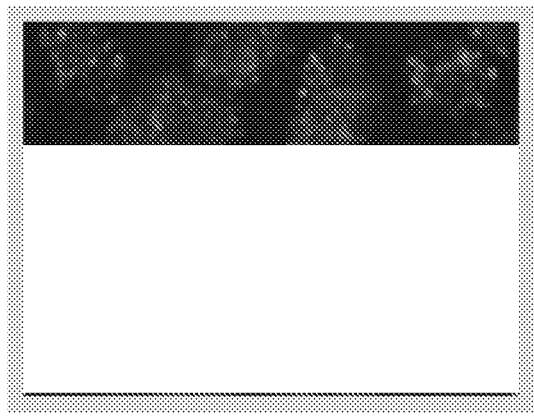
Fig. 35C
Fig. 35D

FIG. 41A

Anti-CD19 scFv | VL | Linker | VH

DIQMTQTTSSLSASLGDRVTISCRASQDTSKYLNWYQQKPDGTVKLLIYHTSRLHSGVPSRFSGSGSGT
DYSLTISNLEQEDIATYFCQQGNTLPYTPGGTKLETTGGGGSGGGGSGGGGSEVKLQESGPGLVAPSQ
SLSVTCTVSGVSLPDYGVSWIRQPPRKGLEWLGVIWGGETTYYNSALKSRLTIIKDRSKSQVFLKMRSL
QTDDTAIYYCAKHYYYGGSYAMDYWGQTSVTVSS (SEQ ID NO. 5)

FIG. 41B

EF-1alpha promoter | T7 promoter | Signal peptide | Anti-CD19 scFv | CD8 hinge | CD8 Transmembrane |
4-1BB | CD3zeta |

```
gagtaattcatacaaaaggactcgcccctgccttgggggaatcccaggacgtcgttaaactccacta
acgtagaaccagagatcgctgctgttccgtgctgagtcgccccgctcgtctcgtcatcactgaggtgag
aagagcatgctgaggctcggcagctccgtgccgtcagtggcagagaagtggcgcgggtaaactgcccagaagt
tggggggaggggttggcaattgaaccggtgcctagaagggggagaacaggtatataagtgcagtagtcgcgtga
tcgtgtactgcgcctttttccgagggtttgccgcaacaggttgccgccagaacaggtaattacttccacgcccctgtgttgttccgggcctg
acgttctttttcacggttatgccgtttgccgcaacaggttgccgccagaacaggtaattacttccacgcccctgtgttgttccgggcctgatt
gcctctcttatccgagctcgagtgaggcctggaagtgggcttgggcctgcttgcgaatctgtctgcaccttcgc
cttgatccgtgcttgagtgctttcgataagtctctagcacatttaaagatcgttccgagggcctgacgcttttt
cctcgtgtctcgctttcgataagtctctagcacatttaaagatcgttccgagggcctgacgcttttt
gcctgtcgctgacatagagtgctgcctgccagcgacacatgcgctgaggcggggcgcgagcgcgcacccg
ttctggcaagatagtgctcgccgctgtaaatgcgtcccagctggccgagggcggggcgcgagcgcgcacccg
ggcggcgacgggcgagtgctgcaagctctcaagctggccgcgctctggtgctgctcgtgagcgagcgccgtatc
agaatcggacgggggtagtctcaaggctgccggctgagcggtcgtgaggcgaaaagatggccgcttccc
```

```
cgcgcctaccggagcagaaacgggcagaaactcctgtatattcaaacaaccattatgagacc
agtacaaactactcaagaggaagatggctgtgctgtagcgcgccccccgcgagagagaaga
actgagagttcaggacgcagagcaggagtacgatgttttggacaagagacgtggccgagat
tgagctcaatctaggacgaagagaacccctcaggaaggcctacgtacagagaagataagatg
tggggaaaagccgacagtgagattgggatgaaagcacctgaaaagagcaagcacatgagatgc
tgaggcctacagtgagattgggatgaaagcacacctgaaaagagcaagcacatgcctttacca
ggtctcagtacagcaggacaccacgacgccctcacatgcaggccctgcccctcgc (SEQ ID NO: 6)
```

FIG. 41C

| Signal peptide | Anti-CD19 seFv | CD8 hinge | CD28 Transmembrane | 4-1BB | CD3zeta |

MALPVTALLPLALLHAARPDIQMTQTTSSLSASLGDRVTISCRASQDISKYLNWYQQKPDGTVKLLI
YHTSRLHSGVPSRFSGSGSGTDYSLTISNLEQEDIATYFCQQGNTLPYTFGGGTKLEITGGGGSGGGGS
GGGGSEVKLQESGPGLVAPSQSLSVTCTVSGVSLPDYGVSWIRQPPRKGLEWLGVIWGSETTYYNSALK
SRLTIIKDNSKSQVFLKMNSLQTDDTAIYYCAKHYYYGGSYAMDYWGQGTSVTVSSTTTPAPRPPTPAP
TIASQPLSLRPEACRPAAGGAVHTRGLDFACDFWVLVVVGGVLACYSLLVTVAFIIFWVRSKRSRLLHS
DYMNMTPRRPGPTRKHYQPYAPPRDFAAYRSKRGRKKLLYIFKQPFMRPVQTTQEEDGCSCRFPEEEEG
GCELRVKFSRSADAPAYKQGQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR (SEQ ID NO: 7)

Fig. 43

| CERTIFICATE OF ANALYSIS | | | |
|---|---|---|---|
| Gene Name | Lenti-T7-CD19-3rd-CAR | Order No. | CBLK-111016-S1B-CAR |
| Lot No. | N.A. | Cloning Vector | pCAR |
| Cloning Sites | EcoRI-BamHI | Insert Size | 1642 bp |
| QC Results | | | |
| Test Items | Specifications | | Results |
| Insert Sequence | Insert sequence results consistent with target | | Pass |
| Vector Sequence | Flanking sequence consistent with expected | | N/A |
| ORF Across Junction | Correct and consistent with target | | N/A |
| Restriction Digest | Expected fragment sizes observed | | N/A |
| PCR Amplification | Correct without non-specific bands | | Pass |
| DNA Quantity/Quality | Actual yield (by A 260) | | 10ug/10ug |
| | Concentration (n/a if lyophilized) | | N/A |
| | Purity (A 260/A280 = 1.8 - 2.0) | | Pass |
| | # of Tubes | | 2 |
| | Matrix | | TE (lyophilized) |
| Endotoxin Test | Verified, <0.1 EU/µg (Endo-Free Preps Only) | | N/A |
| Appearance | Clear, no visible particles | | Pass |
| Label | Correct and white | | Pass |
| Comments | - | | - |

Figure 1-Plate Template Layout

| Parameter | Cell Population % | Cell Viability % | EGFP mRNA Delivery % |
|---|---|---|---|
| UT | 60.14 | 60.71 | 0.58 |
| 1 x 1 7 µl 0.3 Bar 15.5 mm | 63.41 | 39.07 | 1.26 |
| 2 x 2 7 µl 0.3 Bar 15.5 mm | 63.14 | 61 | 0.83 |
| 3 x 3 7 µl 0.3 Bar 15.5 mm | 52.64 | 58.82 | 1.11 |
| 4 x 4 7 µl 0.3 Bar 15.5 mm | 51.31 | 63.3 | 0.84 |
| 5 x 5 7 µl 0.3 Bar 15.5 mm | 44.8 | 61.81 | 1.52 |
| 1 x 1 2 µl 0.3 Bar 15.5 mm | 61.97 | 58.81 | 1.34 |
| 2 x 2 2 µl 0.3 Bar 15.5 mm | 66.64 | 51.66 | 1.06 |
| 3 x 3 2 µl 0.3 Bar 15.5 mm | 64.69 | 56.54 | 1.16 |
| 4 x 4 2 µl 0.3 Bar 15.5 mm | 55.51 | 57.33 | 1.14 |
| 5 x 5 2 µl 0.3 Bar 15.5 mm | 58.37 | 62.27 | 1.07 |

FIG. 61B

1 Enclosing Collar for Ari Mist Spray Head

2 Tip of Ari Mist spray head

3 Well of a double height 96-well filter plate

| | |
|---|---|
| 1 | Enclosing Collar for Ari Mist Spray Head |
| 2 | Tip of Ari Mist spray head |
| 3 | Well of a double height 96-well filter plate |

FIG. 124
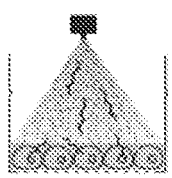
1. Controlled application of delivery solution with cargo, on cell monolayer
2. Transient membrane disruption allows mRNA diffusion through membrane during a short incubation
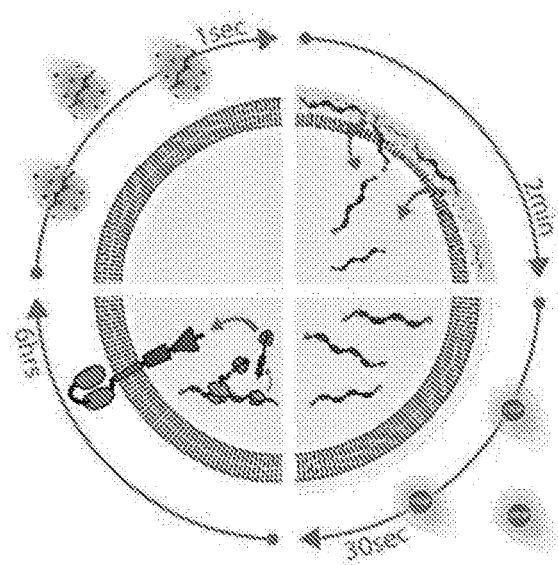
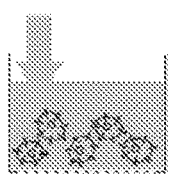
4. Functional engineered cells are maintained in media
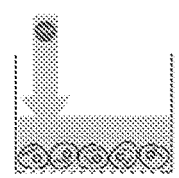
3. Application of stop solution allows membrane to reseal

12400

SEQUENCE LISTING

```
<160> NUMBER OF SEQ ID NOS: 16

<210> SEQ ID NO 1
<211> LENGTH: 867
<212> TYPE: DNA
<213> ORGANISM: Artificial Sequence
<220> FEATURE:
<223> OTHER INFORMATION: encodes for the PD-1 protein

<400> SEQUENCE: 1
atgcagatcc cacaggcgcc ctggccagtc gtctgggcgg tgctacaact gggctggcgg      60
ccaggatggt tcttagactc cccagacagg ccctggaacc cccccacctt ctccccagcc     120
ctgctcgtgg tgaccgaagg ggacaacgcc accttcacct gcagcttctc caacacatcg     180
gagagcttcg tgctaaactg gtaccgcatg agccccagca accagacgga caagctggcc     240
gccttccccg aggaccgcag ccagcccggc caggactgcc gcttccgtgt cacacaactg     300
cccaacgggc gtgacttcca catgagcgtg gtcagggccc ggcgcaatga cagcggcacc     360
tacctctgtg gggccatctc cctggccccc aaggcgcaga tcaaagagag cctgcgggca     420
gagctcaggg tgacagagag aagggcagaa gtgcccacag cccaccccag ccctcaccc     480 aggccagccg gccagttcca aaccctggtg gttggtgtcg tgggcggcct gctgggcagc     540
ctggtgctgc tagtctgggt cctggccgtc atctgctccc gggccgcacg agggacaata     600
ggagccaggc gcaccggcca gcccctgaag gaggaccct cagccgtgcc tgtgttctct     660
gtggactatg gggagctgga tttccagtgg cgagagaaga cccggagcc ccccgtgccc     720 tgtgtccctg agcagacgga gtatgccacc attgtctttc ctagcggaat gggcacctca     780
tcccccgccc gcagggctc agctgacggc cctcggagtg cccagccact gaggcctgag     840
```

```
gatggacact gctcttggcc cctctga                                              867
```

<210> SEQ ID NO 2
<211> LENGTH: 288
<212> TYPE: PRT
<213> ORGANISM: Artificial Sequence
<220> FEATURE:
<223> OTHER INFORMATION: PD1-1 protein amino acid sequence

<400> SEQUENCE: 2

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 3
<211> LENGTH: 20
<212> TYPE: DNA
<213> ORGANISM: Artificial Sequence
<220> FEATURE:
<223> OTHER INFORMATION: crisprRNA

<400> SEQUENCE: 3

```
gcgtgacttc cacatgagcg                                                       20
```

<210> SEQ ID NO 4
<211> LENGTH: 20
<212> TYPE: DNA
<213> ORGANISM: Artificial Sequence
<220> FEATURE:
<223> OTHER INFORMATION: crisprRNA

<400> SEQUENCE: 4
gcagttgtgt gacacggaag                                              20

<210> SEQ ID NO 5
<211> LENGTH: 239
<212> TYPE: PRT
<213> ORGANISM: Artificial Sequence
<220> FEATURE:
<223> OTHER INFORMATION: Anti-CD19 scFv VL-Linker-VH

<400> SEQUENCE: 5

Ile Gln Met Thr Gln Thr Thr Ser Ser Leu Ser Ala Ser Leu Gly Asp
1               5                   10                  15

Arg Val Thr Ile Ser Cys Arg Ala Ser Gln Asp Ile Ser Lys Tyr Leu
            20                  25                  30

Asn Trp Tyr Gln Gln Lys Pro Asp Gly Thr Val Lys Leu Leu Ile Tyr
        35                  40                  45

His Thr Ser Arg Leu His Ser Gly Val Pro Ser Arg Phe Ser Gly Ser
    50                  55                  60

Gly Ser Gly Thr Tyr Ser Leu Thr Ile Ser Asn Leu Glu Gln Glu Asp
65                  70                  75                  80

Ile Ala Thr Tyr Phe Cys Gln Gln Gly Asn Thr Leu Pro Tyr Thr Phe
                85                  90                  95

Gly Gly Gly Thr Lys Leu Glu Ile Thr Gly Gly Gly Ser Gly Gly
            100                 105                 110

Gly Gly Ser Gly Gly Gly Gly Ser Glu Val Lys Leu Gln Glu Ser Gly
        115                 120                 125

Pro Gly Leu Val Ala Pro Ser Gln Leu Ser Val Thr Cys Thr Val Ser
    130                 135                 140

Gly Val Ser Leu Pro Asp Tyr Gly Val Ser Trp Ile Arg Gln Pro Pro
145                 150                 155                 160

Arg Lys Gly Leu Glu Trp Leu Gly Val Ile Trp Gly Ser Glu Thr Thr
                165                 170                 175

Tyr Tyr Asn Ser Ala Leu Lys Ser Arg Leu Thr Ile Ile Lys Asp Asn
            180                 185                 190

Ser Lys Ser Gln Val Phe Leu Lys Met Asn Ser Leu Gln Thr Asp Asp
        195                 200                 205

Thr Ala Ile Tyr Tyr Cys Ala Lys His Tyr Tyr Gly Gly Ser Tyr
    210                 215                 220

Ala Met Asp Tyr Trp Gly Gln Gly Thr Ser Val Thr Val Ser Ser
225                 230                 235

<210> SEQ ID NO 6
<211> LENGTH: 2962
<212> TYPE: DNA
<213> ORGANISM: Artificial Sequence
<220> FEATURE:
<223> OTHER INFORMATION: Nucleotide sequence (codon optimized) of the
      CAR cassette EF-1alpha promoter-T7 promoter-Signal peptide-Anti-
      CD19 scFv-CD8 hinge-CD28 Transmembrane-4-1BB-CD3zeta

<400> SEQUENCE: 6

| | |
|---|---|
| gagtaattca tacaaaagga ctcgcccctg ccttggggaa tcccagggac cgtcgttaaa | 60 |
| ctcccactaa cgtagaaccc agagatcgct gcgttcccgc cccctcaccc gcccgctctc | 120 |
| gtcatcactg aggtggagaa gagcatgcgt gaggctccgg tgcccgtcag tgggcagagc | 180 |
| gcacatcgcc cacagtcccc gagaagttgg ggggaggggg cggcaattga accggtgcct | 240 |
| agagaaggtg gcgcggggta aactgggaaa gtgatgtcgt gtactggctc cgccttttc | 300 |
| ccgagggtgg gggagaaccg tatataagtg cagtagtcgc cgtgaacgtt cttttcgca | 360 |
| acgggtttgc cgccagaaca caggtaagtg ccgtgtgtgg ttcccgcggg cctggcctct | 420 |
| ttacgggtta tggcccttgc gtgccttgaa ttacttccac gccccctggct gcagtacgtg | 480 |
| attcttgatc ccgagcttcg ggttggaagt gggtgggaga gttcgaggcc ttgcgcttaa | 540 |
| ggagccccctt cgcctcgtgc ttgagttgag gcctggcttg ggcgctgggg ccgccgcgtg | 600 |
| cgaatctggt ggcaccttcg cgcctgtctc gctgcttcg ataagtctct agccatttaa | 660 |
| aatttttgat gacctgctgc gacgctttt tctggcaag atagtcttgt aaatgcgggc | 720 |
| caagatctgc acactggtat tcggttttt ggggccgcgg gcggcgacgg ggcccgtgcg | 780 |
| tcccagcgca catgttcggc gaggcggggc ctgcgagcgc ggccaccgag atcggacgg | 840 |
| gggtagtctc aagctggccg gcctgctctg gtgcctggcc tcgcgccgcc gtgtatcgcc | 900 |
| ccgccctggg cggcaaggct ggccggtcg gcaccagttg cgtgagcgga agatggccg | 960 |
| cttccggcc ctgctgcagg gagctcaaaa tggaggacgc ggcgctcggg agagcgggcg | 1020 |
| ggtgagtcac ccacacaaag gaaaagggcc tttccgtcct cagccgtcgc ttcatgtgac | 1080 |
| tccacggagt accgggcgcc gtccaggcac ctcgattagt tctcgagctt ttggagtacg | 1140 |
| tcgtctttag gttgggggga ggggtttat gcgatggagt ttccccacac tgagtgggtg | 1200 |
| gagactgaag ttaggccagc ttggcacttg atgtaattct ccttggaatt tgccctttt | 1260 |
| gagtttggat cttggttcat tctcaagcct cagacagtgg ttcaaagttt ttttcttcca | 1320 |
| tttcaggtgt cgtgattcga attctaatac gactcactat agggccgcca ccatggcctt | 1380 |
| accagtgacc gccttgctcc tgccgctggc cttgctgctc cacgccgcca ggccggacat | 1440 |
| ccagatgaca cagactacat cctccctgtc tgcctctctg ggagacagag tcaccatcag | 1500 |
| ttgcagggca agtcaggaca ttagtaaata tttaaattgg tatcagcaga aaccagatgg | 1560 |
| aactgttaaa ctcctgatct accatacatc aagattacac tcaggagtcc catcaaggtt | 1620 |
| cagtggcagt gggtctggaa cagattattc tctcaccatt agcaacctgg agcaagaaga | 1680 |
| tattgccact tactttttgcc aacagggtaa tacgcttccg tacacgttcg gagggggggac | 1740 |
| caagctggag atcacaggtg gcggtggctc gggcggtggt gggtcgggtg gcggcggatc | 1800 |
| tgaggtgaaa ctgcaggagt caggacctgg cctggtggcg ccctcacaga gcctgtccgt | 1860 |
| cacatgcact gtctcagggg tctcattacc cgactatggt gtaagctgga ttcgccagcc | 1920 |
| tccacgaaag ggtctggagt ggctgggagt aatatgggt agtgaaacca catactataa | 1980 |
| ttcagctctc aaatccagac tgaccatcat caaggacaac tccaagagcc aagttttctt | 2040 |
| aaaaatgaac agtctgcaaa ctgatgacac agccatttac tactgtgcca acattatta | 2100 |
| ctacggtggt agctatgcta tggactactg ggggccaagga acctcagtca ccgtctcctc | 2160 |
| aaccacgacg ccagcgccgc gaccaccaac accggcgccc accatcgcgt cgcagcccct | 2220 |
| gtccctgcgc ccagaggcgt gccggccagc ggcggggggc gcagtgcaca cgaggggggct | 2280 |
| ggacttcgcc tgtgatttct gggtgctggt cgttgtgggc ggcgtgctgg cctgctacag | 2340 |
| cctgctggtg acagtggcct tcatcatctt ttgggtgagg agcaagcgga gcagactgct | 2400 |

```
gcacagcgac tacatgaaca tgaccccccg gaggcctggc cccacccgga agcactacca    2460
gccctacgcc cctcccaggg atttcgccgc ctaccggagc aaacgggggca gaaagaaact    2520 cctgtatata ttcaaacaac catttatgag accagtacaa actactcaag aggaagatgg    2580
ctgtagctgc cgatttccag aagaagaaga aggaggatgt gaactgagag tgaagttcag    2640
caggagcgca gacgccccg cgtacaagca gggccagaac cagctctata acgagctcaa    2700
tctaggacga agagaggagt acgatgtttt ggacaagaga cgtggccggg accctgagat    2760 gggggggaaag ccgagaagga agaaccctca ggaaggcctg tacaatgaac tgcagaaaga    2820
taagatggcg gaggcctaca gtgagattgg gatgaaaggc gagcgccgga ggggcaaggg    2880
gcacgatggc ctttaccagg gtctcagtac agccaccaag gacacctacg acgcccttca    2940
catgcaggcc ctgccccctc gc                                              2962
```

<210> SEQ ID NO 7
<211> LENGTH: 530
<212> TYPE: PRT
<213> ORGANISM: Artificial Sequence
<220> FEATURE:
<223> OTHER INFORMATION: Protein sequence of the CAR cassette Signal
      peptide-Anti-CD19 scFv-CD8 hinge-CD28 Transmembrane-4-1BB-CD3zeta

<400> SEQUENCE: 7

```
Met Ala Leu Pro Val Thr Ala Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gly Gly Gly Ser Glu
    130                 135                 140

Val Lys Leu Gln Glu Ser Gly Pro Gly Leu Val Ala Pro Ser Gln Ser
145                 150                 155                 160

Leu Ser Val Thr Cys Thr Val Ser Gly Val Ser Leu Pro Asp Tyr Gly
                165                 170                 175

Val Ser Trp Ile Arg Gln Pro Pro Arg Lys Gly Leu Glu Trp Leu Gly
            180                 185                 190

Val Ile Trp Gly Ser Glu Thr Thr Tyr Tyr Asn Ser Ala Leu Lys Ser
        195                 200                 205

Arg Leu Thr Ile Ile Lys Asp Asn Ser Lys Ser Gln Val Phe Leu Lys
    210                 215                 220

Met Asn Ser Leu Gln Thr Asp Asp Thr Ala Ile Tyr Tyr Cys Ala Lys
225                 230                 235                 240

His Tyr Tyr Tyr Gly Gly Ser Tyr Ala Met Asp Tyr Trp Gly Gln Gly
                245                 250                 255
```

Thr Ser Val Thr Val Ser Ser Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Phe Trp Val Leu Val Val Val Gly Gly Val Leu Ala
305                 310                 315                 320

Cys Tyr Ser Leu Leu Val Thr Val Ala Phe Ile Ile Phe Val Trp Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
        355                 360                 365

Arg Asp Phe Ala Ala Tyr Arg Ser Lys Arg Gly Arg Lys Lys Leu Leu
    370                 375                 380

Tyr Ile Phe Lys Gln Pro Phe Met Arg Pro Val Gln Thr Thr Gln Glu
385                 390                 395                 400

Glu Asp Gly Cys Ser Cys Arg Phe Pro Glu Glu Glu Glu Gly Gly Cys
                405                 410                 415

Glu Leu Arg Val Lys Phe Ser Arg Ser Ala Asp Ala Pro Ala Tyr Lys
            420                 425                 430

Gln Gly Gln Asn Gln Leu Tyr Asn Glu Leu Asn Leu Gly Arg Arg Glu
        435                 440                 445

Glu Tyr Asp Val Leu Asp Lys Arg Arg Gly Arg Asp Pro Glu Met Gly
    450                 455                 460

Gly Lys Pro Arg Arg Lys Asn Pro Gln Glu Gly Leu Tyr Asn Glu Leu
465                 470                 475                 480

Gln Lys Asp Lys Met Ala Glu Ala Tyr Ser Glu Ile Gly Met Lys Gly
                485                 490                 495

Glu Arg Arg Arg Gly Lys Gly His Asp Gly Leu Tyr Gln Gly Leu Ser
            500                 505                 510

Thr Ala Thr Lys Asp Thr Tyr Asp Ala Leu His Met Gln Ala Leu Pro
        515                 520                 525

Pro Arg
    530

<210> SEQ ID NO 8
<211> LENGTH: 798
<212> TYPE: DNA
<213> ORGANISM: Artificial Sequence
<220> FEATURE:
<223> OTHER INFORMATION: CAR Sequence Alignment validation

<400> SEQUENCE: 8
tcaagcctca gacagtggtt caaagttttt ttcttccatt tcaggtgtcg tgattcgaat      60
tctaatacga ctcactatag ggccgccacc atggccttac cagtgaccgc cttgctcctg     120
ccgctggcct tgctgctcca cgccgccagg ccggacatcc agatgacaca gactacatcc     180
tccctgtctg cctctctggg agacagagtc accatcagtt gcagggcaag tcaggacatt     240
agtaaatatt taaattggta tcagcagaaa ccagatggaa ctgttaaact cctgatctac     300
catacatcaa gattacactc aggagtccca tcaaggttca gtggcagtgg gtctggaaca     360
gattattctc tcaccattag caacctggag caagaagata ttgccactta cttttgccaa     420

| | |
|---|---|
| cagggtaata cgcttccgta cacgttcgga gggggggacca agctggagat cacaggtggc | 480 |
| ggtggctcgg gcggtggtgg gtcggtggc ggcggatctg aggtgaaact gcaggagtca | 540 |
| ggacctggcc tggtggcgcc ctcacagagc ctgtccgtca catgcactgt ctcaggggtc | 600 |
| tcattacccg actatggtgt aagctggatt cgccagcctc cacgaaaggg tctggagtgg | 660 |
| ctgggagtaa tatggggtag tgaaaccaca tactataatt cagctctcaa atccagactg | 720 |
| accatcatca aggacaactc caagagccaa gttttcttaa aaatgaacag tctgcaaact | 780 |
| gatgacacag ccatttac | 798 |

<210> SEQ ID NO 9
<211> LENGTH: 765
<212> TYPE: DNA
<213> ORGANISM: Artificial Sequence
<220> FEATURE:
<223> OTHER INFORMATION: K48306-G106452-1-pCAR-puroless-S (1>765)

<400> SEQUENCE: 9

| | |
|---|---|
| tcaagcctca gacagtggtt caaagttttt ttcttccatt tcaggtgtcg tgattcgaat | 60 |
| tctaatacga ctcactatag ggccgccacc atggccttac cagtgaccgc cttgctcctg | 120 |
| ccgctggcct tgctgctcca cgccgccagg ccggacatcc agatgacaca gactacatcc | 180 |
| tccctgtctg cctctctggg agacagagtc accatcagtt gcagggcaag tcaggacatt | 240 |
| agtaaatatt taaattggta tcagcagaaa ccagatggaa ctgttaaact cctgatctac | 300 |
| catacatcaa gattacactc aggagtccca tcaaggttca gtggcagtgg gtctggaaca | 360 |
| gattattctc tcaccattag caacctggag caagaagata ttgccactta cttttgccaa | 420 |
| cagggtaata cgcttccgta cacgttcgga gggggaccaa agctggagat cacaggtggc | 480 |
| ggtggctcgg gcggtggtgg gtcggtggc ggcggatctg aggtgaaact gcaggagtca | 540 |
| ggacctggcc tggtggcgcc ctcacagagc ctgtccgtca catgcactgt ctcaggggtc | 600 |
| tcattacccg actatggtgt aagctggatt cgccagcctc cacgaaaggg tctggagtgg | 660 |
| ctgggagtaa tatggggtag tgaaaccaca tactataatt cagctctcaa atccagactg | 720 |
| accatcatca aggacaactc caagagccaa gttttcttaa aaatg | 765 |

<210> SEQ ID NO 10
<211> LENGTH: 742
<212> TYPE: DNA
<213> ORGANISM: Artificial Sequence
<220> FEATURE:
<223> OTHER INFORMATION: G106452-1.seq(1>1645)

<400> SEQUENCE: 10

| | |
|---|---|
| gaattctaat acgactcact atagggccgc caccatggcc ttaccagtga ccgccttgct | 60 |
| cctgccgctg gccttgctgc tccacgccgc caggccggac atccagatga cacagactac | 120 |
| atcctccctg tctgcctctc tgggagacag agtcaccatc agttgcaggg caagtcagga | 180 |
| cattagtaaa tatttaaatt ggtatcagca gaaaccagat ggaactgtta aactcctgat | 240 |
| ctaccataca tcaagattac actcaggagt cccatcaagg ttcagtggca gtgggtctgg | 300 |
| aacagattat tctctcacca ttagcaacct ggagcaagaa gatattgcca cttacttttg | 360 |
| ccaacagggt aatacgcttc cgtacacgtt cggaggggg accaagctgg agatcacagg | 420 |
| tggcggtggc tcgggcggtg gtgggtcggg tggcggcgga tctgaggtga aactgcagga | 480 |
| gtcaggacct ggcctggtgg cgccctcaca gagcctgtcc gtcacatgca ctgtctcagg | 540 |
| ggtctcatta cccgactatg gtgtaagctg gattcgccag cctccacgaa agggtctgga | 600 |

```
gtggctggga gtaatatggg gtagtgaaac cacatactat aattcagctc tcaaatccag    660
actgaccatc atcaaggaca actccaagag ccaagttttc ttaaaaatga acagtctgca    720
aactgatgac acagccattt ac                                            742
```

<210> SEQ ID NO 11
<211> LENGTH: 195
<212> TYPE: DNA
<213> ORGANISM: Artificial Sequence
<220> FEATURE:
<223> OTHER INFORMATION: K48306-G106452-1-G106452-1-Seq1- (1>817)

<400> SEQUENCE: 11

```
ttacccgact atggtgtaag ctggattcgc cagcctccac gaaagggtct ggagtggctg     60
ggagtaatat ggggtagtga aaccacatac tataattcag ctctcaaatc cagactgacc    120
atcatcaagg acaactccaa gagccaagtt ttcttaaaaa tgaacagtct gcaaactgat    180
gacacagcca tttac                                                    195
```

<210> SEQ ID NO 12
<211> LENGTH: 1041
<212> TYPE: DNA
<213> ORGANISM: Artificial Sequence
<220> FEATURE:
<223> OTHER INFORMATION: CAR Sequence Alignment Validation

<400> SEQUENCE: 12

```
tactgtgcca acattatta ctacggtggt agctatgcta tggactactg gggccaagga      60
acctcagtca ccgtctcctc aaccacgacg ccagcgccgc gaccaccaac accggccccc    120
accatcgcgt cgcacccct gtccctgcgc ccacaggcgt gccgccagc ggcgggggc      180 gcagtgcaca cgagggggct ccacttcgcc tctgatttct cgctgctcgt cgttgtgggc    240
ggcgtgctgg cctgctacag cctgctggtg acagtggcct tcatcatctt ttgggtgagg    300
agcaagcgga gcagactgct gcacagcgac tacatgaaca tgacccccccg gaggcctcgc    360 cccacccgca agcactacca gcctacgcc cctcccaggg atttcgccgc ctacccgagc    420
aaaccgggca gaaagaaact cctgtatata ttcaaacaac catttatgag accagtacaa    480
actactcaag aggaagatgg ctgtagctcc cgatttccag aagaagaaga aggaggatgt    540
gaactgagag tgaagttcag caggagcgca gacgccccccg cgtacaagca gggccagaac    600
cagctctata cgagctcaa tctaggacga agagaggagt acgatgtttt ggacaagaga    660
cgtggccgga accctgagat ggggggaaag ccgagaagga agaaccctca ggaagggctg    720
tacaatgaac tgcagaaaga taagatggcg gaggcctaca gtgagattgg gatgaaaggc    780
gagggccgga ggggcaaggg gcacgatggc ctttaccagg gtctcagtac agccaccaag    840
gacacctacg acgcccttca catgcaggcc gtgccccctc gctgataacc cggggatcc    900 cgcgactcta gaccgcgtct gcaacaatcr acctctggat tacaaaattt gtgraagatt    960
gactggtatt cttaactatg ttgctccttt taccctatgt ggatacgctg ctttaatgcc    1020
tttgtatcat gctattgctt c                                             1041
```

<210> SEQ ID NO 13
<211> LENGTH: 783
<212> TYPE: DNA
<213> ORGANISM: Artificial Sequence
<220> FEATURE:
<223> OTHER INFORMATION: G106452-1 seq (1>1645)

<400> SEQUENCE: 13

```
tactgtgcca aacattatta ctacggtggt agctatgcta tggactactg gggccaagga      60
acctcagtca ccgtctcctc aaccaccacg ccagcgccgc gaccaccaac accggcgccc     120
accatcgcgt cgcagcccct gtccctgcgc ccagaggcgt gccggccagc ggcgggggc      180
gcagtgcaca cgagggggct ggacttcgcc tgtgatttct gggtgctggt cgttgtgggc     240
ggcgtgctcg cctgctacag cctgctggtg acagtggcct tcatcatctt ttgggtcagg     300
agcaagggga gcagactgct gcacaccgac tacatgaaca tcacccccg gaggcctggc      360
cccacccgga accactacca gccctacgcc cctcccaggg atttcgcggc ctaccggagc     420
aaacggggca gaaagaaact cctgtatata ttcaaacaac catttatcag accagtacaa     480
actactcaag aggaagatgg ctgtacctgc cgatttccag amaagaagaa ggaggatgtg     540
aactgagagt gaagttcatc aggagcgcag acgccccgc ctacaagcag gccagaacc      600
agctctataa cgagctcaat ctaggacgaa gagaggagta ccatgttttg gacamacacg     660
tggcggggac cctgagatgg gggggcacca tccccttta c agggtctca ctacagccac     720
caaggacacc taccacgccc ttcacatcca ggccctgccc gctcgctgat aacccggcga     780
tcc                                                                   783
```

<210> SEQ ID NO 14
<211> LENGTH: 507
<212> TYPE: DNA
<213> ORGANISM: Artificial Sequence
<220> FEATURE:
<223> OTHER INFORMATION: K48306-G106452-1-G106452-1-Seq1-(1>817)

<400> SEQUENCE: 14

```
gcgcccacca tcgcgtcgca gcccctgtcc ctgcgcccag aggcgtgccg gccagcggcg      60
gggggcgcag tgcacacgag ggggctggac ttcgcctgtg atttctgggt gctggtcgtt     120
gtgggcggcg tgctggcctg ctacagcctg ctggtgacag tggccttcat catcttttgg     180
gtgaggagca agcggagcag actgctgcac agcgactaca tgaacatgac ccccggagg     240
cctggcccca cccggaagca ctaccagccc tacgcccctc ccagggatt tcgccgccta     300
cggagcaaac ggggcagaaa gaaactcctg tatatattca acaaccattt atgagaccag     360
tacaaactac tcaagaggaa gatggctgta gctgccgatt ccagaagaa gaagaaggag     420
gatgtgaact gacagtgaag ttcagcagga gcgcagacgc ccccgcgtac aagcagggcc     480
agaaccagct ctataaccag ctcaatc                                        507
```

<210> SEQ ID NO 15
<211> LENGTH: 724
<212> TYPE: DNA
<213> ORGANISM: Artificial Sequence
<220> FEATURE:
<223> OTHER INFORMATION: K4 a 3 0 6-610 64 5 2-1-pCAR-pur oles s -S
      (1>755)

<400> SEQUENCE: 15

```
gtcgttgtgg gcggcgtgct ggcctgctac agcctgctgg tgacagtggc cttcatcatc      60
ttttgggtga ggagcaagcg gagcagactg ctgcacagcg actacatgaa catgaccccc     120
cggaggcctg gccccacccg gaagcactac cagccctacg cccctcccag ggatttcgcc     180
gcctaccgga gcaaacgggg cagaaagaaa ctcctgtata tattcaaaca accatttatg     240
agaccagtac aaactactca agaggaagat ggctgtagct gccgatttcc agaagaagaa     300
```

```
gaaggaggat gtgaactgag agtgaagttc agcaggagcg cagacgcccc cgcgtacaag    360
cagggccaga accagctcta taacgagctc aatctaggac gaagagagga gtacgatgtt    420
ttggacaaga gacgtggccg ggaccctgag atgggggaa agccgagaag gaagaaccct     480
caggaaggcc tgtacaatga actgcagaaa gataagatgg cggaggccta cagtgagatt    540
gggatgaaag gcgagcgccg gaggggcaag gggcaccatc ccctttacca gggtctcact    600
acagccacca aggaccccta ccacgccctt cacatccagg ccctgccccc tcgctgataa    660
cccgmcgatc ccccgactct acaccgcgtc tggaacaatc aacctctgga ttacaaaatt    720
tgtg                                                                 724

<210> SEQ ID NO 16
<211> LENGTH: 745
<212> TYPE: DNA
<213> ORGANISM: Artificial Sequence
<220> FEATURE:
<223> OTHER INFORMATION: K4 83 0 6-610 64 52-1-G10 6 4 5 2-1-Seq2 -
      (1>745)

<400> SEQUENCE: 16
gaggagcaag cggagcagac tgctgcacag cgactacatg aacatgaccc cccggaggcc     60 tggcccccacc cggaagcact accagcccta cgcccctccc agggatttcg ccgcctaccg    120
gagcaaacgg ggcagaaaga aactcctgta tatattcaaa caaccattta tgagaccagt    180
acaaactact caagaggaag atggctgtag ctgccgattt ccagaagaag aagaaggagg    240
atgtgaactg agagtgaagt tcagcaggag cgcagacgcc cccgcgtaca agcagggcca    300
gaaccagctc tataacgagc tcaatctagg acgaagagag gagtacgatg ttttggacaa    360
gagacgtggc cgggaccctg agatgggggg aaagccgaga aggaagaacc ctcaggaagg    420
cctgtacaat gaactgcaga aagataagat ggcggaggcc tacagtgaga ttgggatgaa    480
aggcgagcgc cggaggggca aggggcacga tgcccttac caggctctca gtacagccac    540
craggacacc taccacgccc ttcacatcca ggccctgccc cctcgctgat aacccggggg    600
atcccgcgac tctacacggg gtctggaaca atcaacctct ggattacaaa atttgtgaaa    660
gattgactgg tattcttaac tatgttgctc cttttacgct atgtggatac gctgctttaa    720
tgcctttgta tcatgctatt gcttc                                          745
```

VECTOR-FREE INTRACELLULAR DELIVERY BY REVERSIBLE PERMEABILIZATION

CROSS-REFERENCE TO RELATED APPLICATIONS

This application is a national stage application filed under 35 U.S.C. § 371, of International Patent Application No. PCT/IB17/001713, filed Dec. 21, 2017, which claims the benefit of and priority to U.S. Provisional Patent Application No. 62/438,298, filed Dec. 22, 2016, U.S. Provisional Patent Application No. 62/528,963 filed Jul. 5, 2017, and U.S. Provisional Patent Application No. 62/536,831 filed Jul. 25, 2017, the entire contents of each of which is hereby expressly incorporated by reference herein.

INCORPORATION BY REFERENCE OF SEQUENCE LISTING

The contents of the sequence listing text file named "048831-516001WO_Sequence_Listing_ST25.txt", which was created on Dec. 21, 2017 and is 31,000 bytes in size, is hereby incorporated by reference in its entirety.

FIELD OF THE INVENTION

The invention relates to the delivery of agents into mammalian cells.

BACKGROUND OF THE INVENTION

Variability in cell transfection efficiency exists among different cell types. Transfection of suspension cells, e.g., non-adherent cells, has proven to be very difficult using conventional methods. Thus, a need exists for compositions and methods to facilitate transfection of such cells.

SUMMARY OF THE INVENTION

The invention provides a solution to the problem of delivering payload/cargo compounds and compositions into non-adherent cells. Accordingly, a method of delivering a payload across a plasma membrane of a non-adherent cell comprises the steps of providing a population of non-adherent cells and contacting the population of cells with a volume of an isotonic aqueous solution, the aqueous solution including the payload and an alcohol at greater than 5 percent (v/v) concentration. For example, the alcohol comprises ethanol, e.g., greater than 10% ethanol. In some examples, the aqueous solution comprises between 20-30% ethanol, e.g., 27% ethanol.

The aqueous solution for delivering cargo to cells comprises a salt, e.g., potassium chloride (KCl) in between 12.5-500 mM. For example, the solution is isotonic with respect to the cytoplasm of a mammalian cell such as a human T cell. Such an exemplary isotonic delivery solution 106 mM KCl.

The methods are used to deliver any cargo molecule or molecules to mammalian cells, adherent or non-adherent and are particularly useful to deliver cargo to non-adherent cells because of the difficulties associated with doing so prior to the invention. In some examples, the non-adherent cell comprises a peripheral blood mononuclear cell, e.g., the non-adherent cell comprises an immune cell such as a T cell (T lymphocyte). An immune cell such as a T cell is optionally activated with a ligand of CD3, CD28, or a combination thereof. For example, the ligand is an antibody or antibody fragment that binds to CD3 or CD28 or both.

The method involves delivering the cargo in the delivery solution to a population of non-adherent cells comprising a monolayer. For example, the monolayer is contacted with a spray of aqueous delivery solution. The method delivers the payload/cargo (compound or composition) into the cytoplasm of the cell and wherein the population of cells comprises a greater percent viability compared to delivery of the payload by electroporation or nucleofection—a significant advantage of the Soluporation system.

Any compound or composition can be delivered. For example, the payload comprises a messenger ribonucleic acid (mRNA), e.g., a mRNA that encodes a gene-editing composition. For example, the gene editing composition reduces the expression of an immune checkpoint inhibitor such as PD-1 or PD-L1. In some examples, the mRNA encodes a chimeric antigen receptor (CAR).

In certain embodiments, the monolayer of non-adherent/suspension cells resides on a membrane filter. In some embodiments, the membrane filter is vibrated following contacting the cell monolayer with a spray of the delivery solution. The membrane filter may be vibrated or agitated before, during, and/or after spraying the cells with the delivery solution.

Also within the invention is a system comprising: a housing configured to receive a plate comprising a well; a differential pressure applicator configured to apply a differential pressure to the well; a delivery solution applicator configured to deliver atomized delivery solution to the well; a stop solution applicator configured to deliver a stop solution to the well; and a culture medium applicator configured to deliver a culture medium to the well. A stop solution is one that lacks a cell membrane permeabilizing agent, e.g., ethanol. An example phosphate buffered saline or any physiologically-compatible buffer solution. The system optionally further comprises: an addressable well assembly configured to: align the differential pressure applicator adjacent the well for applying the differential pressure to the well; align the delivery solution applicator adjacent the well for delivering the atomized delivery solution to the well; align the stop solution applicator adjacent the well to deliver the stop solution to the well; and/or align the culture medium applicator adjacent the well to deliver the culture medium to the well.

The addressable well assembly can include a movable base-plate configured to receive the plate comprising the well and move the plate in at least one dimension. The addressable well assembly can include a mounting assembly configured to couple to the delivery solution applicator, the stop solution applicator and the culture medium applicator.

The delivery solution applicator can include a nebulizer. The delivery solution applicator can be configured to deliver 10-300 micro liters of the delivery solution per actuation.

The system can include a temperature control system configured to control a temperature of the delivery solution and/or of the plate comprising the well.

The system can include an enclosure configured to control an environment of the plate comprising the well.

The differential pressure applicator can include a nozzle assembly configured to form a seal with an opening of the well and to deliver a vapor to the well to increase or decrease pressure within the well, thereby driving a liquid portion of the culture medium from the well such that a layer of cells remains within the well.

The stop solution applicator can comprise a needle emitter configured to couple to a stop solution reservoir.

The culture medium applicator can comprise a needle emitter configured to couple to a culture medium reservoir.

The system can further comprise a controller configured to: receive user input; operate the delivery solution applicator to deliver the atomized delivery solution to a cellular monolayer within the well; incubate, for a first incubation period, the cellular monolayer after application of the delivery solution; operate, in response to expiration of the first incubation period, the stop solution applicator to deliver the stop solution to the cellular monolayer; and incubate, for a second incubation period and in response to application of the stop solution, the cellular monolayer. The controller can be further configured to: iterate operation of the delivery solution applicator, incubation for the first incubation period, operation of the stop solution applicator, and incubation for the second incubation period for a predetermined number of iterations.

The system can further comprise a controller configured to: operate the positive pressure system to remove supernatant from the well to create a cellular monolayer within the well.

The delivery solution applicator can include a spray head and a collar encircling a distal end of the spray head, wherein the collar is configured to prevent contamination between wells in a multi-well plate, wherein the collar is configured to provide a gap between the plate and the collar.

The delivery solution applicator can include a spray head and a film encircling a distal end of the spray head.

The system can further comprise a vibration system coupled to a membrane holder and configured to vibrate a membrane.

The system can further comprise the plate, wherein the well is configured to contain a population of non-adherent cells.

The delivery solution includes an isotonic aqueous solution, the aqueous solution including the payload and an alcohol at greater than 5 percent (v/v) concentration. The alcohol can comprise ethanol. The aqueous solution can comprise greater than 10% ethanol. The aqueous solution can comprise between 20-30% ethanol. The aqueous solution can comprise 27% ethanol. The aqueous solution can comprise between 12.5-500 mM KCl. The aqueous solution can comprise between 106 mM KCl.

The non-adherent cells can comprise a peripheral blood mononuclear cell. The non-adherent cells can comprise an immune cell. The non-adherent cells can comprise non-adherent cell comprises a T lymphocyte. The population of non-adherent cells can comprise a monolayer.

The payload can comprise a messenger ribonucleic acid (mRNA). The mRNA can encode a gene-editing composition. For example, the gene editing composition reduces the expression of PD-1. The mRNA can encode a chimeric antigen receptor.

The system can be used to deliver a cargo compound or composition to a mammalian cell.

In another aspect, a composition comprises an isotonic aqueous solution, the aqueous solution comprising KCl at a concentration of 10-500 mM and ethanol at greater than 5 percent (v/v) concentration for use to deliver a cargo compound or composition to a mammalian cell. The KCl concentration can be 106 mM and said alcohol concentration can be 27%.

The compounds that are loaded into the MPS composition are processed or purified. For example, polynucleotides, polypeptides, or other agents are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Purified also defines a degree of sterility that is safe for administration to a human subject, e.g., lacking infectious or toxic agents. In the case of tumor antigens, the antigen may be purified or a processed preparation such as a tumor cell lysate.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

A small molecule is a compound that is less than 2000 Daltons in mass. The molecular mass of the small molecule is preferably less than 1000 Daltons, more preferably less than 600 Daltons, e.g., the compound is less than 500 Daltons, 400 Daltons, 300 Daltons, 200 Daltons, or 100 Daltons.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

(FIG. 19A). Media was removed from cells seeded in a 96-well filter plate by either centrifugation or positive pressure (FIG. 19B). GFP mRNA was delivered by Soluporation and expression assessed by flow cytometry.

FIG. 23 is a photograph of an Ari Mist Nebulizer payload fluidic control using a pinch valve. Image demonstrates the fluidic control of the payload solution to the Ari Mist nebulizer on the test rig used for optimisation of atomisation of the delivery solution. The ari mist nebulizer (1) is connected to a pinch valve (2) connected to an Elveflow delivery solution reservoir (3).

FIG. 24 is a dot plot showing Ari Mist Test Rig Longitudinal Data. Graph demonstrates GFP mRNA efficiency to T-cells using the Ari Mist nebulizer gathered over the course of the optimisation experiments. The data demonstrates average uptake efficiency of up to 25% and high reproducibility across replicates.

FIG. 25 is a dot plot showing Ultrasonic 180 kHz Test Rig Longitudinal Data. Graph demonstrates GFP mRNA efficiency to T-cells using the Ultrasonic nebulizer gathered over the course of the optimisation experiments. The data demonstrates average uptake efficiency of up to 30% and high reproducibility across replicate.

FIG. 26 is a dot plot showing Nasal Head Test Rig Longitudinal Data. Graph demonstrates GFP mRNA efficiency to T-cells using the MAD nasal head nebulizer gathered over the course of the optimisation experiments. The data demonstrates average uptake efficiency of up to 22% with reduced reproducibility across replicates compared to the Ari Mist and Ultrasonic spray head.

FIG. 27A and FIG. 27B are bar graphs showing results from a comparison of atomiser height above cells. GFP expression was assessed in T cells following delivery of mRNA with the atomiser height set at 31, 26, 12 or 11 mm.

FIG. 28 is a bar graph showing a comparison of delivery solution volumes. GFP expression in T cells following delivery of GFP mRNA in delivery solution of different volumes (4, 1 or 0.5 μl).

FIG. 29 is a bar graph showing a comparison of salt concentrations. GFP mRNA was added to delivery solution containing 12 mM KCl (Hypotonic) or 106 mM KCl (Isotonic). "Hypotonic" and "isotonic" refer to tonicity relative to cell cytoplasm. Expressions levels at 24 hr were assessed by flow cytometry.

(FIG. 33B) For electroporation, delivery efficiency was 92.9% (+/−0.6%) and cell survival was 73.0% (+/−9.8%). (FIG. 33C) The transfection score ((transfected cells/total cells)×(viable cells/total cells)) was 0.33 (+/−0.05) for the current subject matter technology and 0.51 (+/−0.13) for electroporation with no significant difference between the scores, p=0.25.

FIG. 35A is a bar graph, FIG. 35B is a line graph, and FIGS. 35C and 35D are photographs showing a comparison of fluorescence intensity between Solupore and Nucleofection-mediated delivery of cargo. The Median fluorescence intensity produced by human T cells 24 hr post-delivery of GFP mRNA was compared between Solupore and Nucleofection (FIG. 35A) and a histogram showing the increase in intensity (FIG. 35B). An example image of T cells aggregates expressing GFP following Soluporation (brighter) and Nucleofection.

(FIG. 37A) 10 kDa dextran-Alexa488 was delivered into A549 cells and analysed by fluorescence microscopy at 30 sec, 1 min, 2 min and 3 min post-delivery (10× mag.). (FIG. 37B) A549 were pretreated with Dynasore (4 mM) or chloropromazine (20 μM) to inhibit clathrin-mediated endocytosis or Nystatin (20 μg/ml) or EIPA (100 μM) to inhibit caveolar-mediated endocytosis and micropinocytosis respectively (n=3). None of these inhibitors blocked the uptake of EGFP mRNA. (FIG. 37C) Lipofectamine 2000 was used as a positive control for endocytosis-mediated delivery. GFP expression was significantly reduced in lipofected cells treated with Dynasore (n=3). (FIG. 37D) To examine recovery of the cell membrane after permeabilization, delivery solution was sprayed onto A549 cells in the absence of cargo and at subsequent time points (0 to 182.5 min) medium was removed and 50 μl propidium iodide (100 μg/ml) in PBS added. After 2 min incubation the PI solution was removed and the cells were harvested. For basal levels of PI uptake, untreated cells received 50 μl PI in PBS. PI uptake was analysed by flow cytometry and the data indicate that the cells remain permeable to PI for up to 6 min post-treatment but then reseal and prevent uptake thereafter (n=3). Error bars represent standard error (SE) across three experiments (n=3). ***p<0.001, student's t test for independent means.

Figure 41B:
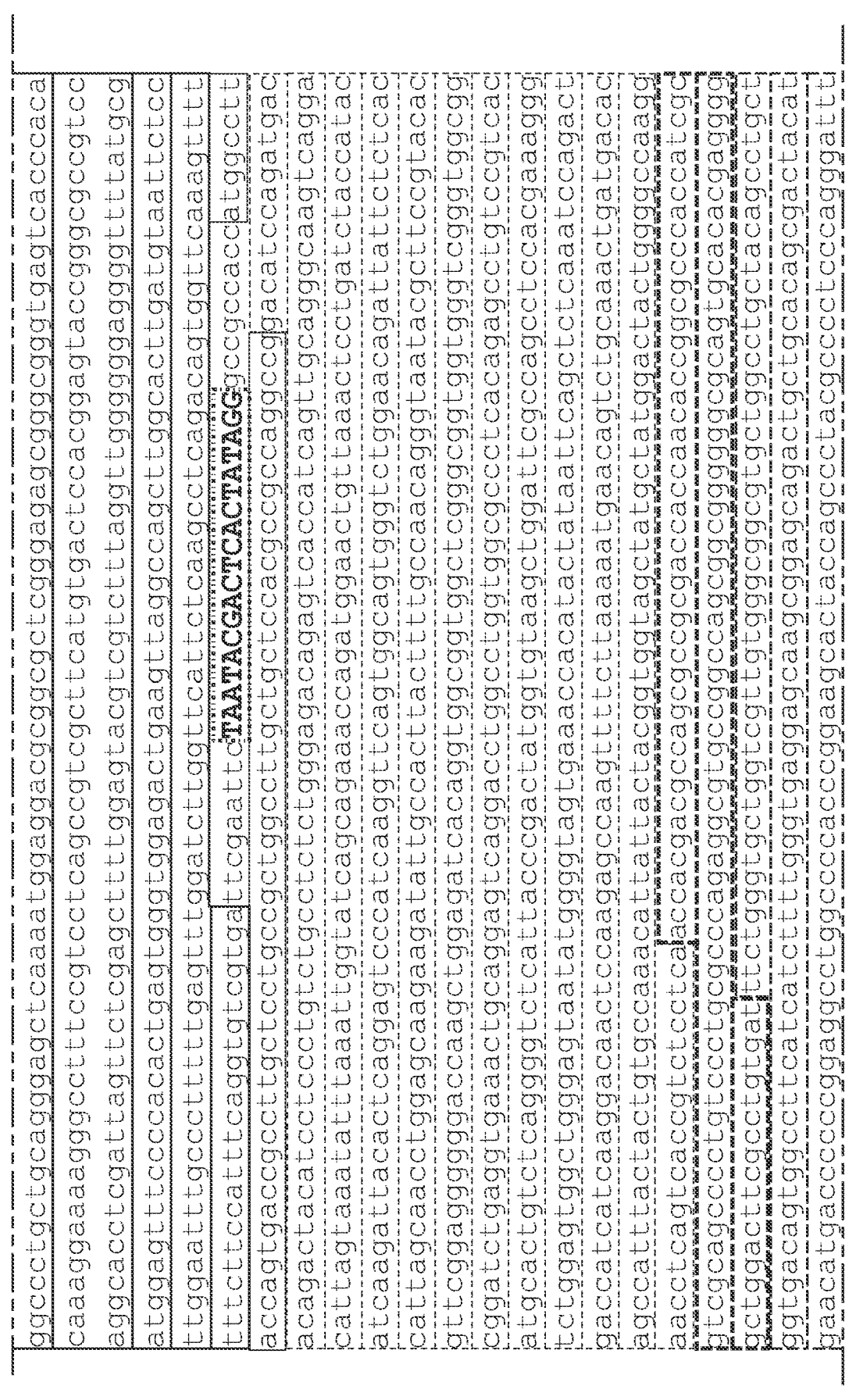

FIG. 41A is a schematic depicting the sequence of single-chain variable fragment (scFv).

FIG. 41B is a schematic depicting the nucleotide sequence (codon optimized) of the CAR cassette.

FIG. 41C is a schematic depicting the protein sequence of the CAR cassette.

FIG. 43 is a table showing the QC results and Certificate of Analysis of the commercially sourced CAR vector.

Figure 44A:
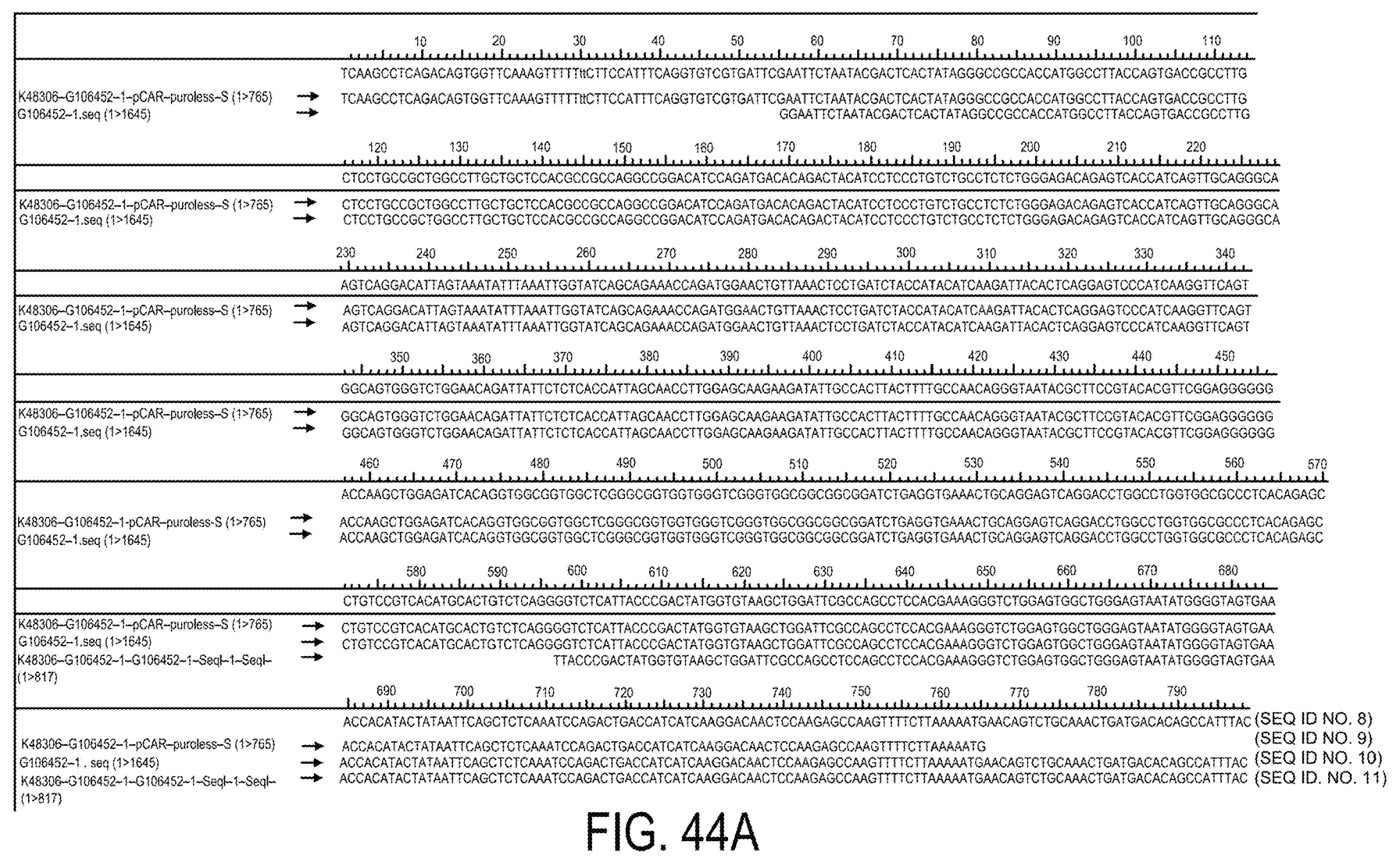

FIG. 44A-FIG. 44B are is a schematic depicting the CAR sequence alignment validation of the commercially sourced CAR vector.

FIG. 53A. Human CD45+ cells were detected in mice that received untreated (UT) PBMC and soluporated (Sol) PBMC. Low numbers of human CD45+ cells were detected in mice that received nucleofected (Nuc) PBMC. FIG. 53B. The presence of CD4+ cells was confirmed in Groups 2, 5 and 6. FIG. 53C. The presence of CD8+ cells was confirmed in Groups 2, 5 and 6.

FIG. 61A is a bar graph and FIG. 61B is a table showing data demonstrating lack of GFP mRNA delivery using the Certus Flex Digital Dispensing technology. (FIG. 61A) Graph depicts representative data demonstrating lack of mRNA delivery using the Certus Flex. Cell viability was not adversely affected using this system. (FIG. 61B) Corresponding data set detailed in table.

(FIG. 62A). Graph demonstrates data comparing delivery efficiency without an enclosing collar (− collar), with the enclosing collar (+ collar) and with the enclosing collar with a 1 mm gap between the collar and the 96-well plate (+ collar and 1 mm gap). Results indicate the addition of the enclosing collar had a negative impact on the spray which was reversed when a 1 mm gap was left between the collar and the well plate. (FIG. 62B) Image demonstrates the enclosing collar set-up. The collar is inserted onto the Ari Mist spray head. The spray head is positioned 27 mm over the well of a double height plate which leaves a 1 mm gap between the collar and the top of the well plate. Delivery efficiency was not impacted with this set-up.

FIG. 90 illustrates a distal end of the nozzle as it contacts a well of a 96-well filter plate.

FIG. 120 is a plot showing data that characterizes force profiles for a LB-100 nebulizer corresponding to various test parameters.

Figure 121:
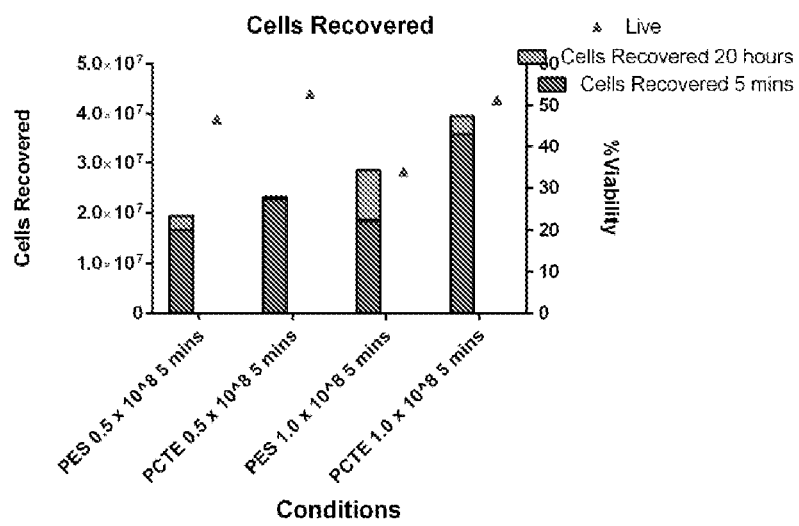

FIG. 121 is a plot showing data characterizing cell recovery and viability following cell monolayer formation. Representative data demonstrates cell recovery from PES and PCTE filter membranes. A cell suspension at two different concentrations was applied to a 63 mm stirred cell unit. Pressure in the range of 100-250 mbar was applied for 10 seconds. Following formation of the cell monolayer, the filter was rinsed and cells counted and viability analysed. Data shows cell recovery and viability is improved from the PCTE (track-edged) filters.

Figure 122:
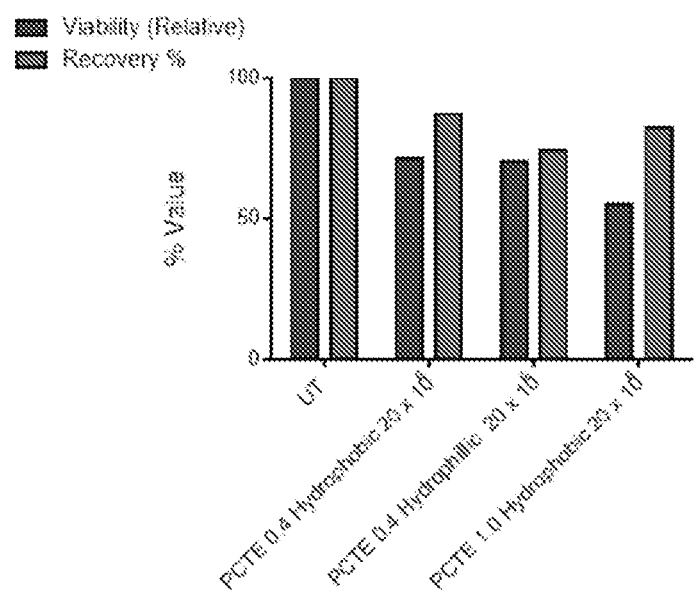

FIG. 122 is another plot showing data characterizing cell recover and viability following cell monolayer formation.

Figure 123:
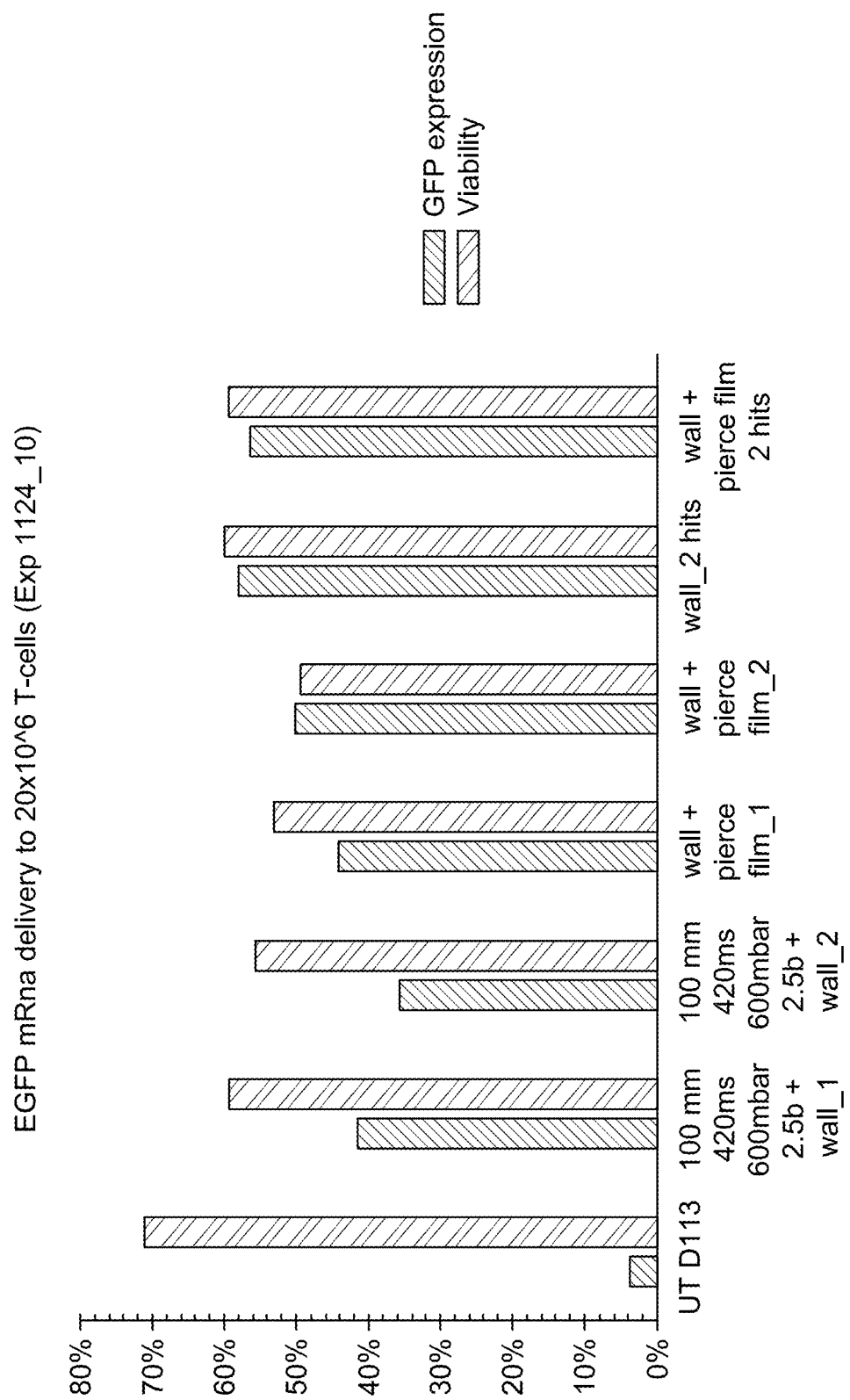

FIG. 123 is another plot showing data characterizing deliver efficiency using a LB-100 nebulizer. Representative data demonstrates delivery efficiency of GFP mRNA into T-cells using the LB-100 nebulizer across different parameters tested (100 mm distance, 420 ms spray duration, 600 mbar pressure corresponding to 100 µl volume delivered and 2.5 bar air pressure). In addition, the presence of walls and an enclosing film was tested. 100 µl delivery solution was atomised using the LB-100 onto a monolayer of $20 \times 10^6$ T-cells in a 40 mm diameter target area. Delivery efficiency of up to 50% was achieved with a single spray and up to 58% with a double spray protocol. Average viability across treatment groups was 60%.

FIG. 124 a diagram illustrating a mechanism of action.

Figure 125:
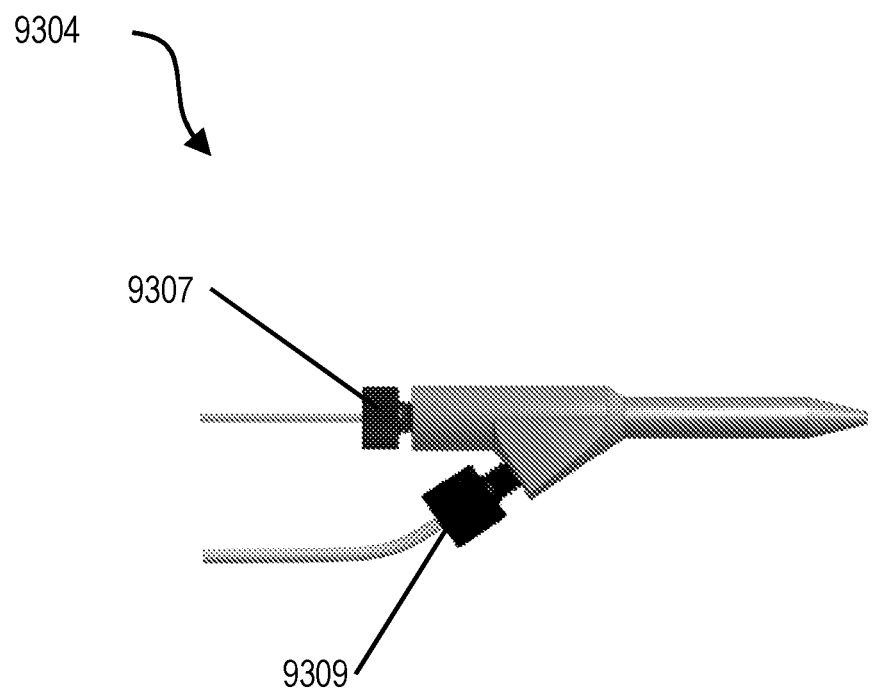

FIG. 125 is an embodiment of an Ari Mist nebulizer. Shown here are the connections for liquid and air to the nebulizer. Described in U.S. Pat. Nos. 5,411,208; 6,634,572 and Canadian Patents #2,112,093 & 2,384,201.

Figure 126:
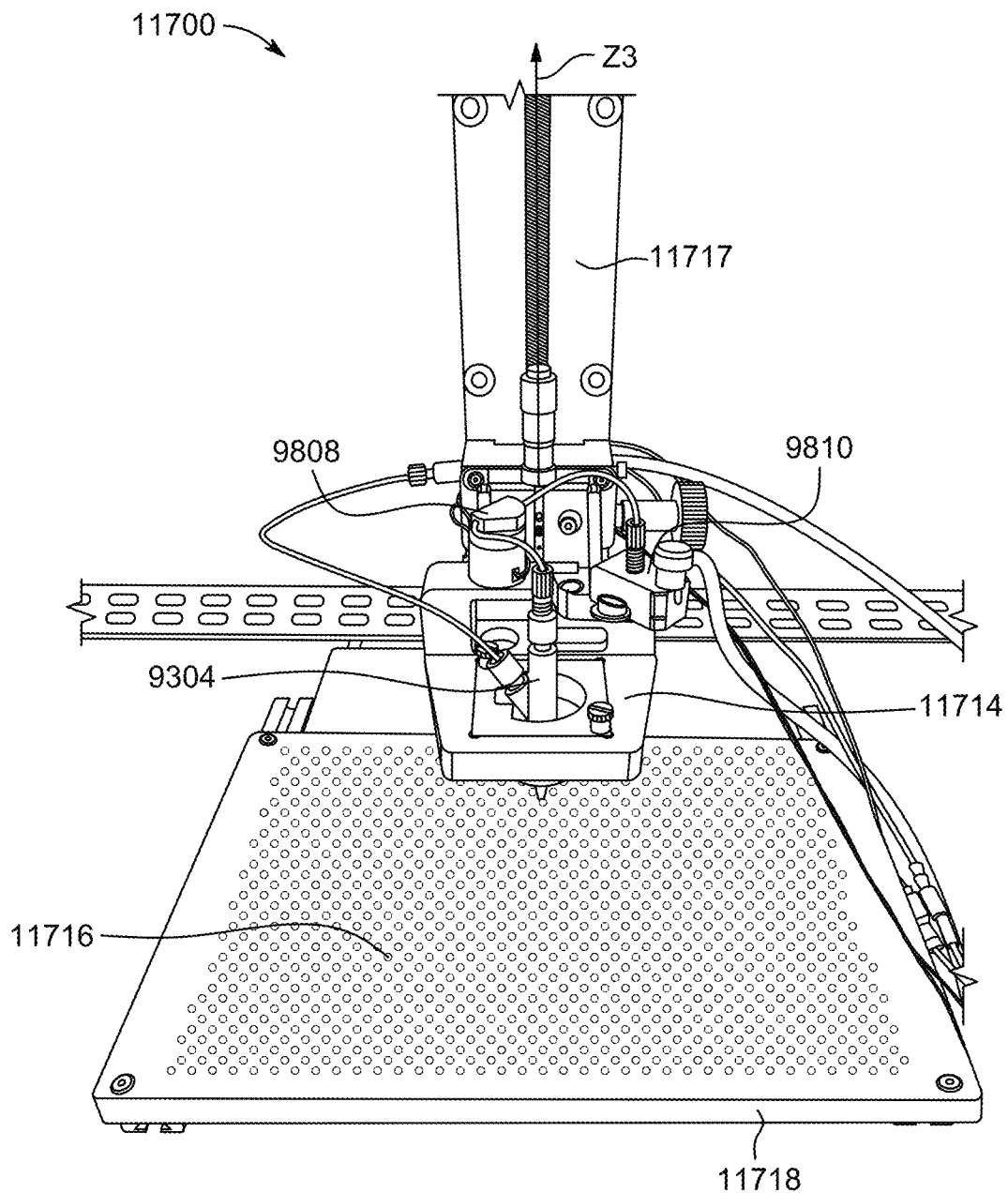

FIG. 126 is an exemplary embodiment of a payload delivery system (Rig 1).

Figure 127:
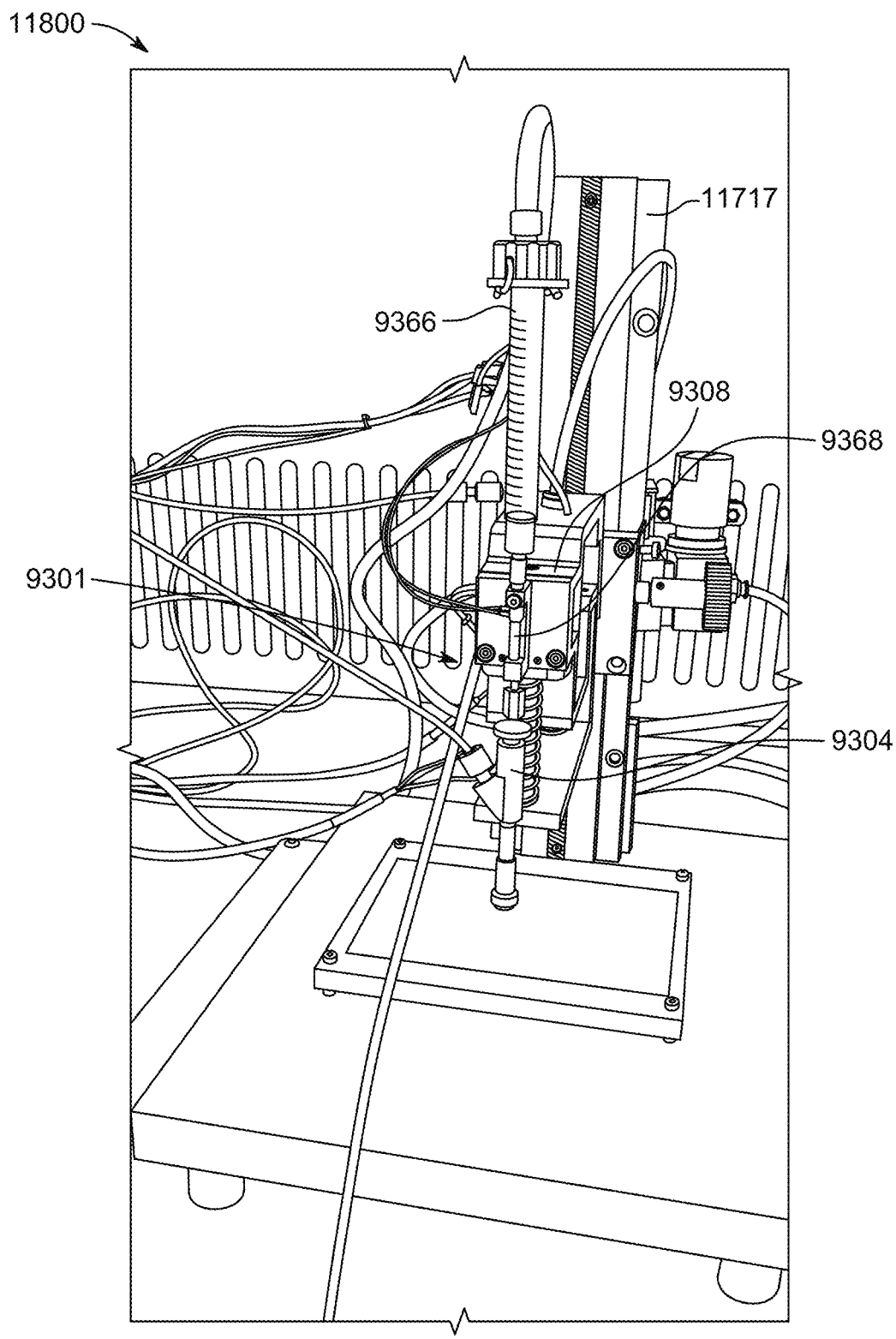

FIG. 127 is an exemplary embodiment of a payload delivery system (Rig 3).

Figure 128:
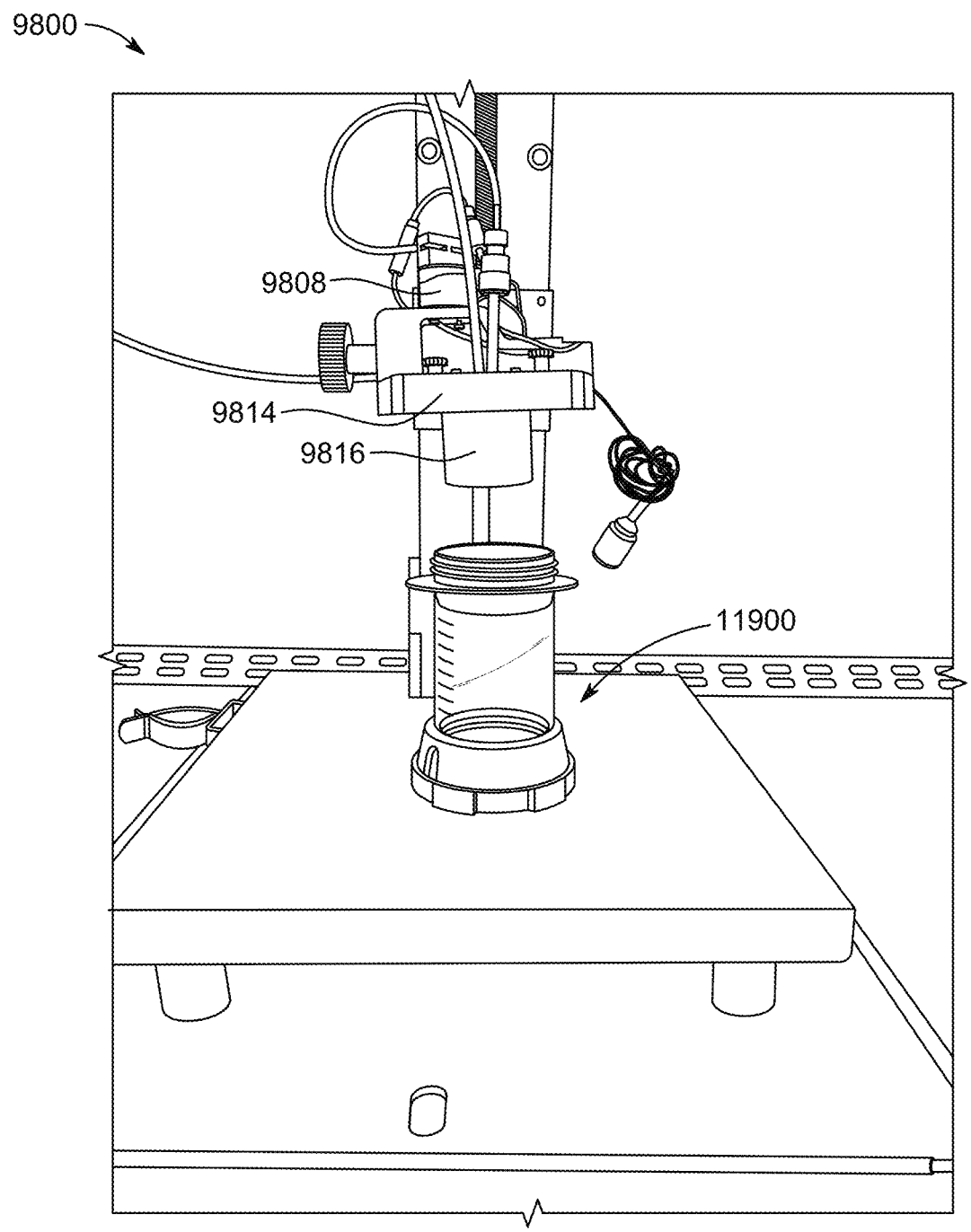

FIG. 128 is an exemplary embodiment of a payload delivery system (Rig 4).

Figure 129:
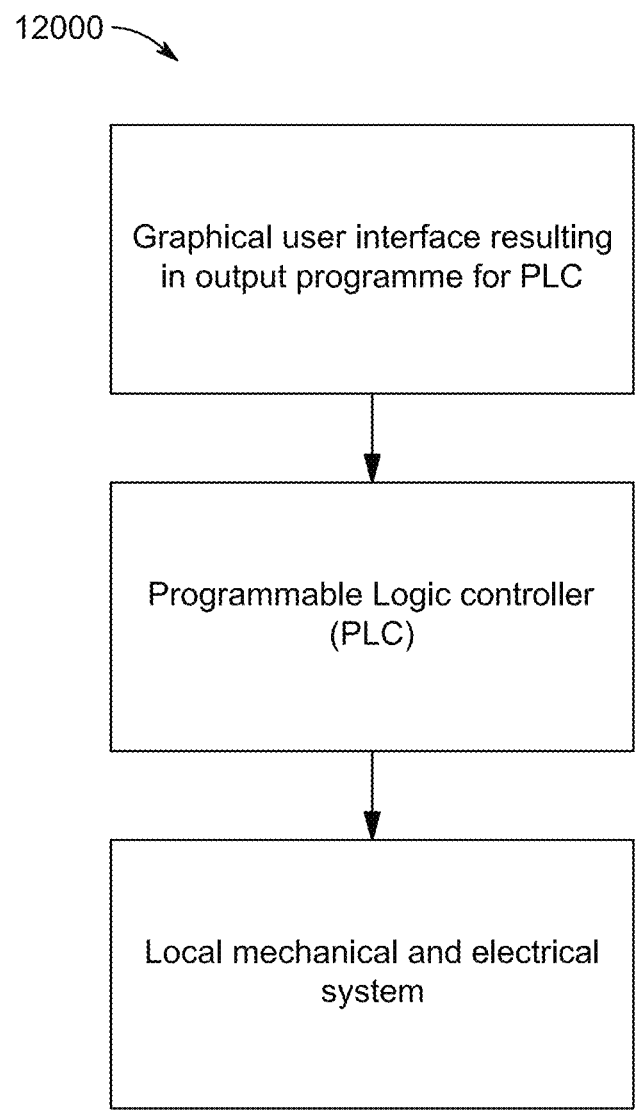

FIG. 129 is a schematic of a software platform including graphical user interface used to output a program to a PLC which provides local control to the mechanical and electrical system.

Figure 130:
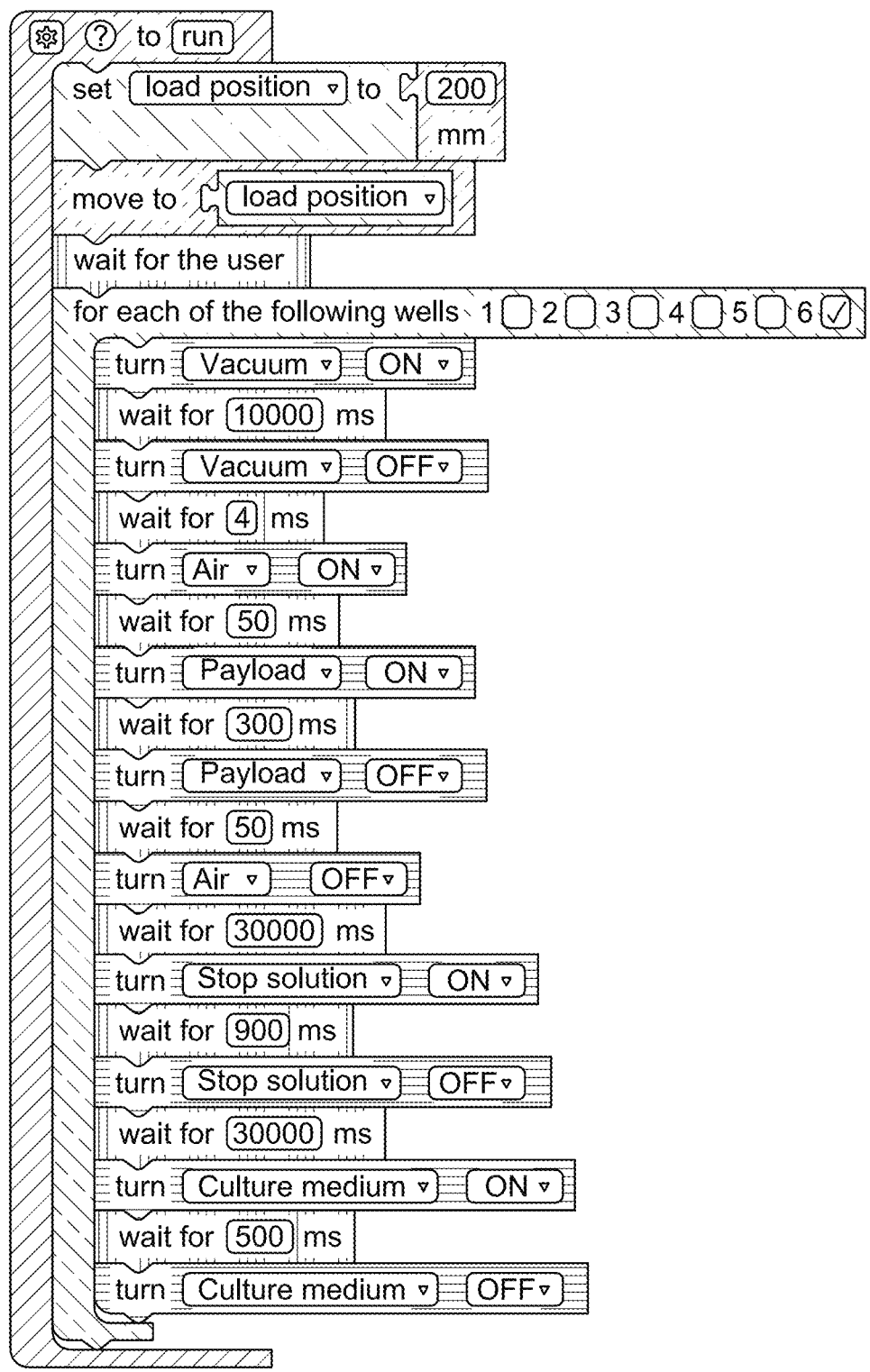

FIG. 130 is example of graphical user interface experiment canvas according to some aspects of the current subject matter. The user interface includes an experiment canvas which allows the user to vary parameters. The parameters which can be varied by the user include the location and number of wells to be addressed, the sequence of steps including vacuum or positive pressure, dispense of payload, stop solution and culture medium and the volume delivered. The user can also modify the actuator speed and the incubation times.

Figure 131:
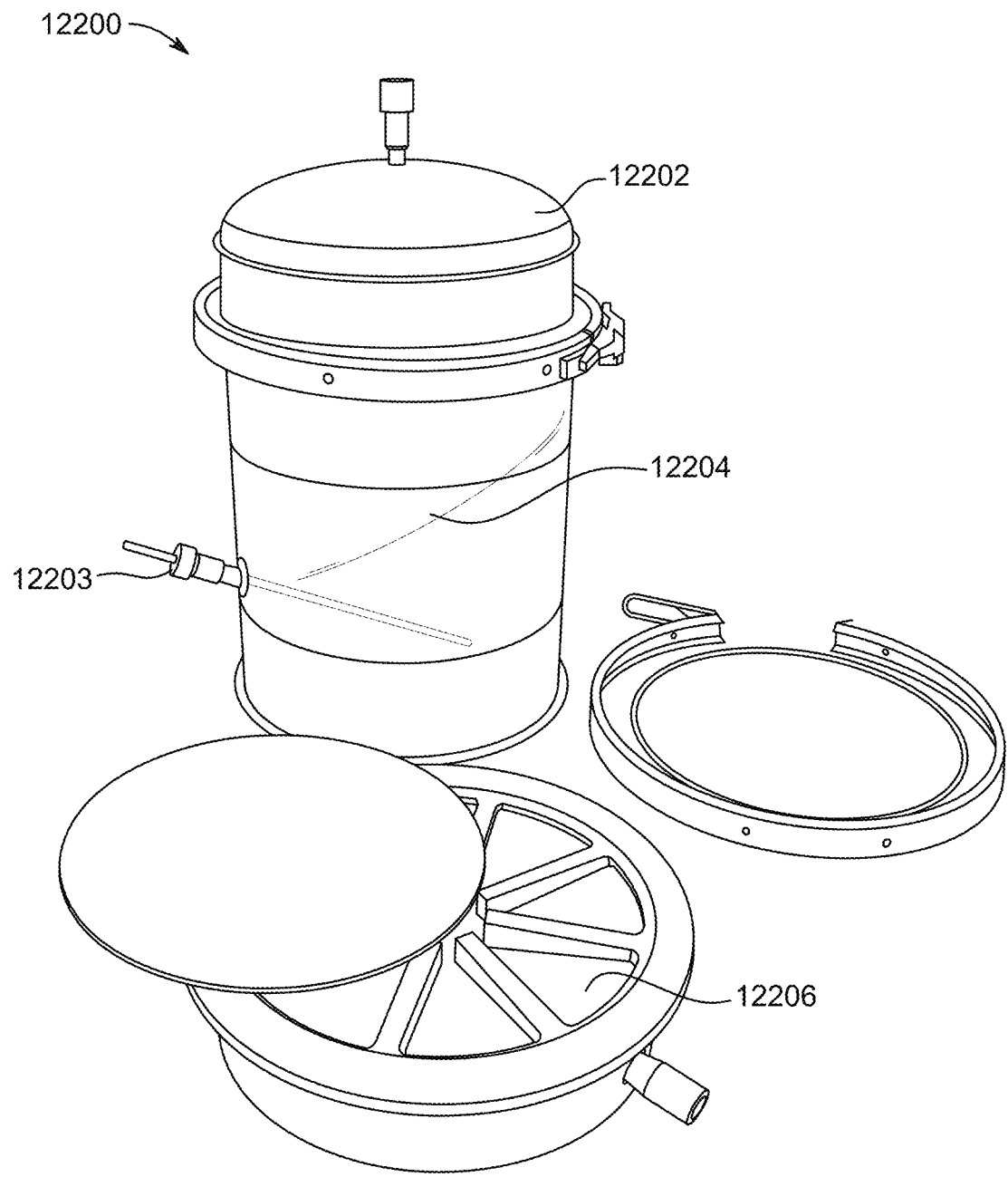

FIG. 131 is exemplary embodiment of a closed stirred cell system configured to facilitate forming a monolayer of cells. As shown in the illustrated example, the closed stirred cell system 12200 includes a cap 12202 a body 12204 which forms a chamber wall, a cell introducer 12203, and a chamber base 12208, which includes a membrane holder.

Figure 132:
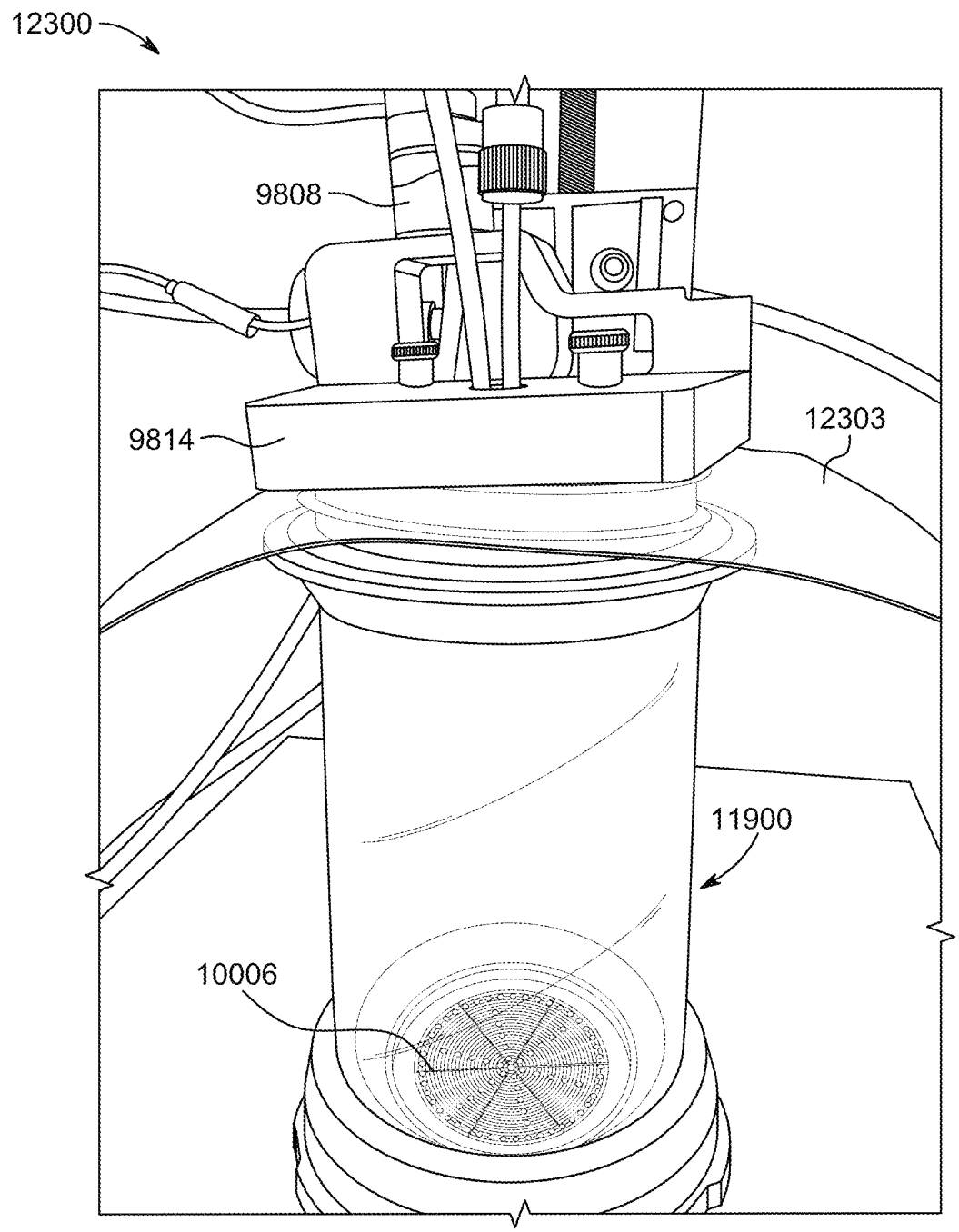

FIG. 132 is an exemplary Midi system. Shown is the 63 mm stirred cell unit containing the 44 mm membrane holder (which has been modified to include additional holes to promote better filtration). An enclosing film is visible adhered to the top of the stirred cell unit. The spray head holder containing the LB-100 has been inserted into the chamber to a distance of 82 mm from the emitter tip to the surface of the filter membrane.

Figure 133:
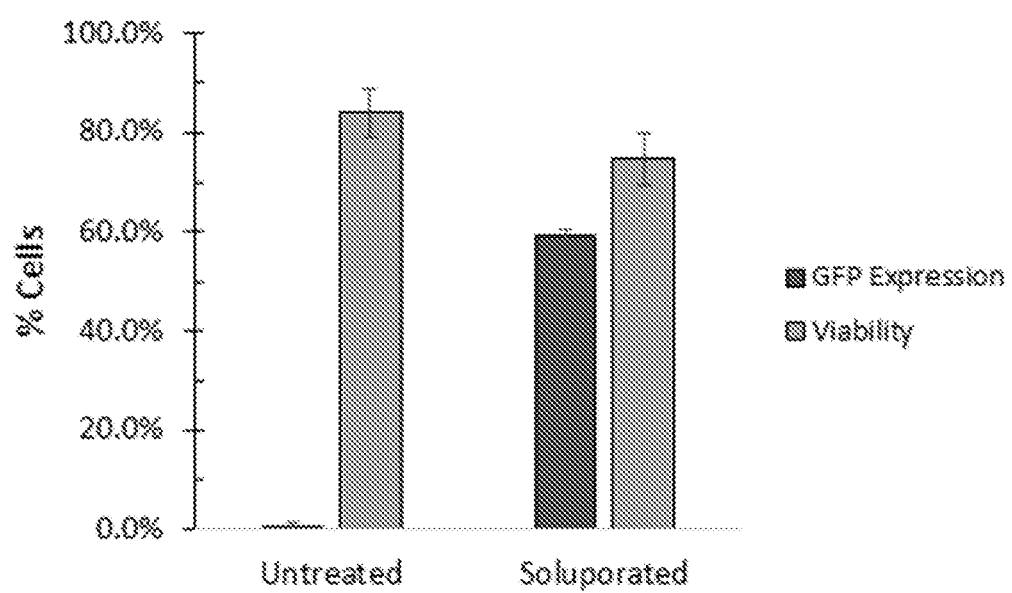

FIG. 133 is a plot showing data characterizing the delivery efficiency and viability using the LB-100 nebulizer. Graph demonstrates average delivery efficiency of 59.63%±1.2 and average viability data of 74.6%±5.3 across 3 technical repeats. The cell monolayer was formed using a 0.4 μm PCTE filter membrane and 20×10$^7$ cells and application of 120 mbar pressure for 40 s. The LB-100 spray parameters were 2.5 bar pressure; 600 mbar 400 ms spray duration (100 μl volume) and 82 mm distance. The data represents results from three experiments characterizing the delivery efficiency and viability.

Figure 134:
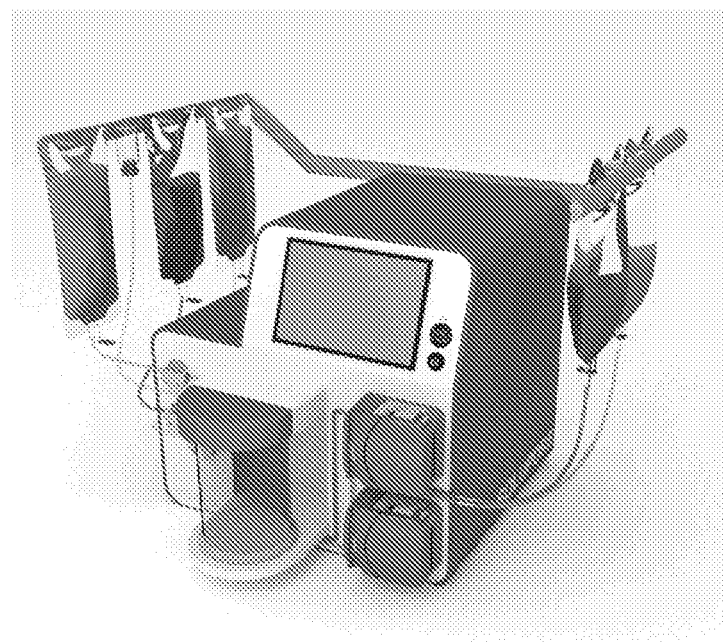

FIG. 134 is an embodiment of an example delivery system for clinical use.

DETAILED DESCRIPTION

Difficulty in transfecting molecules into non-adherent cells has plagued research and therapeutic, e.g., cell therapy, gene therapy, genetic alteration, for decades. A reason for the difficulty in transfecting such cells may be that non-adherent cells lack cell surface heparan sulfate proteoglycans, molecules are responsible for adhesion of cells to the extracellular matrix. Transfection methods such as electroporation and/or nucleofections have drawbacks in that they compromise the viability of cells, the ability of the cells to resume proliferation after treatment, and the function of the cells, e.g., immune activity of lymphocytes. The transfection compositions and methods described herein (Soluporation) do not have such drawbacks and therefore are characterized as having significant advantages over earlier methods of introducing cargo molecules into mammalian cells, e.g., difficult-to-transfect non-adherent/suspension cells.

The invention is based on the surprising discovery that compounds or mixtures of compounds (compositions) are delivered into the cytoplasm of eukaryotic cells by contacting the cells with a solution containing a compound(s) to be delivered (e.g., payload) and an agent that reversibly permeates or dissolves a cell membrane. Preferably, the solution is delivered to the cells in the form of a spray, e.g., aqueous particles. (see, e.g., PCT/US2015/057247 and PCT/IB2016/001895, hereby incorporated in their entirety by reference). For example, the cells are coated with the spray but not soaked or submersed in the delivery compound-containing solution. Exemplary agents that permeate or dissolve a eukaryotic cell membrane include alcohols and detergents such as ethanol and Triton X-100, respectively. Other exemplary detergents, e.g., surfactants include polysorbate 20 (e.g., Tween 20), 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), sodium dodecyl sulfate (SDS), and octyl glucoside.

An example of conditions to achieve a coating of a population of coated cells include delivery of a fine particle spray, e.g., the conditions exclude dropping or pipetting a bolus volume of solution on the cells such that a substantial population of the cells are soaked or submerged by the volume of fluid. Thus, the mist or spray comprises a ratio of volume of fluid to cell volume. Alternatively, the conditions comprise a ratio of volume of mist or spray to exposed cell area, e.g., area of cell membrane that is exposed when the cells exist as a confluent or substantially confluent layer on a substantially flat surface such as the bottom of a tissue culture vessel, e.g., a well of a tissue culture plate, e.g., a microtiter tissue culture plate.

"Cargo" or "payload" are terms used to describe a compound, or composition that is delivered via an aqueous solution across a cell plasma membrane and into the interior of a cell.

In an aspect, delivering a payload across a plasma membrane of a cell includes providing a population of cells and contacting the population of cells with a volume of an aqueous solution. The aqueous solution includes the payload and an alcohol content greater than 5 percent concentration. The volume of the aqueous solution may be a function of exposed surface area of the population of cells, or may be a function of a number of cells in the population of cells.

In another aspect, a composition for delivering a payload across a plasma membrane of a cell includes an aqueous solution including the payload, an alcohol at greater than 5 percent concentration, greater than 46 mM salt, less than 121 mM sugar, and less than 19 mM buffering agent. For example, the alcohol, e.g., ethanol, concentration does not exceed 50%.

One or more of the following features can be included in any feasible combination. The volume of solution to be delivered to the cells is a plurality of units, e.g., a spray, e.g., a plurality of droplets on aqueous particles. The volume is described relative to an individual cell or relative to the exposed surface area of a confluent or substantially confluent (e.g., at least 75%, at least 80% confluent, e.g., 85%, 90%, 95%, 97%, 98%, 100%) cell population. For example, the volume can be between $6.0\times10^{-7}$ microliter per cell and $7.4\times10^{-4}$ microliter per cell. The volume is between $4.9\times10^{-6}$ microliter per cell and $2.2\times10^{-3}$ microliter per cell. The volume can be between $9.3\times10^{-6}$ microliter per cell and $2.8\times10^{-5}$ microliter per cell. The volume can be about $1.9\times10^{-5}$ microliters per cell, and about is within 10 percent. The volume is between $6.0\times10^{-7}$ microliter per cell and $2.2\times10^{-3}$ microliter per cell. The volume can be between $2.6\times10^{-9}$ microliter per square micrometer of exposed surface area and $1.1\times10^{-6}$ microliter per square micrometer of exposed surface area. The volume can be between $5.3\times10^{-8}$ microliter per square micrometer of exposed surface area and $1.6\times10^{-7}$ microliter per square micrometer of exposed surface area. The volume can be about $1.1\times10^{-7}$ microliter per square micrometer of exposed surface area. About can be within 10 percent.

Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel.

Contacting the population of cells with the volume of aqueous solution can be performed by gas propelling the aqueous solution to form a spray. The gas can include nitrogen, ambient air, or an inert gas. The spray can include discrete units of volume ranging in size from, lnm to 100 µm, e.g., 30-100 µm in diameter. The spray includes discrete units of volume with a diameter of about 30-50 µm. A total volume of aqueous solution of 20 µl can be delivered in a spray to a cell-occupied area of about 1.9 cm$^2$, e.g., one well of a 24-well culture plate. A total volume of aqueous solution of 10 µl is delivered to a cell-occupied area of about 0.95 cm$^2$, e.g., one well of a 48-well culture plate. Typically, the aqueous solution includes a payload to be delivered across a cell membrane and into cell, and the second volume is a buffer or culture medium that does not contain the payload. Alternatively, the second volume (buffer or media) can also contain payload. In some embodiments, the aqueous solution includes a payload and an alcohol, and the second volume does not contain alcohol (and optionally does not contain payload). The population of cells can be in contact with said aqueous solution for 0.1 10 minutes prior to adding a second volume of buffer or culture medium to submerse or suspend said population of cells. The buffer or culture medium can be phosphate buffered saline (PBS). The population of cells can be in contact with the aqueous solution for 2 seconds to 5 minutes prior to adding a second volume of buffer or culture medium to submerse or suspend the population of cells. The population of cells can be in contact with the aqueous solution, e.g., containing the payload, for 30 seconds to 2 minutes prior to adding a second volume of buffer or culture medium, e.g., without the payload, to submerse or suspend the population of cells. The population of cells can be in contact with a spray for about 1-2 minutes prior to adding the second volume of buffer or culture medium to submerse or suspend the population of cells. During the time between spraying of cells and addition of buffer or culture medium, the cells remain hydrated by the layer of moisture from the spray volume.

The aqueous solution can include an ethanol concentration of 5 to 30%. The aqueous solution can include one or more of 75 to 98% H$_2$O, 2 to 45% ethanol, 6 to 91 mM sucrose, 2 to 500 mM KCl, 2 to 35 mM ammonium acetate, and 1 to 14 mM (4-(2-hydroxyethyl)-1-piperazineethane-sulfonic acid) (HEPES). For example, the delivery solution contains 106 mM KCl and 27% ethanol.

The population of cells can include adherent cells or non-adherent cells. The adherent cells can include at least one of primary mesenchymal stem cells, fibroblasts, monocytes, macrophages, lung cells, neuronal cells, fibroblasts, human umbilical vein (HUVEC) cells, Chinese hamster ovary (CHO) cells, and human embryonic kidney (HEK) cells or immortalized cells, such as cell lines. In preferred embodiments, the population of cells comprises non-adherent cells, e.g., the % non-adherent cells in the population is at least 50%, 60%, 75%, 80%, 90%, 95%, 98%, 99% or 100% non-adherent cells. Non-adherent cells primary cells as well as immortalized cells (e.g., cells of a cell line). Exemplary non-adherent/suspension cells include primary hematopoietic stem cell (HSC), T cells (e.g., CD3+ cells, CD4+ cells, CD8+ cells), natural killer (NK) cells, cytokine-induced killer (CIK) cells, human cord blood CD34+ cells, B cells, or cell lines such as Jurkat T cell line.

The payload can include a small chemical molecule, a peptide or protein, or a nucleic acid. The small chemical molecule can be less than 1,000 Da. The chemical molecule can include MitoTracker® Red CMXRos, propidium iodide, methotrexate, and/or DAPI (4',6-diamidino-2-phenylindole). The peptide can be about 5,000 Da. The peptide can include ecallantide under trade name Kalbitor, is a 60 amino acid polypeptide for the treatment of hereditary angioedema and in prevention of blood loss in cardiothoracic surgery), Liraglutide (marketed as the brand name Victoza, is used for the treatment of type II diabetes, and Saxenda for the treatment of obesity), and Icatibant (trade name Firazyer, a peptidomimetic for the treatment of acute attacks of hereditary angioedema). The small-interfering ribonucleic acid (siRNA) molecule can be about 20-25 base pairs in length, or can be about 10,000-15,000 Da. The siRNA molecule can reduces the expression of any gene product, e.g., knockdown of gene expression of clinically relevant target genes or of model genes, e.g., glyceraldehyde-3phosphate dehydrogenase (GAPDH) siRNA, GAPDH siRNA-FITC, cyclophilin B siRNA, and/or lamin siRNA. Protein therapeutics can include peptides, enzymes, structural proteins, receptors, cellular proteins, or circulating proteins, or fragments thereof. The protein or polypeptide be about 100-500,000 Da, e.g., 1,000-150,000 Da. The protein can include any therapeutic, diagnostic, or research protein or peptide, e.g., beta-lactoglobulin, ovalbumin, bovine serum albumin (BSA), and/or horseradish peroxidase. In other examples, the protein can include a cancer-specific apoptotic protein, e.g., Tumor necrosis factor-related apoptosis inducing protein (TRAIL).

An antibody is generally be about 150,000 Da in molecular mass. The antibody can include an anti-actin antibody, an anti-GAPDH antibody, an anti-Src antibody, an anti-Myc ab, and/or an anti-Raf antibody. The antibody can include a green fluorescent protein (GFP) plasmid, a GLuc plasmid and, and a BATEM plasmid. The DNA molecule can be greater than 5,000,000 Da. In some examples, the antibody can be a murine-derived monoclonal antibody, e.g., ibritumomab tiuxetin, muromomab-CD3, tositumomab, a human antibody, or a humanized mouse (or other species of origin) antibody. In other examples, the antibody can be a chimeric monoclonal antibody, e.g., abciximab, basiliximab, cetuximab, infliximab, or rituximab. In still other examples, the antibody can be a humanized monoclonal antibody, e.g., alemtuzamab, bevacizumab, certolizumab pegol, daclizumab, gentuzumab ozogamicin, trastuzumab, tocilizumab, ipilimumamb, or panitumumab. The antibody can comprise an antibody fragment, e.g., abatacept, aflibercept, alefacept, or etanercept. The invention encompasses not only an intact monoclonal antibody, but also an immunologically-active antibody fragment, e. g., a Fab or (Fab)2 fragment; an engineered single chain Fv molecule; or a chimeric molecule, e.g., an antibody which contains the binding specificity of one antibody, e.g., of murine origin, and the remaining portions of another antibody, e.g., of human origin.

The payload can include a therapeutic agent. A therapeutic agent, e.g., a drug, or an active agent", can mean any compound useful for therapeutic or diagnostic purposes, the term can be understood to mean any compound that is administered to a patient for the treatment of a condition. Accordingly, a therapeutic agent can include, proteins, peptides, antibodies, antibody fragments, and small molecules. Therapeutic agents described in U.S. Pat. No. 7,667,004 (incorporated herein by reference) can be used in the methods described herein. The therapeutic agent can include at least one of cisplatin, aspirin, statins (e.g., pitavastatin, atorvastatin, lovastatin, pravastatin, rosuvastatin, simvastatin, promazine HCl, chloropromazine HCl, thioridazine HCl, Polymyxin B sulfate, chloroxine, benfluorex HCl and phenazopyridine HCl), and fluoxetine. The payload can include a diagnostic agent. The diagnostic agent can include a detectable label or marker such as at least one of methylene blue, patent blue V, and indocyanine green. The payload can include a fluorescent molecule. The payload can include a detectable nanoparticle. The nanoparticle can include a quantum dot.

The population of non-adherent cells can be substantially confluent, such as greater than 75 percent confluent. Confluency of cells refers to cells in contact with one another on a surface. For example, it can be expressed as an estimated (or counted) percentage, e.g., 10% confluency means that 10% of the surface, e.g., of a tissue culture vessel, is covered with cells, 100% means that it is entirely covered. For example, adherent cells grow two dimensionally on the surface of a tissue culture well, plate or flask. Non-adherent cells can be spun down, pulled down by a vacuum, or tissue culture medium aspiration off the top of the cell population, or removed by aspiration or vacuum removal from the bottom of the vessel. The population of cells can form a monolayer of cells.

The alcohol can be selected from methanol, ethanol, isopropyl alcohol, butanol and benzyl alcohol. The salt can be selected from NaCl, KCl, $Na_2HPO_4$, $KH_2PO_4$, and $C_2H_3O_2NH$. In preferred embodiments, the salt is KCl. The sugar can include sucrose. The buffering agent can include 4-2-(hydroxyethyl)-1-piperazineethanesulfonic acid.

The present subject matter relates to a method for delivering molecules across a plasma membrane. The present subject matter finds utility in the field of intra-cellular delivery, and has application in, for example, delivery of molecular biological and pharmacological therapeutic agents to a target site, such as a cell, tissue, or organ. The method of the present subject matter comprises introducing the molecule to an aqueous composition to form a matrix; atomizing the matrix into a spray; and contacting the matrix with a plasma membrane.

This present subject matter relates to a composition for use in delivering molecules across a plasma membrane. The present subject matter finds utility in the field of intra-cellular delivery, and has application in, for example, delivery of molecular biological and pharmacological therapeutic agents to a target site, such as a cell, tissue, or organ. The composition of the present subject matter comprises an alcohol; a salt; a sugar; and/or a buffering agent.

In some implementations, demonstrated is a permeabilisation technique that facilitates intracellular delivery of molecules independent of the molecule and cell type. Nanoparticles, small molecules, nucleic acids, proteins and other molecules can be efficiently delivered into suspension cells or adherent cells in situ, including primary cells and stem cells, with low cell toxicity and the technique is compatible with high throughput and automated cell-based assays.

The example methods described herein include a payload, wherein the payload includes an alcohol. By the term "an alcohol" is meant a polyatomic organic compound including a hydroxyl (—OH) functional group attached to at least one carbon atom. The alcohol may be a monohydric alcohol and may include at least one carbon atom, for example methanol. The alcohol may include at least two carbon atoms (e.g. ethanol). In other aspects, the alcohol comprises at least three carbons (e.g. isopropyl alcohol). The alcohol may include at least four carbon atoms (e.g., butanol), or at least seven carbon atoms (e.g., benzyl alcohol). The example payload may include no more than 50% (v/v) of the alcohol, more preferably, the payload comprises 2-45% (v/v) of the alcohol, 5-40% of the alcohol, and 10-40% of the alcohol. The payload may include 20-30% (v/v) of the alcohol.

Most preferably, the payload delivery solution includes 25% (v/v) of the alcohol. Alternatively, the payload can include 2-8% (v/v) of the alcohol, or 2% of the alcohol. The alcohol may include ethanol and the payload comprises 5, 10, 20, 25, 30, and up to 40% or 50% (v/v) of ethanol, e.g., 27%. Example methods may include methanol as the alcohol, and the payload may include 5, 10, 20, 25, 30, or 40% (v/v) of the methanol. The payload may include 2-45% (v/v) of methanol, 20-30% (v/v), or 25% (v/v) methanol. Preferably, the payload includes 20-30% (v/v) of methanol. Further alternatively, the alcohol is butanol and the payload comprises 2, 4, or 8% (v/v) of the butanol.

In some aspects of the present subject matter, the payload is in an isotonic solution or buffer.

According to the present subject matter, the payload may include at least one salt. The salt may be selected from NaCl, KCl, $Na_2HPO_4$, $C_2H_3O_2NH_4$ and $KH_2PO_4$. For example, KCl concentration ranges from 2 mM to 500 mM. In some preferred embodiments, the concentration is greater than 100 mM, e.g., 106 mM.

According to example methods of the present subject matter, the payload may include a sugar (e.g., a sucrose, or a disaccharide). According to example methods, the payload comprises less than 121 mM sugar, 6-91 mM, or 26-39 mM sugar. Still further, the payload includes 32 mM sugar (e.g., sucrose). Optionally, the sugar is sucrose and the payload comprises 6.4, 12.8, 19.2, 25.6, 32, 64, 76.8, or 89.6 mM sucrose.

According to example methods of the present subject matter, the payload may include a buffering agent (e.g. a weak acid or a weak base). The buffering agent may include a zwitterion. According to example methods, the buffering agent is 4-(2-hydroxyethyl)-1-piperazineethanesulfonic acid. The payload may comprise less than 19 mM buffering agent (e.g., 1-15 mM, or 4-6 mM or 5 mM buffering agent). According to example methods, the buffering agent is 4-(2-hydroxyethyl)-1-piperazineethanesulfonic acid and the payload comprises 1, 2, 3, 4, 5, 10, 12, 14 mM 4-(2-hydroxyethyl)-1-piperazineethanesulfonic acid. Further preferably, the payload comprises 5 mM 4-(2-hydroxyethyl)-1-piperazineethanesulfonic acid.

According to example methods of the present subject matter, the payload includes ammonium acetate. The payload may include less than 46 mM ammonium acetate (e.g., between 2-35 mM, 10-15 mM, ore 12 mM ammonium acetate). The payload may include 2.4, 4.8, 7.2, 9.6, 12, 24, 28.8, or 33.6 mM ammonium acetate.

The volume of aqueous solution performed by gas propelling the aqueous solution may include compressed air (e.g. ambient air), other implementations may include inert gases, for example, helium, neon, and argon.

In certain aspects of the present subject matter, the population of cells may include adherent cells (e.g., lung, kidney, immune cells such as macrophages) or non-adherent cells (e.g., suspension cells).

In certain aspects of the present subject matter, the population of cells may be substantially confluent, and substantially may include greater than 75 percent confluent. In preferred implementations, the population of cells may form a single monolayer.

According to example methods, the payload to be delivered has an average molecular weight of up to 20,000,000 Da. In some examples, the payload to be delivered can have an average molecular weight of up to 2,000,000 Da. In some implementations, the payload to be delivered may have an average molecular weight of up to 150,000 Da. In further implementations, the payload to be delivered has an average molecular weight of up to 15,000 Da, 5,000 Da or 1,000 Da.

The payload to be delivered across the plasma membrane of a cell may include a small chemical molecule, a peptide or protein, a polysaccharide or a nucleic acid or a nanoparticle. A small chemical molecule may be less than 1,000 Da, peptides may have molecular weights about 5,000 Da, siRNA may have molecular weights around 15,000 Da, antibodies may have molecular weights of about 150,000 Da and DNA may have molecular weights of greater than or equal to 5,000,000 Da. In preferred embodiments, the payload comprises mRNA.

According to example methods, the payload includes 3.0-150.0 µM of a molecule to be delivered, more preferably, 6.6-150.0 µM molecule to be delivered (e.g. 3.0, 3.3, 6.6, or 150.0 µM molecule to be delivered). In some implementations, the payload to be delivered has an average molecular weight of up to 15,000 Da, and the payload includes 3.3 µM molecules to be delivered.

According to example methods, the payload to be delivered has an average molecular weight of up to 15,000 Da, and the payload includes 6.6 µM to be delivered. In some implementations, the payload to be delivered has an average molecular weight of up to 1,000 Da, and the payload includes 150.0 µM to be delivered.

According to further aspects of the present subject matter, a method for delivering molecules of more than one molecular weight across a plasma membrane is provided; the method including the steps of: introducing the molecules of more than one molecular weight to an aqueous solution; and contacting the aqueous solution with a plasma membrane.

In some implementations, the method includes introducing a first molecule having a first molecular weight and a second molecule having a second molecular weight to the payload, wherein the first and second molecules may have different molecular weights, or wherein, the first and second molecules may have the same molecular weights. According to example methods, the first and second molecules may be different molecules.

In some implementations, the payload to be delivered may include a therapeutic agent, or a diagnostic agent, including, for example, cisplatin, aspirin, various statins (e.g., pitavastatin, atorvastatin, lovastatin, pravastatin, rosuvastatin, simvastatin, promazine HCl, chloropromazine HCl, thioridazine HCl, Polymyxin B sulfate, chloroxine, benfluorex HCl and phenazopyridine HCl), and fluoxetine. Other therapeutic agents include antimicrobials (aminoclyclosides (e.g. gentamicin, neomycin, streptomycin), penicillins (e.g., amoxicillin, ampicillin), glycopeptides (e.g., avoparcin, vancomycin), macrolides (e.g., erythromycin, tilmicosin, tylosin), quinolones (e.g., sarafloxacin, enrofloxin), streptogramins (e.g., viginiamycin, quinupristin-dalfoprisitin), carbapenems, lipopeptides, oxazolidinones, cycloserine, ethambutol, ethionamide, isoniazrid, para-aminosalicyclic acid, and pyrazinamide). In some examples, an anti-viral (e.g., Abacavir, Aciclovir, Enfuvirtide, Entecavir, Nelfinavir, Nevirapine, Nexavir, Oseltamivir Raltegravir, Ritonavir, Stavudine, and Valaciclovir). The therapeutic may include a protein-based therapy for the treatment of various diseases, e.g., cancer, infectious diseases, hemophilia, anemia, multiple sclerosis, and hepatitis B or C.

Additional exemplary payloads can also include detectable markers or labels such as methylene blue, Patent blue V, and Indocyanine green.

The methods described herein may also include the payload including of a detectable moiety, or a detectable nanoparticle (e.g., a quantum dot). The detectable moiety may include a fluorescent molecule or a radioactive agent (e.g., $^{125}$I). When the fluorescent molecule is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, p-phthaldehyde and fluorescamine. The molecule can also be detectably labeled using fluorescence emitting metals such as $^{152}$Eu, or others of the lanthanide series. These metals can be attached to the molecule using such metal chelating groups as diethylenetriaminepentacetic acid (DTPA) or ethylenediaminetetraacetic acid (EDTA). The molecule also can be detectably labeled by coupling it to a chemiluminescent compound. The presence of the chemiluminescent-tagged molecule is then determined by detecting the presence of luminescence that arises during the course of chemical reaction. Examples of particularly useful chemiluminescent labeling compounds are luminol, isoluminol, theromatic acridinium ester, imidazole, acridinium salt and oxalate ester.

In additional embodiments, the payload to be delivered may include a composition that edits genomic DNA (i.e., gene editing tools). For example, the gene editing composition may include a compound or complex that cleaves, nicks, splices, rearranges, translocates, recombines, or otherwise alters genomic DNA. Alternatively or in addition, a gene editing composition may include a compound that (i) may be included a gene-editing complex that cleaves, nicks, splices, rearranges, translocates, recombines, or otherwise alters genomic DNA; or (ii) may be processed or altered to be a compound that is included in a gene-editing complex that cleaves, nicks, splices, rearranges, translocates, recombines, or otherwise alters genomic DNA. In various embodiments, the gene editing composition comprises one or more of (a) gene editing protein; (b) RNA molecule; and/or (c) ribonucleoprotein (RNP).

In some embodiments, the gene editing composition comprises a gene editing protein, and the gene editing protein is a zinc finger nuclease (ZFN), a transcription activator-like effector nuclease (TALEN), a Cas protein, a Cre recombinase, a Hin recombinase, or a Flp recombinase. In additional embodiments, the gene editing protein may be a fusion proteins that combine homing endonucleases with the modular DNA binding domains of TALENs (megaTAL). For example, megaTAL may be delivered as a protein or alternatively, a mRNA encoding a megaTAL protein is delivered to the cells.

In various embodiments, the gene editing composition comprises a RNA molecule, and the RNA molecule comprises a sgRNA, a crRNA, and/or a tracrRNA.

In certain embodiments, the gene editing composition comprises a RNP, and the RNP comprises a Cas protein and a sgRNA or a crRNA and a tracrRNA. Aspects of the present subject matter are particularly useful for controlling when and for how long a particular gene-editing compound is present in a cell.

In various implementations of the present subject matter, the gene editing composition is detectable in a population of cells, or the progeny thereof, for (a) about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution, or (b) less than about 0.5, 1, 2, 3, 4, 5, 6, 7, 8, 9, 10, 12, 24, 48, 60, 72, 0.5-2, 0.5-6, 6-12 or 0.5-72 hours after the population of cells is contacted with the aqueous solution.

In some embodiments, the genome of cells in the population of cells, or the progeny thereof, comprises at least one site-specific recombination site for the Cre recombinase, Hin recombinase, or Flp recombinase.

Aspects of the present invention relate to cells that comprise one gene editing compound, and inserting another gene editing compound into the cells. For example, one component of an RNP could be introduced into cells that express or otherwise already contain another component of the RNP. For example, cells in a population of cells, or the progeny thereof, may comprise a sgRNA, a crRNA, and/or a tracrRNA. In some embodiments the population of cells, or the progeny thereof, expresses the sgRNA, crRNA, and/or tracrRNA. Alternatively or in addition, cells in a population of cells, or the progeny thereof, express a Cas protein.

Various implementations of the subject matter herein include a Cas protein. In some embodiments, the Cas protein is a Cas9 protein or a mutant thereof. Exemplary Cas proteins (including Cas9 and non-limiting examples of Cas9 mutants) are described herein.

In various aspects, the concentration of Cas9 protein may range from about 0.1 to about 25 µg. For example, the concentration of Cas9 may be about 1 µg, about 5 µg, about 10 µg, about 15 µg, or about 20 µg. Alternatively, the concentration of Cas9 may range from about 10 ng/µL to about 300 ng/µL; for example from about 10 ng/µL to about 200 ng/µl; or from about 10 ng/µL to about 100 ng/µl, or from about 10 ng/µL to about 50 ng/µl.

In certain embodiments, the gene editing composition comprises (a) a first sgRNA molecule and a second sgRNA molecule, wherein the nucleic acid sequence of the first sgRNA molecule is different from the nucleic acid sequence of the second sgRNA molecule; (b) a first RNP comprising a first sgRNA and a second RNP comprising a second sgRNA, wherein the nucleic acid sequence of the first sgRNA molecule is different from the nucleic acid sequence of the second sgRNA molecule; (c) a first crRNA molecule and a second crRNA molecule, wherein the nucleic acid sequence of the first crRNA molecule is different from the nucleic acid sequence of the second crRNA molecule; (d) a first crRNA molecule and a second crRNA molecule, wherein the nucleic acid sequence of the first crRNA molecule is different from the nucleic acid sequence of the second crRNA molecule, and further comprising a tracrRNA molecule; or (e) a first RNP comprising a first crRNA and a tracrRNA and a second RNP comprising a second crRNA and a tracrRNA, wherein the nucleic acid sequence of the first crRNA molecule is different from the nucleic acid sequence of the second crRNA molecule.

In aspects, the ratio of the Cas9 protein to guide RNA may be 1:1, 1:2, 1:3, 1:4, 1:5, 1:6, 1:7, 1:8, 1:9, or 1:10.

In embodiments, increasing the number of times that cells go through the delivery process (alternatively, increasing the number of doses), may increase the percentage edit; wherein, in some embodiments the number of doses may include 1, 2, 3, 4, 5, 6, 7, 8, 9, or 10 doses.

In various embodiments, the first and second sgRNA or first and second crRNA molecules together comprise nucleic acid sequences complementary to target sequences flanking a gene, an exon, an intron, an extrachromosomal sequence, or a genomic nucleic acid sequence, wherein the gene, an exon, intron, extrachromosomal sequence, or genomic nucleic acid sequence is about 1, 2, 3, 4, 5, 6, 10, 20, 30, 40, 50, 60, 70, 80, 90, 100, 1-100, kilobases in length or is at least about 1, 2, 3, 4, 5, 6, 10, 20, 30, 40, 50, 60, 70, 80, 90, 100, 1-100, kilobases in length. In some embodiments, the use of pairs of RNPs comprising the first and second sgRNA or first and second crRNA molecules may be used to create a polynucleotide molecule comprising the gene, exon, intron, extrachromosomal sequence, or genomic nucleic acid sequence.

In certain embodiments, the target sequence of a sgRNA or crRNA is about 12 to about 25, or about 12, 13, 14, 15, 16, 17, 18, 19, 20, 21, 22, 23, 24, 25, 17-23, or 18-22, nucleotides long. In some embodiments, the target sequence is 20 nucleotides long or about 20 nucleotides long.

In various embodiments, the first and second sgRNA or first and second crRNA molecules are complementary to sequences flanking an extrachromosomal sequence that is within an expression vector.

Aspects of the present subject matter relate to the delivery of multiple components of a gene-editing complex, where the multiple components are not complexed together. In some embodiments, gene editing composition comprises at least one gene editing protein and at least one nucleic acid, wherein the gene editing protein and the nucleic acid are not bound to or complexed with each other.

The present subject matter allows for high gene editing efficiency while maintaining high cell viability. In some embodiments, at least about 10, 20, 30, 40, 50, 60, 70, 80, 90, 95, 99%, 1-99%, or more of the population of cells, or the progeny thereof, become genetically modified after contact with the aqueous solution. In various embodiments, at least about 10, 20, 30, 40, 50, 60, 70, 80, 90, 95, 99%, 1-99%, or more of the population of cells, or the progeny thereof, are viable after contact with the aqueous solution.

In certain embodiments, the gene editing composition induces single-strand or double-strand breaks in DNA within the cells. In some embodiments the gene editing composition further comprises a repair template polynucleotide. In various embodiments, the repair template comprises (a) a first flanking region comprising nucleotides in a sequence complementary to about 40 to about 90 base pairs on one side of the single or double strand break and a second flanking region comprising nucleotides in a sequence complementary to about 40 to about 90 base pairs on the other side of the single or double strand break; or (b) a first flanking region comprising nucleotides in a sequence complementary to at least about 20, 25, 30, 35, 40, 45, 50, 60, 70, 80, or 90 base pairs on one side of the single or double strand break and a second flanking region comprising nucleotides in a sequence complementary to at least about 20, 25, 30, 35, 40, 45, 50, 60, 70, 80, or 90 base pairs on the other side of the single or double strand break. Non-limiting descriptions relating to gene editing (including repair templates) using the CRISPR-Cas system are discussed in Ran et al. (2013) Nat Protoc. 2013 November; 8(11): 2281-2308, the entire content of which is incorporated herein by reference. Embodiments involving repair templates are not limited to those comprising the CRISPR-Cas system.

In various implementations of the present subject matter, the volume of aqueous solution is delivered to the population of cells in the form of a spray. In some embodiments, the volume is between $6.0 \times 10^{-7}$ microliter per cell and $7.4 \times 10^{-4}$ microliter per cell. In certain embodiments, the spray comprises a colloidal or sub-particle comprising a diameter of 10 nm to 100 µm. In various embodiments, the volume is between $2.6 \times 10^{-9}$ microliter per square micrometer of exposed surface area and $1.1 \times 10^{-6}$ microliter per square micrometer of exposed surface area.

In some embodiments, the RNP has a size of approximately 100 Å×100 Å×50 Å or 10 nm×10 nm×5 nm. In various embodiments, the size of spray particles is adjusted to accommodate at least about 1, 2, 3, 4, 5, 6, 7, 8, 9, 10, or more RNPs per spray particle.

For example, contacting the population of cells with the volume of aqueous solution may be performed by gas propelling the aqueous solution to form a spray. In certain embodiments, the population of cells is in contact with said aqueous solution for 0.01-10 minutes (e.g., 0.1 10 minutes) prior to adding a second volume of buffer or culture medium to submerse or suspend said population of cells.

In various embodiments, the population of cells includes at least one of primary or immortalized cells. For example, the population of cells may include mesenchymal stem cells, lung cells, neuronal cells, fibroblasts, human umbilical vein (HUVEC) cells, and human embryonic kidney (HEK) cells, primary or immortalized hematopoietic stem cell (HSC), T cells, natural killer (NK) cells, cytokine-induced killer (CIK) cells, human cord blood CD34+ cells, B cells. Non limiting examples of T cells may include CD8+ or CD4+ T cells. In some aspects, the CD8+ subpopulation of the CD3+ T cells are used. $CD8^+$ T cells may be purified from the PBMC population by positive isolation using anti-CD8 beads. In some aspects primary NK cells are isolated from PBMCs and GFP mRNA may be delivered by platform delivery technology (i.e., 3% expression and 96% viability at 24 hours). In additional aspects, NK cell lines, e.g., NK92 may be used.

Cell types also include cells that have previously been modified for example T cells, NK cells and MSC to enhance their therapeutic efficacy. For example: T cells or NK cells that express chimeric antigen receptors (CAR T cells, CAR NK cells, respectively); T cells that express modified T cell receptor (TCR); MSC that are modified virally or non-virally to overexpress therapeutic proteins that complement their innate properties (e.g. delivery of Epo using lentiviral vectors or BMP-2 using AAV-6) (reviewed in Park et al, Methods, 2015 August; 84-16.); MSC that are primed with non-peptidic drugs or magnetic nanoparticles for enhanced efficacy and externally regulated targeting respectively (Park et al., 2015); MSC that are functionalised with targeting moieties to augment their homing toward therapeutic sites using enzymatic modification (e.g. Fucosyltransferase), chemical conjugation (eg. modification of SLeX on MSC by using N-hydroxy-succinimide (NHS) chemistry) or non-covalent interactions (eg. engineering the cell surface with palmitated proteins which act as hydrophobic anchors for subsequent conjugation of antibodies) (Park et al., 2015). For example, T cells, e.g., primary T cells or T cell lines, that have been modified to express chimeric antigen receptors (CAR T cells) may further be treated according to the invention with gene editing proteins and or complexes containing guide nucleic acids specific for the CAR encoding sequences for the purpose of editing the gene(s) encoding the CAR, thereby reducing or stopping the expression of the CAR in the modified T cells.

Aspects of the present invention relate to the expression vector-free delivery of gene editing compounds and complexes to cells and tissues, such as delivery of Cas-gRNA ribonucleoproteins for genome editing in primary human T cells, hematopoietic stem cells (HSC), and mesenchymal stromal cells (MSC). In some example, mRNA encoding such proteins are delivered to the cells.

Various aspects of the CRISPR-Cas system are known in the art. Non-limiting aspects of this system are described, e.g., in U.S. Pat. No. 9,023,649, issued May 5, 2015; U.S. Pat. No. 9,074,199, issued Jul. 7, 2015; U.S. Pat. No. 8,697,359, issued Apr. 15, 2014; U.S. Pat. No. 8,932,814, issued Jan. 13, 2015; PCT International Patent Application Publication No. WO 2015/071474, published Aug. 27, 2015; Cho et al., (2013) Nature Biotechnology Vol 31 No 3 pp 230-232 (including supplementary information); and Jinek et al., (2012) Science Vol 337 No 6096 pp 816-821, the entire contents of each of which are incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2 and in the NCBI database as under accession number Q99ZW2.1. UniProt database accession numbers A0A0G4DEU5 and CDJ55032 provide another example of a Cas9 protein amino acid sequence. Another non-limiting example is a *Streptococcus thermophilus* Cas9 protein, the amino acid sequence of which may be found in the UniProt database under accession number Q03JI6.1. In some embodiments, the unmodified CRISPR enzyme has DNA cleavage activity, such as Cas9. In certain embodiments the CRISPR enzyme is Cas9, and may be Cas9 from *S. pyogenes* or *S. pneumoniae*. In various embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

In certain embodiments, a Cas9 nickase may be used in combination with guide sequence(s), e.g., two guide sequences, which target respectively sense and antisense strands of the DNA target. This combination allows both strands to be nicked and used to induce NHEJ.

As a further example, two or more catalytic domains of Cas9 (RuvC I, RuvC II, and RuvC III) may be mutated to produce a mutated Cas9 substantially lacking all DNA cleavage activity. A D10A mutation may be combined with one or more of H840A, N854A, or N863A mutations to produce a Cas9 enzyme substantially lacking all DNA cleavage activity. In certain embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than *S. pyogenes*, mutations in corresponding amino acids may be made to achieve similar effects.

In certain embodiments, a protein being delivered (such as a Cas protein or a variant thereof) may include a subcellular localization signal. For example, the Cas protein within a RNP may comprise a subcellular localization signal.

Depending on context, a fusion protein comprising, e.g., Cas9 and a nuclear localization signal may be referred to as "Cas9" herein without specifying the inclusion of the nuclear localization signal. In some embodiments, the payload (such as an RNP) comprises a fusion-protein that comprises a localization signal. For example, the fusion-protein may contain a nuclear localization signal, a nucleolar localization signal, or a mitochondrial targeting signal. Such signals are known in the art, and non-limiting examples are described in Kalderon et al., (1984) Cell 39 (3 Pt 2): 499-509; Makkerh et al., (1996) Curr Biol. 6 (8):1025-7; Dingwall et al., (1991) Trends in Biochemical Sciences 16 (12): 478-81; Scott et al., (2011) BMC Bioinformatics 12:317 (7 pages); Omura T (1998) J Biochem. 123(6):1010-6; Rapaport D (2003) EMBO Rep. 4(10):948-52; and Brocard & Hartig (2006) Biochimica et Biophysica Acta (BBA)—Molecular Cell Research 1763(12):1565-1573, the contents of each of which are hereby incorporated herein by reference. In various embodiments, the Cas protein may comprise more than one localization signals, such as 2, 3, 4, 5, or more nuclear localization signals. In some embodiments, the localization signal is at the N-terminal end of the Cas protein and in other embodiments the localization signal is at the C-terminal end of the Cas protein.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis.

Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme corresponding to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. In some embodiments, the degree of complementarity is 100%. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In certain embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions.

CRISPR-Cas technology which facilitates genome engineering in a wide range of cell types is evolving rapidly. It has recently been shown that delivery of the Cas9-gRNA editing tools in the form of ribonucleoproteins (RNPs) yields several benefits compared with delivery of plasmids encoding for Cas9 and gRNAs. Benefits include faster and more efficient editing, fewer off-target effects, and less toxicity. RNPs have been delivered by lipofection and electroporation but limitations that remain with these delivery methods, particularly for certain clinically relevant cell types, include toxicity and low efficiency. Accordingly, there is a need to provide a vector-free e.g., viral vector-free, approach for delivering biologically relevant payloads, e.g., RNPs, across a plasma membrane and into cells. "Cargo" or "payload" are terms used to describe a compound, or composition that is delivered via an aqueous solution across a cell plasma membrane and into the interior of a cell.

The current subject matter relates to delivery technology that facilitates delivery of a broad range of payloads to cells with low toxicity. Genome editing may be achieved by delivering RNPs to cells using some aspects of the current subject matter. Levels decline thereafter until Cas9 is no longer detectable. The delivery technology per se does not deleteriously affect the viability or functionality of Jurkat and primary T cells. The current subject matter enables gene editing via Cas9 RNPs in clinically relevant cell types with minimal toxicity.

The transient and direct delivery of CRISPR/Cas components such as Cas and/or a gRNA has advantages compared to expression vector-mediated delivery. For example, an amount of Cas, gRNA, or RNP can be added with more precise timing and for a limited amount of time compared to the use of an expression vector. Components expressed from a vector may be produced in various quantities and for variable amounts of time, making it difficult to achieve consistent gene editing without off-target edits. Additionally, pre-formed complexes of Cas and gRNAs (RNPs) cannot be delivered with expression vectors.

In one aspect, the present subject matter describes cells attached to a solid support, (e.g., a strip, a polymer, a bead, or a nanoparticle). The support or scaffold may be a porous or non-porous solid support. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present subject matter. The support material may have virtually any possible structural configuration. Thus, the support configuration may be spherical, as in a bead, or cylindrical, as in the inside surface of a test tube, or the external surface of a rod. Alternatively, the surface may be flat such as a sheet, or test strip, etc. Preferred supports include polystyrene beads.

In other aspects, the solid support comprises a polymer, to which cells are chemically bound, immobilized, dispersed, or associated. A polymer support may be a network of polymers, and may be prepared in bead form (e.g., by suspension polymerization). The cells on such a scaffold can be sprayed with payload containing aqueous solution according to the invention to deliver desired compounds to the cytoplasm of the scaffold. Exemplary scaffolds include stents and other implantable medical devices or structures.

The present subject matter further relates to apparatus, systems, techniques and articles for delivery of payloads across a plasma membrane. The present subject matter also relates to an apparatus for delivering payloads such as proteins or protein complexes across a plasma membrane. The current subject matter may find utility in the field of intra-cellular delivery, and has application in, for example, delivery of molecular biological and pharmacological therapeutic agents to a target site, such as a cell, tissue, or organ.

In some implementations, an apparatus for delivering a payload across a plasma membrane can include an atomizer having at least one atomizer emitter and a support oriented relative to the atomizer. The method further comprises the step of atomizing the payload prior to contacting the plasma membrane with the payload.

The atomizer can be selected from a mechanical atomizer, an ultrasonic atomizer, an electrospray, a nebuliser, and a Venturi tube. The atomizer can be a commercially available atomizer. The atomizer can be an intranasal mucosal atomization device. The atomizer can be an intranasal mucosal atomization device commercially available from LMA Teleflex of NC, USA. The atomizer can be an intranasal mucosal atomization device commercially available from LMA Teleflex of NC, USA under catalogue number MAD300.

The atomizer can be adapted to provide a colloid suspension of particles having a diameter of 30-100 μm prior to contacting the plasma membrane with the payload. The atomizer can be adapted to provide a colloid suspension of particles having a diameter of 30-80 μm. The atomizer can be adapted to provide a colloid suspension of particles having a diameter of 50-80 μm.

The atomizer can include a gas reservoir. The atomizer can include a gas reservoir with the gas maintained under pressure. The gas can be selected from air, carbon dioxide, and helium. The gas reservoir can include a fixed pressure head generator. The gas reservoir can be in fluid communication with the atomizer emitter. The gas reservoir can include a gas guide, which can be in fluid communication with the atomizer emitter. The gas guide can be adapted to allow the passage of gas therethrough. The gas guide can include a hollow body. The gas guide can be a hollow body having open ends. The gas guide can include a hollow body having first and second open ends. The gas guide can be a hollow body having first and second opposing open ends. The diameter of the first open end can be different to the diameter of the second open end. The diameter of the first open end can be different to the diameter of the second open end. The diameter of the first open end can be greater than the diameter of the second open end. The first open end can be in fluid communication with the gas reservoir. The second open end can be in fluid communication with the atomizer emitter.

The apparatus can include a sample reservoir. The sample reservoir can be in fluid communication with the atomizer. The sample reservoir can be in fluid communication with the atomizer emitter. The gas reservoir and the sample reservoir can both be in fluid communication with the atomizer emitter.

The apparatus can include a sample valve located between the sample reservoir and the gas reservoir. The apparatus can include a sample valve located between the sample reservoir and the gas guide. The sample valve can be adapted to adjust the sample flow from the sample reservoir. The sample valve can be adapted to allow continuous or semi-continuous sample flow. The sample valve can be adapted to allow semi-continuous sample flow. The sample valve can be adapted to allow semi-continuous sample flow of a defined amount. The sample valve is adapted to allow semi-continuous sample flow of 0.5-100 μL. The sample valve can be adapted to allow semi-continuous sample flow of 10 μL. The sample valve can be adapted to allow semi-continuous sample flow of 1 μL to an area of 0.065-0.085 cm$^2$.

The atomizer and the support can be spaced apart. The support can include a solid support. The support can include a plate including sample wells. The support can include a plate including sample wells selected from 1, 6, 9, 12, 24, 48, 384, 1536 or more wells. Alternatively, the support comprises a plate, e.g., a scaled up configuration that can accommodate a monolayer with more cells than a microtiter plate. The solid support can be formed from an inert material. The solid support can be formed from a plastic material, or a metal or metal alloy, or a combination thereof. The support can include a heating element. The support can include a resistive element. The support can be reciprocally mountable to the apparatus. The support can be reciprocally movable relative to the apparatus. The support can be reciprocally movable relative to the atomizer. The support can be reciprocally movable relative to the atomizer emitter. The support can include a support actuator to reciprocally move the support relative to the atomizer. The support can include a support actuator to reciprocally move the support relative to the atomizer emitter. The support can include a support actuator to reciprocally move the support relative to the longitudinal axis of the atomizer emitter. The support can include a support actuator to reciprocally move the support transverse to the longitudinal axis of the atomizer emitter.

The longitudinal axis of the spray zone can be coaxial with the longitudinal axis or center point of the support and/or the circular well of the support, to which the payload is to be delivered. The longitudinal axis of the atomizer emitter can be coaxial with the longitudinal axis or center point of the support and/or the circular well of the support. The longitudinal axis of the atomizer emitter, the longitudinal axis of the support, and the longitudinal axis of the spray zone can be each coaxial. The longitudinal length of the spray zone may be greater than the diameter (may be greater than double) of the circular base of the spray zone (e.g., the area of cells to which the payload is to be delivered).

The apparatus can include a valve located between the gas reservoir and the atomizer. The valve can be an electromagnetically operated valve. The valve can be a solenoid valve. The valve can be a pneumatic valve. The valve can be located at the gas guide. The valve can be adapted to adjust the gas flow within the gas guide. The valve can be adapted to allow continuous or semi-continuous gas flow. The valve can be adapted to allow semi-continuous gas flow. The valve can be adapted to allow semi-continuous gas flow of a defined time interval. The valve can be adapted to allow semi-continuous gas flow of a one second time interval. The apparatus can include at least one filter. The filter can include a pore size of less than 10 µm. The filter can have a pore size of 10 µm. The filter can be located at the gas guide. The filter can be in fluid communication with the gas guide.

The apparatus can include at least one regulator. The regulator can be an electrical regulator. The regulator can be a mechanical regulator. The regulator can be located at the gas guide. The regulator can be in fluid communication with the gas guide. The regulator can be a regulating valve. The pressure within the gas guide can be 1.0-2.0 bar. The pressure within the gas guide can be 1.5 bar. The pressure within the gas guide can be 1.0-2.0 bar, and the distance between the atomizer and the support can be less than or equal to 31 mm. The pressure within the gas guide can be 1.5 bar, and the distance between the atomizer and the support can be 31 mm. The pressure within the gas guide can be 0.05 bar per millimeter distance between the atomizer and the support. The regulating valve can be adapted to adjust the pressure within the gas guide to 1.0-2.0 bar. The regulating valve cam be adapted to adjust the pressure within the gas guide to 1.5 bar. The or each regulating valve can be adapted to maintain the pressure within the gas guide at 1.0-2.0 bar. The or each regulating valve can be adapted to maintain the pressure within the gas guide at 1.5 bar.

The apparatus can include two regulators. The apparatus can include first and second regulators. The first and second regulator can be located at the gas guide. The first and second regulator can be in fluid communication with the gas guide. The first regulator can be located between the gas reservoir and the filter. The first regulator can be adapted to adjust the pressure from the gas reservoir within the gas guide to 2.0 bar. The first regulator can be adapted to maintain the pressure within the gas guide at 2.0 bar. The second regulator can be located between the filter and the valve.

The atomizer emitter can be adapted to provide a conical spray zone (e.g., a generally circular conical spray zone). The atomizer emitter can be adapted to provide a 30° conical spray zone. The apparatus further can include a microprocessor to control any or all parts of the apparatus. The microprocessor can be arranged to control any or all of the sample valve, the support actuator, the valve, and the regulator. The apparatus can include an atomizer having at least one atomizer emitter; and a support oriented relative to the atomizer; the atomizer can be selected from a mechanical atomizer, an ultrasonic atomizer, an electrospray, a nebuliser, and a Venturi tube. The atomizer can be adapted to provide a colloid suspension of particles having a diameter of 30-100 µm. The apparatus can include a sample reservoir and a gas guide, and a sample valve located between the sample reservoir and the gas guide. The sample valve can be adapted to allow semi-continuous sample flow of 10-100 µL. The atomizer and the support can be spaced apart and define a generally conical spray zone there between; and the distance between the atomizer and the support can be approximately double the diameter of the circular base of the area of cells to which molecules are to be delivered; the distance between the atomizer and the support can be 31 mm and the diameter of the circular base of the area of cells to which molecules are to be delivered can be 15.5 mm. The apparatus can include a gas guide and the pressure within the gas guide is 1.0-2.0 bar. The apparatus can include at least one filter having a pore size of less than 10 μm.

The aqueous solution and/or composition can be saponin-free.

The details of one or more variations of the subject matter described herein are set forth in the accompanying drawings and the description below. Other features and advantages of the subject matter described herein will be apparent from the description and drawings, and from the claims.

Optimisation of T Cell Preparation for Soluporation

Optimization of T cell culture conditions for maximal efficiency of mRNA delivery using the vector-free reversible permeabilization method is described below. The vector-free method for intracellular delivery of macromolecules and nucleic acids described herein has demonstrated success in facilitating the delivery of gene-editing tools such as CRISPR/Cas9 and mRNA to mammalian cells such as primary human immune cells. Culture conditions for efficient transfer of mRNA to human T cells using the vector-free delivery platform were determined.

Considerable differences exist in the ex vivo activation of human lymphocytes amongst clinical groups and T-cell engineering companies. There is no single standardised protocol for expansion of primary human T cells, therefore, a comprehensive evaluation of culture media, additives, activation methods and timing schedules was undertaken to identify the optimal ex vivo culturing conditions that promote maximal efficiency transfer of mRNA using the vector-free reversible permeabilization method technology. Herein, the cell isolation protocol and the results/conclusions of each experiment undertaken is described.

To address suspension cells (i.e., non-adherent cells), a centrifugation step was developed as part of the delivery process. This step was developed to enable formation of an exposed monolayer of suspension cells. The centrifugation step allows for both formation of the monolayer and removal of the supernatant in one step. In contrast, with adherent cells, the cells were already in monolayer formation and medium were removed by pipetting.

Materials and Methods

Cell culture and transfection. Human peripheral blood mononuclear cells (PBMC) were recovered by centrifugation over a Percoll gradient from Leuko Pak (AllCells Alameda, CA). $CD3^+$ enriched lymphocytes were isolated by magnetically activated cell sorting using CD3 Microbeads (Miltenyi). Cells were cryopreserved in 10% dimethyl sulphoxide (DMSO) and foetal bovine serum (FBS). Following initial thawing from stock aliquots, $CD3^+$ T cells were cultured in human recombinant interleukin-2 (IL-2) with primary and co-stimulatory antibody activation using various protocols (see below) in a humidified tissue culture incubator at 37° C. and 5% $CO_2$.

Delivery procedure. Activated T cells were seeded at $1.5\times10^6$ cells per well of a 96-well filter plate (Acroprep, 1.2 μm Supor membrane; Pall, USA). Media was removed from the wells by centrifugation at 300×g for 5 min. 7 μl of delivery solution (32 mM sucrose, 12 mM potassium chloride, 12 mM ammonium acetate, 5 mM HEPES and 27% ethanol in molecular grade water (all from Sigma-Aldrich)) containing 4 µg GFP mRNA was then sprayed into each well using the vector-free delivery spray instrument. The atomizer used in the instrument was a MAD Nasal™ intranasal mucosal atomization device (Wolfe Tory Medical Inc, Salt Lake City, USA). The atomizer was held on a retort stand at 26 mm above the bottom of the well and was connected to a 6 bar compressor (Circuit Imprimé Français, Bagneux Cedex, France) via polyurethane tubing (6 mm outside diameter, 4 mm inside diameter; SMC, Tokyo, Japan). The delivery solution containing the cargo was pipetted into a delivery port located at the top of the atomizer and the spray was generated at 1.5 Bar using a spray actuator button (SMC, Tokyo, Japan). Following delivery, the cells were incubated in this solution for 2 min prior to the addition of 50 µl Stop Solution (0.5×PBS). Thirty seconds later T cell media was added (100 µl) and cells were allowed to recover at 37° C. and 5% $CO_2$ overnight. Uptake and viability were assessed at 24 h post-delivery.

Cell viability, FACS Sample Preparation and Analysis. To assess cell viability following the vector-free method of delivery, 7-Aminoactinomycin D (7-AAD) (Sigma) was used to stain the cells. Briefly, cells were in washed in PBS+1% foetal bovine serum (FACS buffer) followed by incubation with 7-AAD (1:40 for 5-10 min protected from light at room temperature), followed by resuspension in PBS+1% FBS (FACS buffer). Samples were processed on the BD Accuri C6 flow cytometer (Becton Dickinson, USA) and data was analysed using the C6 software. Cell debris was excluded from whole cells using forward and side scatter parameters. Single cells were selected by excluding doublets in the FSC height vs FSC are plot. GFP expression was analysed on gated viable cells.

Media, Activation Reagents and Timing

Figure 1:
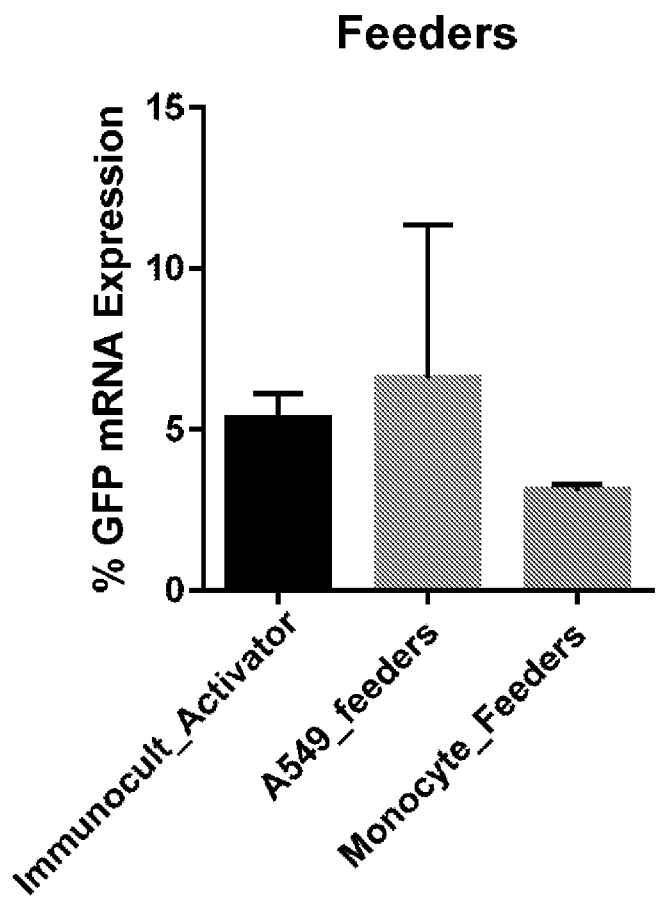
FIG. 1 is a bar graph illustrating the assessment of feeder cells as a method of T cell activation. GFP mRNA was delivered to T cells cultured in cRPMI medium.

Four media for T cell culture and expansion were evaluated using mRNA, e.g., model cargo GFP mRNA, as cargo and GFP expression as an indicator of successful culture methodology. cRPMI was tested which is a serum-containing media typically used in the culture of primary immune cells. However, as serum is a highly variable supplement in cell-culture media, three serum-free and xeno-free expansion media, optimised for the in vitro culture of human T cells were also evaluated.

cRPMI was prepared using RPMI, heat-inactivated fetal bovine serum (PBS) (10% v/v), penicillin-streptomycin, L-glutamine and supplemented with IL-2 (100 U/ml). cRPMI was utilised as culture medium in experiments that assessed the performance of various T-cell proliferation protocols. The first proliferation protocol tested was ImmunoCult™ Human CD3/CD28 T-cell Activator which consists of a soluble tetrameric antibody complex that bind CD3 and CD28 cell surface ligands on the T lymphocytes. It was evaluated alongside an alternative method of activation which use "feeder" cells as a means of presenting antigen to the T cell receptor (TCR) to induce proliferation of the T cell (FIG. 1).

T Cell Activation Using PBMC or A549 as Feeder Cells

Autologous PBMC were transferred to the tissue culture plate. After 2 hr incubation, the supernatant was removed leaving the adhered monocytes. T cells cultured in cRPMI were added to the plate and allowed to co-incubate with the monocytes for several days. In a similar protocol, the A549 cell line was left to adhere for up to 2 h. Medium was removed and T cells were added to the plate and left to co-incubate prior to delivery of mRNA using the vector-free delivery technology. Uptake efficiencies using feeder cells were variable both inter and intra-experiment (FIG. 1), therefore, ImmunoCult™ Human CD3/CD28 T-cell Activator reagent was utilised in further evaluations.

T Cell Activation Using Dynabeads®

Figure 2A:
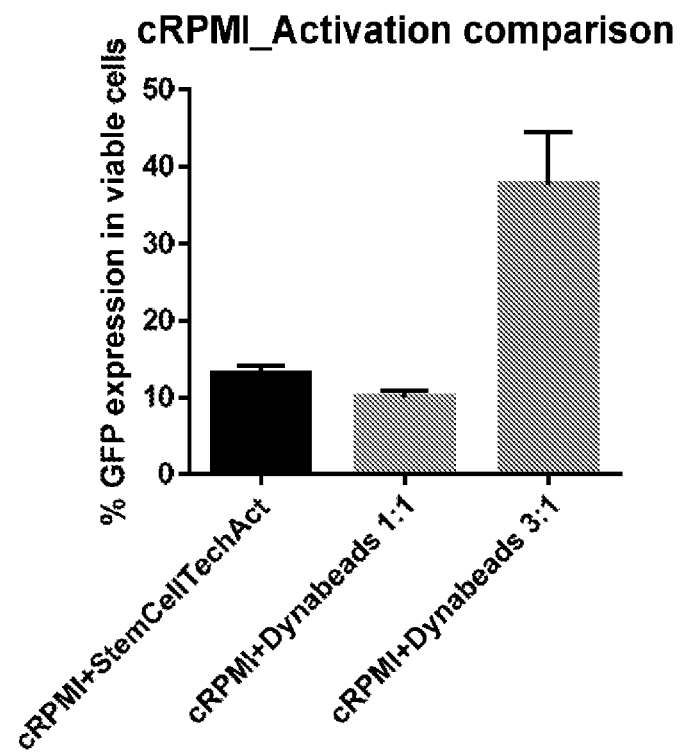
FIG. 2A is a bar graph illustrating results of RPMI media comparing StemCellTech reagent vs Dynabeads at 2 concentrations.
Figure 2B:
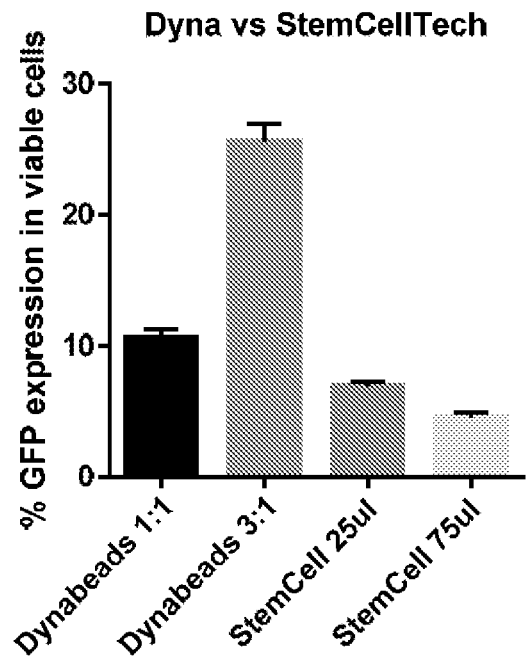
FIG. 2B is a bar graph illustrating that the experiment (from FIG. 2A) was repeated to include StemCell tech reagent at 3 times recommended concentration but didn't have any effect.

T cells are activated using methods known in the art, e.g., antibodies that bind to cell surface proteins such as CD3 and/or CD28, feeder cells, and/or magnetic beads comprising immunostimulatory molecules. For example, Dynabeads® were examined as an alternative to ImmunoCult™ Human CD3/CD28 T-cell Activator. Dynabeads® are superparamagnetic beads coated with antibodies against human CD3 and CD28 that provide the primary and co-stimulatory signals necessary for T cell activation and expansion. The bead-to-cell ratio recommended is 1:1, however, another condition using 3 beads per cell was also used to assess whether more efficient and rapid expansion could positively affect uptake of mRNA into T cells using the Soluporation delivery method. Increasing the bead-to-cell ratio significantly improved percentage uptake (FIG. 2A). A repeat experiment was then carried out to include the ImmunoCult™ Human CD3/CD28 T-cell Activator at 3 times the concentration recommended by the manufacturer, however, this concentration did not result in the same improvement in efficiency observed using Dynabeads (FIG. 2B)

Culture Medium: Prime XV

Figure 3:
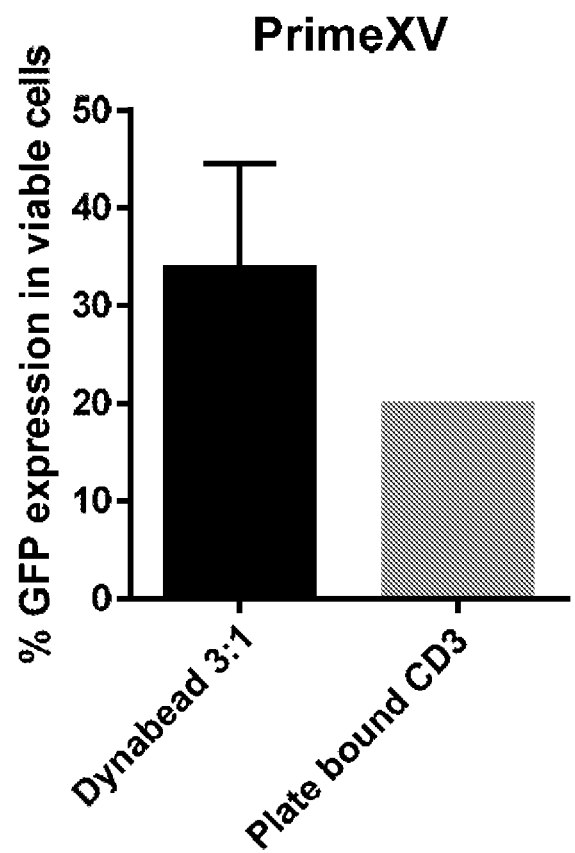
FIG. 3 is a bar graph illustrating the improvement in uptake using Prime XV culture medium and activation with Dynabeads (3:1 bead to cell).

Cell-compatible culture media are used in the delivery methods. For example, Prime-XV (Irvine Scientific) is a first serum-free and animal component free media that was tested with vector-free delivery technology. Based on positive data observed using Dynabeads at a 3:1 bead to cell ratio (FIG. 2 and FIGS. 2A and 2B), it was decided to continue using this method of activation to test alternative culture media. This medium was tested using Dynabeads to induce proliferation alongside an alternative activation method which stimulates T cell proliferation by binding anti-human CD3 antibody to cell culture plates followed by the addition of soluble anti-CD28 to the media. Dynabead-activated T cells cultured in Prime XV demonstrated significantly better uptake efficiency (up to 50%) compared to those cells stimulated using soluble α-CD3/CD28 (<20%) (FIG. 3).

Figure 4A:
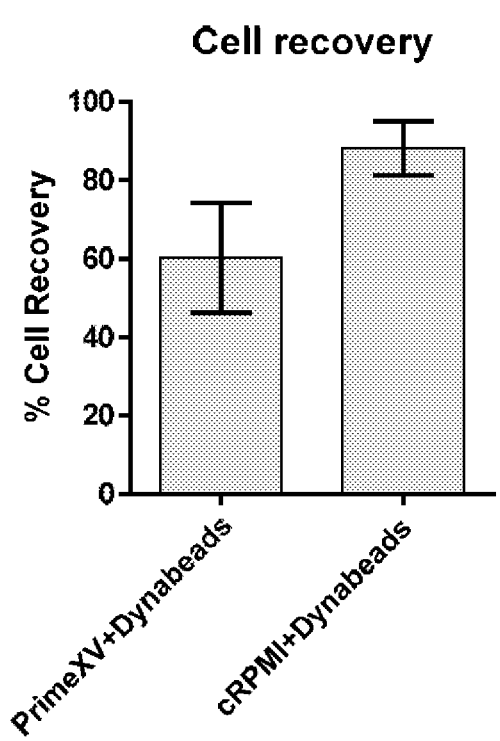
FIG. 4A is a bar graph illustrating poor cell recovery when cultured in Prime XV medium.
Figure 4B:
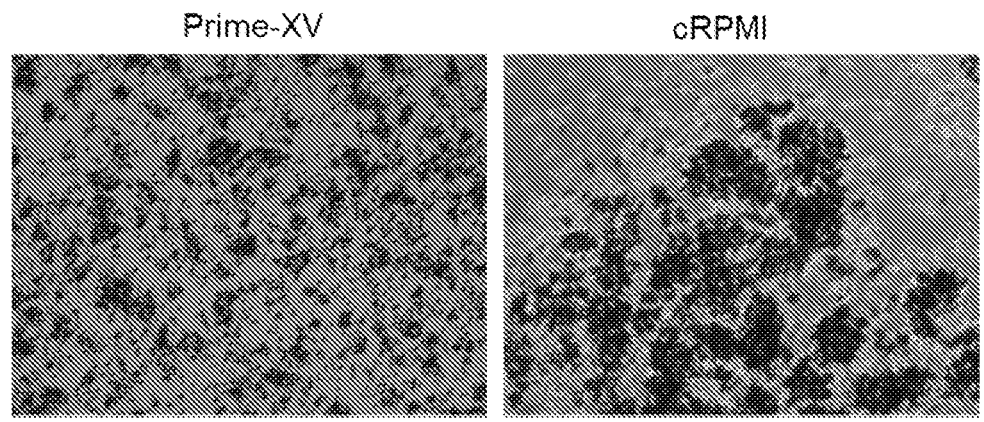
FIG. 4B are images depicting poor cell recovery and variability in cell proliferation when cultured in Prime XV. Cells were activated using Dynabeads (3:1).

Although delivery to T cells cultured in Prime XV did improve uptake of mRNA using the vector-free technology, it was associated with cell-handling issues, e.g., removing the cells from culture 24 h after initial seeding and recovery of cells from the Dynabeads upon washing (FIGS. 4A and 4B).

Culture Medium: Supplementary Cytokines

In some examples, the cell culture media was supplemented with a higher concentration of IL-2 (200 U/ml instead of 100 U/ml) to enhance the rate of proliferation (Tumeh P, et al., *J Immunother* 2010. 33(6): 759-768 and Besser M J, et al., *Cytotherapy* 2009. 11:206-217).

Culture Medium: Immunocult

Figure 5:
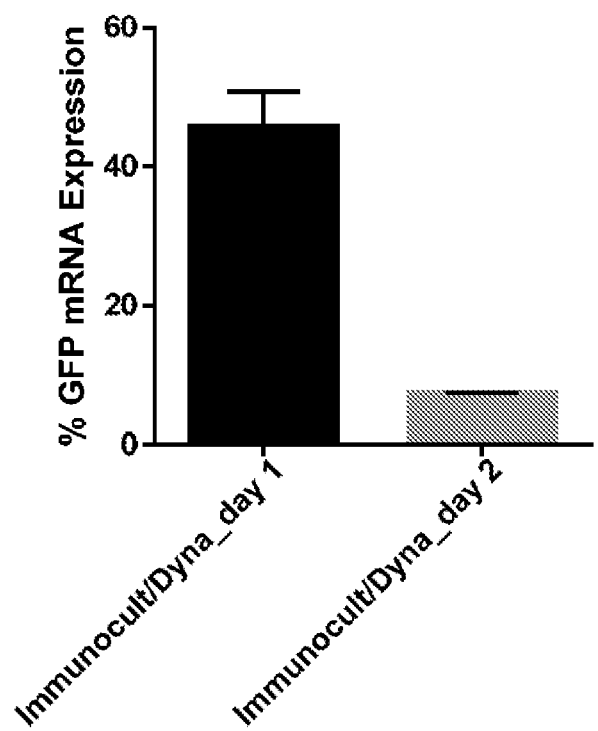
FIG. 5 is a bar graph illustrating results of Dynabead-activated T cells cultured in Immunocult culture media.

Immunocult™-XF Expansion Medium (StemCell Technologies) was evaluated. Like Prime XV, it is also a serum-free, xeno-free T cell culture medium. In this example, T cells were cultured in Immunocult Expansion Medium and activated using Dynabeads® bead to cell ratio of 3 to 1. GFP mRNA was delivered to the cells at day 1 and day 2 post-activation and assessed for uptake 24 h later (FIG. 5).

Timing of Delivery Post-Activation of T Cells

Cells are activated for between 15 to 21 hr, with 19 hr being preferred.

Figure 6:
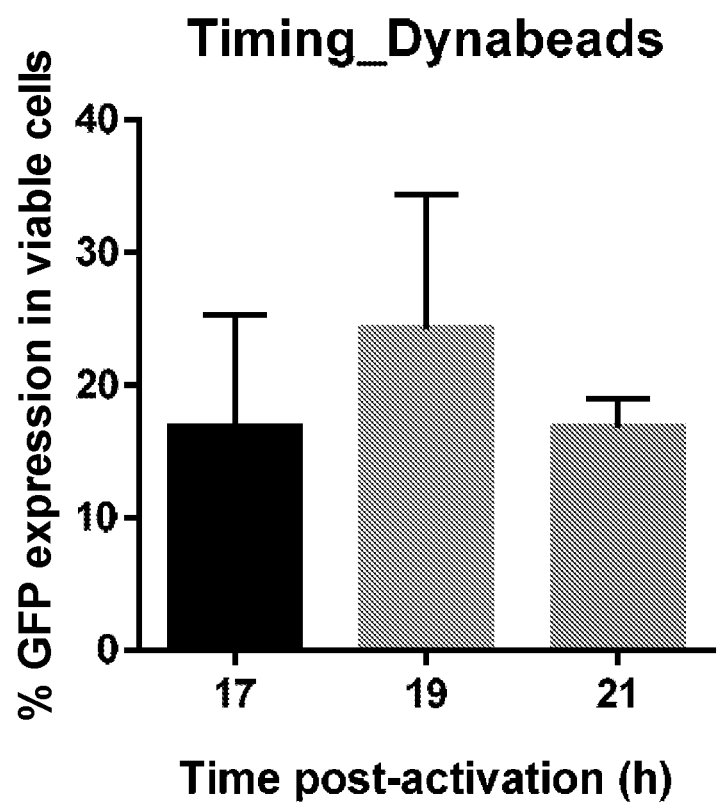
FIG. 6 is a bar graph illustrating the optimum post-activation window for delivery of mRNA to T cells using Dynabeads as activation reagent.

A preferred "window" for delivery post-activation after addition of Dynabeads was identified. mRNA was delivered using the vector-free technology at several time points. Optimal GFP expression was observed when mRNA payload, e.g., model payload GFP mRNA, was delivered at 19 h post-activation compared with 17 h and 21 h (FIG. 6). Studies were undertaken to determine if there was a correlation between increased cell size and time post-activation. Cell size was estimated using the forward scatter (FSC) data obtained from flow cytometry analysis. It was observed that maximal transfection efficiency correlated with a time when cells were actively increasing in size. Exemplary results are depicted in Table below:

TABLE

Timing of delivery post-activation of T cells

| | Time post-activation when GFP mRNA delivered | | |
|---|---|---|---|
| | 17 h | 19 h | 21 h |
| GFP expression at 24 h post-delivery (Mean of 4 replicates) | 16.78% | 24.23% | 16.77% |
| Size (FSC) | 2378956 | 2449816 | 2514971 |

T Cell Activation Using TransAct

Figure 7:
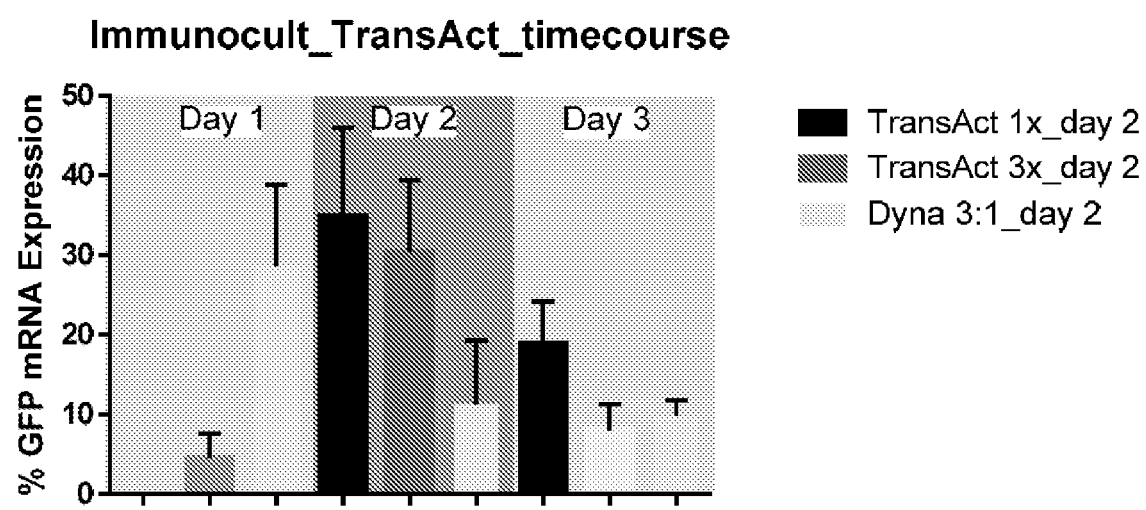
FIG. 7 is a bar graph illustrating TransAct vs Dynabead in Immunocult time course.

T cell TransAct™ (Miltenyi) is a colloidal reagent consisting of a nanomatrix conjugated to CD3 and CD28 agonist which provide signals for activation and expansion of T cells. It provides benefits over Dynabeads® as excess reagent can be removed by centrifugation without the need for magnetic separation and the beads from the cells and all the subsequent washing. Thus, this reagent was evaluated over a three-day period using Immunocult as the culture medium to determine the preferred day for delivery of mRNA by the vector-free delivery technology described herein. TransAct initiates T cell proliferation less aggressively than Dynabeads. Therefore, optimum delivery of mRNA to T cells was observed 24 h later than that demonstrated using bead activation, however, this was accompanied by an enhancement in transfection efficiency (FIG. 7).

Culture Medium: TexMACS

Figure 8:
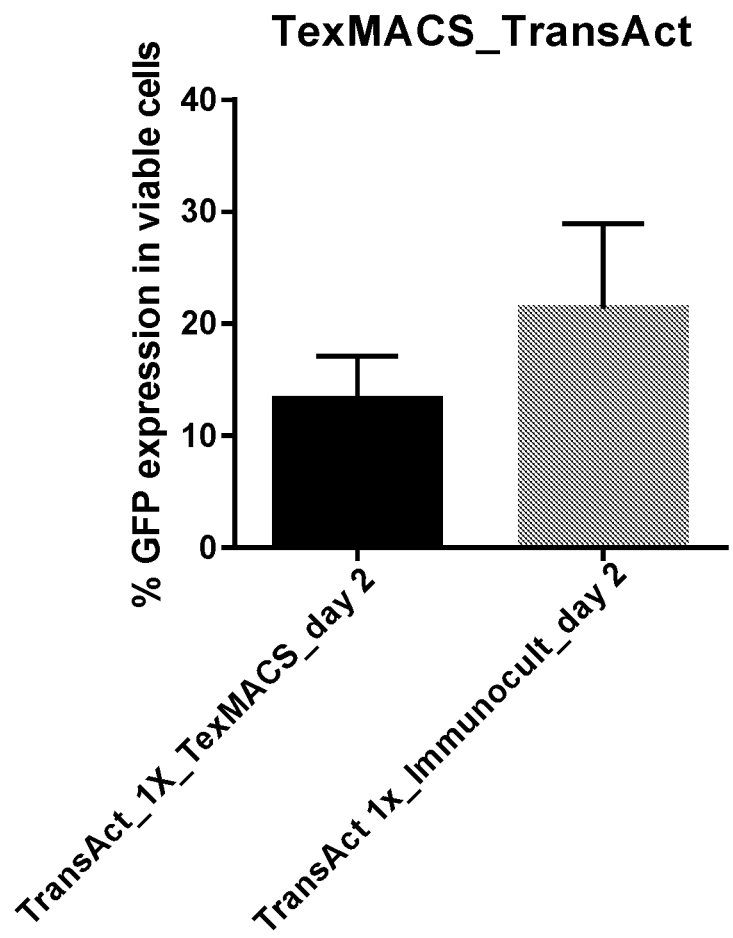
FIG. 8 is a bar graph illustrating results of TexMACS vs Immunocult using TransAct as T cell activator.
Figure 9:
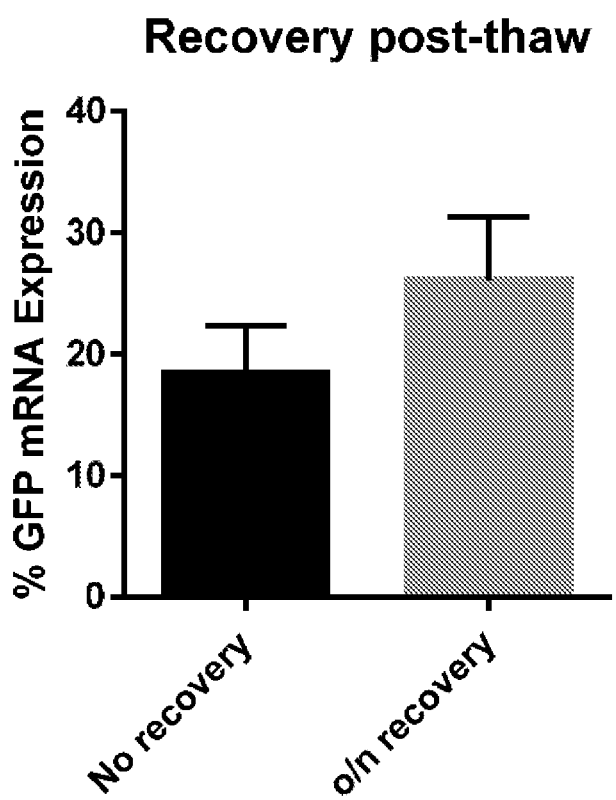
FIG. 9 is a bar graph illustrating results of cells left to recover prior to activation demonstrated higher uptake efficiency to those activated immediately post-thaw.

TexMACS (Miltenyi Biotech) was also tested as an alternative serum-free medium for T-cell culture. This T cell stimulation and expansion reagent was useful but not routinely used going forward (FIG. 8).

Effect of Post-Thaw Recovery Period Prior to Activation

The benefit for delivery to allow cells to recover overnight before addition of activation reagent compared with adding the recovery agent immediately after thawing without a recovery period was evaluated. Upon thawing of T cells from liquid nitrogen storage, cells were left to recover overnight in culture medium alone before the addition of activation reagent. This step resulted in a 30% improvement in transfection efficiency. In some examples, fresh primary non-adherent cells are used in the method; in other examples, primary non-adherent cells are frozen, e.g., for storage, and then thawed prior to the payload deliver method. The method may thus optionally include a freeze/thaw step of primary non-adherent cells. These data indicate that a recovery period (after thawing) prior to activation is useful.

Cell Culture Density

Figure 10:
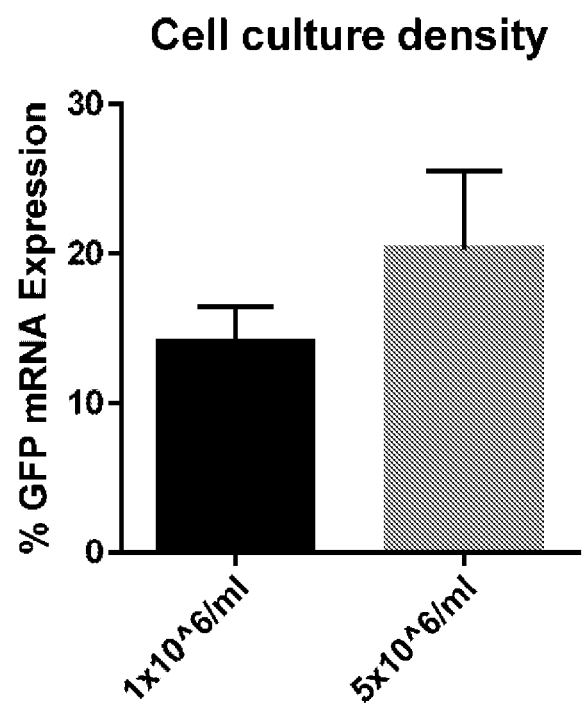
FIG. 10 is a bar graph illustrating results of cells cultured at a higher cell density prior to delivery using the vector-free delivery technology. A higher cell density ($5\times10^6$/ml) correlated with higher uptake efficiency.

Cells were cultured in Immunocult Expansion medium at various seeding densities ($1\times10^6$/ml and $5\times10^6$/ml) prior to the vector-free delivery. The density at which cells are cultured prior to Soluporation is between $1-5\times10^6$/mL]. Higher seed number led to an enhancement in uptake efficiency (FIG. 10).

T Cell Activation Using Zinc

Figure 11:
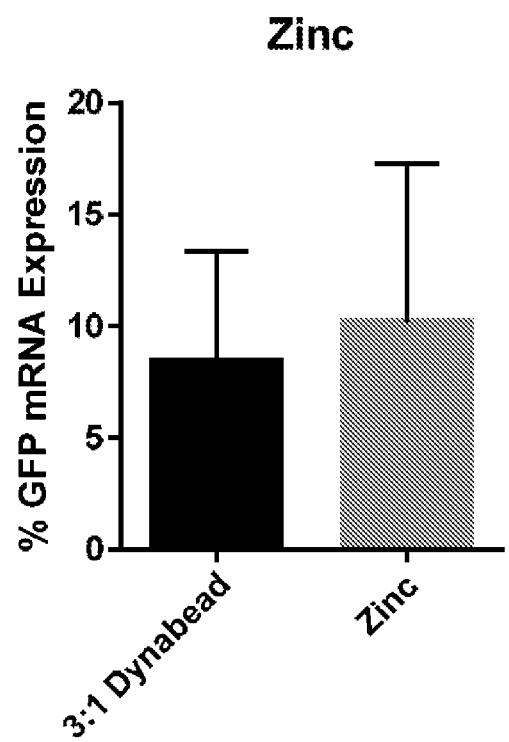
FIG. 11 is a bar graph illustrating that the addition of zinc chloride to the culture media resulted in higher uptake efficiency.

Zinc influx can support T cell activation (Yu M, et al., *J. Exp. Med.* 208 (4):775-785) but may also improve transfection of nucleic acid (Niedzinski E J, et al. *Mol Ther* 2003 7(3): 396-400). Zinc improved T cell proliferation in two independent experiments (FIG. 11). A trend towards an enhancement of transfection efficiency was observerd. Thus, zinc is an optional component of the cell culture medium at the activation step The range of zinc concentration ranges from 0.03 mM to 3 mM.

Optimization of T Cell Culture Conditions for Maximal Efficiency of mRNA Delivery Evaluation of multiple culture media, activation methods, supplementation and time courses has resulted in a preconditioning protocol that maximises the transfection efficiency of mRNA, e.g., the model payload GFP mRNA, to human primary T cells using the vector-free delivery technology. In this evaluation, cells were cultured in Immunocult™ T Cell Expansion Medium supplemented with 200 U/ml of IL-2 at a density of $5\times10^6$/ml. Cells were left to recover overnight post-thaw before the addition of 1× T cell TransAct™ (Miltenyi) for 48 h prior to vector-free delivery of nucleic acid.

Figure 12:
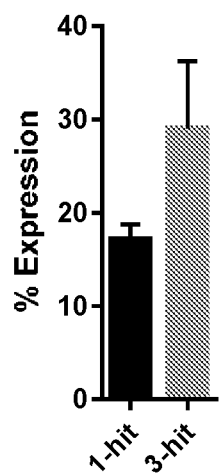
FIG. 12 is a bar graph showing that multiple hits on CD4+ T cells were negatively selected using CD8 microbeads. Cells were transfected with GFP mRNA by soluporation. Multiple hits improved uptake over 3 donors tested.

Human peripheral blood mononuclear cells (PBMC) were recovered by centrifugation over a Percoll gradient from Leuko Pak (AllCells Alameda, CA). CD4 enriched T cells were isolated by negative selection to recover a purified population using anti-CD8 microbeads and the flow-through was collected from an LD column (Miltenyi). Cells were cultured in standard cell culture media, e.g., complete RPMI using RPMI basal medium, heat-inactivated fetal bovine serum (FBS) (10% v/v), penicillin-streptomycin, L-glutamine and supplemented with IL-2 (200 U/ml). Cells were left to recover for 4 hours before the addition Dynabeads® at a bead to cell ratio of 3 to 1. mRNA was delivered to the cells at day 1 post-activation and assessed for uptake 24 h later. Multiple hits in this cell type achieved higher uptake efficiency, >30% (FIG. 12).

Figure 13:
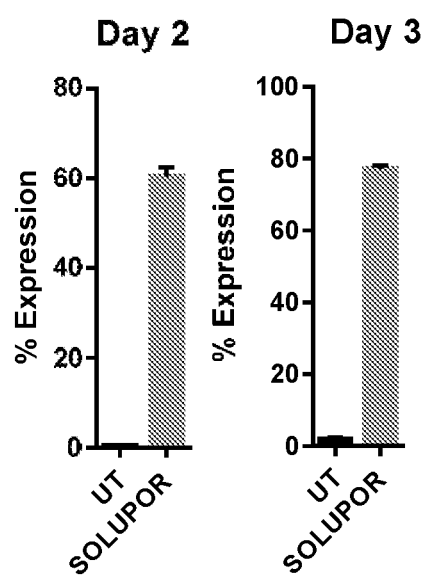
FIG. 13 is a bar graph showing expression of transfected mRNA by PBMC-initiated T cells. T cells were enriched from PBMC for 2-3 days. Cells were transfected with GFP mRNA by soluporation.

T cells were enriched from PBMC cultured in X-VIVO 15 supplemented with 2 mM GlutaMAX, 10 mM HEPES and 5% Human AB Serum and 250 IU/ml IL-2. Cells were seeded at a density of $1\times10^6$/mL and supplemented with anti-CD3 and anti-CD28 antibodies (Miltenyi) prior to culture. mRNA, e.g. test payload GFP mRNA, was delivered to the cells by soluporation at either day 2 or day 3 post-initiation and assessed for uptake 24 h later (FIG. 13).

Optimisation of T Cell Monolayer Formation

A cell monolayer is a culture in which cells are oriented in a single layer on substrate. The substrate is generally a plate, e.g., a microtiter plate, a flask, Petri dish, membrane, or filter upon which the cells lie. In cell culture, a monolayer refers to a layer of cells in which cells are substantially side by side and often touching each other on the same surface. The cells are adherent cells (cells that attach to a substrate) or non-adherent cells (cells that float or are suspended in culture media). Adherent cells grow on a substrate, attach, and thereby form a monolayer. A monolayer can also be made from non-adherent or "suspension cells". The terms "non-adherent cells" and "suspension cells" are used interchangeably herein.

A number of techniques may be employed to make a cell monolayer from non-adherent or suspension cells prior to delivery of a payload to the cells. Such techniques include allowing a culture suspension cells to settle on substrate, centrifugation, exposure to a vacuum, exposure to positive pressure, use of magnetic T-cell activation beads and/or deposition onto a membrane (e.g., the use of a transwell insert system, described below.)

Transwell Insert

Figure 14A:
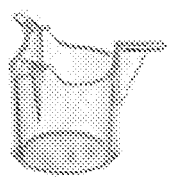
FIG. 14A is a diagram.
Figure 14B:
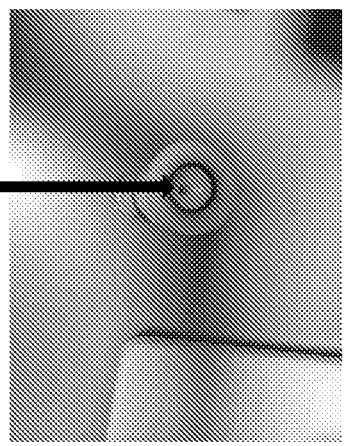
FIG. 14B is a photograph.
Figure 14C:
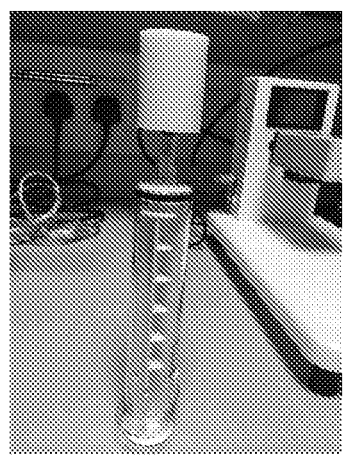
FIG. 14C is a photograph showing membrane inserts. An example image of a ThinCert 12-well insert (FIG. 14A). An image of the insert device whereby the insert would be placed within the O-ring as indicated by the arrow (FIG. 14B). The device attached to a syringe to allow a vacuum to be applied to the insert to remove the media (FIG. 14C).
Figure 15:
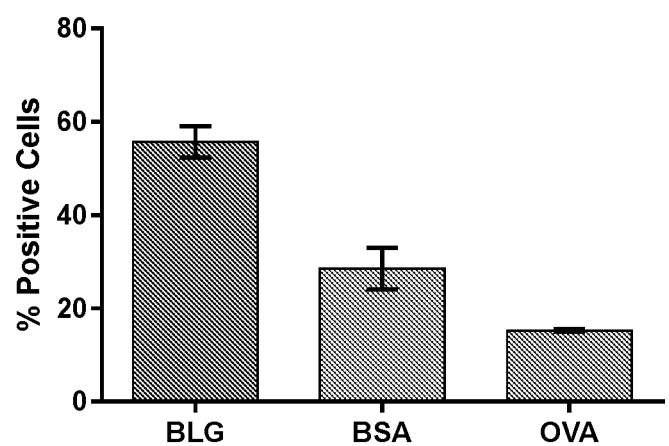
FIG. 15 is a bar graph showing Solupore delivery of cargo to suspension cells (non-adherent cells). Fluorescently-labelled beta-lactoglobulin (BLG), bovine serum albumin (BSA) or ovalbumin (OVA) was delivered to a monolayer of Jurkat cells formed using the insert device. Expression levels were analysed by flow cytometry.

In order to form a monolayer of suspension cells that would allow the cells to be presented optimally to the spray, a transwell insert system was used. Cells were seeded at $1\times10^6$ in 400 μl per insert and the media was removed by placing the transwell insert (Greiner bio-one; CAT #655640; 12 Well ThinCert; PET 0.4 μm) into a device that allowed a vacuum to be applied to the bottom of the insert (between −0.5 bar and −0.65 bar; see FIGS. 14A, B, C). Once the media was removed the remaining cells formed a monolayer to which the spray can be applied. Non-adherent cells such as PBMCs, primary T-cells, or a cell line, e.g., Jurkat T cells, were added to the insert system, the vacuum applied and the insert placed into a 12 well plate and sprayed with delivery solution (10 μl) containing test payload such as either fluorescently-labelled beta-lactoglobulin (BLG), bovine serum albumin (BSA) or ovalbumin (OVA). Stop solution (50 μl) was applied after a 2 minute incubation and 30 s later normal media (100 μl) was applied. Expression levels of 55.6, 28.5 and 15.3% were achieved (FIG. 15). The insert system was found to be useful as an exemplary technique to generate a monolayer using non-adherent cells.

96-Well Polyethersulfone (PES) Plate

Permeable membranes that allow filtering of culture media are also useful to generate cell monolayers. Such membranes include cellulose nitrate membranes, cellulose acetate or PES membranes.

Figure 16A:
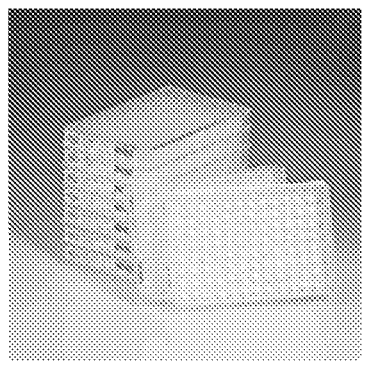
FIG. 16A is a photograph of microtiters plates (PES filter plate)
Figure 16B:
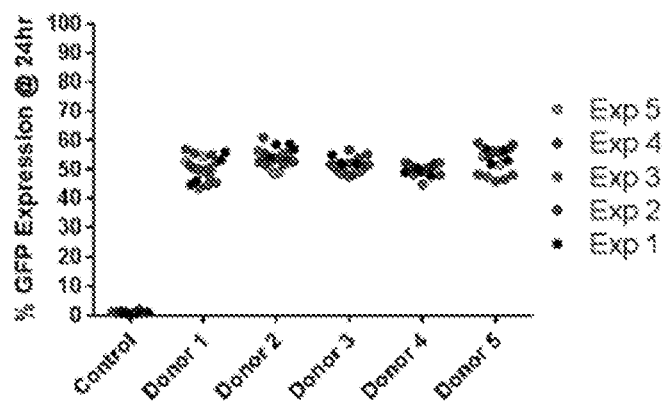
FIG. 16B and FIG. 16C are dot plots showing expression of product from transfected mRNA. An example image of the Acroprep Advance, Supor membrane, 96-well filter plate (FIG. 16A). GFP expression levels from 5 random donors across 5 experiments 24 hr post mRNA delivery to T cells (FIG. 16B). Relative viability of T cells 24 hr post mRNA delivery to T cells (FIG. 16C).
Figure 16C:
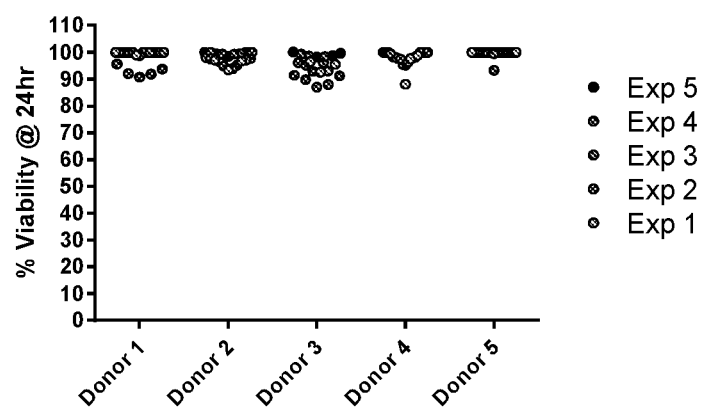

Such a membrane-based system was assessed to create a suspension cell monolayer. 96-well filter bottomed plates provide a 96-well format with a filter bottom to the well. The Pall Supor filter plate (AcroPrep Advance; PES 1.2 μm, CAT #8039) was assessed. $1\times10^6$ human primary T cells were seeded in 100 μl per well and the plate centrifuged at 300×g for 5 min. Once the media was removed by centrifugation, and the remaining cells formed a monolayer, the plate was placed within the Solupore device and cells sprayed with delivery solution containing mRNA. Stop solution (50 μl) was applied after a 2 minute incubation and 30 s later normal media (100 μl) was applied. The cells were incubated for 2 hours before the process was repeated. At the end of this spray the cells were incubated overnight at 37° C. and 5% $CO_2$ in a humidified incubator and assessed for GFP fluorescence by flow cytometry. GFP expression levels of 52%±3.6 across 5 donors and 5 experiments was achieved with a viability of 97%±3.3 (FIGS. 16A, B, C). The PES plate contains a mesh-like filter in which cells may become irretrievable. Other filter types, such as track-etched, were assessed. A track-etched membrane is a thin (~5-25 microns) polymer membrane the pores of which are formed by irradiating the initial non-porous material with high-energy particles and subsequent etching (usually by caustic etchant (for example NaOH)) of latent tracks to form pores through the membrane of a given diameter.

96-Well Polycarbonate Track-Etched (PCTE) Plate

Figure 17:
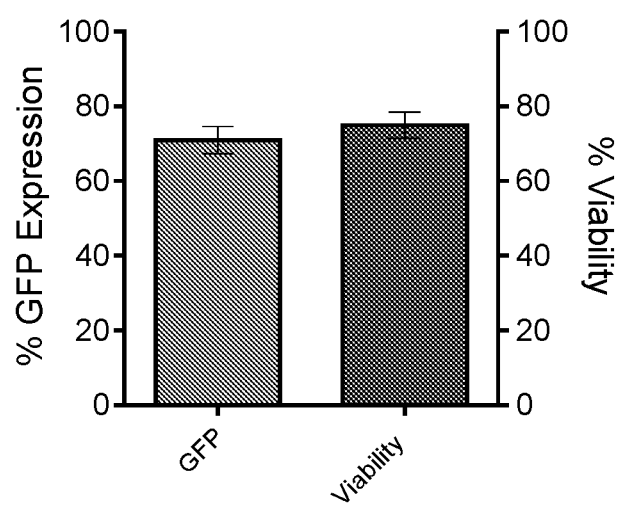
FIG. 17 is a bar graph showing the results of cargo delivery using a PCTE filter plate. Viability and GFP expression 24 hr post mRNA delivery to T cells using a PCTE 96-well plate.
Figure 18:
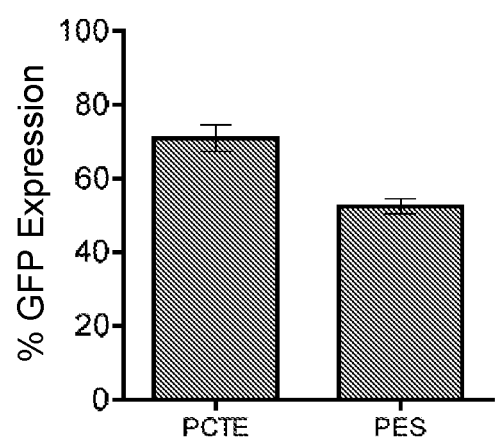
FIG. 18 is bar graph showing mRNA expression after cargo delivery to cells (comparison of 96-well filter plates). GFP expression in T cells following mRNA delivery. A monolayer of cells were formed in either a PCTE or PES filter plate.

Alternative membrane filter systems may be used for generation of a cell monolayer of non-adherent cells. For example, an alternative filter plate with 0.4 μm hydrophilic PCTE filter was obtained from Agilent technologies. Human primary T cells were seeded at $2.5\times10^5$ cells per 100 μl per well and centrifuged at 350×g for 2 min Once the media was removed and the cell monolayer formed, the plate was placed within the Solupore device and cells sprayed with delivery solution containing a test payload such as GFP mRNA. Stop solution (50 μl) was applied after a 2 minute incubation and 30 s later normal media (100 μl) was applied. The cells were incubated for 2 hours before the process was repeated. At the end of this spray the cells were incubated overnight at 37° C. and 5% $CO_2$ in a humidified incubator and assessed for GFP fluorescence by flow cytometry. GFP expression levels of 72%±5 was achieved with a viability of 75.0%±3.5 (FIG. 17). The results of a comparison of PES and PCTE plates is shown in FIG. 18 and shows that uptake is enhanced when using the PCTE plates. Thus, a hydrophilic membrane filter, optionally track-etched, is a useful exemplary membrane and is preferred in some embodiments.

Media Removal

Figure 19A:
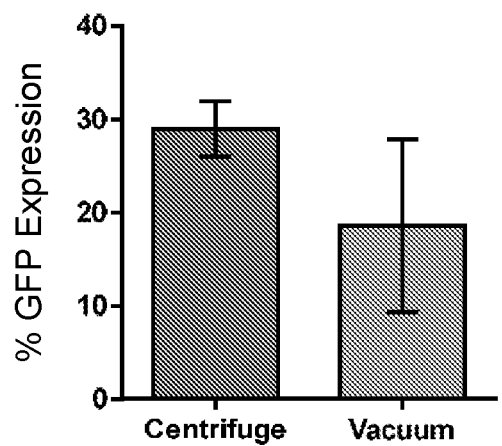
FIG. 19A-FIG. 19B are bar graphs showing expression of transfected mRNA. A comparison of media removal methods. Media was removed from cells seeded in a 96-well filter plate by either centrifugation or vacuum pressure.
Figure 19B:
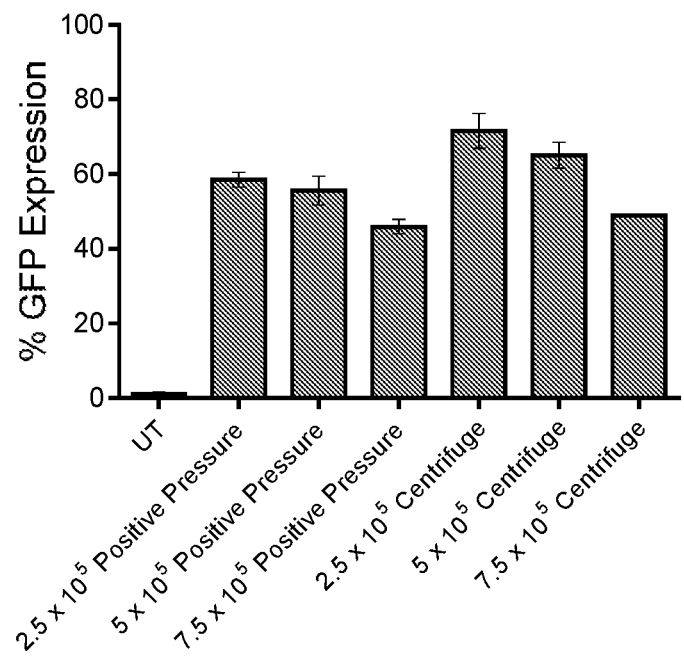
Figure 20A:
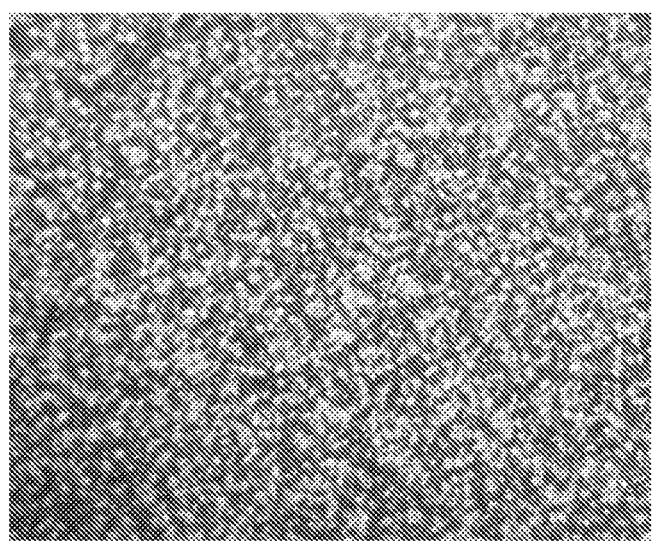
FIG. 20A and FIG. 20B are photographs of cells. Monolayer formation using Dynabead bound cells (FIG. 20A). Media was removed by pipetting and GFP mRNA was delivered by Soluporation. GFP expression was detected 24 hr later by fluorescence microscopy (FIG. 20B).
Figure 20B:
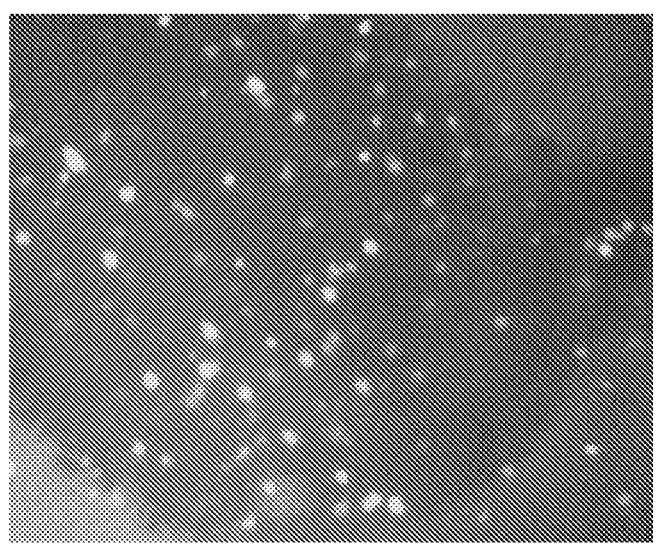
Figure 105:
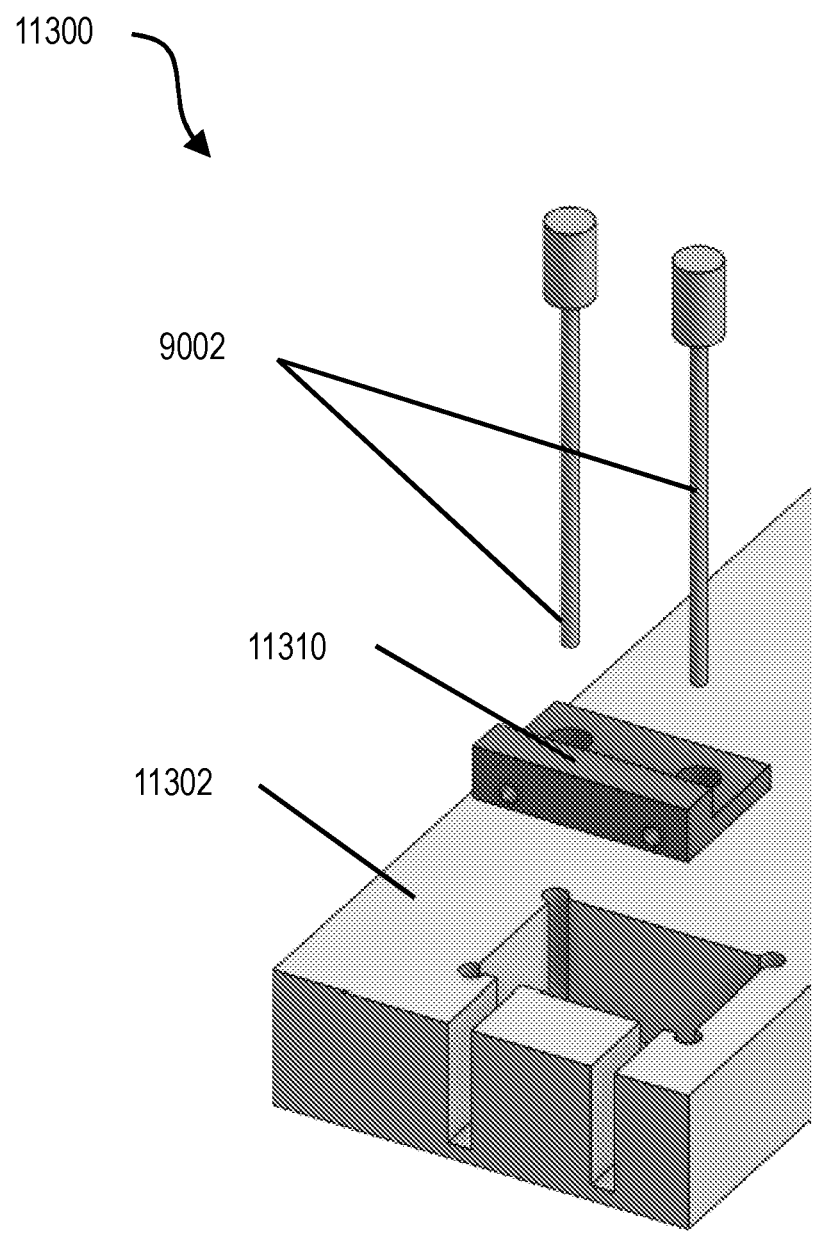
FIG. 105 is an exploded perspective view of a portion of the mounting assembly shown in FIG. 90.
Figure 106:
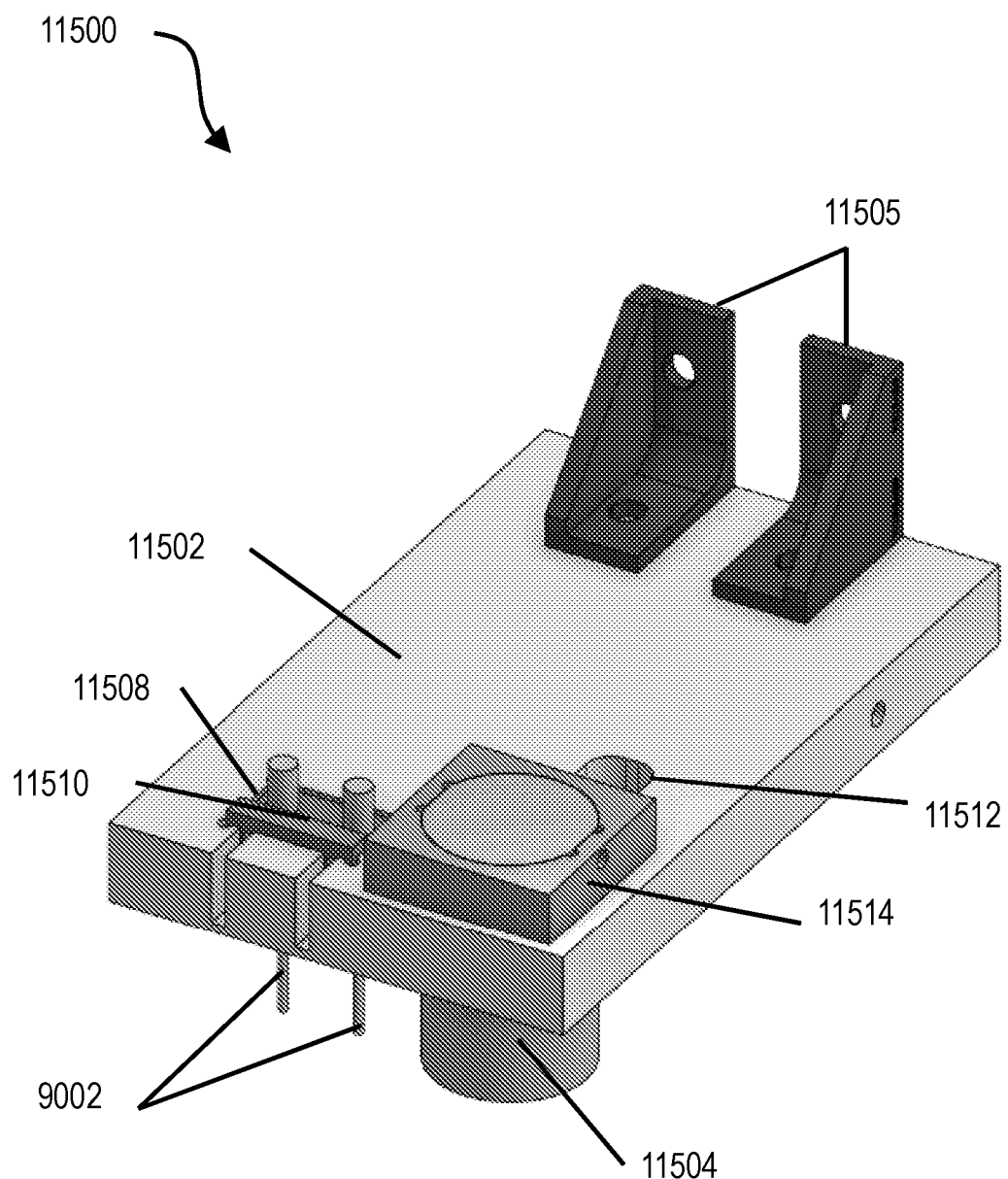
FIG. 106 is a perspective view of another embodiment of a mounting assembly that can releasably retain needle emitters and an ultrasonic atomizer.
Figure 107:
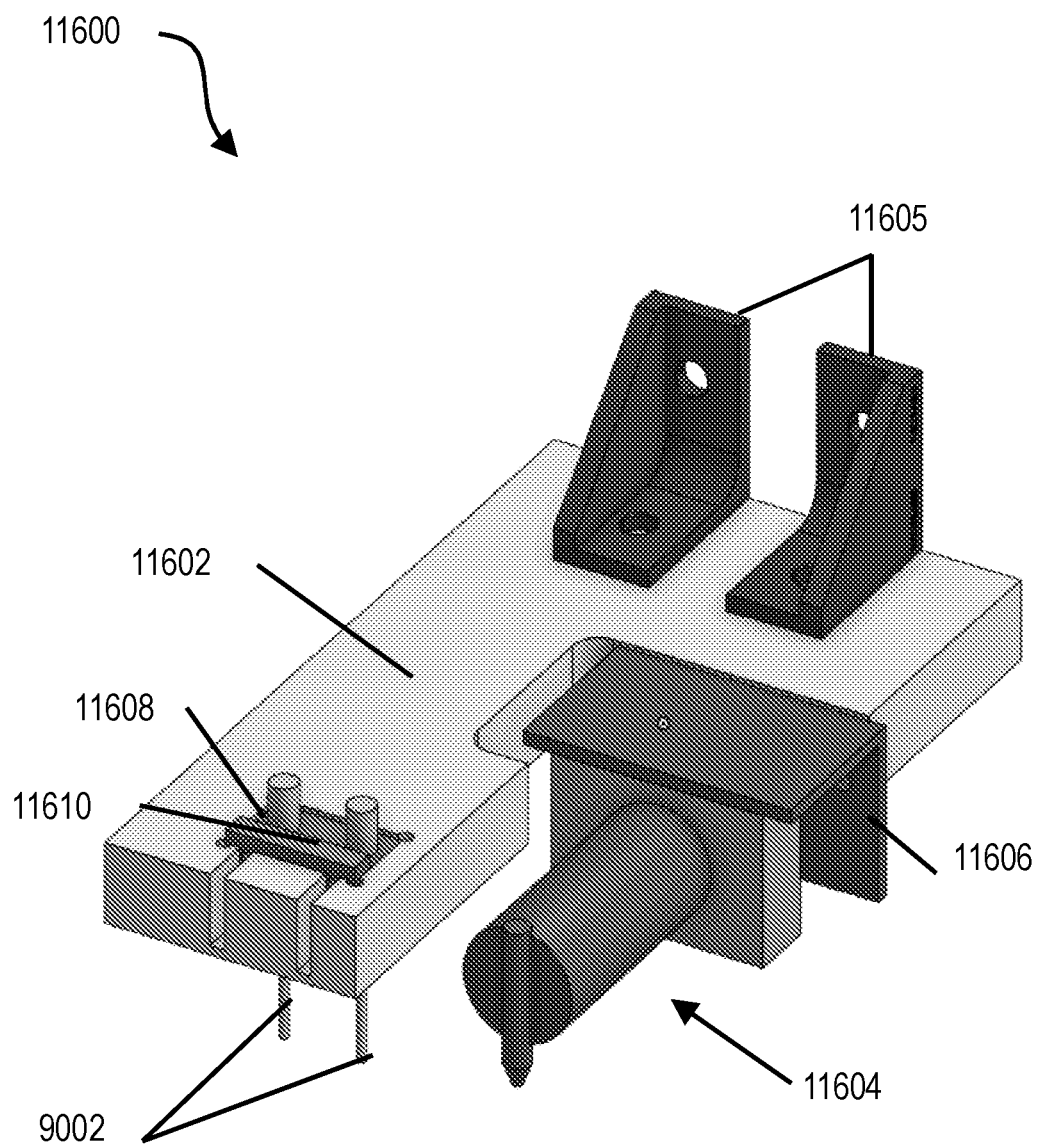
FIG. 107 is a perspective view of an embodiment of a mounting assembly that can releasably retain needle emitters and a nebulizer.

The method for removal of media from the cells was also addressed. Using the filter plates, centrifugation, vacuum pressure and positive pressure were assessed. $1\times10^6$ human primary T cells were seeded per well in a 96-well filter plate (Pall; Supor, 1.2 μm; CAT #8039). The media was removed by either centrifugation at 300×g for 5 min or by vacuum pressure (−20 mBar, 30 s; see FIG. 105-107). The cell monolayer was sprayed with 4 μl of delivery solution containing 0.57 μg/μl of GFP mRNA. Stop solution (50 μl) was applied after a 2 minute incubation and 30 s later normal media (100 μl) was applied. The cells were incubated overnight at 37° C. and 5% $CO_2$ in a humidified incubator and assessed for GFP fluorescence by flow cytometry (FIG. 19A, B). In another experiment, human primary T cells were seeded at $2.5\times10^5$ cells in 100 μl per well of the Agilent PCTE filter plate (Agilent; PCTE 0.4 μm). The media was removed by either centrifugation (350×g for 2 min), or positive pressure (200 mBar for 1 min;). Once the media was removed and the cell monolayer formed the plate was placed within the Solupore device and cells sprayed with delivery solution containing GFP mRNA. Stop solution (50 μl) was applied after a 2 minute incubation and 30 s later normal media (100 μl) was applied. The cells were incubated for 2 hours before the process was repeated. At the end of this spray the cells were incubated overnight at 37° C. and 5% $CO_2$ in a humidified incubator and assessed for GFP fluorescence by flow cytometry (FIG. 19A, B). Vacuum pressure is used to remove the media from the wells to provide a cell monolayer. Optionally, both positive pressure and centrifugation are used to produce monolayers. In some embodiments, the latter technique is preferred.

Magnetic Beads

An alternative method combines the use of the T cell activation beads (e.g., DynaBeads 3:1 ratio) and a magnet. After overnight activation, the T cells (bound to the DynaBeads) were seeded in a 96-well plate. A magnet was placed underneath the wells and the media removed by pipette. The magnet holds the beads and cells in place while the media is removed. mRNA was then delivered by Soluporation. GFP expression was detected 24 hr later by fluorescence microscopy.

mRNA Delivery to MSCs

To confirm delivery to cells in a monolayer, mesenchymal stromal cells (either primary human or iPSC-derived) were seeded in 96-well plates so that by 24 hrs the confluency was 80-90%.

Delivery of mRNA, e.g., test payload/cargo GFP mRNA, to BM-MSCs and iPSC-MSCs was evaluated. The delivery of various cargo compounds such as 10 kDa dextran to primary human BM-MSCs using a vector-free method for intracellular delivery involving reversible permeabilization was previously reported (O'Dea S, et al., *PLoS One*. 2017. 30; 12(3):e0174779). A method for delivery of functional molecules such as mRNA was also evaluated. A reporter GFP mRNA was used to evaluate mRNA delivery efficiency to BM-derived and iPSC-derived MSCs.

Figure 21A:
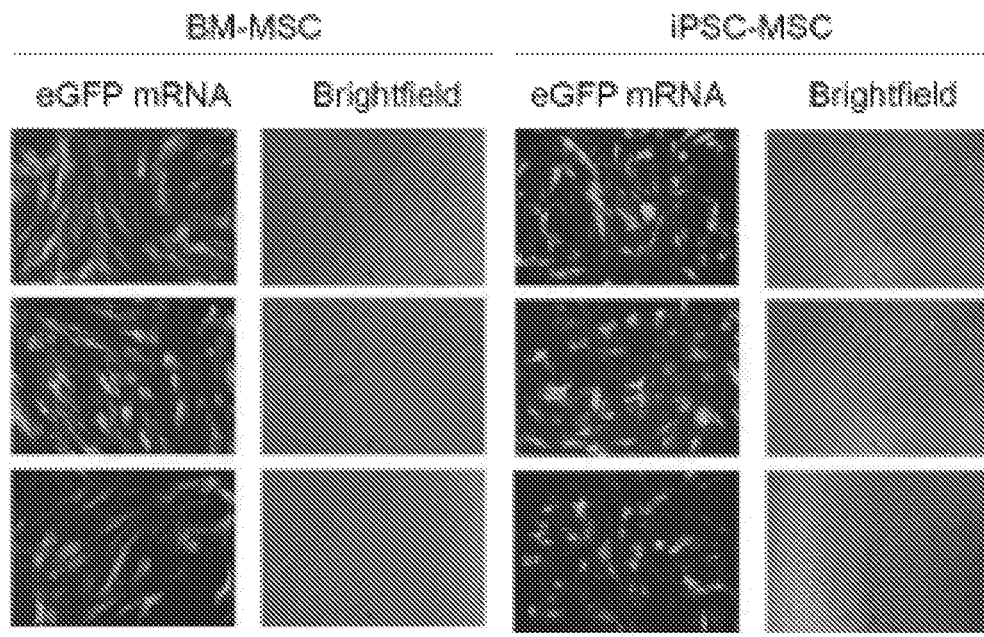
FIG. 21A is a series of photographic images illustrating the delivery of GFP mRNA to MSCs. GFP RNA was delivered to BM-MSCs and iPSC-MSCs using the vector-free reversible permeabilization method and analysed by fluorescence microscopy (10× magnification).
Figure 21B:
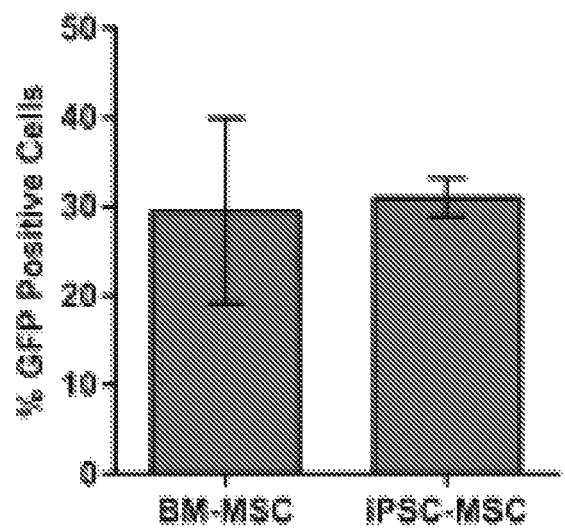
FIG. 21B is a bar graph illustrating delivery of GFP mRNA by MSCs analysed by flow cytometry; n=3, data are depicted as the mean±standard deviation.
Figures 22A, 22B:
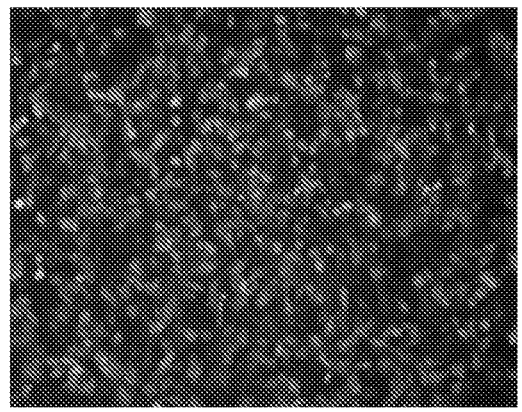
FIG. 22A is a table and FIG. 22B is a photograph of cells showing a green fluorescent marker. Uptake of Alexa 488 Dextran 10KD using the ultrasonic nebulizer. Representative data demonstrating uptake of dextran into U2OS cells using the ultrasonic nebulizer (a) Table summarising the data where up to 64% dextran uptake was achieved and (b) Fluorescence micrograph showing green Dextran-Alex488.
Figure 24:
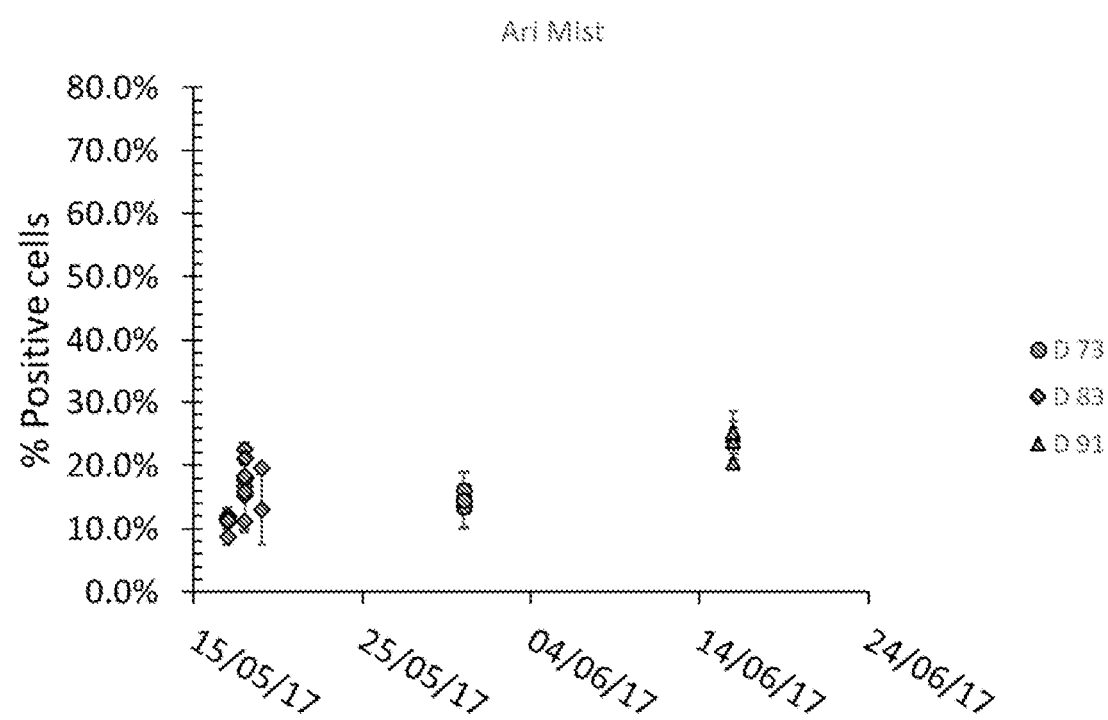
Figure 25:
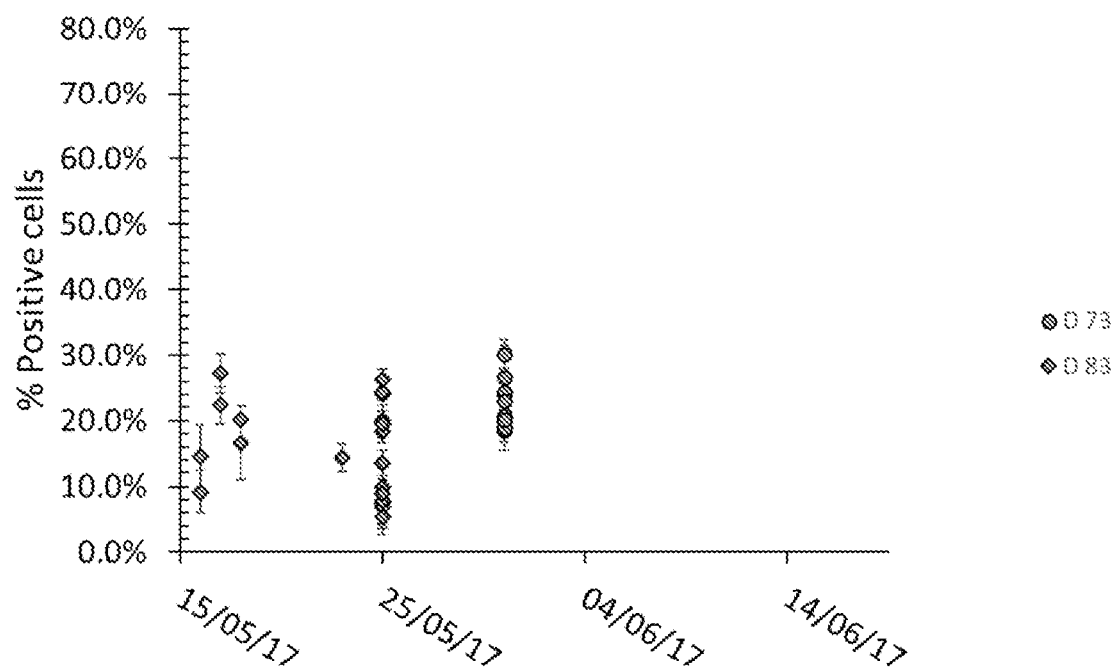
Figure 26:
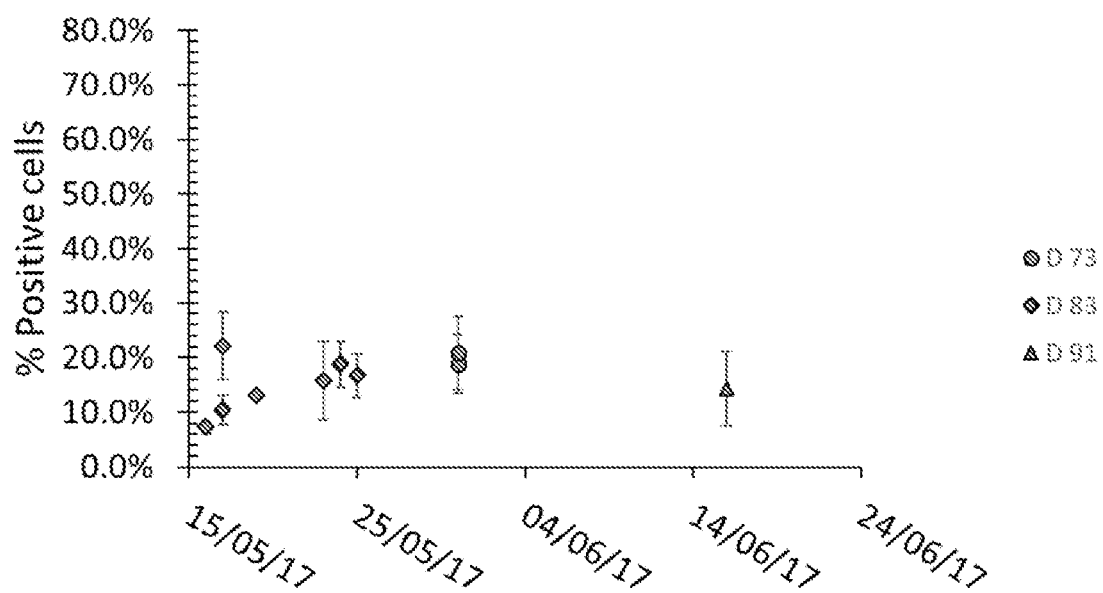
Figure 27A:
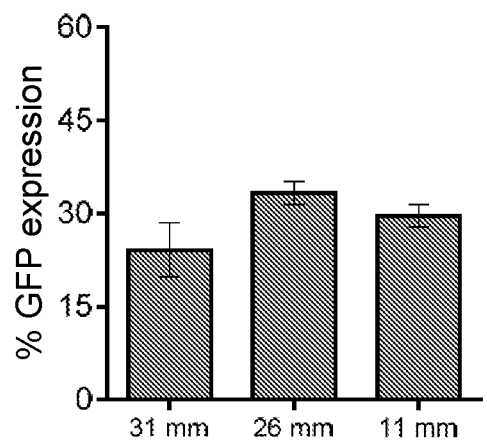
Figure 27B:
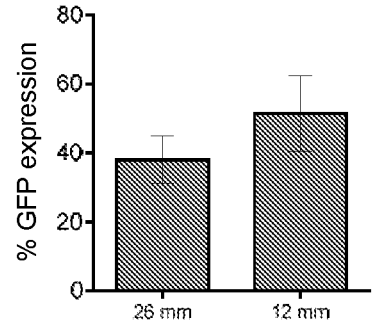

Multiple treatments, e.g., three doses of GFP mRNA, were delivered to BM-MSCs and iPSC-MSCs over 2 days. Fluorescence microscopy confirmed expression of GFP protein in cells 24 hr following delivery of the final dose of mRNA (FIG. 72A). Flow cytometry analysis indicated delivery efficiencies of 29.5±10.4% and 31.0±2.2% (n=3) in BM-MSCs and iPSC-MSCs respectively (FIG. 21A, B).

Optimisation of Atomisation of Delivery Solution

The Mucosal Atomization Device (MAD Nasal™) spray head, used to atomize the payload solution dispenses volume of milliliters while soluporation works with micro-litres volumes. The use of a microliter volume atomizer/droplet delivery system is preferable.

Figure 58:
FIG. 58 is a photograph of a Certus Flex set-up. Image demonstrates Certus flex set-up with delivery solution loaded in Channel 1, Stop solution loaded in Channel 2 and Culture medium loaded in Channel 3.
Figure 59:
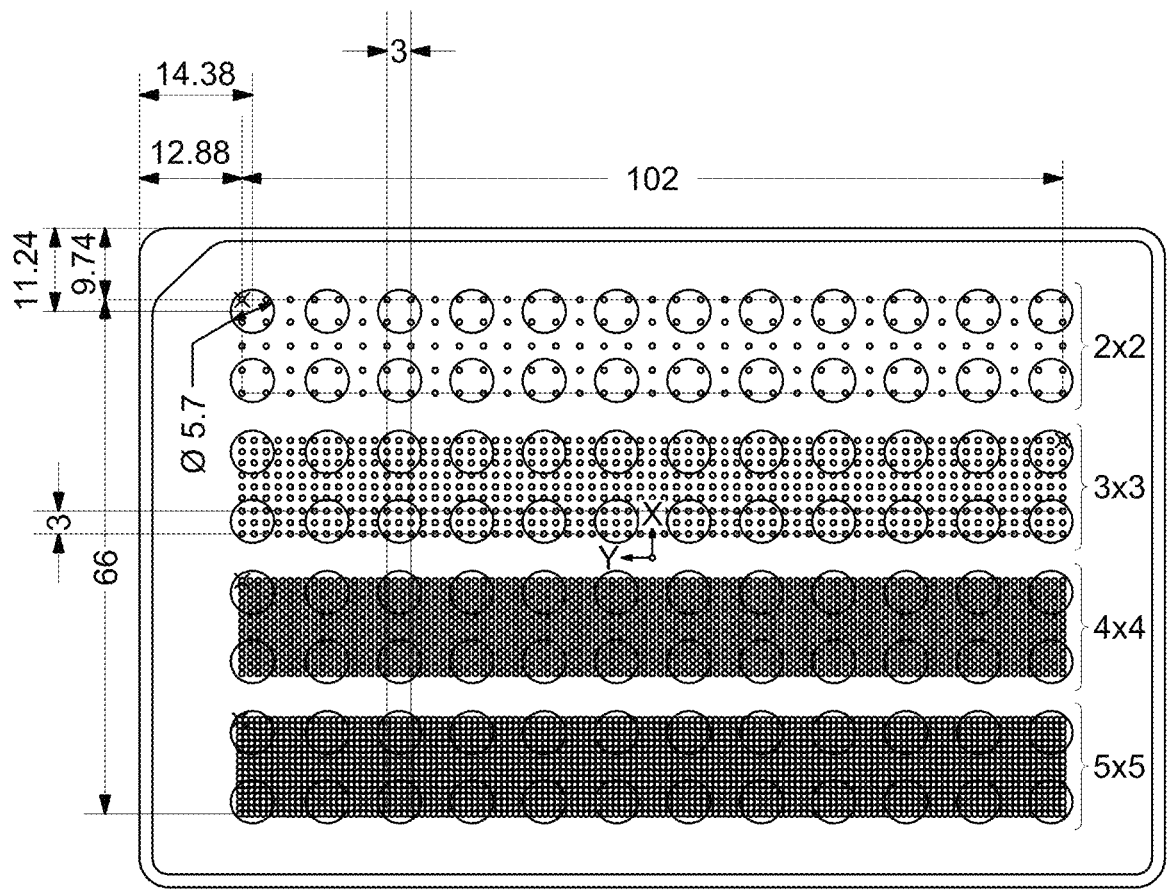
FIG. 59 is a diagram of a Droplet Array Pattern. Figure demonstrates the droplet array pattern tested and is further described in Table 1. The total volume delivered into the well was 2 μl or 7 μl and the number of droplets increased from 4 to 25. This corresponded to droplet volumes ranging from 0.08 to 0.5 μl.

Alternative spray heads were investigated for two main purposes: increasing the uptake and improving reproducibility across replicates (intra-experiment) and across experiments (inter-experiment). An assessment of alternative atomiser devices was undertaken to find which was optimal for mRNA delivery to T cells. The atomiser allows the application of the delivery solution in dropletised form to the cell monolayer. In addition to identification of the atomiser, a controller device was designed and built which allowed fine control of the atomisation process. A variety of parameter sets were tested to find the optimal parameters for delivery of mRNA to T-cells.

The results indicated that a microliter volume delivery device such as the Ari Mist nebuliser and 180 kHz ultrasonic nebuliser gave comparable uptake and reproducibility while cell viability was slightly higher with Ari Mist. Such a microliter volume delivery device such as the Ari Mist head was preferred and can be incorporated into an automated solution since it is smaller in size, easier to handle and does not require a power box to operate. Other units such as the Burgener nebulisation technology (U.S. Pat. No. 6,634,572, hereby incorporated by reference) also was suitable for the scaling up of soluporation. Taken together, the Ari Mist and other Burgener nebulizers were used moving forward for automation and scaling.

Atomization of the Delivery Solution to Produce Monodispersed Droplets

A cell membrane permeabilizing solution can be delivered onto a monolayer of cells using a variety of methods. For example, the permeabilizing solution can be atomized using ultrasonication or it can be nebulized using a pneumatic nebulizer.

Both air-assisted ultrasonication and pneumatic nebulization were tested as delivery methods. A total of eight different spray heads were tested: three ultrasonic heads namely 60 KHz (Sonaer), 130 kHz (Sonaer) and 180 kHz (Sonotek Echo) and five pneumatic nebulizers namely Ari Mist, X-175, PFA 250, T2100 and Peek Mira Mist (Burgener Research)

Ultrasonication tests were performed at 60 kHz, 130 kHz, and 180 kHz. Liquid can be driven to an ultrasonic nozzle by a pumping system, and it can be atomized into a fine mist spray using high frequency sound vibrations.

A curtain of gas (air) can assist the process. An auxiliary piece called shaper is mounted around the ultrasonic head and the function of the air is to shape the mist of liquid ultrasonicated. For example, the air had the dual function of shaping the spray as well as promoting the payload to enter the cells. This was possible because the air fed through the shaper was at pressure beyond that used for shaping function.

Testing with the ultrasonic nebulizer yielded results useful for delivery of caro/payload to mammalian cells, e.g., non-adherent cells. Up to 60% Dextran-Alexa488 (model cargo) was delivered to U2OS cells using the 180 kHz ultrasonic head (FIG. 22A, B).

Piezoelectric transducers can be used to impart electrical input into mechanical energy in the form of vibrations, which created capillary waves in the liquid when introduced into the nozzle, and resulted in atomization of the liquid. Each ultrasonic probe worked at a given resonant frequency. The operating frequency can determine the size of the liquid droplets generated. The size of the droplets can also be affected to a lesser extent by the power at which the ultrasonic probe is operated. An ancillary air stream can be used to help control and shape the spray.

An exemplary ultrasonic spray emitter generates a fine spray, with narrow size distribution of the droplets which in turn results in even deposition of the delivery solution and payload onto cells. Reducing the volume delivered and reducing the ethanol concentration, e.g., with respect to the preferred parameters evaluated for the MAD nasal spray head, improved delivery efficiency and improved viability with the ultrasonic spray head.

Additional nebulizers to generate droplets (microliter volume) were tested such as Ari Mist, Peek Mira Mist, T2100, X175 and PFA250 nebulizer (Burgener Research). These exemplary nebulizers operate on compressed gases and require a pump to supply the sample solution. These exemplary atomizers have two parallel channels, one for the gas (air) and the other one for the liquid to be nebulized. Both paths end at the tip of the nebulizer with an orifice for the gas and an exit for the liquid. The gas flow can draw the liquid into the gas stream. The impact with the gas molecules can break the liquid into small droplets, resulting in nebulization.

The Burgener nebulizers (U.S. Pat. No. 6,634,572) tested differ in inner diameter, material and optimal flow rate. In preliminary tests, the nebulizers gave comparable expression of cargo mRNA. Characterisation of the droplet size revealed droplets ranging from 1-20 μm, with the peak number of droplets in the range of 5-7 μm. The average particle size as defined by the Sauter mean ($D_{32}$) diameter is 13 μm (see http://www.burgener.com/EnhancedData.html)] Amongst the suite of Burgener's nebulizers tested the Ari Mist was chosen as the preferential spray head based on several factors: uptake and viability were good, its specs (optimal flow-rate, inner diameter) matched the characteristics of the pumping system, its inner diameter (225 μm) was small enough to handle low volumes of liquid without the inconvenience of clogging.

Certus Digital Dispensing Technology

The Certus Flex liquid dispensing instrument was equipped with an 8 channel dispensing head (Cat. #D196057) and two valve sizes (0.10 nozzle diameter, 0.03 travel (Cat. #21765) and 0.15 nozzle diameter, 0.03 travel (Cat. #21766). Each channel is individually controlled using the Certus proprietary software and electronics. The Certus Flex enables contactless dispensing of liquid and large molecules using Gyger micro valve technology and air pressure control. Volumes in the nano litre (nl) range can be delivered with high precision (100 nl with CV 5%; CV represents coefficient of variation or relative standard deviation).

Delivery mRNA to T cells through the generation of small droplets in the nanoliter (nl) to μl size range was examined to evaluate the feasibility of delivering mRNA to T-cells using the Certus Flex microfluidic platform.

$CD3^+$ T-cells were activated using, e.g., either Dynabeads or TransAct. Cells were seeded at $1.5\times10^6$ cells per well of a 96-well filter plate (PES). The plate was centrifuged, e.g., for 5 mins at 300×g to remove the cell culture medium. Delivery solution was dispensed to each well through Channel 1 with the parameters listed in Table 1. A total volume of microliter amounts, e.g., 2 or 7 µl, was delivered in droplets ranging in volume from 7 to 0.08 µl. The volume of the droplet was determined by the number of drops dispensed into the well. FIG. 58, represents the droplet array pattern tested (FIG. 58). The valve type, pressure and height were varied as outlined in Table 2. Cells were incubated for 2 minutes following application of the delivery solution. 50 µl Stop solution was added though Channel 2 and incubated for 30 s. 100 culture medium was added though Channel 3. The plates were incubated at 37 degrees for 24 hrs prior to analysis (FIG. 58).

Figure 61A:
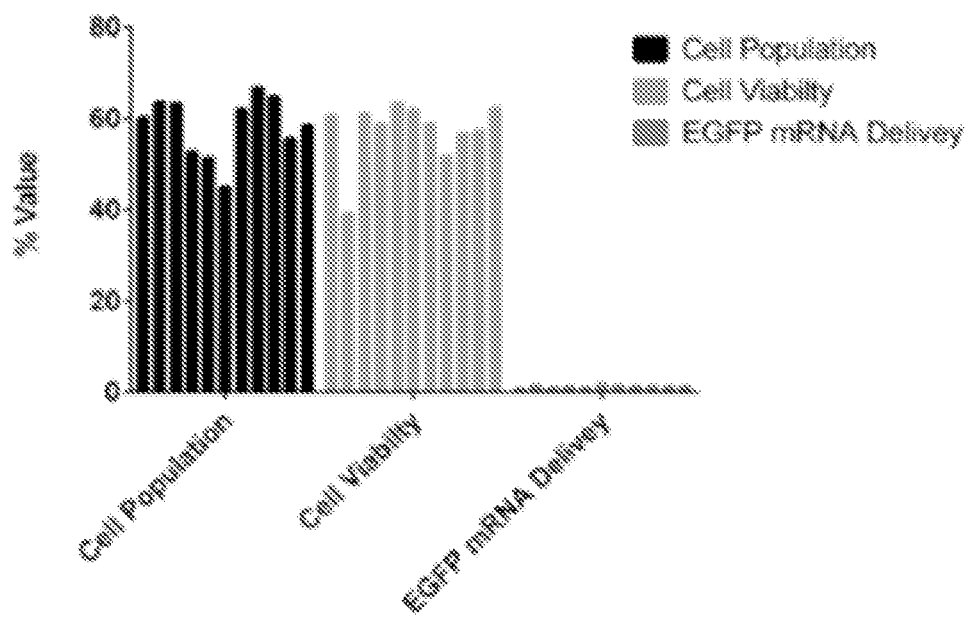
Figure 62A:
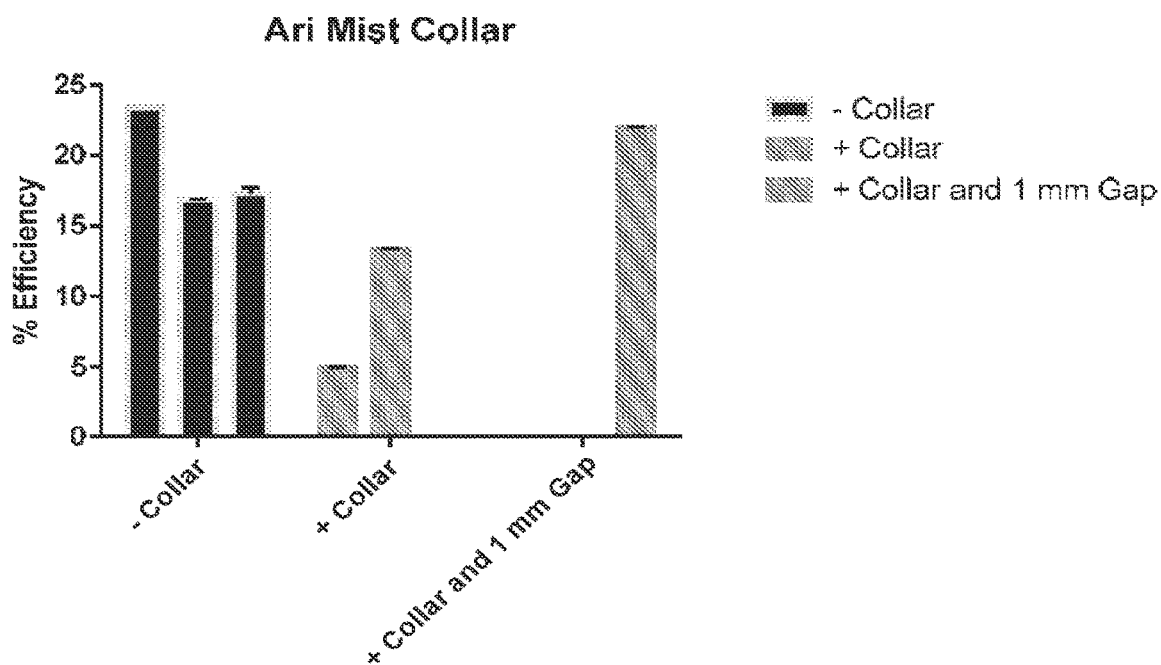
FIG. 62A is a bar graph showing the effect of a collar and FIG. 62B is a photograph showing a collar. Testing of an Enclosing collar on the Ari Mist spray head.
Figure 62B:
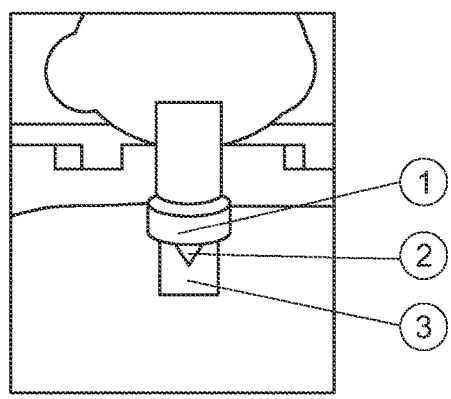

The results indicate that cell viability was comparable to untreated cells using this system. No delivery of GFP mRNA was observed using this system. This was seen across all parameters tested (FIG. 61). Thus, using the Certus Digital Dispensing Technology to delivery droplets in the nl-µl range did not result in uptake of GFP mRNA to T-cells.

TABLE 1

Plate Delivery Template Parameters

| Orientation | Points per plate | Points per well | Volume per point (2 µl delivery) | Volume per point (7 µl delivery) |
|---|---|---|---|---|
| 1 × 1 | 96 | 1 | 2 | 7 |
| 2 × 2 | 1761 | 4 | 0.5 | 1.75 |
| 3 × 3 | 4001 | 9 | 0.222222222 | 0.777777778 |
| 4 × 4 | 6901 | 16 | 0.125 | 0.437 |
| 5 × 5 | 11021 | 25 | 0.08 | 0.28 |

TABLE 2

Dispensing head channel configuration

| Channel | Valve | Solution | Dispense Volume | Pressure | Height | Incubation time |
|---|---|---|---|---|---|---|
| 1 | 0.10, 0.03 | Delivery-EGFP mRNA | 2/7 µl | 0.3/0.6 Bar | 15.5/31 mm | 120 secs |
| 2 | 0.15, 0.03 | Stop Solution | 50 µl | 0.3 Bar | 15.5/31 mm | 30 secs |
| 3 | 0.15, 0.03 | Culture Medium | 100 µl | 0.3 Bar | 15.5/31 mm | 24 hrs (incubator) |

Instrumentation to Enable Fine Control of the Spray

A test rig was built to control the critical spray parameters and enable mechanisation of the spray. The plate containing the cell suspension was centrifuged prior to being placed on the test rig. The delivery solution containing the payload was loaded into the elveflow fluidic reservoir or a syringe system. Fluidic control of the delivery solution containing the payload was brought about either using a pinch valve or using a micro valve. Addition of the stop and culture medium was done manually.

Fluidic control of the delivery solution containing the payload was brought about using two systems, an elveflow-pinch valve system and a syringe-micro valve system. The syringe-micro valve system was shown to have benefit over the elveflow-pinch valve system.

a) Fluidic Control of the Delivery Solution Containing the Payload
(i) Elveflow-Pinch Valve Elveflow refers to a microfluidic reservoir which was used with a 1.5 ml Eppendorf tube or 50 ml falcon tube depending on the sample reservoir size required (Elvesys, Innovation centre, 83 avenue Philippe Auguste, 75011, Paris, FRANCE). Pinch valve can refer to any pinch valve where an example is the Electronic Clippard pinch valve (Clippard, 7390 Colerain Avenue, Cincinnati, OH 45239, USA) The fluidic control can be achieved by fluid control system that can apply a constant pressure to an elveflow fluidic reservoir to drive the fluid through a pinch valve (FIG. 23). A volume of fluid that can be dispensed can be controlled by: an amount of pressure applied; a length of time the valve is open; and/or a diameter of the tubing used.

The valve can be activated by a metal-oxide-semiconductor field-effect transistor (MOS FET) which can be controlled by a microprocessor.

(ii) Syringe-Micro Valve

Figure 54:
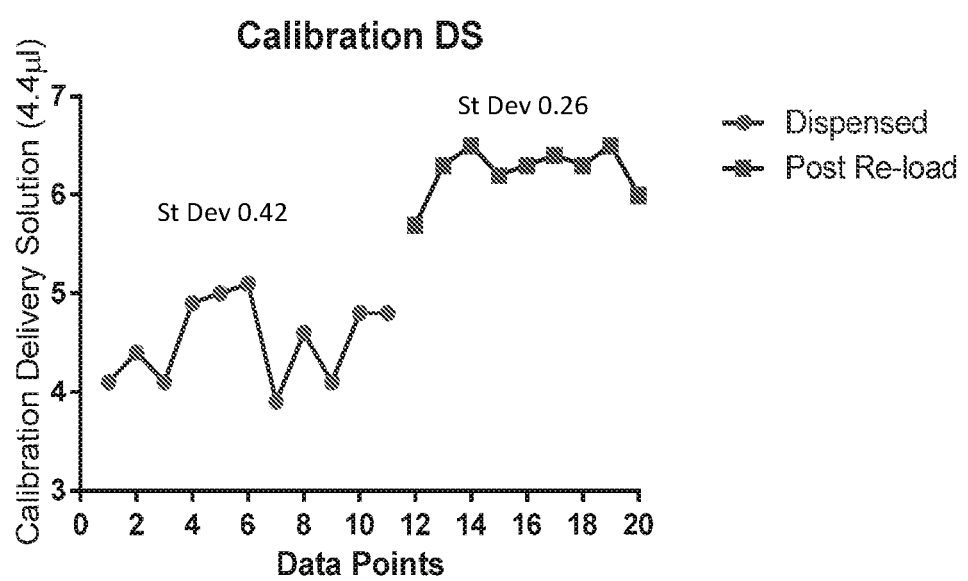
FIG. 54 is a line graph showing calibration data for the delivery solution using the elveflow-pinch valve system. Graph demonstrates calibration data for repeated atomisation of 4 μl volume of delivery solution. The orange bar shows the volume measured from 11 repeat sprays of delivery solution where the expected volume was 4 μl. Data demonstrates a relative standard deviation (% RSD) of 9.38% at this volume range. The pink bar shows the volume measured from 9 repeat sprays following re-load of the sample reservoir. These data highlight the limitations with the elveflow-pinch valve system which include lack of precision and accuracy when spraying 4 μl volumes and a lack of calibration holding following re-load of the system.
Figure 63A:
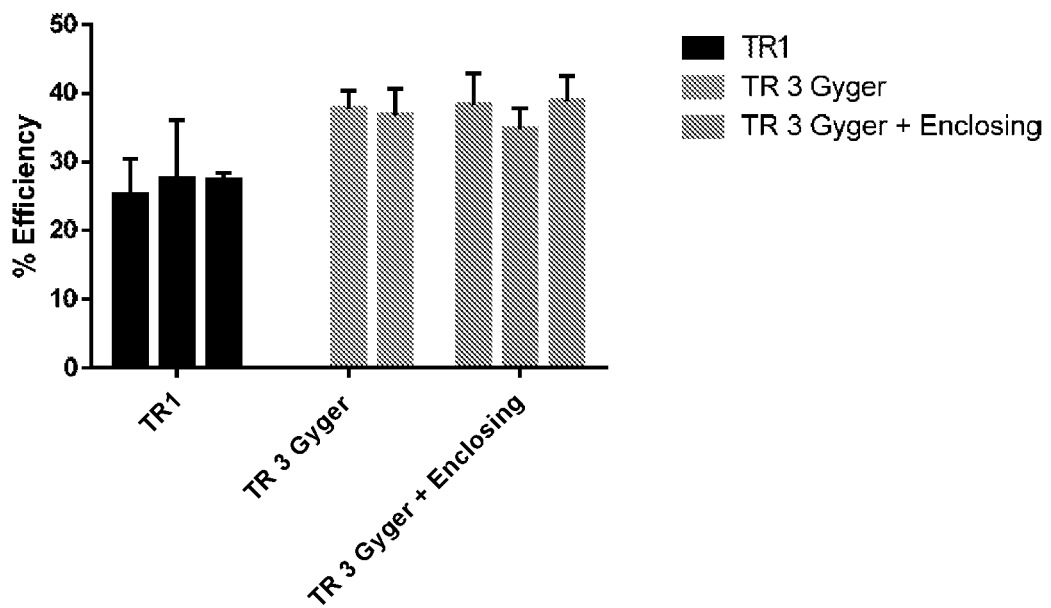
FIG. 63A is a bar graph showing the results of testing with a Gyger valve.
Figure 63B:
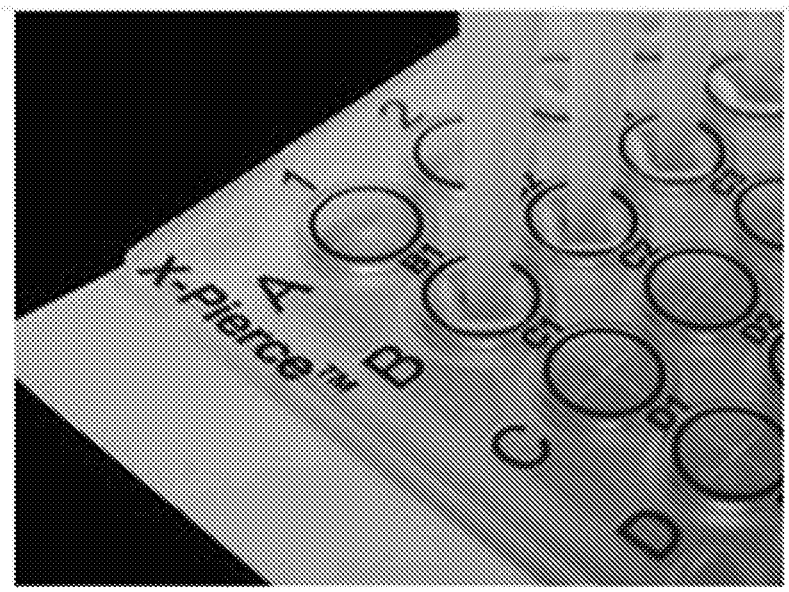
FIG. 63B is a photographic image of X-pierce film. Graph presents data from three independent experiments comparing delivery efficiency on Test Rig 1 (which utilises a Clippard pinch valve), Test Rig 3 (which utilizes a Gyger micro valve) and Test rig 3 and an X-pierce film on a PCTE filter plate. Note: only two experiments were done comparing the TR3 and Gyger valve only (TR3 Gyger). The results demonstrate increased delivery efficiency when the Gyger micro valve (TR3 Gyger) was used in place of the Clippard valve (TR1). The addition of the X-pierce film on the PCTE plate did not have any effect on this delivery efficiency (TR3 Gyger+enclosing). Each bar represents a single experiment with a minimum of 4 replicates.

The Elveflow-pinch valve system described above had limitations:
  Calibration of the system did not hold when the elveflow sample reservoir was reloaded.
  There was poor accuracy and precision in dispensing volumes lower than 5 µl (For low volumes (<5 µl) the relative standard deviation was approximately 9% over repeated dispenses These data were generated in Avectas and are summarised in FIG. 54. Calibration data for the delivery solution using the elveflow-pinch valve system.
To address these limitations, a new fluidic system was used.
This can involve using a micro valve fluidic system such as the Gyger microvalve (SMLD300, Fritz Gyger AG, Bodmerstrasse 12, 3645 Gwatt (Thun), Switzerland). This system includes a syringe sample reservoir connected to a micro valve which is connected to the Air Mist nebulizer. This system had greater accuracy and precision when delivering volumes in the range of 1 µl to 100 µl. A comparison of delivery efficiency using the microvalve and pinch valve demonstrates no difference in delivery efficiency (FIG. 63A, B)

b) Fluidic Control of the Air
Air pressure is optionally controlled by solenoid valve.

c) Electronics to Control Spray Actuation
To enable electronically controlled spray actuation, a system was designed using a microprocessor based development board to allow easy development of time controlled sequences. The development board used the microprocessor, e.g., PIC16F1619. The spray actuation time and fluid delivery time can be manipulated through the development board's interface software. The microprocessor development board enables pulsing of the nebulizer spray.

Figure 28:
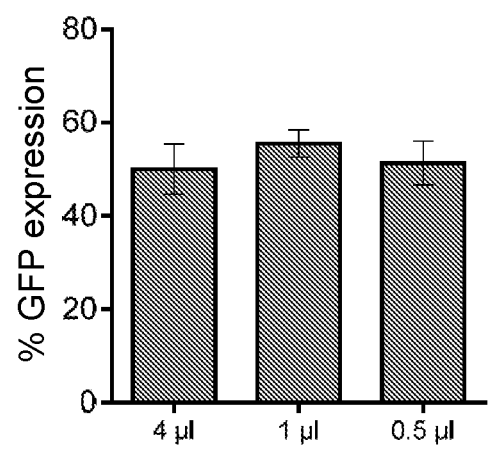

This system was then upgraded to utilise the high speed and repeatable PLC technology (programmable logic controller) to better align with industry standards and to serve as proof of concept for the automated Solupore™ technology (which is based on ultra-high-speed Programmable Logic Controller (PLC) technology). The Test Rig controller consisted of a PLC with a Gyger controller and a program which communicates between the two pieces of hardware. There is operator interaction to the hardware via a momentary push button.

d) Alignment of the Spray Head

A sprayhead such as the Ari Mist nebulizer parallel path design produces a spray which is off centre from the nebulizer tip. Using a custom spray head holder equipped with a goniometer, the alignment of the spray head can be adjusted.

Identification of Optimal Parameters for Delivery of mRNA into T-Cells

Work was carried out to characterise and optimise the spray with the three ultrasonic heads and Ari Mist head. The character of the various sprays was assessed using high speed camera recording. The force of the spray experienced by the cell monolayer was determined by force sensor analysis. In some cases, the volume delivered into the wells of a 96 well plate was assessed using a colorimetric assay For the optimisation study the following parameters were tested, in the ranges indicated:

a) Air pressure: 0.5-2 bar
b) Volume delivered: 1-7 μl
c) Height of atomiser to target area: 26 and 31 mm
d) Length of spray actuation: 50-900 ms
e) Flow rate: 1-20 μl/s
f) Power of ultrasonic probe: 40-80%
g) Spray head: Ari Mist, Ultrasonic 60 kHz, Ultrasonic 130 kHz, Ultrasonic 180 kHz Numerous sets of parameter combinations were tested with the three ultrasonic probes as well as with the Ari Mist nebulisers, using EGFP mRNA as the payload.

All sets of parameters resulted in GFP expression, with uptake varying from 5% to 30%.

Amongst the ultrasonic emitters, 180 kHz proved to be more effective compared to the 130 kHz and 60 kHz ultrasonic heads in delivering payloads to T-cells. The test results indicated that payloads had been delivered to T-cells successfully, at an efficiency of approximately 15-28%, with high level of consistency between replicates (±1%). The health of the cells was maintained following delivery (85% relative viability).

Uptake and reproducibility obtained with Ari Mist, 180 kHz ultrasonic and Mad Nasal spray heads was compared. Results are presented in the longitudinal data plots for Ari Mist, 180 kHz ultrasonic and Mad Nasal spray heads (FIGS. 24, 25, and 26, respectively). The longitudinal data also show the progress in the optimisation of the delivery parameters over the weeks. The uptake improved reaching 20-30% positive cells with 180 kHz ultrasonic (FIG. 25) and Ari Mist (FIG. 24) while it fluctuated below 20% when cells were soluporated using MAD nasal spray head (FIG. 26).

Improved reproducibility was observed when ultrasonic or Burgener nebulisers were used (FIGS. 24, 25), in comparison to the MAD nasal spray head (FIG. 26). The reproducibility of the uptake was expressed through standard deviation (StDev). A major goal of evaluating other spray heads was to identify nebulisers that gave standard deviation of the uptake within replicates of one experiment as narrow as possible. Considering the longitudinal data, by averaging the standard deviation of the uptake across all experiments, the 180 kHz ultrasonic spray head the average standard deviation of the uptake was 2.4%, with Ari Mist was 2.1% while with MAD nasal was 4.5%. In both cases there was an improvement over the MAD nasal nebuliser.

The results indicated that the Ari Mist and 180 kHz ultrasonic nebulisers gave comparable levels of delivery efficiency with between 20 and 30% GFP positive cells detected. The cell viability was higher with the Ari Mist head. Furthermore, this nebuliser is smaller, easier to handle and does not require to be powered to operate. All these reasons contributed to selection of a nebulizer, e.g., Ari Mist nebuliser, as spray head for soluporation and the optimal delivery parameters evaluated for mRNA delivery, e.g, as shown in Table 4.1. This set of parameters was the result of a wide screening and became the starting point for a further study of refined optimisation whereby in addition to volume, distance and length of spray other parameters such as constituents of the delivery solution, cell number and filter plate were finely tuned to further improve mRNA delivery. Table 4.1 shows a list of parameters and the ranges tested including the preferred parameters for delivery of mRNA (e.g., model cargo GFP mRNA) to T-cells. Table 4.1 includes ranges tested and preferred parameters for both the benchtop Flexi (benchtop) and the Midi (scaled-up) systems.

Optimisation of the Steps for Application of Delivery Solution to Cells

Atomiser Height

A number of parameters were assessed in order to increase uptake efficiency and expression of mRNA in human primary T cells. The height at which the AriMist atomiser was assessed to observe if an effect on GFP mRNA delivery to T cells existed. $1\times10^6$ human primary T cells were seeded per well in a 96-well filter plate (Pall; Supor, 1.2 μn; CAT #8039). The plate was centrifuged at 300×g for 5 min and the cell monolayer was sprayed with 4 μl of delivery solution containing 0.57 μg/μl of GFP mRNA. The atomiser height was assessed at 31, 26 and 11 mm above the bottom of the well (a comparison of 26 mm vs 12 mm was assessed in another experiment). Stop solution (50 μl) was applied after a 2 minute incubation and 30 s later normal media (100 μl) was applied. The cells were incubated overnight at 37° C. and 5% $CO_2$ in a humidified incubator and assessed for GFP fluorescence by flow cytometry. Uptake of mRNA by T cells was achieved when the atomiser was placed 31 and 26 mm above the bottom of the well. In some cases, a percentage of the 4 μl delivered did not enter the well. A preferred height of 12 mm above the bottom of the well was chosen (FIG. 27A, B). This allowed accurate dosing of payload and prevented overspray contaminating other wells. The reduction in height also allowed for a reduction in volume delivered. Range of height is between 11 mm and 31 mm above bottom of well (filter).

Volume Delivered

A comparison of volumes was undertaken to determine the optimal volume delivered that would allow the greatest uptake of mRNA by T cells. $1\times10^6$ human primary T cells were seeded per well in a 96-well filter plate (Pall; Supor, 1.2 μm; CAT #8039). The plate was centrifuged at 300×g for 5 min and the cell monolayer was sprayed with 4, 1 or 0.5 μl of delivery solution containing 0.57 μg/μl of GFP mRNA. Stop solution (50 μl) was applied after a 2 minute incubation and 30 s later normal media (100 μl) was applied. The cells were incubated overnight at 37° C. and 5% $CO_2$ in a humidified incubator and assessed for GFP fluorescence by flow cytometry. An optimal volume of 1 µl per well was determined (FIG. 28). The Solupore test rig system allows the volume sprayed to be adjusted by altering either the pressure applied to the ElveFlow or by the duration that the valve remains open. For the first condition, the duration of the valve opening was set at 280 ms and the pressure was set at 70 mBar. The second condition reduced the valve opening time to 140 ms and the pressure set at 140 mBar. The optimal method was to reduce the valve opening time to 140 ms.

Tonicity of Delivery Solution

Previous experiments used a delivery solution that was hypotonic when compared to the cell. An assessment of delivery solutions where the tonicity was altered by the further addition of KCl was conducted. Human primary T cells were seeded at $1\times10^6$ per well in a 96-well filter plate (Pall; Supor, 1.2 µm; CAT #8039). The plate was centrifuged at 300×g for 5 min and the cell monolayer was sprayed with 4 µl of delivery solution containing 0.57 µg/µl of GFP mRNA. In the first condition, the delivery solution contained 12.5 mM KCl resulting in a solution hypotonic to the cell. The second condition contained 106 mM KCl resulting in a solution isotonic to the cell cytoplasm. Other concentrations between 10 mM and 500 mM, e.g., 12.5 mM KCl, 328 and 500 mM KCl, were also tested. At higher tonicity, 328 and 500 mM KCl and GFP expression was demonstrated at a reduced level. Thus, the useful range is from 12.5 to 500 mM, e.g., 50-150 mM, e.g., 100-125 mM, e.g., 100-110 mM, with 106 mM being a preferred concentration of KCl.

Figure 29:
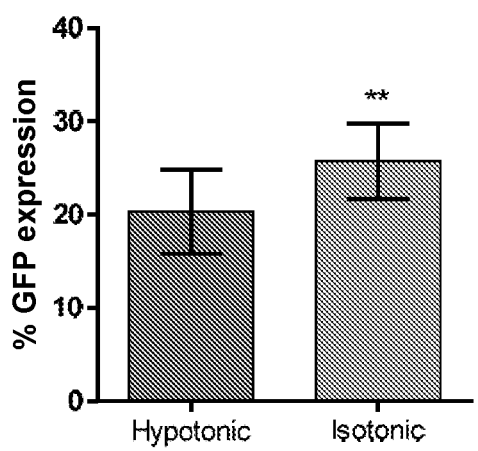

Once the cells were sprayed, Stop solution (50 µl) was applied after a 2 minute incubation and 30 s later normal media (100 µl) was applied. The cells were incubated overnight at 37° C. and 5% $CO_2$ in a humidified incubator and assessed for GFP fluorescence by flow cytometry. An optimal concentration of 106 mM KCl, which was isotonic to the cell, was determined (FIG. 29).

Multiple "Hits"

Figure 30:
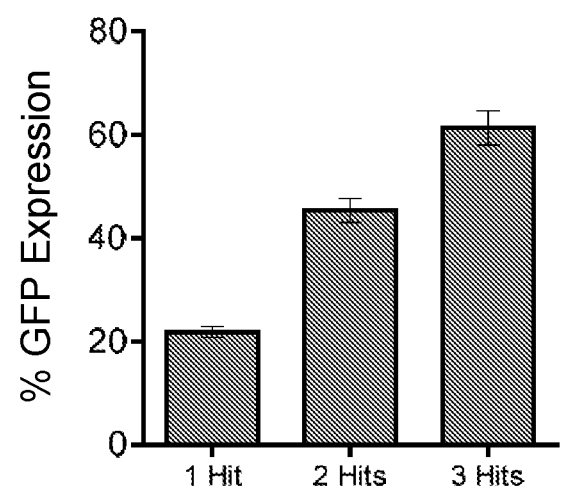
FIG. 30 is a bar graph showing a comparison of the number of "Hits". T cells were sprayed (Hit) once, twice or three times, with a 2 hour incubation in between each spray. GFP expression was assessed by flow cytometry 24 hr later.

Due to the gentle nature of the Solupore technology, the cells can be addressed on numerous occasions, without a drop in the cell viability or functionality. An assessment of the preferred number of "hits" (treatments) was undertaken with, e.g., a 1-, 2- and 3-hit strategy. Human primary T cells were seeded at $1\times10^6$ cells per well in a 96-well filter plate (Pall; PES, 1.2 µm). The plate was centrifuged at 300×g for 5 min and the cell monolayer was sprayed with 1 µl of delivery solution containing 0.57 µg/µl of GFP mRNA. Once the cells were sprayed, Stop solution (50 µl) was applied after a 2 minute incubation and 30 s later normal media (100 µl) was applied. For the 2-hit strategy the cells were incubated for 2 hours before the spray process was repeated and the 3-hit strategy had a further repeat after a 2 hour incubation. Before each additional hit, and at the end of the 2 hr incubation, the wells containing the cell suspension were sealed using a film (e.g., Parafilm M) and the plate was placed on top of an agitator, e.g., a vortex mixer, and held for 15 s. The cell suspension was then pipette mixed 3 times. The vibration from the vortex and the mixing enabled the orientation of the cells to be "shuffled" prior to the subsequent hits. Cells were incubated overnight at 37° C. and 5% $CO_2$ in a humidified incubator and assessed for GFP fluorescence by flow cytometry. The 3-hit strategy appeared to be optimal when looking at uptake, viability and cell yield (FIG. 30).

Cell Seeding Density

Figure 31:
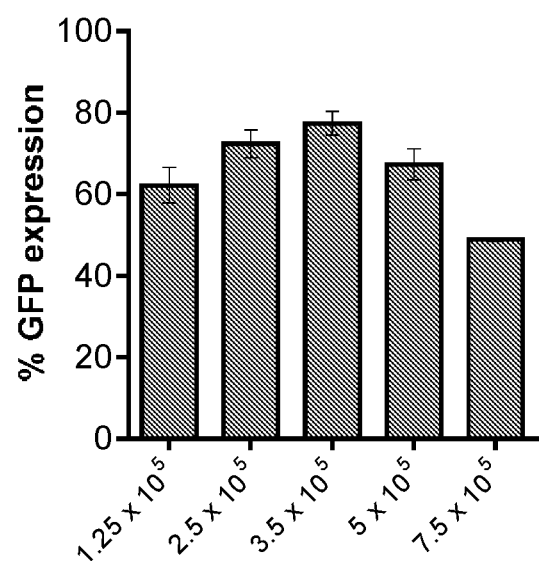
FIG. 31 is a bar graph showing a comparison of T cell seeding densities. T cells were seeded at 1.25, 2.5, 3.5, 5 and $7.5 \times 10^5$ cells per well and GFP mRNA delivered by Soluporation. GFP expression was assessed at 24 hr by flow cytometry.
Figure 32:
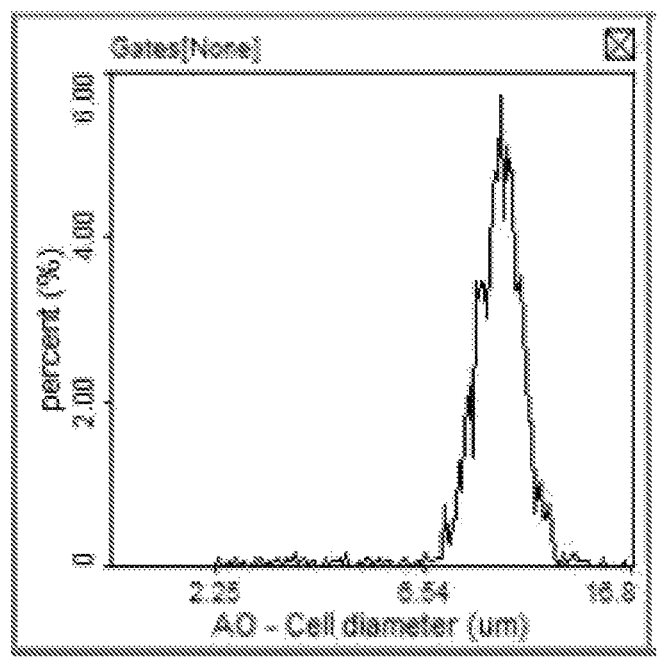
FIG. 32 is a line graphs showing distribution of cell diameter. Average T cell diameter (9.5 μm) at 24 hr post addition of DynaBeads (3:1 Bead to cell ratio).

An assessment of the optimal T cell seeding density using the Agilent PCTE plate was undertaken. Human primary T cells were seeded at 1.25, 2.5, 3.5, 5 and $7.5\times10^5$ cells per well in a 96-well filter plate (Agilent; PCTE, 0.4 µm). The plate was centrifuged at 350×g for 2 min and the cell monolayer was sprayed with 1 µl of delivery solution containing 0.57 µg/µl of mRNA. Once the cells were sprayed, Stop solution (50 µl) was applied after a 2 minute incubation and 30 s later normal media (100 µl) was applied. The cells were incubated for 2 hours before the process was repeated. At the end of this spray the cells were incubated overnight at 37° C. and 5% $CO_2$ in a humidified incubator and assessed for GFP fluorescence by flow cytometry. The seeding density of $3.5\times10^5$ cells was shown to be optimal (FIG. 31). The average T cell size following Dynabead activation is ~9.5 µm (70.9 µm$^2$; FIG. 32). To confirm the seeding density, the density based on the average diameter of an activated T cell and the area of the addressable area of the filter well (19.6 mm$^2$) was calculated. From the calculation the number of cells that would form a monolayer on the filter is approximately $2.77\times10^5$.

Masking

Figure 60A:
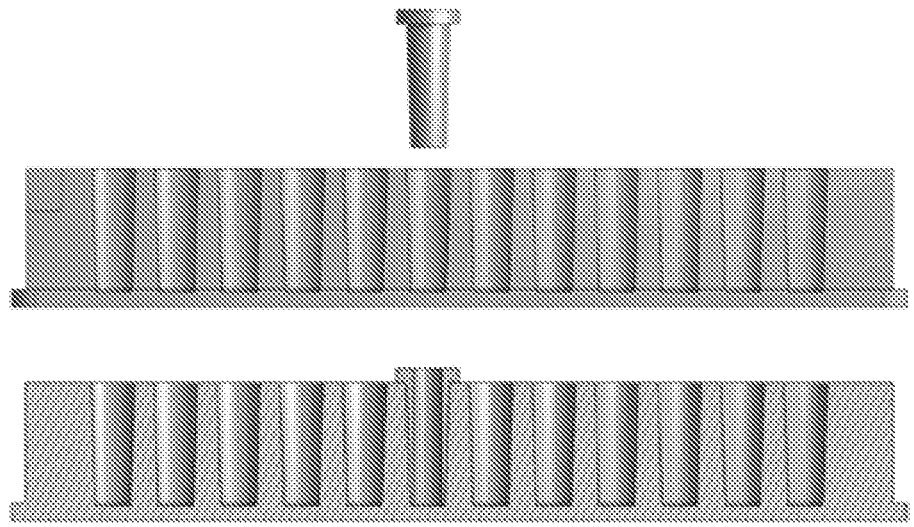
FIG. 60A is a diagram and FIG. 60B is a bar graph a seeding mask and the effect of a seeding mask, respectively. A comparison of GFP mRNA expression in cells that were seeded into a well of a PCTE plate in the presence or absence of a seeding mask (FIG. 60A). GFP expression was measured 24 hr post delivery (FIG. 60B).
Figure 60B:
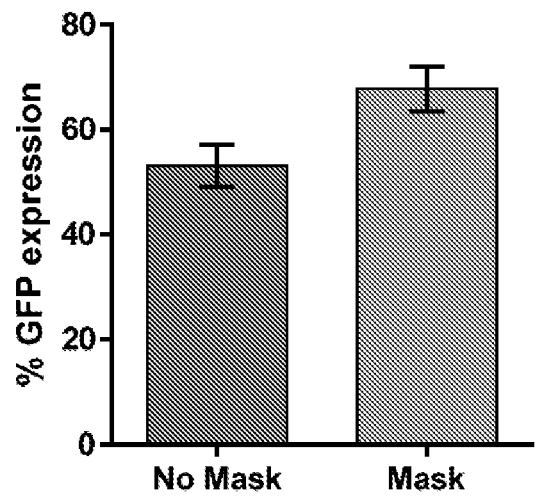

It was noted previously that a region of negative cells existed around the edge of the well. It is possible that this edge-effect exists due to either (or combinations of): poor spray targeting; increased volume around edge due to meniscus; or ineffective droplet impact at edge; pressure turbulence at the edges. A strategy to overcome the edge-effect would be to produce a seeding mask that would be present during seeding and removed after centrifugation which would prevent cells from being seeded close to the well edge. To test this theory the masks were placed into the PCTE plate wells reducing the diameter of the well from 5.2 to 4 mm $2.5\times10^5$ cells human T cells were seeded within the mask and $3.5\times10^5$ unmasked wells as a control. The plate was centrifuged at 350×g for 2 min and the masks were removed before spraying the cells. This meant that cells were seeded only up to about 0.5 mm from the walls of the well. The cells were sprayed with delivery solution containing 0.57 µg/µl of GFP mRNA using a 1-hit strategy. At the end of the process the cells were incubated overnight at 37° C. and 5% $CO_2$ in a humidified incubator and assessed for GFP fluorescence by flow cytometry. The results showed that the sample from the masked wells gave 67.7% uptake but the samples without the mask had 53.1% uptake, suggesting that there is an edge effect and that by having the mask present for seeding negates this (FIGS. 60A, B). Thus, optionally cells are prevented from being seeded up to the edge of the well, thereby leading to an increase in transfection efficiency.

Force

Figure 55:
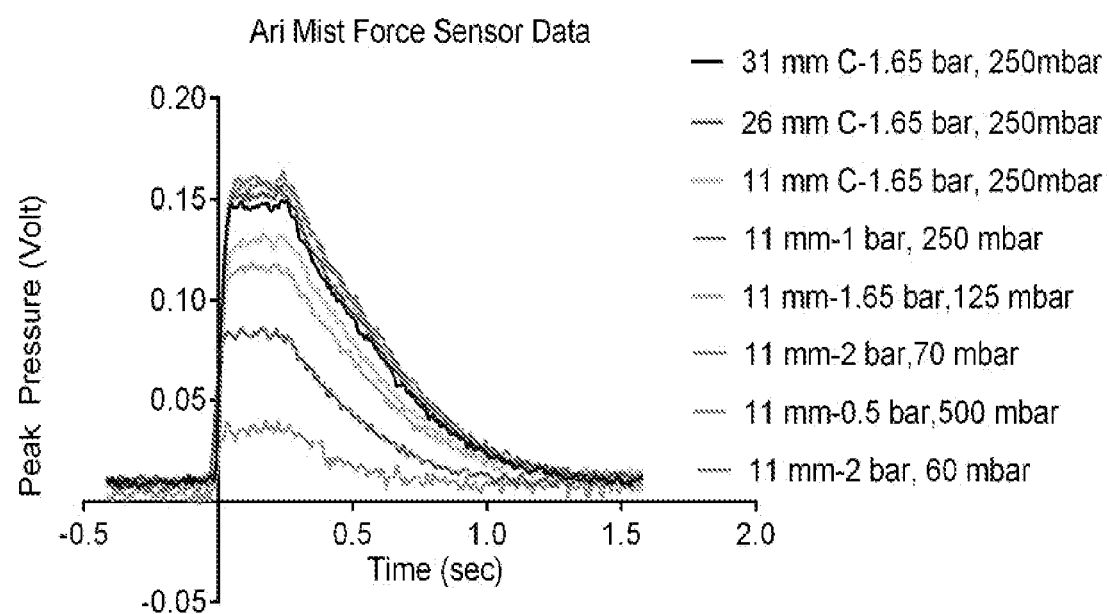
FIG. 55 is a is a line graph showing Force Sensor Parametrisation 1. A force sensor was placed at 31, 26 or 11 mm below the Ari Mist atomiser and the pressure of air driven through the atomiser adjusted from 0.5 Bar to 2 Bar. The amount of liquid dispensed was also altered by adjusting the amount of pressure applied to the Elveflow system. The peak pressure experienced by the sensor is measured in Volts.
Figure 56:
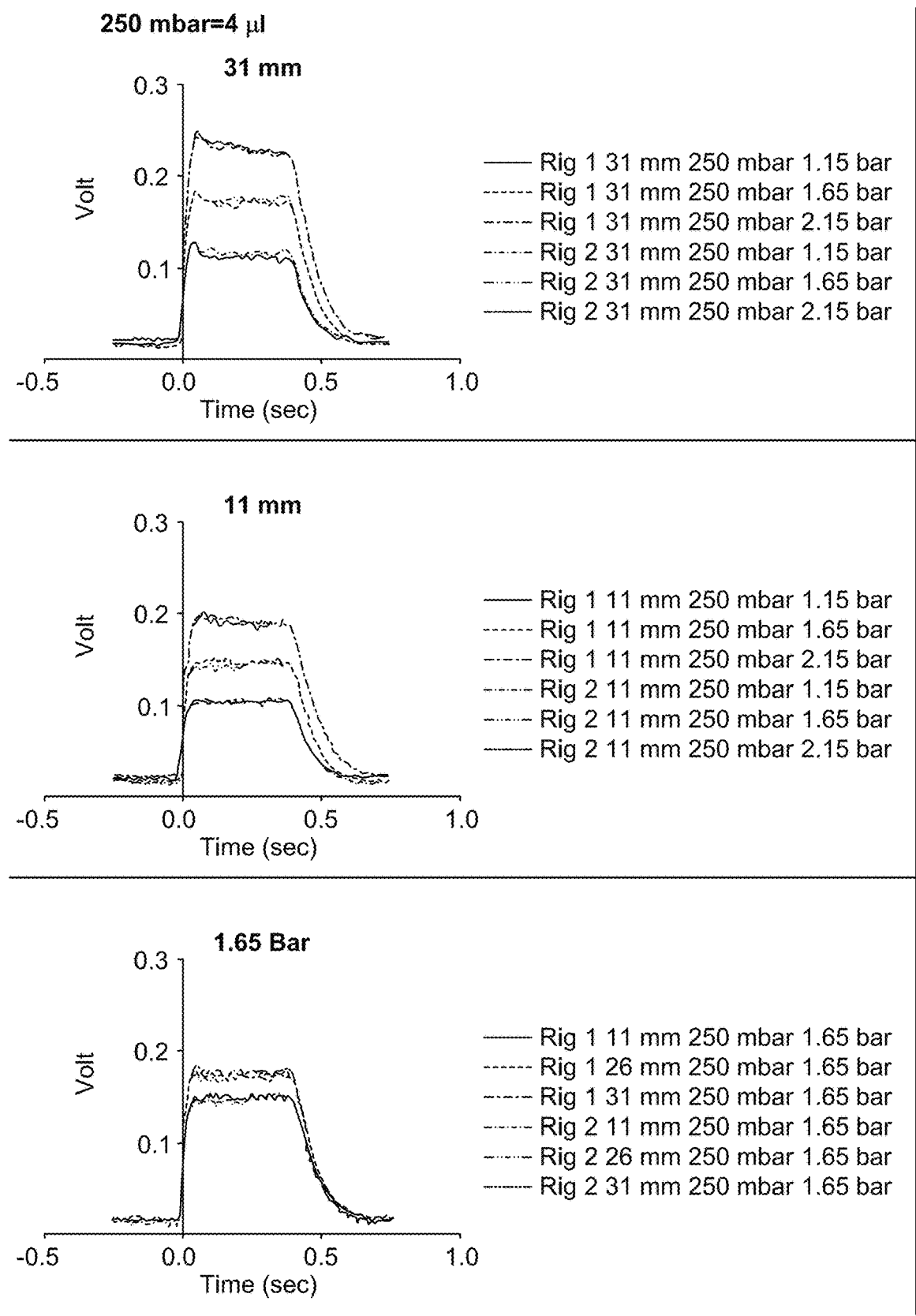
FIG. 56 is a series of line graphs showing Force Sensor Parametrisation 2. A force sensor was placed at 31, 26 or 11 mm below the Arimist atomiser and the pressure of air driven through the atomiser adjusted from 1.15 Bar to 2.15 Bar. The peak pressure experienced by the sensor is measured in Volts.
Figure 56:
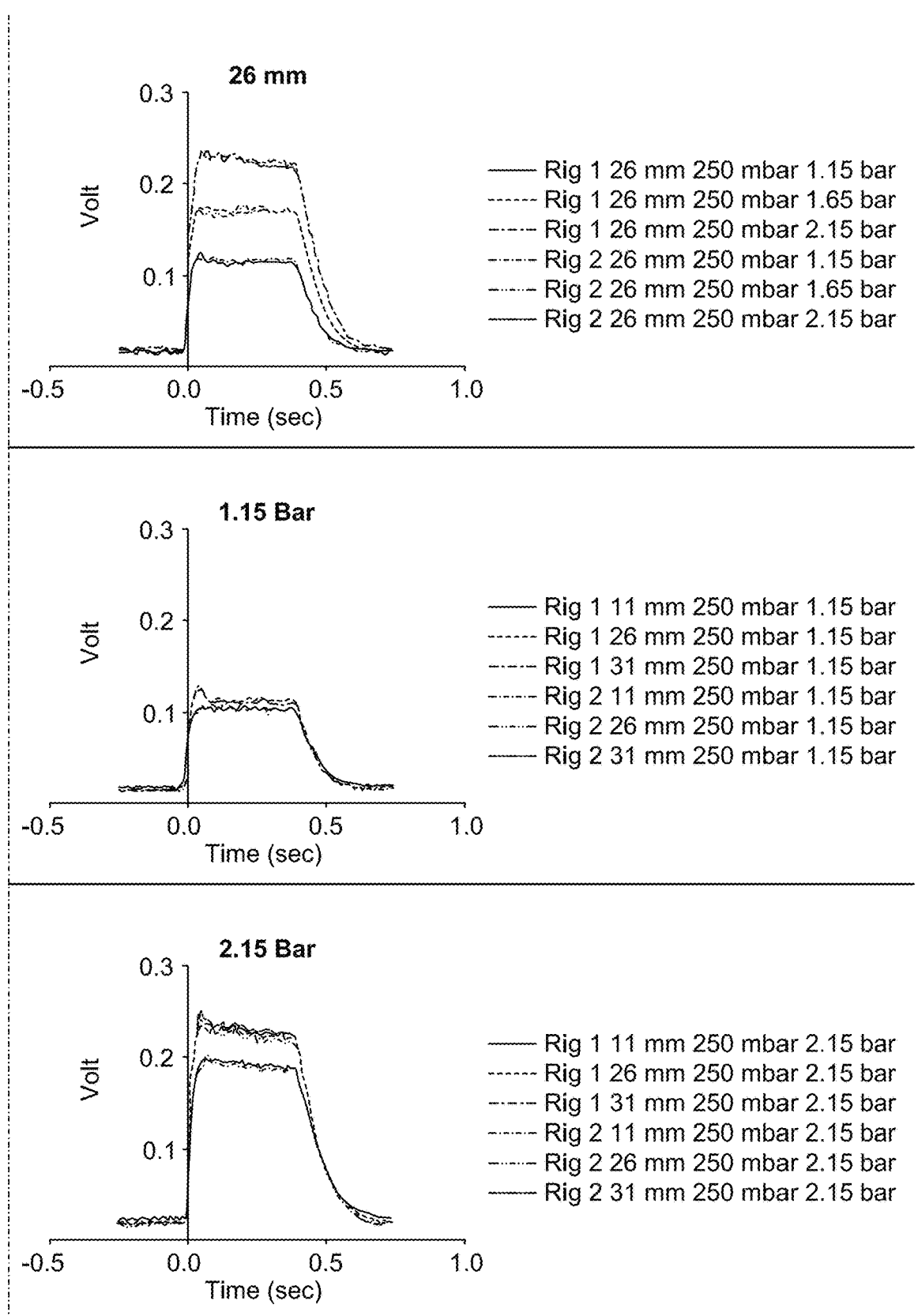
Figure 57:
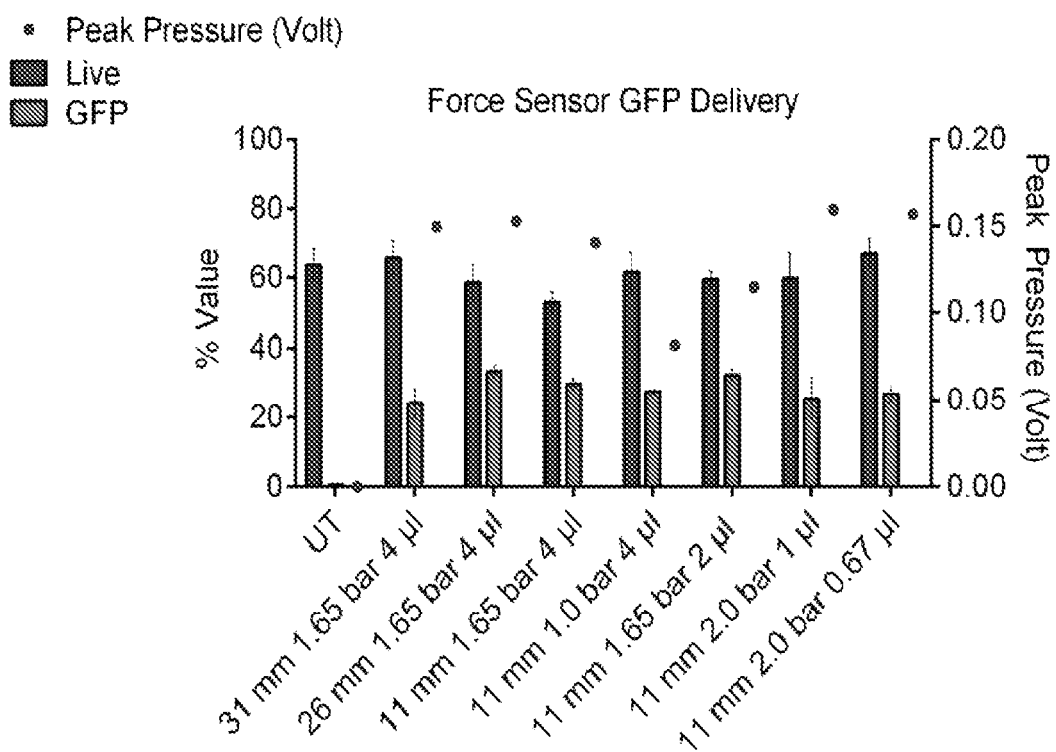
FIG. 57 is a bar graph showing Force Sensor GFP Delivery. GFP expression, Viability (Live) and Peak Pressure (Volt) depicted following GFP mRNA delivery with variable air pressures and volumes.

To examine the correlation between force exerted from the spray and uptake, force sensor analysis was conducted at different heights and pressures to establish a baseline of results. The pressure that drives the air through the atomizer was adjusted from 0.5 to 2 Bar and the force experienced at the bottom of the well was measured using a force sensor. The height was also adjusted to 31, 26 and 11 mm. The results indicated that air pressure was the single largest factor that affects the force exhibited by the spray with a small drop in force at the lower height of 11 mm With a force of 2.0 bar at 11 mm, the same force is experienced with the larger heights and the normal pressure of 1.65 bar (FIG. 55). This experiment was repeated with a more robust analysis of what affects the force exerted by the spray. Again, the air pressure was the greatest contributing factor to force exerted by the spray (FIG. 56). At lower pressures, the force experience at different heights becomes negligible with force at 1.15 bar at heights of 11, 26 and 31 mm being indistinguishable. At 2.15 bar, the force at the 26 and 31 mm height was greater than the 11 mm. This can be explained with the fact the larger height with higher pressure drags more air from the atmosphere into the spray path thus increasing the mass of the spray, due to force=mass×acceleration. The same parameters from FIG. 4.11 were then tested to correlate the force profile with GFP mRNA uptake in CD3+ T-Cells. $1\times10^6$ human primary T cells were seeded per well in a 96-well filter plate (Pall; Supor, 1.2 μm; CAT #8039). The plate was centrifuged at 300×g for 5 min and the cell monolayer was sprayed with 4, 2, 1 or 0.67 μl of delivery solution containing 0.57 μg/μl of GFP mRNA. Stop solution (50 μl) was applied after a 2 minute incubation and 30 s later normal media (100 μl) was applied. The cells were incubated overnight at 37° C. and 5% $CO_2$ in a humidified incubator and assessed for GFP fluorescence by flow cytometry. The GFP expression results indicated that GFP mRNA uptake can be achieved under a wide range on conditions varying in delivery volume, distance and air pressure (FIG. 57). Force experienced by the spray does not directly correlate with uptake. While there may be a minimum force required to achieve uptake and a maximum before we see a loss in viability, this range is broad (1-2 bar).

Ranges of conditions suitable for delivery of mRNA to non-adherent cells, e.g., T cells such as primary human T cells, are summarized below.

| | Benchtop Flexi - Range | Midi - Range |
|---|---|---|
| | Spray | |
| Atomiser | Any Nebuliser | Any Nebuliser |
| Distance | 2-60 mm | 10-300 mm |
| Pressure | 0.1-6.0 Bar | 0.1-6.0 Bar |
| Spray duration (air/liquid) | 50-3000 ms/ 50-2900 ms | 50-3000 ms/ 50-2900 ms |
| Flow rate | 50-1000 μl/min | 2000-100,000 μl/min |
| | Delivery solution | |
| KCl Concentration | 5-1000 mM | 5-1000 mM |
| Ethanol | 5-50% | 5-50% |
| Volume sprayed | 0.2 to 100 μl | 20-3000 μl |
| mRNA/hit | 0.1-75 ug | 0.1-2250 ug |
| | Hits | |
| Number of hits | 1-10 | 1-10 |
| Shuffle between hits | No/Yes | Yes |
| | Monolayer formation possibilities | |
| Seeding density | 0.25-10 × $10^4$ per $mm^2$ | 0.25-10 × $10^4$ per $mm^2$ |
| Vacuum | 5 s-300 s @ −10-−1000 mBar | n.d. |
| Centrifugation | 30 s-5 min @ 100-1000 x g | n.d. |
| Positive pressure | 5 s-300 s @ 10-1000 mBar | 5 s-300 s @ 10-1000 mBar |
| Filter type/pore size | PES/PCTE 0.1-8.0 μm | PES/PCTE/PETE 0.1-8.0 μm |

The preferred, e.g., optimal, conditions for delivering mRNA to T cells is outlined in Table 4.1

TABLE 4.1

Conditions for mRNA delivery to T cells over time.

| | Bench Flexi - Optimal | Bench Flexi - Ranges | Midi - Optimal | Midi - Ranges |
|---|---|---|---|---|
| | | Spray | | |
| Atomiser | AriMist | MAD Nasal/ Ultrasonic emitters (60-180 kHz)/ Burgener Research Nebulizers (AriMist/PEEK MiraMist/PFA250/X-175/1-2100) | LB-100 | LB-100/T-2100 |
| Distance | 12 mm | 11-31 mm | 82 mm | 62-140 mm |
| Pressure | 1.65 Bar | 0.5-3.0 Bar | 2.5 Bar | 1-6 Bar |
| Spray duration (air/liquid) | 240 ms/140 ms | 130-1000 ms/50-900 ms | 520 ms/420 ms | 380-800 ms/280-700 ms |
| Flow rate | 7.14 μl/s | 21.2-7.14 μl/s | 238 μl/s | 100-500 μl/s |
| | | Delivery Solution | | |
| KCl Concentration | 106 mM | 12.5-106 mM | 106 mM | 12.5-106 mM |
| Ethanol | 27% | 20-30% | 24% | 20-30% |
| Volume sprayed | 1 μl | 0.5 to 10 μl | 100 μl | 30-300 μl |
| mRNA/hit | 0.57 μg | 0.57-2.28 μg | 10.0 μg | 3-60 μg |
| | | Hits | | |
| Number of hits | 2 | 1-4 | 2 | 1-2 |
| Shuffle between hits | Yes | No/Yes | Yes | Yes |
| | | Monolayer formation possibilities | | |
| Seeding density | 1.8 × $10^4$ per $mm^2$ | 1.3-4 × $10^4$ per $mm^2$ | 1.5 × $10^4$ per $mm^2$ | 1.3-4 × $10^4$ per $mm^2$ |
| Vacuum | n.d. | 10 s-120 s @ −10-150 mBar | n.d. | n.d. |
| Centrifugation | 2 min @ 350 g | 30 s-5 min @ 150-350 x g | n.d. | n.d. |
| Positive pressure | 45 s @ 100 mbar | 10s-120 s 10-150 mBar | 40 s @ 120 mbar | 20-80 s @ 100-200 mBar |
| Filter type/pore size | PCTE/0.4 μm | PES/PCTE 0.4-3.0 μm | PCTE/0.4 μm | PES/PCTE/PETE 0.2-5.0 μm |

Transfection Comparison Delivery and viability compared with electroporation—electroporation is a widely used method for vector-free intracellular delivery. Therefore, delivery efficiency and cell viability levels using the delivery method of the current subject matter was compared with electroporation.

Figure 33A:
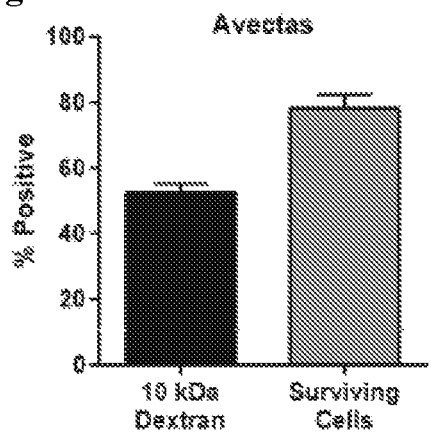
FIG. 33A-FIG. 33C are bar graphs showing delivery and viability of Avectas (Soluporation) compared with electroporation. At (FIG. 33A) delivery efficiency of 10 kDa dextran-Alexa488 to A549 cells was 52.8% (+/−2.7%) as quantified by flow cytometry and cell survival compared with untreated control cells was 78.3% (+/−4.1%) as determined by propidium iodide exclusion and flow cytometry.
Figure 33B:
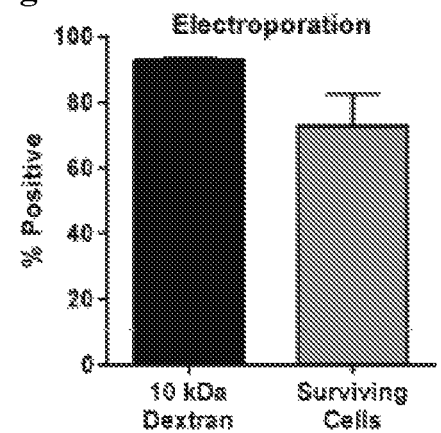

When 3 µM of model payload, 10 kDa dextran-Alexa488, was delivered to A549 cells using the current subject matter technology, delivery efficiency was 52.8% (+/−2.7%) compared with 92.9% (+/−0.6%) for electroporation (FIGS. 33A, B, C). The percentage of cells that survived the delivery process was analysed by propidium iodide exclusion and flow cytometric analysis. For the current subject matter technology, cell survival compared with untreated control cells was 78.3% (+/−4.1%) compared with 73.0% (+/−9.8%) for electroporation (FIGS. 33A, B, C).

Figure 33C:
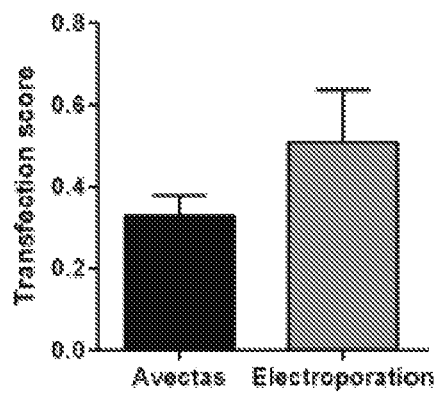

For most delivery methods, effective delivery must be balanced with maintenance of cell viability. In order to examine this balance, a transfection score ((transfected cells/total cells)×(viable cells/total cells)) was used to obtain an aggregate characterisation of cell loss, cell viability and transfection efficiency for the current subject matter delivery technology compared with electroporation. A score of 1.0 would indicate 100% transfection efficiency, 100% cell viability and that no cells were lost during the procedure. The transfection score for the current subject matter technology was 0.33 (+/−0.05) and for electroporation was 0.51 (+/−0.13) with no significant difference between the scores (FIG. 33C).

Figure 34:
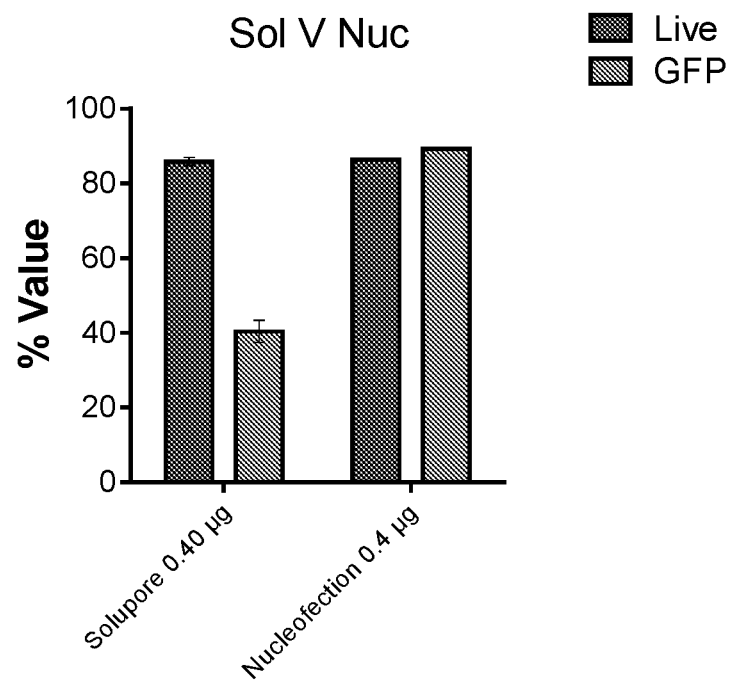
FIG. 34 is a bar graph showing a comparison of Soluporation and Nucleofection. Human T cells were transfected with GFP mRNA using either Solupore or Nucleofection. GFP expression and cell viability (7-AAD) was analysed 24 hr later by flow cytometry.
Figure 36:
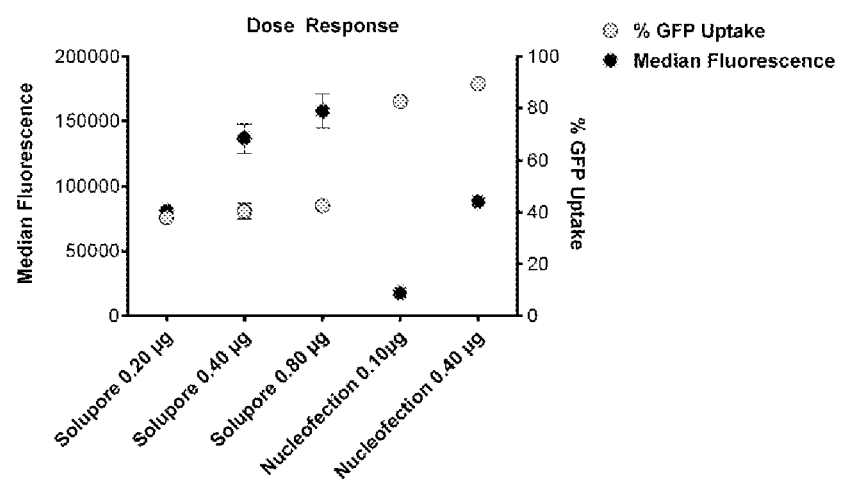
FIG. 36 is a dot plot showing a comparison of fluorescence intensity and GFP expression between Solupore and Nucleofection with different amounts of mRNA delivered. A dose response in the Median fluorescence intensity produced by human T cells 24 hr post delivery of different amounts of GFP mRNA was observed post Soluporation and Nucleofection.

A comparison of Solupore and Nucleofection (4D; Lonza) delivery of mRNA to human T cells was undertaken to benchmark the current technology. The amount of mRNA delivered (µg) was matched per cell. For Soluporation, human primary T cells were seeded at 1×10$^6$ cells per well in a 96-well filter plate (Pall; PES, 1.2 µm). The plate was centrifuged at 300×g for 5 min and the cell monolayer was sprayed with 1 µl of delivery solution containing 0.57 µg/µl of GFP mRNA. Once the cells were sprayed, Stop solution (50 µl) was applied after a 2 minute incubation and 30 s later normal media (100 µl) was applied. The cells were incubated overnight at 37° C. and 5% $CO_2$ in a humidified incubator and assessed for GFP fluorescence by flow cytometry. For Nucleofection, 5×10$^6$ human primary T cells were washed in PBS and resuspended in 40 µl P3 buffer containing 2 µg GFP mRNA (Lonza). The cells were then added to the nucleocuvette strip and nucleofected as per instructions. 100 µl media was added to each well and transferred to recovery flask containing 10 mls media. The cells were incubated overnight at 37° C. and 5% $CO_2$ in a humidified incubator and assessed for GFP fluorescence by flow cytometry. GFP mRNA expression levels were 40.3% and 89.3%, respectively (FIG. 34). The average median fluorescent intensity from 5 experiments and 2 donors was 203,059 and 113,895, respectively (FIGS. 35A, B, C, D). A dose response of mRNA delivered by each technology is shown in FIG. 36.

Endocytosis Independent

Diffusion of cargo into cells and resealing of plasma membrane. Having demonstrated the ability of this method to deliver a broad range of cargoes to a range of cells types, the mechanism of cargo uptake into cells and the reversal of the cell permeability was examined A limitation of other delivery techniques is their dependence on active uptake pathways such as endocytosis which can lead to sequestration of the cargo rendering it unavailable to function in the cell. For example, liposome-mediated delivery involves both clathrin- and caveolar-mediated endocytosis (Cui S, Wang B, Zhao Y, Chen H, Ding H, Zhi D, et al. Transmembrane routes of cationic liposome-mediated gene delivery using human throat epidermis cancer cells. Biotechnol Lett. 2014; 36(1):1-7. doi: 10.1007/s10529-013-1325-0. PubMed PMID: 24068499; PubMed Central PMCID: PMCPMC3889874.) while iTOP delivery involves macropinocytosis (D'Astolfo D S, Pagliero R J, Pras A, Karthaus W R, Clevers H, Prasad V, et al. Efficient intracellular delivery of native proteins. Cell. 2015; 161(3):674-90. doi: 10.1016/j.cell.2015.03.028. PubMed PMID: 25910214.).

Figure 37A:
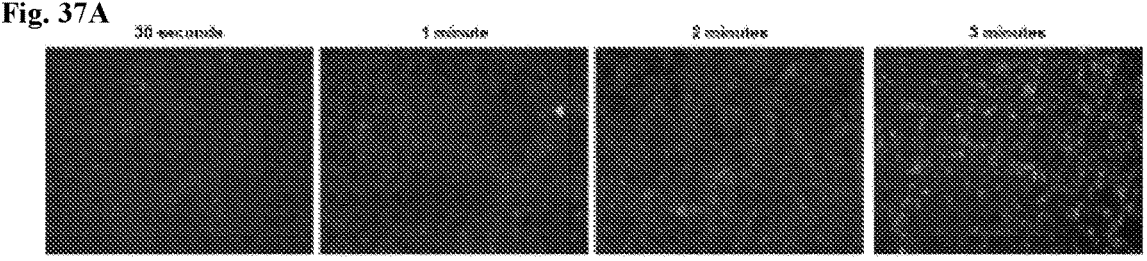
FIG. 37A is a photograph.
Figure 37B:
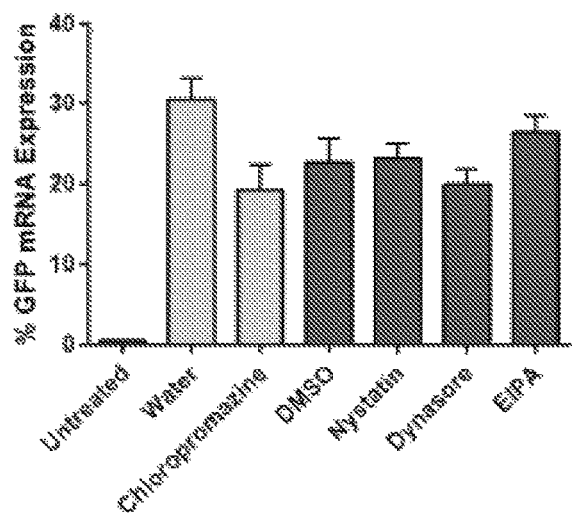
FIG. 37B, 37C, and FIG. 37D are bar graphs showing evaluation of delivery of cargo into cells. Diffusion of cargo into cells and resealing of plasma membrane.
Figure 37C:
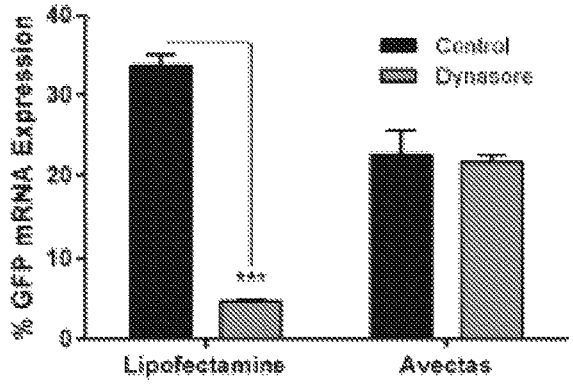
Figure 37D:
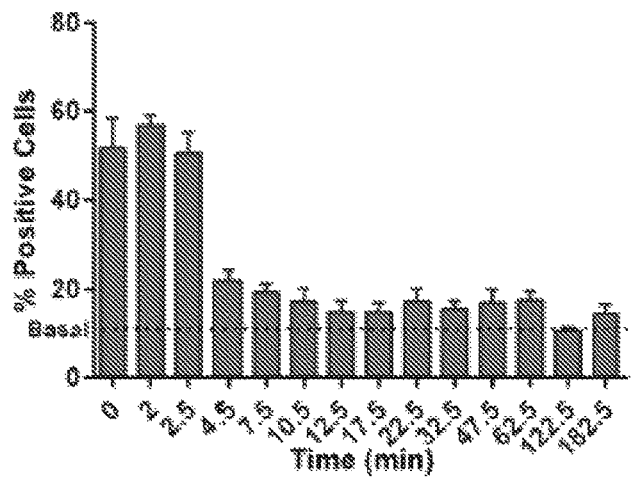

During the experiments using Soluporation, immediate uptake of cargo into cells was observed. Using 10 kDa dextran-FITC as a model cargo, within 30 sec of applying the delivery solution, before Stop solution was added, cargo was visible within the cells (FIGS. 37A, B, C, C). The rapid influx of cargo into the cells indicates that it is unlikely that delivery involves endocytosis. The results showing loading of a wide range of molecular species into a range of cell types indicates that a diffusion mechanism through the cell membrane is the mechanism of entry of macromolecules into the cells. To test the contribution of alternate uptake mechanisms such as active pathways and internalization in endocytotic vesicles, A549 cells were pretreated with Dynasore (4 mM) or chloropromazine (20 µM) to inhibit clathrin-mediated endocytosis or Nystatin (20 µg/ml) or EIPA (100 µM) to inhibit caveolar-mediated endocytosis and micropinocytosis respectively. Expression of EGFP mRNA remained unchanged in the presence of these inhibitors indicating that this method results in direct delivery into the cytoplasm of cells and does not rely on endocytosis (FIG. 37C). Furthermore, in addition to following the procedure reported by D'Astolfo et al. (D'Astolfo et al. 2015), Lipofectamine 2000 was included as a positive control to confirm Dynasore-mediated inhibition of clathrin-mediated endocytosis (FIG. 37C).

It was noted that the delivery method was very gentle on cells with little if any cell death or damage evident. The method allows the permeabilised plasma membrane to reseal rapidly, hence retaining high levels of cell viability. To examine the rate of recovery of the cell membrane after permeabilization, delivery solution was applied to A549 cells in the absence of cargo. At subsequent time points (0 to 182.5 min), this delivery solution was removed and 50 µl PBS containing propidium iodide (PI) (100 µg/ml) is added. After 2 min incubation, the PI solution was removed and the cells were harvested. PI uptake was analysed by flow cytometry. For basal levels of PI uptake, untreated cells received 50 µl PI in PBS. The results demonstrate that the cells remain permeable to PI for several minutes but reseal over a period of 6 min post treatment (FIG. 37C). After 6 minutes there is no further uptake. Thus not only do the cells load within 2 minutes of exposure to the delivery solution, but the membrane has effectively recovered its integrity within 6 minutes of beginning the procedure. These data indicate that delivery of agents using Soluporation does not involve endocytosis.

Gene Editing in T Cells

In order to demonstrate another functional output of T cells following delivery of cargo, gene editing of T cells was assessed using CRISPR/Cas9 RNP delivery.

CRISPR/Cas9 RNP Delivery. A two guide RNA strategy was employed to knockdown the PDCD1 gene [ATGCAGATCCCACAGGCGCCCTGGCCAGTCGTCT-GGGCGGTGCTACAACTGGGCTG GCGGCCAGGAT-GGTTCTTAGACTCCCCAGACAGGCCCTGGAACCC-CCCCACCTTCTC CCCAGCCCTGCTCGTGGTGACC-GAAGGGGACAACGCCACCTTCACCTGCAGCTT-CTC CAACACATCGGAGAGCTTCGTGCTAAACTG- GTACCGCATGAGCCCCAGCAACCAGA CGG- ACAA-GCTGGCCGCCTTCCCCGAGGACCGCAGCCAGCCC-GGCCAGGACTGCCGC TTCCGTGTCACACAACT-GCCCAACGGGCGTGACTTCCACATGAGCGTGGT-CAGGGC CCGGCGCAATGACAGCGGCACCTACCT-CTGTGGGGCCATCTCCCTGGCCCCCAAGG CGCA-GATCAAAGAGAGCCTGCGGGCAGAGCTCAGGG-TGACAGAGAGAAGGGCAGA AGTGCCCACAGCC-CACCCCAGCCCCTCACCCAGGCCAGCCGGCCAG-TTCCAAACCC TGGTGGTTGGTGTCGTGGGCGGC-CTGCTGGGCAGCCTGGTGCTGCTAGTCTGGGTCC TGGCCGTCATCTGCTCCCGGGCCGCACGAGG-GACAATAGGAGCCAGGCGCACCGGC CAGCCCCT-GAAGGAGGACCCCTCAGCCGTGCCTGTGTTCTCT-GTGGACTATGGGGA GCTGGATTTCCAGTGGCG-AGAGAAGACCCCGGAGCCCCCCGTGCCCTGT-GTCCCTG AGCAGACGGAGTATGCCACCATTGT-CTTTCCTAGCGGAATGGGCACCTCATCCCCCG CC-CGCAGGGGCTCAGCTGACGGCCCTCGGAGTG-CCCAGCCACTGAGGCCTGAGGAT GGACACT-GCTCTTGGCCCCTCTGA] (SEQ ID NO:1), which encodes for the PD-1 protein.

MQIPQAPWPVVWAVLQLGWRPGWFLDSPDRP-WNPPTFSPALLVVTEGDNATFT CSFSNTSESFVLN-WYRMSPSNQTDKLAAFPEDRSQPGQDCRFRVTQL-PNGRDFHMSVV RARRNDSGTYLCGAISLAPKAQ-IKESLRAELRVTERRAEVPTAHPSPSPRPAGQFQTLVV GVVGGLLGSLVLLVWVLAVICSRAARGTIGARRT-GQPLKEDPSAVPVFSVDYGELDFQ WREKTPEPP-VPCVPEQTEYATIVFPSGMGTS SPARRGSADGPR-SAQPLRPEDGHCSWPL (PD1-1 protein amino acid sequence, SEQ ID NO:2). Equimolar amounts of crisprRNA (a mixture of both GCGTGACTTCCACATGAGCG (SEQ ID NO:3) and GCAGTTGTGTGACACGGAAG (SEQ ID NO:4) crisprRNAs, also equimolar amounts; (Su, S. et al. CRISPR-Cas9 mediated efficient PD-1 disruption on human primary T cells from cancer patients. Sci. Rep. 6, 20070; doi: 10.1038/srep20070 (2016)) and tracrRNA were incubated for 10 min at RT. 5 µg Cas9 (IDT) was then added so that the final molar ratio of Cas9 to guide RNA was 1:3 and incubated for a further 10 min at RT. Cas9 RNPs (in buffer, with α-crystallin (220 µM) and Ethanol (25% v/v)) were delivered to T cells by using the vector-free intracellular delivery method described. Using the vector-free delivery method described herein, RNPs were delivered to $1.5 \times 10^6$ cells per treatment and PD-1 expression was analysed at 72 h post-transfection.

Cell viability. FACS Sample Preparation and Analysis: Cell viability following the vector-free intracellular delivery method, delivery was assessed using 7-AAD viability staining solution (Sigma). Cells were in washed in PBS+1% fetal bovine serum (FACS buffer) followed by incubation with 7-AAD (1:40 for 5-10 min protected from light at room temperature), followed by resuspension in PBS+1% FBS (FACS buffer). PD-1 labelling was carried out using APC-conjugated anti-human CD279 (PD-1) (Biolegend) and processed on the BD Accuri C6 flow cytometer (Becton Dickinson, USA). Data was analysed using the C6 software. Cell debris was excluded from whole cells using forward and side scatter parameters. Single cells were selected by excluding doublets in the FSC height vs FSC are plot. GFP expression was analyzed on gated viable cells.

Knock-down of immune check point gene expression such as PD-1 expression in T cells following vector-free delivery of CRISPR/Cas9 RNPs CRISPR/Cas9 RNPs targeting the PDCD1 gene were delivered to T cells using either the vector-free intracellular delivery method described herein or by electroporation. PD-1 expression was analysed by flow cytometry 72 h post-transfection.

Figure 38A:
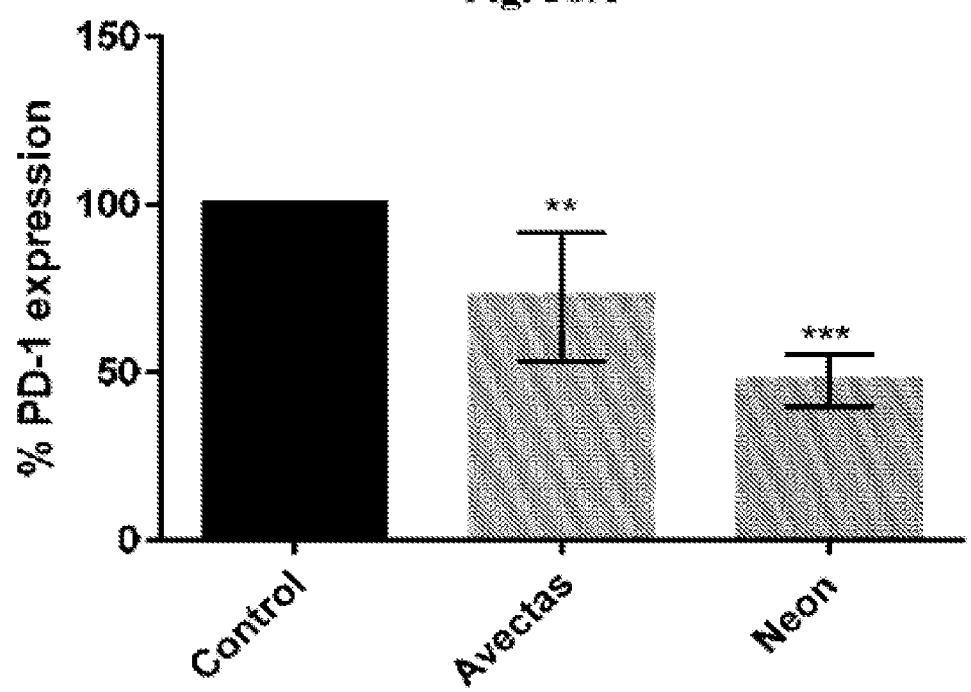
FIG. 38A is a bar graph illustrating the PD-1 surface expression on T cells. Data shown are the mean of five independent experiments where control group is normalised to 100%.
Figure 38B:
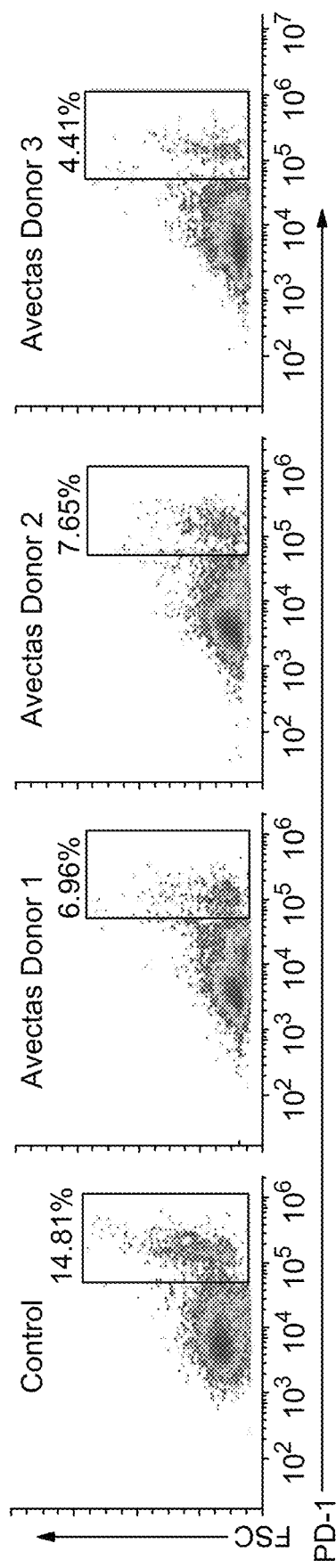
FIG. 38B are photographic images illustrating PD-1 surface expression on T cells determined at 72 h post-transfection by flow cytometry. Data shown is from one independent experiment.

Delivery of CRISPR/Cas9 gene editing tools to activated T cells resulted in a 28% reduction in PD-1 expression by the vector-free intracellular delivery method described herein compared with 53% inhibition in electroporated cells (FIGS. 38A, B).

Figure 39:
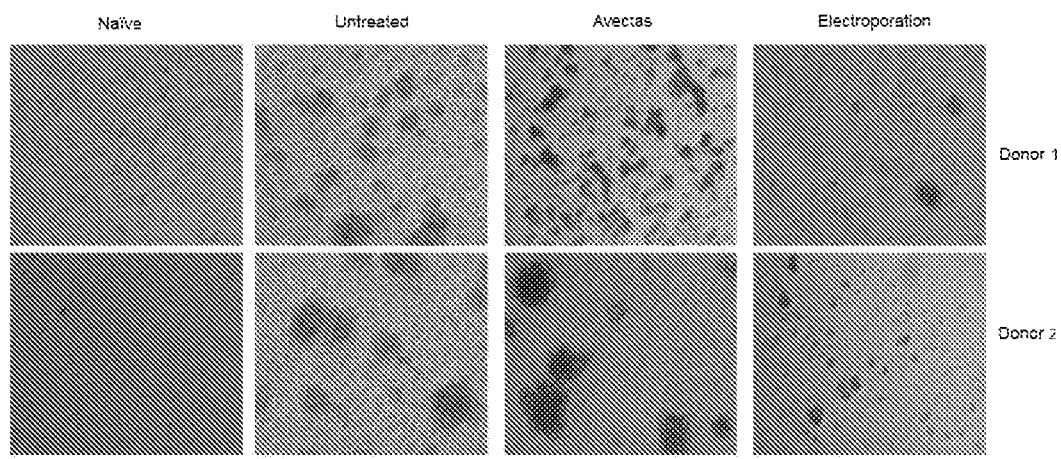
FIG. 39 are photographic images showing that T cell clones at day 4 post treatment (see arrows) by light microscope, indicating good proliferation and activation of the T cells in untreated controls and the vector-free intracellular delivery method described herein treated cells. Significantly fewer clones were observed in those cells that underwent electroporation. Data shown is one independent experiment.
Figure 40:
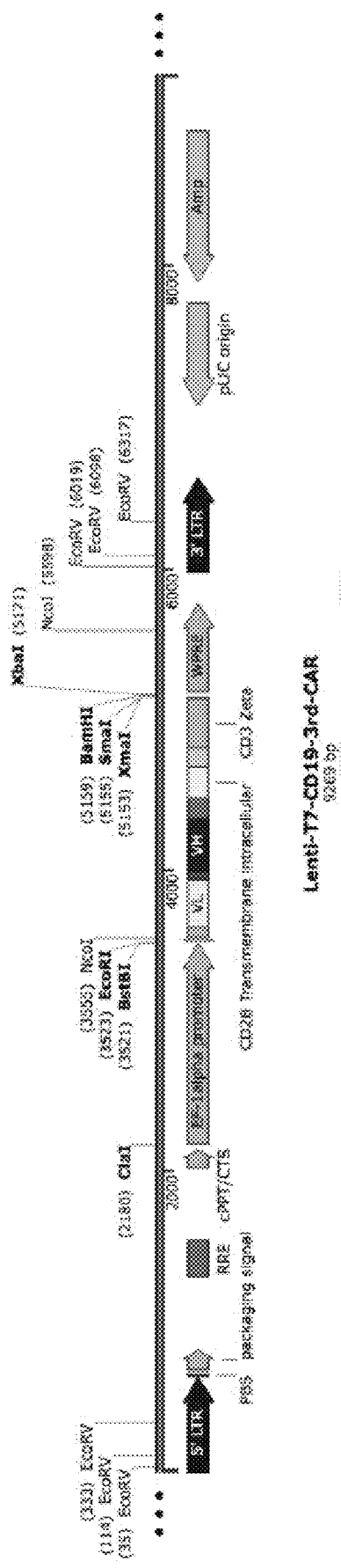
FIG. 40 is a schematic of CAR construction of Lenti-T7-CD19-3rd-CAR vector.
Figure 42:
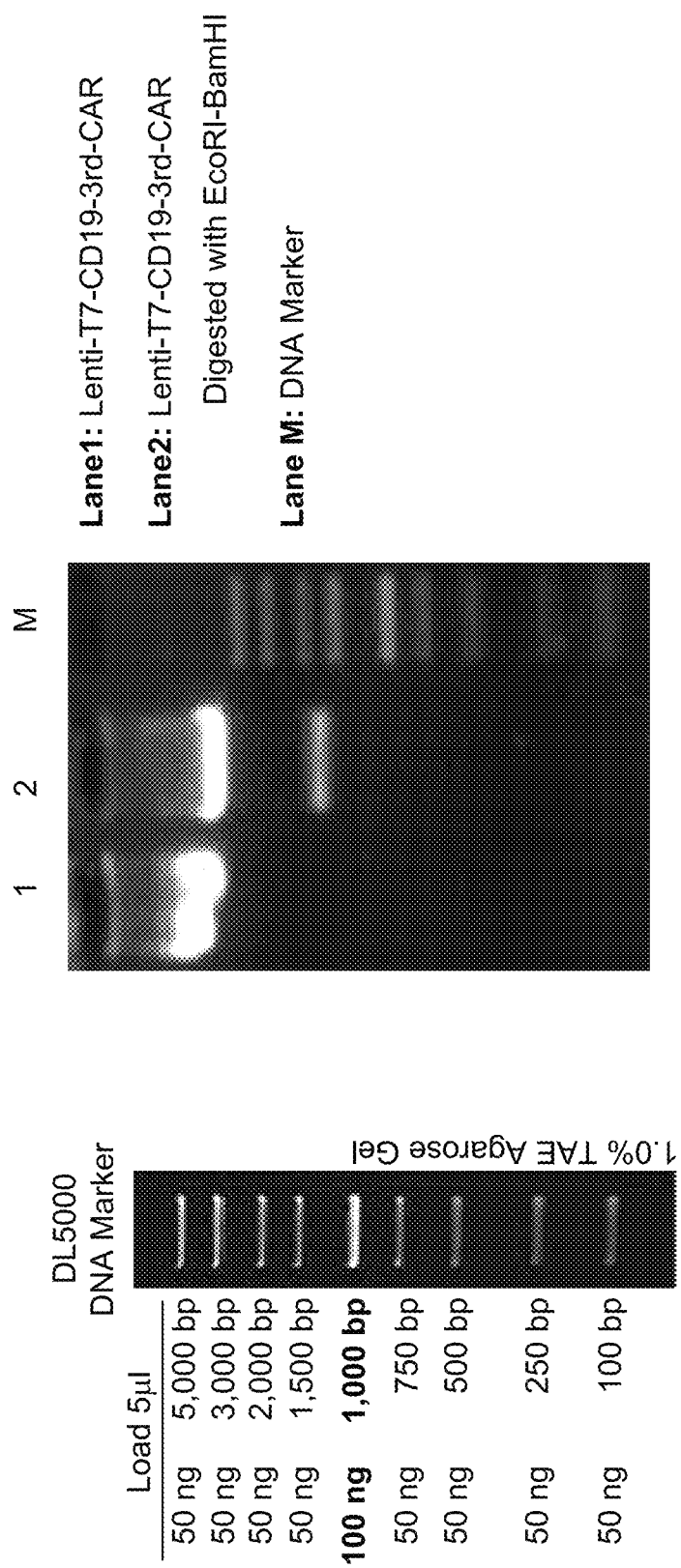
FIG. 42 is a photographic image showing the Restriction Digestion Map of the CAR vector.
Figure 44B:
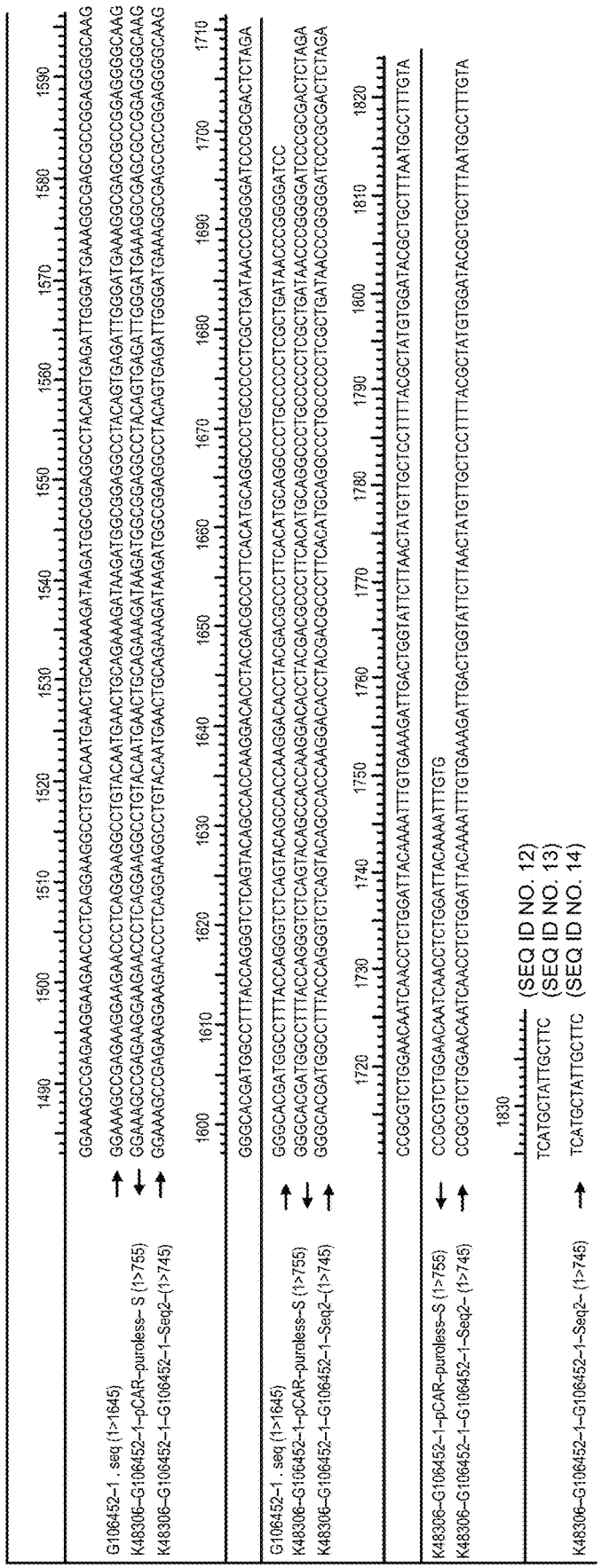

The proliferative capacity of gene-edited cells was assessed over a 4-day period by observing the formation of T cell aggregates in culture. Following delivery of RNPs, cells were returned to culture. After 4 days, cells were observed using a microscope. Cell aggregation in the vector-free intracellular method-transfected cells was similar to untreated control activated cells indicating that they were not affected by the vector-free intracellular delivery method described. In contrast, the growth rate of electroporated cells was significantly affected as indicated by significantly fewer cell aggregates (FIG. 39)

CAR-T: Expression of Chimeric Antigen Receptor (CAR) in Primary T Cells Following mRNA Delivery mRNA generated from a commercially sourced CD19 CAR plasmid was successfully delivered to human-derived activated T cells. Surface expression of the CAR was detected by flow cytometry with up to 50% of the population positive for CAR expression.

Materials and Methods

Cell culture. Human peripheral blood mononuclear cells (PBMC) were recovered by centrifugation over a Percoll gradient from Leuko Pak (AllCells Alameda, CA). CD3$^+$ enriched lymphocytes were isolated by magnetically activated cell sorting using CD3 Microbeads (Miltenyi). Cells were cryopreserved in 10% dimethyl sulphoxide (DMSO) and foetal bovine serum (FBS). Following initial thawing from stock aliquots, CD3$^+$ T cells were cultured in human recombinant interleukin-2 (IL-2) with primary and co-stimulatory antibody activation using various protocols (see below) in a humidified tissue culture incubator at 37° C. and 5% $CO_2$.

Construction of CD19 CAR Plasmid

Figure 86:
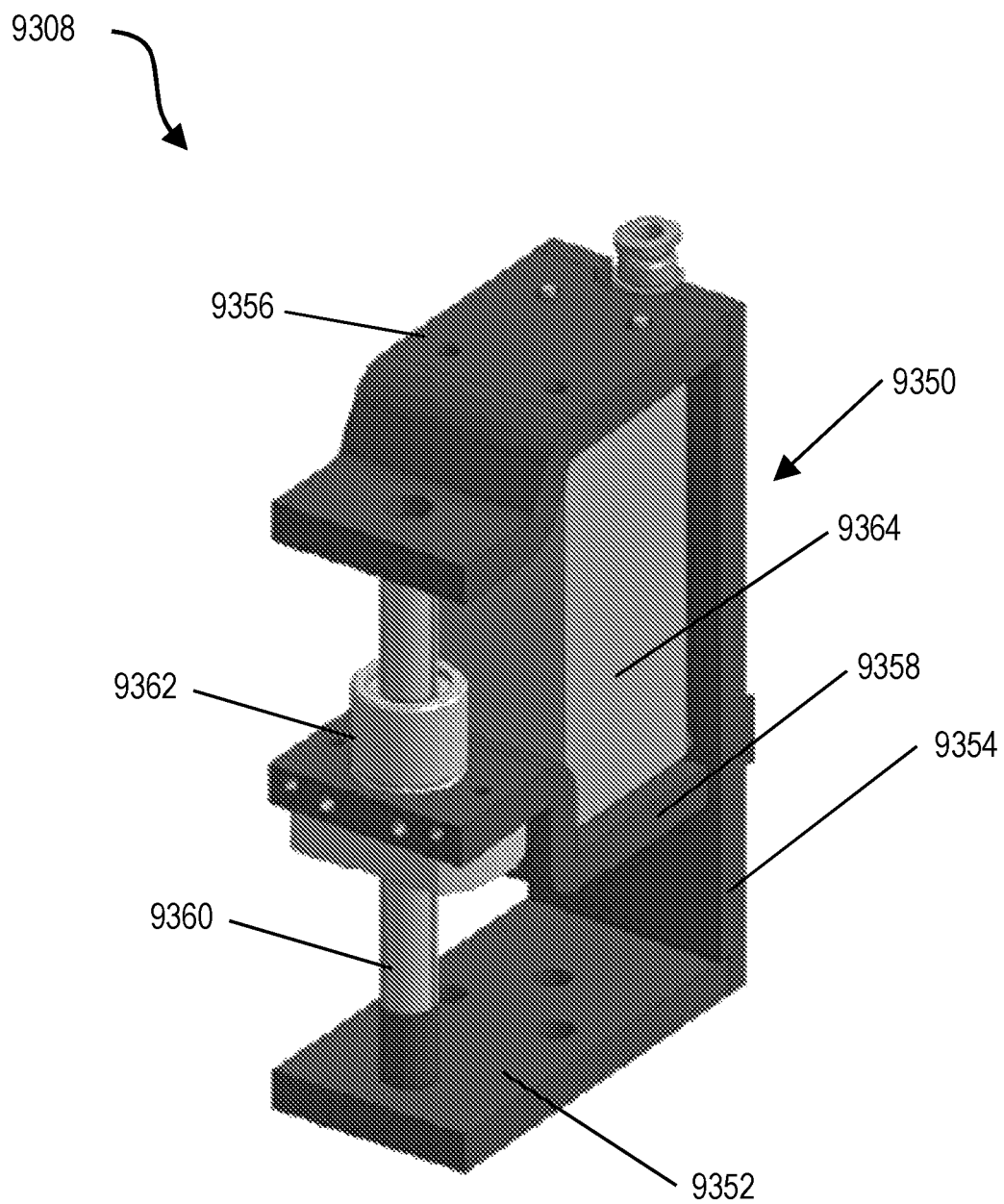
FIG. 86 is an enlarged view of a modular fluidic head module that enables movement in a vertical direction.
Figure 87:
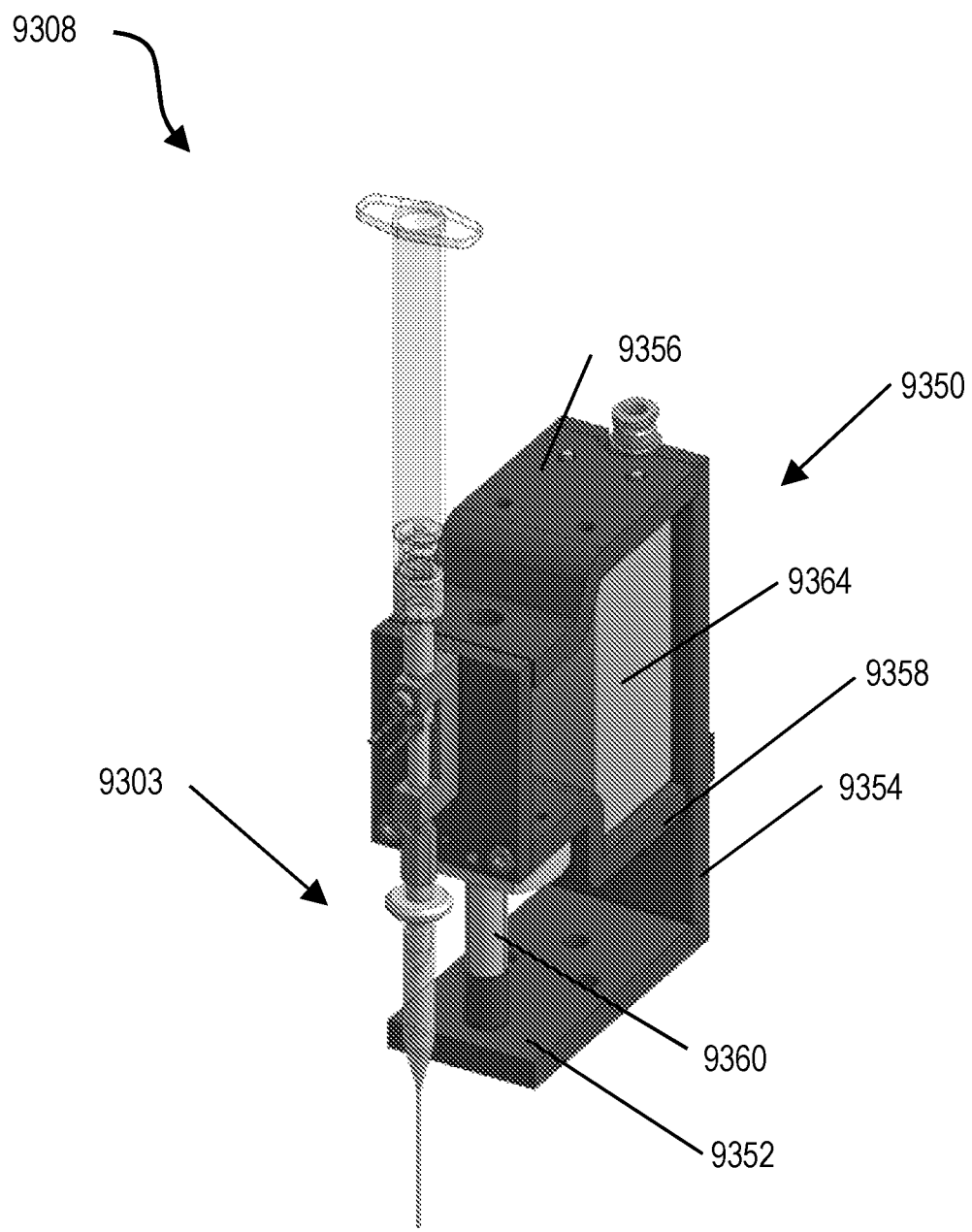
FIG. 87 is the modular fluidic head module shown in FIG. 86, with a needle assembly attached thereto. The needle assembly is used to dispense a culture medium and a stop solution.
Figure 88:
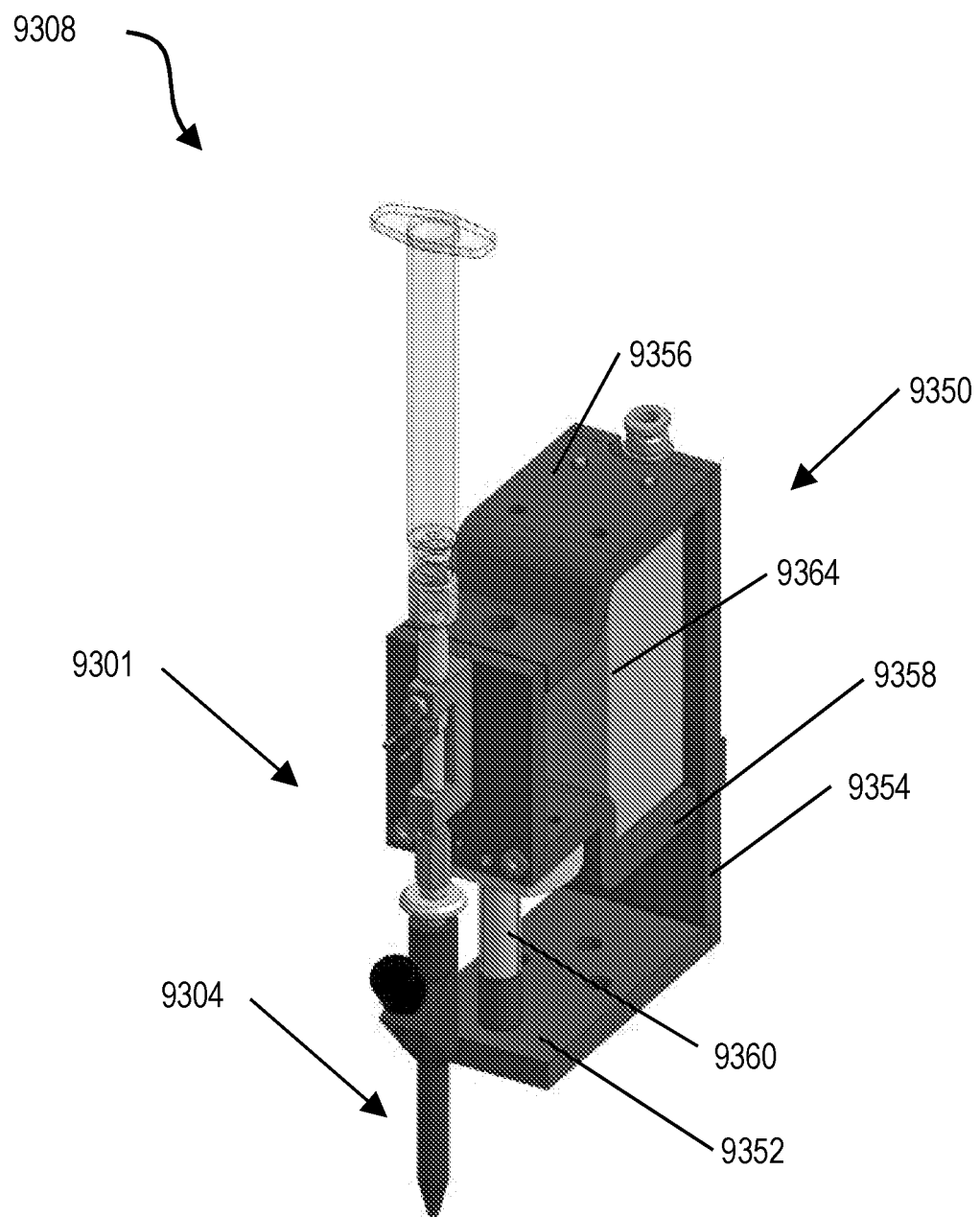
FIG. 88 is the modular fluidic head module shown in FIG. 86, with a nebulizer assembly attached thereto. The nebulizer assembly is used for atomization of a payload and delivery solution to deliver the solution to cells.
Figure 89:
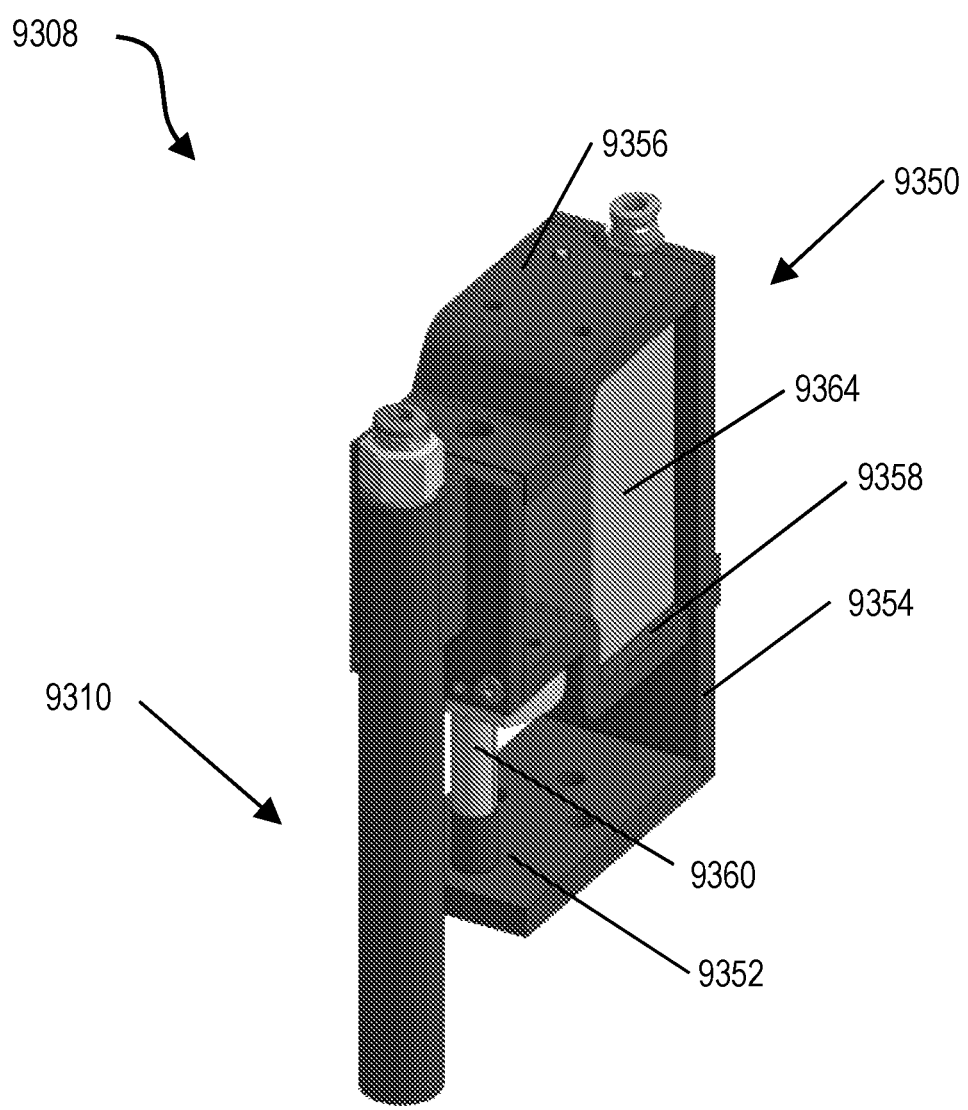
FIG. 89 modular fluidic head module shown in FIG. 86, with a positive pressure nozzle assembly attached thereto. The positive pressure nozzle assembly is used for removal of a culture medium.
Figure 90:
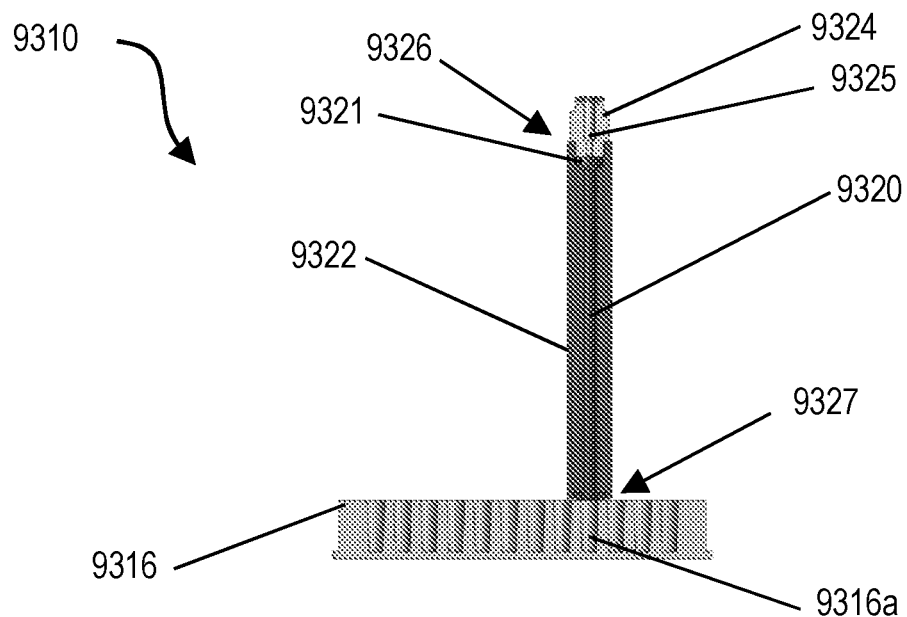
FIG. 90 is a side view of a positive pressure nozzle of the positive pressure system shown in FIGS. 84-85, used for removal of a culture medium.

A CD19 CAR plasmid was sourced commercially (Creative Biolabs, NY, USA) and mRNA generated from the plasmid. The full length of chimeric antigen receptor (CAR) was synthesized and subcloned into lentivirus vector. The insert was confirmed by Sanger sequencing. The structure of CAR vector is illustrated in FIG. 86. The amino acid sequence of scFv (Anti-CD19 scFv VL-Linker-VH) is depicted in FIG. 87A. The nucleotide sequence (codon optimized) of the CAR cassette is depicted in FIG. 87B. The amino acid sequence of the CAR cassette is depicted in FIG. 87C. The Restriction Digestion map is depicted in FIG. 88. The Quality Control results of the vector design is depicted in FIG. 89. The CAR sequence alignment validation is depicted in FIG. 90. The sequence alignment results showed that the sequence of the constructed plasmid was in accordance with the design.

CAR mRNA Delivery

4 µg of mRNA (from CD19 CAR plasmid described above) was added to Buffer and Ethanol (27% v/v) also added and delivered to $1.5 \times 10^6$ T cells using technology described herein to $1.5 \times 10^6$. 24 hr later the cells were harvested and analysed for mRNA expression using flow cytometry.

Flow Cytometry

Biotinylated protein L (AcroBiosystems) was reconstituted in phosphate buffered saline (PBS) at 1 mg/ml. For FACS staining, $1 \times 10^6$ cells were harvested and washed three times with ice cold PBS containing 4% bovine serum albumin (BSA) wash buffer. After wash, cells were resuspended in 0.2 ml of the wash buffer and incubated with 1 μg of Protein L for 45 minutes at 4° C. Cells were washed a further three times and then incubated in the dark with 10 μl of PE-conjugated streptavidin in 0.2 ml of wash buffer. To assess cell viability following the vector-free delivery method described herein, 7-AAD (Sigma) was used to stain the cells. Briefly, cells were in washed in PBS+1% fetal bovine serum (FACS buffer) followed by incubation with 7-AAD (1:40 for 5-10 min protected from light at room temperature), followed by resuspension in PBS+1% FBS (FACS buffer). Samples were processed on the BD Accuri C6 flow cytometer (Becton Dickinson, USA) and data was analysed using the C6 software. Cell debris was excluded from whole cells using forward and side scatter parameters. Single cells were selected by excluding doublets in the FSC height vs FSC are plot. CAR-T expression was analysed on gated viable cells.

Figure 45:
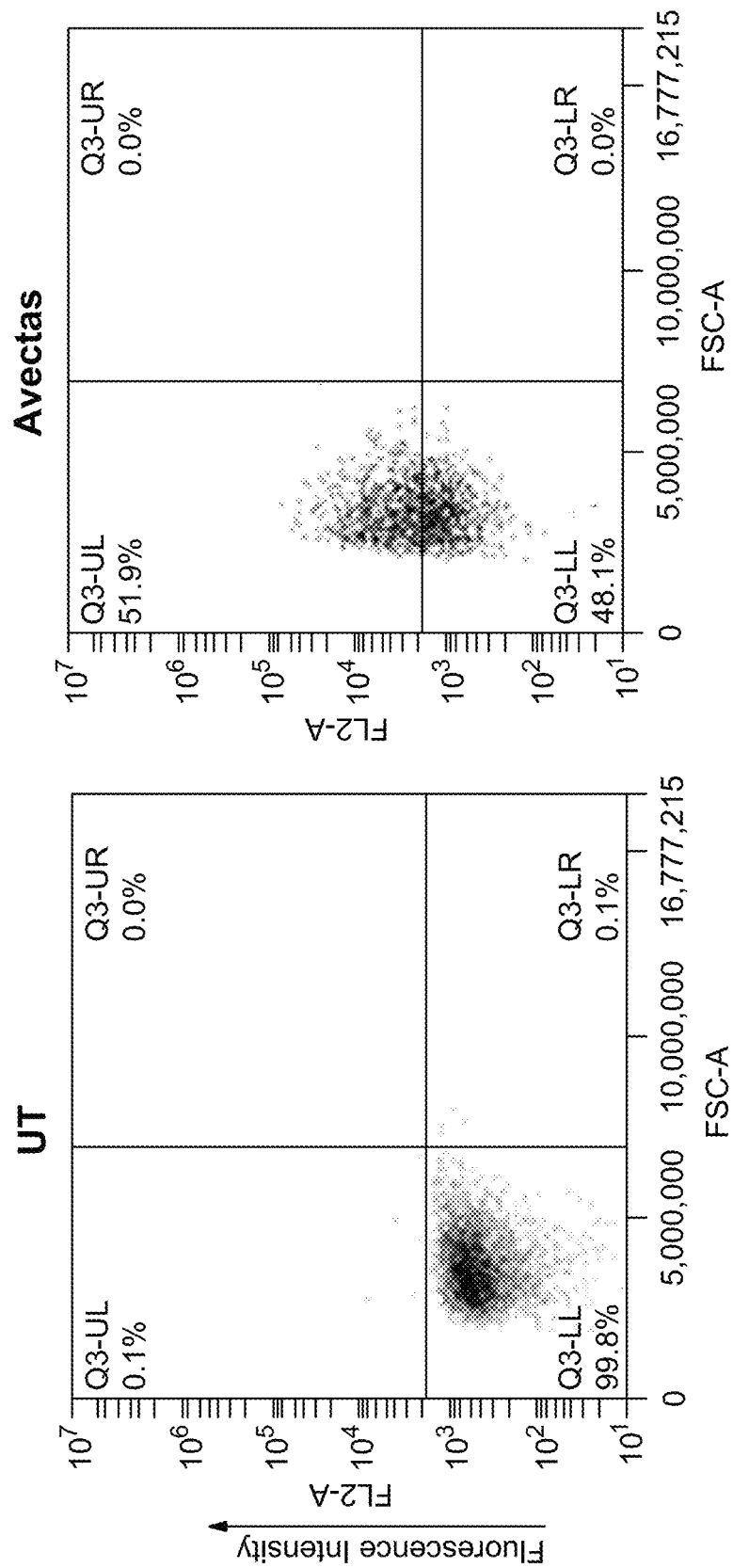
FIG. 45 is a dot plot of flow cytometry data showing CAR expression in human primary T cells following mRNA delivery by the vector-free delivery technology described herein.
Figure 46A:
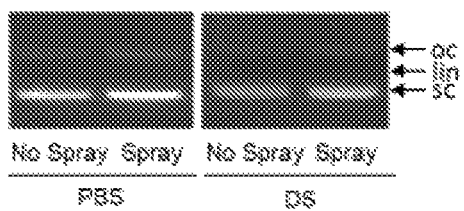
FIG. 46A is a photograph of an electrophoretic gel and FIG. 46B is a bar graph showing supercoiled vs open circular nucleic acids.
Figure 46B:
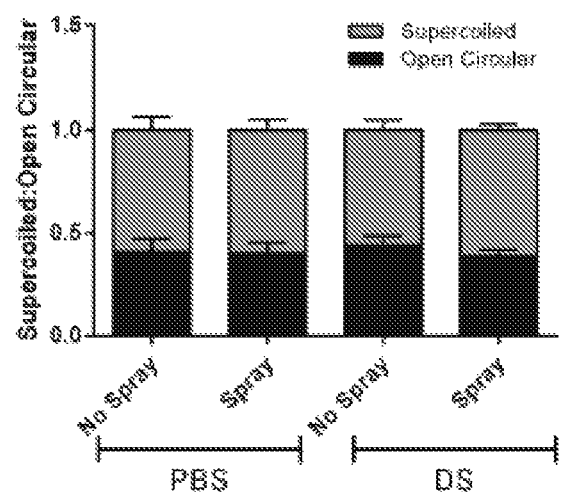

Untransfected cells were used as untreated controls (UT). A shift in fluorescence intensity was observed using the delivery method for treated cells was indicative of CAR expression following mRNA delivery (FIG. 45).

Assessment of Functionality of T Cells Post-Soluporation

In order to demonstrate that the functionality of T cells transfected using Solupore technology is equivalent to or better than cells transfected using electroporation, e.g., with the Neon electroporator, and nucleofection, e.g., using the Lonza 4D nucleofector. Cell membrane protein expression, gene expression, cell proliferation rate, in vitro functionality and in vivo functionality assays were carried out.

(i) T Cell Membrane Protein Expression Analysis

The goal of this study was to determine whether expression of cell surface proteins on T cells was affected by the soluporation process and to compare with electroporation and nucleofection.

Method: Activated T cells were seeded at $1.5 \times 10^6$ cells per well of a 96-well filter plate (Acroprep, 1.2 μm Supor membrane; Pall, USA). Media was removed from the wells by centrifugation at 300×g for 5 min. 7 μl of delivery solution (32 mM sucrose, 12 mM potassium chloride, 12 mM ammonium acetate, 5 mM HEPES and 27% ethanol in molecular grade water (all from Sigma-Aldrich)) containing 4 μg GFP mRNA was then sprayed into each well using the vector-free delivery spray instrument. Following delivery, the cells were incubated in this solution for 2 min prior to the addition of 50 μl Stop Solution (0.5×PBS). Thirty seconds later T cell media was added (100 μl) and cells were allowed to recover at 37° C. and 5% $CO_2$ overnight. For electroporation and nucleofection, $5 \times 10^6$ cells and $2.5 \times 10^6$ cells were used respectively per transfection. GFP expression and viability were assessed at 6 h and 24 h post-delivery.

Figure 47A:
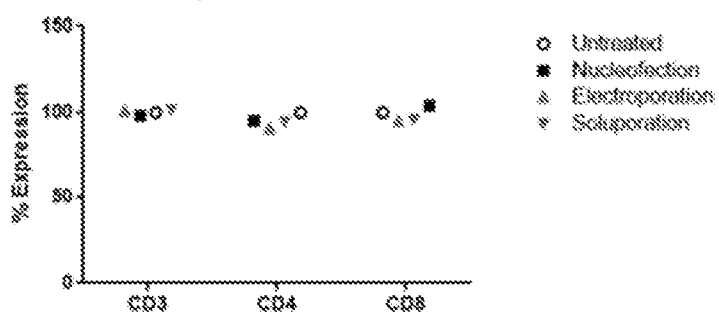
FIG. 47A-FIG. 47B are dot plots showing the effect of transfection methods on expression of CD4 and CD8 on T cells. The expression of cell surface CD4 and CD8 was examined 6 hr and 24 hr after either nucleofection, electroporation (Neon) or Soluporation. At 6 hr, expression levels were similar to untreated control cells. However, at 24 hr, expression in soluporated cells and nucleofected cells was similar to control untreated cells whereas expression was significantly reduced in electroporated cells.
Figure 47B:
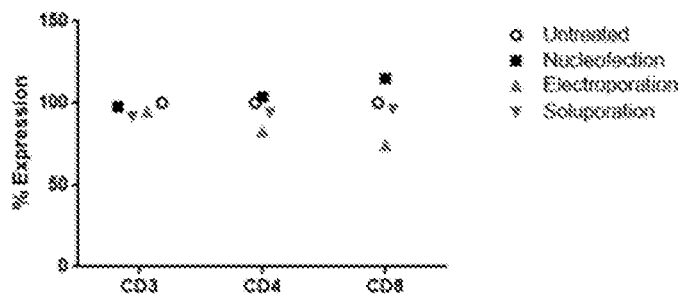

The expression of cell surface CD4 and CD8 was examined at 6 hr and 24 hr after either nucleofection, electroporation or Soluporation. At 6 hr post-transfection, the percentage of T cells expressing CD4 and CD8 was unchanged compared to untreated control cells for each transfection method. However, at 24 hr, expression was significantly reduced in electroporated cells whereas expression in soluporated cells and nucleofected cells was similar to control untreated cells (FIG. 47A, B).

(ii) Global mRNA Expression Analysis

The goal of this study was to obtain a molecular signature of cellular perturbation induced by the soluporation process, and to compare that signature with electroporation and nucleofection. 16 samples were analysed using mRNA microarrays: two donor T cells were taken, samples included an untreated control, neon, nucleofector and Solupore transfected cells with GFP-mRNA, at 6 hr and 24 hr time points.

Method: Activated T cells were seeded at $1.5 \times 10^6$ cells per well of a 96-well filter plate (1.2 μm PES membrane; Pall, USA). Media was removed from the wells by centrifugation at 300×g for 5 min. 1 μl of delivery solution (32 mM sucrose, 12 mM potassium chloride, 12 mM ammonium acetate, 5 mM HEPES and 27% ethanol in molecular grade water (all from Sigma-Aldrich)) containing 0.2 μg GFP mRNA was then sprayed into each well using the vector-free delivery spray instrument. Following the spray, cells were incubated in this solution for 2 min prior to the addition of 50 μl Stop Solution (0.5×PBS). Thirty seconds later T cell media was added (100 μl). A second spray was carried out 2 hrs after the first. Cells transferred to an incubator at 37° C. and 5% $CO_2$. For electroporation and nucleofection, $5 \times 10^6$ cells and $2.5 \times 10^6$ cells were used respectively per transfection. GFP expression and viability were assessed at 6 h and 24 h post-delivery.

Figure 48A:
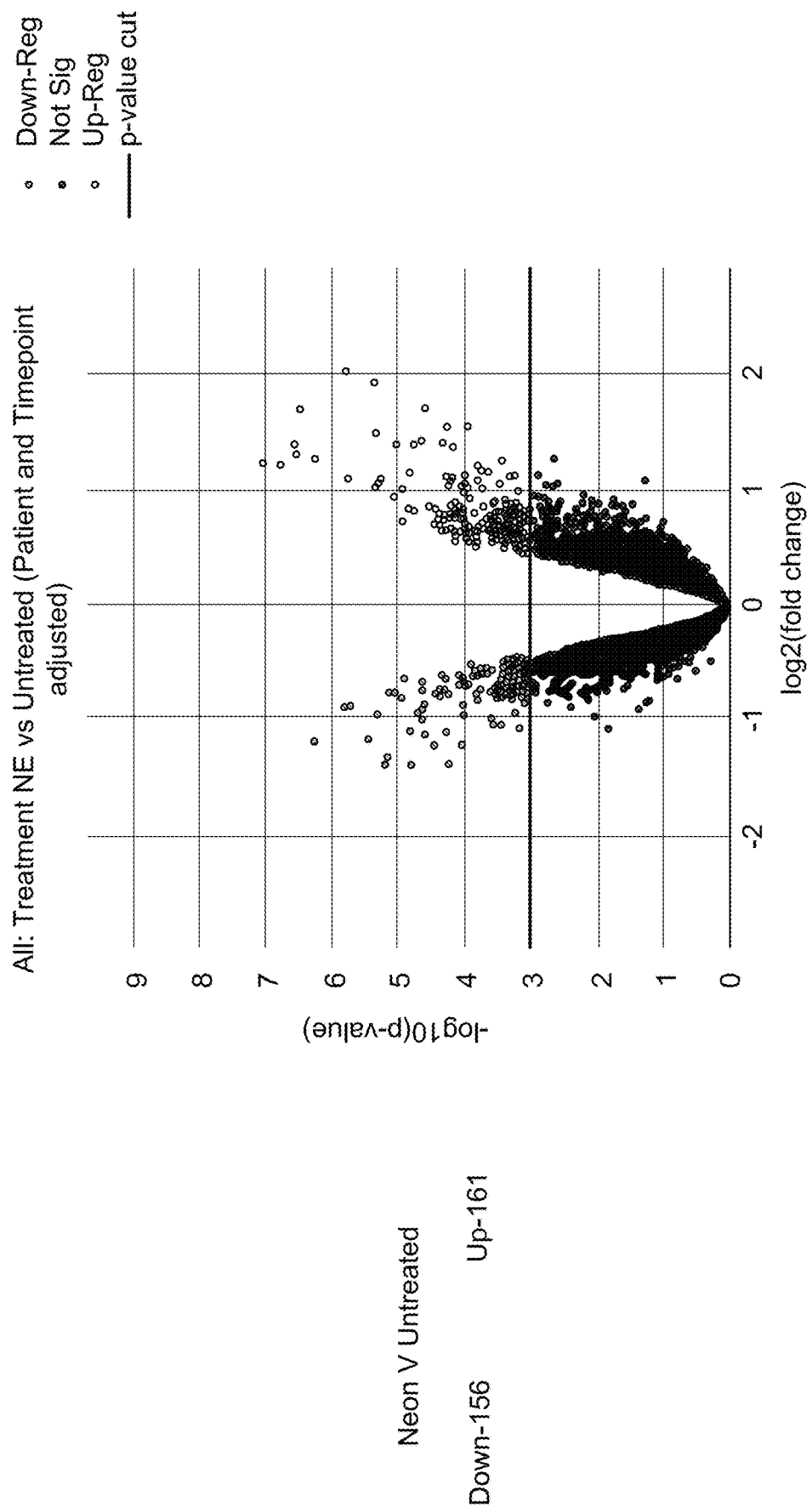
FIG. 48A-FIG. 48C are dot plots showing a mRNA microarray analysis. Cells were transfected with GFP mRNA. The highest level of gene expression changes occurred in Neon electroporation treatments. Of the 20,893 genes analysed, Solupore had 32 changed, nucleofection had 24 changed and electroporation had 317 changed.
Figure 48B:
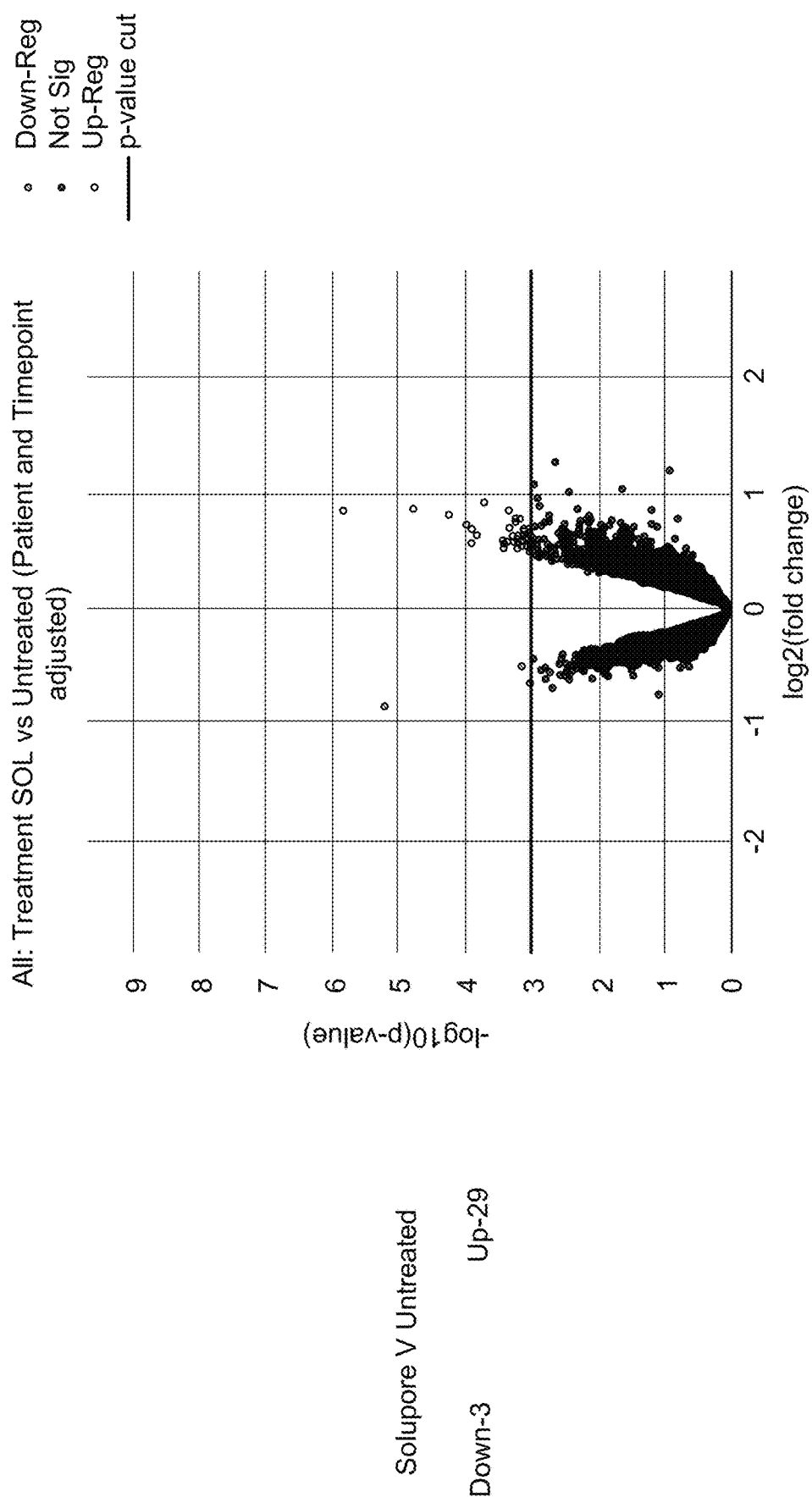
Figure 48C:
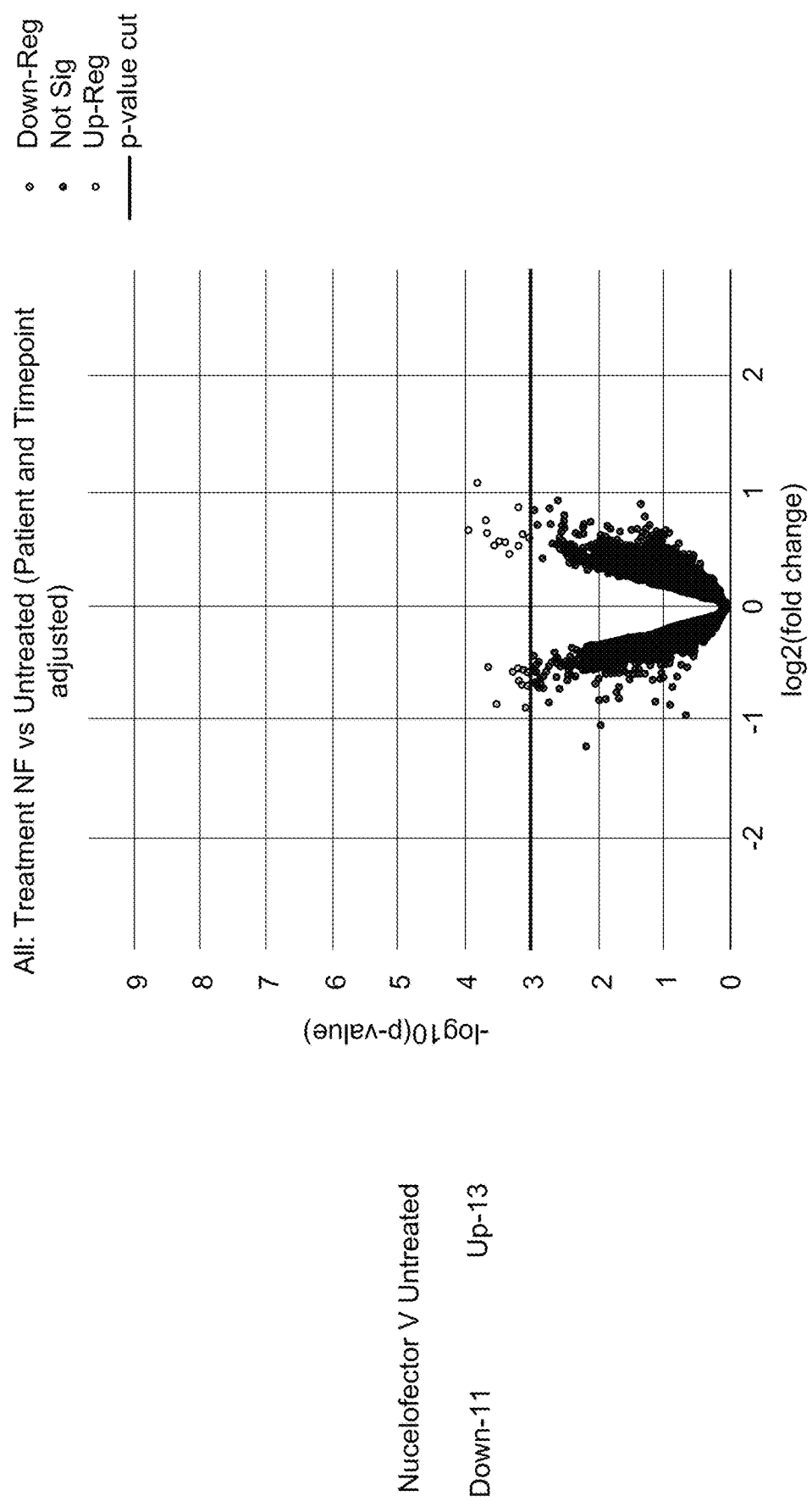

The highest level of gene expression changes occurred in Neon electroporation treatments. However, a drawback of electroporation is reduced viability and functionality of the treated cells post-electroporation. Of the 20,893 mRNAs analysed, Neon electroporation had a combined total of 317 changed over all timepoints (6 hr and 24 hr) and both donors, Solupore had 32 changed (Tables 5.1 and 5.2) and nucleofector had 24 changed (Tables 5.3 and 5.4; FIG. 48A, B, C). Notably, the background level of false positives for this microarray analysisis approximately 10%. For Solupore and nucleofection, the number of genes changed was only slightly above this threshold, demonstrating that Solupore and Nucleofector cause a minimal level of perturbation to cell gene expression. The high level of gene expression changes indicates that the Neon electroporation process perturbs the cells more than Soluporation of nucleofection. Cell perturbation is undesirable; therefore, the data indicate that Neon electroporation is less desirable as a transfection method compared with Soluporation and nucleofection. Soluporation is associated with several significant advantages compared to electroporation and nucleofection. Such advantages include high level reliable delivery of cargo, e.g., mRNA, to primary human cells, while preserving the integrity, function, and proliferation capabilities of the cells treated.

TABLE 5.1

List of gene expression changes in soluporated cells compared with untreated control cells at 6 hr post transfection. (Numbers indicate fold change compared with untreated control cells.)

| | | | |
|---|---|---|---|
| FOSB | FosB proto-oncogene, AP-1 transcription factor subunit | Osteoclast differentiationIL-1 | 2.673 |
| DMTF1 | cyclin D binding myb like transcription factor 1 | — | 1.954 |
| ATF3 | activating transcription factor 3 | HTLV-I infection | 2.983 |
| SLITRK5 | SLIT and NTRK like family member 5 | — | −2.155 |
| PPIL6 | peptidylprolyl isomerase like 6 | — | 2.34 |
| ARRDC4 | arrestin domain containing 4 | — | 2.602 |

TABLE 5.1-continued

List of gene expression changes in soluporated cells compared with untreated control cells at 6 hr post transfection. (Numbers indicate fold change compared with untreated control cells.)

| Symbol | Description | KEGG Pathways | FC |
|---|---|---|---|
| TSC22D3 | TSC22 domain family member 3 | — | 2.858 |
| FSD1L | fibronectin type III and SPRY domain containing 1 like | — | 2.377 |
| SNX9 | sorting nexin 9 | — | 1.863 |
| PPP1R15A | protein phosphatase 1 regulatory subunit 15A | Protein processing in endoplasm | 2.033 |
| — | — | — | 1.715 |
| PIFO | primary cilia formation | — | 1.816 |
| RASGEF1B | RasGEF domain family member 1B | — | 2.622 |
| TMEM154 | transmembrane protein 154 | — | 1.869 |
| TTC30B | tetratricopeptide repeat domain 30B | — | 2.734 |
| TCP11L2 | t-complex 11 like 2 | — | 3.804 |
| KLF6 | Kruppel like factor 6 | — | 1.674 |
| — | — | — | −1.644 |
| CCDC173 | coiled-coil domain containing 173 | — | 1.974 |
| — | — | — | 2.008 |
| IL1RN | interleukin 1 receptor antagonist | — | 2.021 |
| NPIPB3 | nuclear pore complex interacting protein family member B3 | — | 1.77 |
| GPCPD1 | glycerophosphocholine phosphodiesterase 1 | Glycerophospholipid metabolic | 1.967 |
| MGEA5 | meningioma expressed antigen 5 (hyaluronidase) | Insulin resistance | 1.811 |
| ZC2HC1A | zinc finger C2HC-type containing 1A | — | 1.762 |
| EPC2 | enhancer of polycomb homolog 2 | — | 1.803 |
| NPIPB11 | nuclear pore complex interacting protein family member B1 | — | 1.772 |
| ZNF440 | zinc finger protein 440 | — | 1.653 |

The data indicate that only a low number (e.g., negligible) of changes in gene expression occur in soluporated cells at 6 hr post transfection.

The data indicate that only a low number (e.g., negligible) of changes in gene expression occur in soluporated cells at 24 hr post transfection.

TABLE 5.2

List of gene expression changes in soluporated cells compared with untreated control cells at 24 hr post transfection. Numbers indicate fold change compared with untreated control cells.

| Symbol | Description | KEGG Pathways | FC |
|---|---|---|---|
| CXCL13 | C-X-C motif chemokine ligand 13 | Cytokine-cytokine receptor | 2.525 |
| FAM198B | family with sequence similarity 198 member B | — | 2.337 |
| — | — | — | −1.918 |
| GPM6A | glycoprotein M6A | — | 1.925 |
| — | — | — | 2.013 |
| GTF2H5 | general transcription factor IIH subunit 5 | Basal transcription factors | 1.796 |
| — | — | — | 1.881 |
| TREML2 | triggering receptor expressed on myeloid cells life | — | 1.882 |
| HFE2 | hemochromatosis type 2 (juvenile) | — | −1.998 |
| SCUBE3 | signal peptide, CUB domain and EGF like domain | — | −1.77 |
| TCTEX1D2 | Tctex1 domain containing 2 | — | 1.825 |
| WLS | wntless Wnt ligand secretion mediator | — | 1.713 |
| — | — | — | −1.766 |
| — | — | — | −1.859 |
| — | — | — | 1.797 |
| CNTN5 | contactin 5 | — | −1.706 |
| ZFP2 | ZFP2 zinc finger protein | — | −1.883 |
| SNX9 | sorting nexin 9 | — | 1.738 |
| — | — | — | 1.891 |
| — | — | — | 1.75 |
| TSSK4 | testis specific serine kinase 4 | — | 1.829 |
| ADAMTS6 | ADAM metallopeptidase with thrombospondin t | — | −1.725 |
| WIPI1 | WD repeat domain, phosphoinositide interacting | Autophagy - otherAutopha | 1.655 |
| — | — | — | −2.062 |
| OSBPL10 | oxysterol binding protein like 10 | — | −1.817 |
| — | — | — | −1.782 |
| UBASH3A | ubiquitin associated and SH3 domain containing | — | 1.703 |
| — | — | — | 1.757 |
| — | — | — | 1.654 |
| OR52A5 | olfactory receptor family 52 subfamily A member | Olfactory transduction | −1.632 |
| SMCO4 | single-pass membrane protein with coiled-coil d | — | −1.647 |
| C19orf38 | chromosome 19 open reading frame 38 | — | −1.776 |
| WDR19 | WD repeat domain 19 | — | 1.834 |

TABLE 5.3

List of gene expression changes in nucleofected cells compared with untreated control cells at 6 hr post transfection. Numbers indicate fold change compared with untreated control cells.

| | | | |
|---|---|---|---|
| EFHC2 | EF-hand domain containing 2 | — | 2.883 |
| NEK11 | NIMA related kinase 11 | — | 2.206 |
| QPCT | glutaminyl-peptide cyclotransferase | — | −2.059 |
| — | — | — | 1.78 |
| RNF125 | ring finger protein 125 | RIG-I-like receptor signaling . . . | −2.219 |
| — | — | — | 1.763 |
| GJB2 | gap junction protein beta 2 | — | 1.827 |
| PIFO | primary cilia formation | — | 1.801 |
| FSD1L | fibronectin type III and SPRY domain containing 1 like | — | 2.099 |
| LOC654841 | uncharacterized LOC654841 | — | 1.92 |
| ADGRG1 | adhesion G protein-coupled receptor G1 | — | 1.836 |
| — | — | — | 1.631 |
| CDKL2 | cyclin dependent kinase like 2 | — | 1.701 |
| LY96 | lymphocyte antigen 96 | NF-kappa B signaling pathwayTol | 1.975 |
| APBB1IP | amyloid beta precursor protein binding family B member | Rap1 signaling pathwayPlatelet a | 1.643 |

The data indicate that only a low number (e.g., negligible) of changes in gene expression occur in nucleofected cells at 6 hr post transfection.

TABLE 5.4

List of gene expression changes in nucleofected cells compared with untreated control cells at 24 hr post transfection. Numbers indicate fold change compared with untreated control cells.

| | | | |
|---|---|---|---|
| GJB2 | gap junction protein beta 2 | — | 2.446 |
| CMPK2 | cytidine/uridine monophosphate kinase 2 | Pyrimidine metabolism | 2.056 |
| WLS | wntless Wnt ligand secretion mediator | — | 1.994 |
| BEX5 | brain expressed X-linked 5 | — | −2.038 |
| — | — | — | 1.927 |
| IL17F | interleukin 17F | Cytokine-cytokine receptor int . . . IL-17 signaling pathwayTh | −1.818 |
| OSBPL10 | oxysterol binding protein like 10 | — | −2.018 |
| — | — | — | −1.788 |
| SYNGR3 | synaptogyrin 3 | — | −1.793 |
| TET2 | tet methylcytosine dioxygenase 2 | — | −1.9 |
| — | — | — | 1.875 |
| NLRP7 | NLR family pyrin domain containing 7 | NOD-like receptor signaling pa . . . | −1.963 |
| NAPB | NSF attachment protein beta | — | 2.417 |
| IRF1 | interferon regulatory factor 1 | Prolactin signaling pathwayPertussisHepatitis CHuman pap | 2.265 |
| IL2 | interleukin 2 | Cytokine-cytokine receptor int . . . PI3K-Akt signaling pathway | −2.421 |
| ARMC4 | armadillo repeat containing 4 | — | 1.714 |
| MRC1 | mannose receptor, C type 1 | PhagosomeTuberculosis | 1.88 |
| — | — | — | −1.717 |
| RPS6KC1 | ribosomal protein S6 kinase C1 | — | 2.005 |
| — | — | — | −1.64 |
| BEND3 | BEN domain containing 3 | — | 1.751 |
| IL13RA1 | interleukin 13 receptor subunit alpha 1 | Cytokine-cytokine receptor int . . . Jak-STAT signaling pathway | 1.715 |
| DEFB118 | defensin beta 118 | — | −1.788 |
| SERGEF | secretion regulating guanine nucleotide exchange family | — | −1.671 |
| USP37 | ubiquitin specific peptidase 37 | — | −1.634 |
| SOS1 | SOS Ras/Rac guanine nucleotide exchange factor 1 | MAPK signaling pathwayErbB signaling pathwayRas signaling | 1.752 |
| — | — | — | 1.948 |
| LOC729970 | hCG2028352-like | — | 1.63 |

The data indicate that only a low number (e.g., negligible) of changes in gene expression occur in nucleofected cells at 24 hr post transfection.

(iii) Cell Proliferation Analysis

For therapeutic applications, it is necessary that T cells are able to proliferate following modifications. Therefore, the ability of T cells to proliferate following soluporation, electroporation and nucleofection was examined. The cells capacity to proliferate post-cryopreservation and thaw was also tested.

Method: Activated T cells were seeded at $1.5 \times 10^6$ cells per well of a 96-well filter plate (Acroprep, 1.2 μm Supor membrane; Pall, USA). 1 μl of delivery solution containing 0.2 μg GFP mRNA was then sprayed into each well. A second spray was carried out 2 hrs later. For electroporation and nucleofection, $5 \times 10^6$ cells and $2.5 \times 10^6$ cells were used per transfection. Cells were transferred to an incubator at 37° C. and 5% $CO_2$. The next day, cells were harvested and counted. Cells were then re-seeded at $0.5 \times 10^6$/ml by adding additional media+IL-2 each day for 7 days. In another experiment, cells were cryopreserved in 10% DMSO and foetal bovine serum 24 hrs post-transfection. Cells were thawed and seeded at $0.5 \times 10^6$/ml on day 0 in Immunocult media+IL-2. Cells were counted and re-seeded by adding additional media each day for 5 days.

Figure 49:
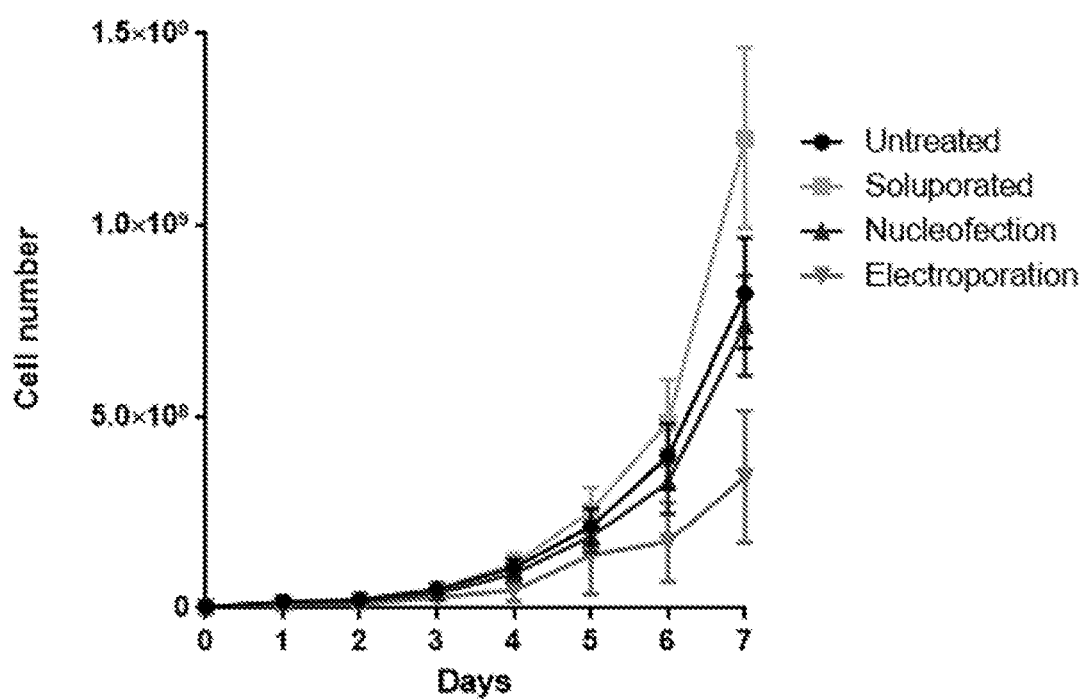
FIG. 49 is a line graph showing cell proliferation. T cells were transfected with GFP mRNA and cells were counted each subsequent day for 7 days. Proliferation rates in soluporated and nucleofected cells were similar to untreated control cells whereas the ability of Neon electroporated cells was reduced compared with control cells.
Figure 50:
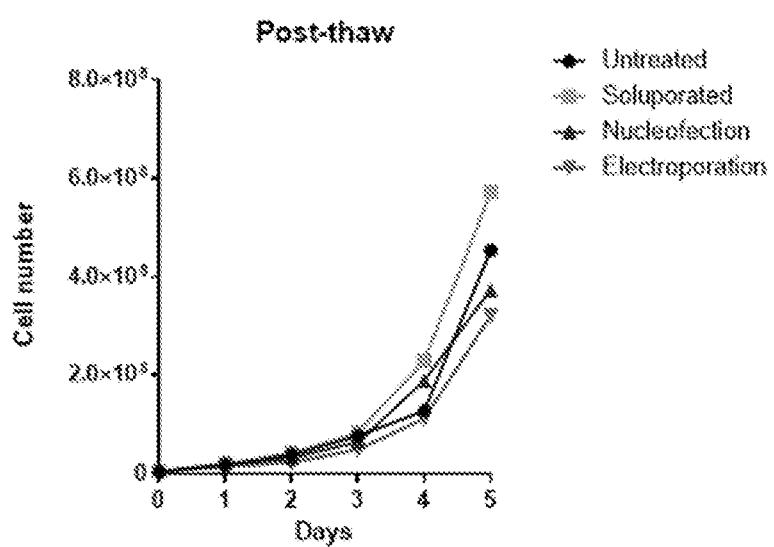
FIG. 50 is a line graph showing cell proliferation post-cryopreservation. T cells were transfected with GFP mRNA and cells were cryopreserved in 10% DMSO and foetal bovine serum 24 hrs post-transfection. Cells were thawed and seeded at $0.5 \times 10^6$/ml on day 0 in Immunocult media+ IL-2. Cells were counted and re-seeded by adding additional media each day for 5 days. Proliferation rates in soluporated and nucleofected cells were similar to untreated control cells whereas the ability of electroporated (e.g., Neon) cells was reduced compared with control cells.

T cells were transfected and cells were counted each subsequent day for 7 days. Proliferation rates in soluporated and nucleofected cells were similar to untreated control cells whereas the ability of Neon electroporated cells was reduced compared with control cells (FIG. 49). Proliferation was unaffected by Soluporation post-cryopreservation and subsequent thaw (FIG. 50). These data indicate that a significant drawback of electroporation and/or nucleofection is a cell proliferation stall. A significant advantage of the Solupore system is the absence of a cell proliferation stall.

(iv) Interferon-Gamma (IFNg) Secretion Analysis

For therapeutic applications, it is necessary that T cells are able to produce IFNg following modifications. Therefore, the ability of T cells to produce IFNg following soluporation, electroporation and nucleofection was examined Two different activation methods were examined, phorbol myristate acetate/ionomycin (PMA/I) and Dynabeads. The cells ability to secrete IFN-γ was also tested post-cryopreservation and thaw following soluporation.

Method: Activated T cells were seeded at $1.5 \times 10^6$ cells per well of a 96-well filter plate (Acroprep, 1.2 μm Supor membrane; Pall, USA). 1 μl of delivery solution containing 0.2 μg GFP mRNA was then sprayed into each well. A second spray was carried out 2 hrs later. For electroporation and nucleofection, $5 \times 10^6$ cells and $2.5 \times 10^6$ cells were used respectively per transfection. Cells were allowed to recover at 37° C. and 5% $CO_2$. The next day, cells were harvested and counted. Cells were then re-seeded at $0.5 \times 10^6$/ml by adding additional media+IL-2 each day for 7 days, after which the cells were allowed to return to a resting state by monitoring cell size. This was approximately 2 weeks after initial activation. Cells were then re-stimulated with either Dynabeads or a PMA/Ionomycin cocktail for 4 hrs, after which the supernatants were recovered and stored at −20° C. until cytokine analysis. IFN-γ ELISA (Biotechne) were carried out on all samples. In another experiment, Soluporated, nucleofected and electroporated cells were harvested and counted 24 h after transfection. Cells were then re-seeded at $0.5 \times 10^6$/ml by adding additional media+IL-2 each day for 7 days, after which the cells were allowed to return to a resting state by monitoring cell size. This was approximately 2 weeks after initial activation. Cells were then re-stimulated with either Dynabeads or a PMA/Ionomycin cocktail for 4 hrs, after which the supernatants were recovered and stored at −20° C. until cytokine analysis. IFN-γ ELISA (Biotechne) were carried out on all samples.

Figure 51:
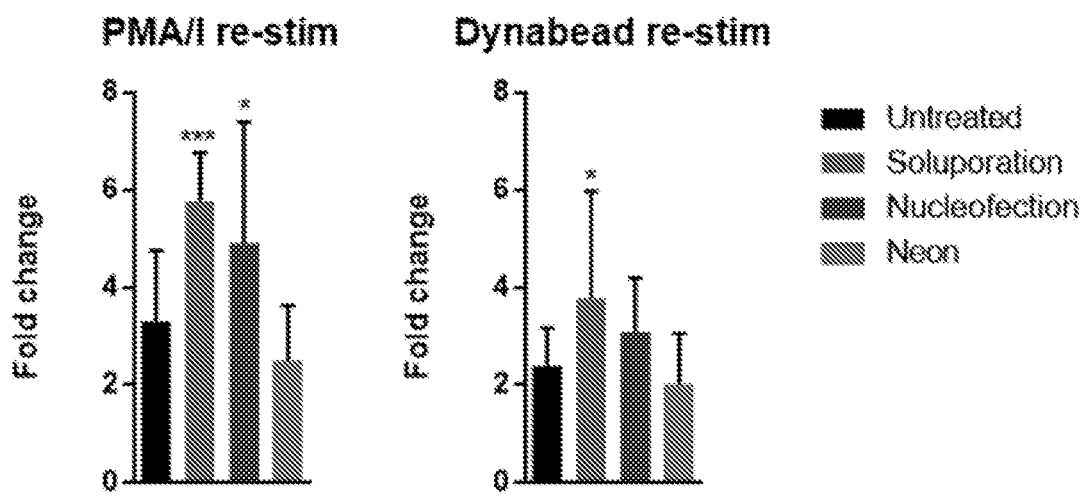
FIG. 51 is a series of bar graphs showing Interferon-gamma (IFNg) production. IFNg production, measured at 14 days post transfection, was not reduced in T cells following soluporation, nucleofection or electroporation compared with control cells.
Figure 52:
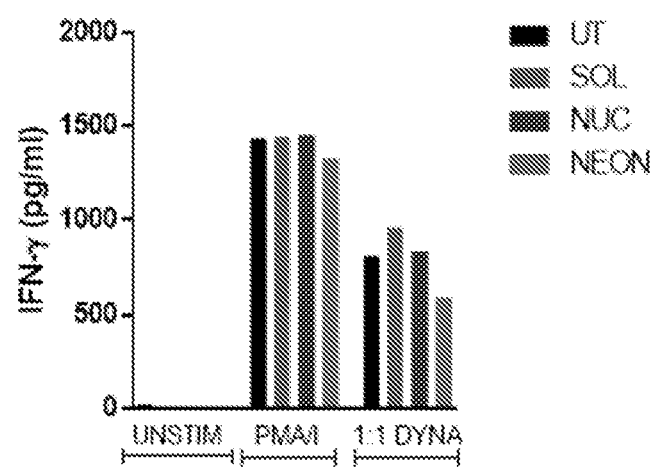
FIG. 52 is a bar graph showing IFNg production. Soluporated, nucleofected, electroporated and untreated cells were cryopreserved 24 h post-transfection. Cells were then re-stimulated with either Dynabeads or a PMA/Ionomycin cocktail for 4 hrs and their supernatants were analysis for IFN-γ production.

IFNg production was not reduced in T cells following soluporation, nucleofection or electroporation compared with control cells (FIG. 51). Freshly thawed soluporated cells did not lose their capacity to secrete IFN-γ when compared to untreated controls (FIG. 52).

(v) In Vivo Engraftment in T Cells Following Delivery of 3 kDa Dextran

In order to determine the effect of Solupore technology on T cell functionality, the capacity of transfected PBMC to induce GvHD in a NSG mouse model was studied. NOD scid gamma mice (NSG mice) is an art-recognized immunodeficient laboratory mouse strain from The Jackson Laboratory.)

If transfected cells were adversely affected by the Solupore delivery technology, their ability to engraft and induce Graft versus Host Disease (GvHD) would be impaired. A comparison with nucleofection was also carried out. It was impractical to include Neon electroporation as a comparator because the high loss of cells in the process would require an unfeasibly high number of cells to be electroporated.

Method: 3 kDa Dextran-Alexa488 was delivered to $20 \times 10^6$ and $5 \times 10^6$ PBMC by soluporation and nucleofection respectively. Soluporation was carried out using the 44.45 mm Stirred Cell system. A monolayer of cells was formed on a 1 μm PCTE hydrophilic membrane (Sterlitech) by applying a pressure of 100 mbar for 15-25 secs until all media was removed. 5 ml of delivery solution containing 3 μM Dextran 3000 was prepared and loaded into the LP100 atomiser. Cells were soluporated and after 1 min and 30 sec, the membrane was gently transferred to a 60-mm cell culture grade petri dish. After 2 mins, 1 ml of stop solution was added to the membrane and left to incubate for 30 seconds, after which time, 4 ml of media was added to the cells. The petri dish was transferred to an incubator at 37° C. with 5% $CO^2$ for 30 mins. For nucleofection, $5 \times 10^6$ cells were used per transfection. Cells were harvested, washed twice in 1×PBS and resuspended according the weight of the mouse i.e. $1 \times 10^6$ per gram. injected intravenously via the tail vein based on weight per mouse ($1 \times 10^6$ per gram). Mice were weighed 2-3 times weekly and monitored for the appearance of GvHD-like symptoms. Peripheral blood was collected between 9-12 days post-injection and processed for flow cytometry analysis. Similarly, blood and spleen were collected at the end of the study and prepared for analysis.

Figure 53A:
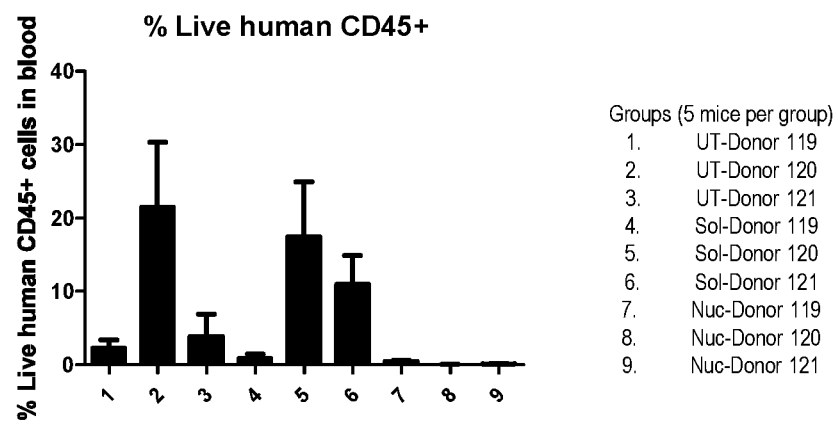
FIG. 53A-FIG. 53C are bar graphs showing evaluation of CD 45+ cells post-treatment. Analysis of blood at Day 14 following injection of human PBMC into NSG mice.
Figure 53B:
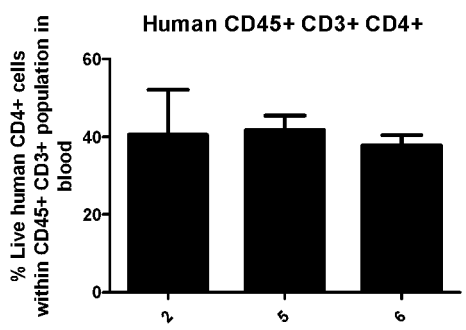
Figure 53C:
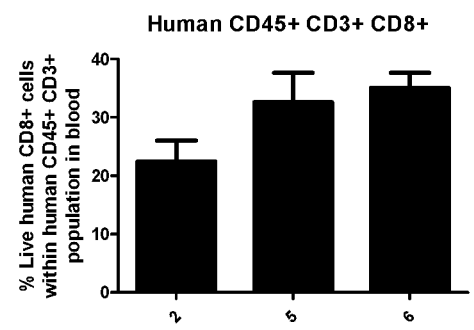

PBMC were isolated from three different donors (D119, D120, D121) and cells from each donor were soluporated or nucleofected. There were four groups of NOD scid gamma (NSG) mice, with 5 mice per group, for the study. The groups were: 1. No cells 2. UT 3. Soluporation 4. Nucleofection (4 groups×5 mice p/group×3 donors=60 mice). Cells were injected into the mice on Day 0. Animals were monitored daily and GvHD symptoms were present by Day 14 post injection in all animals that received cells indicating that cells were viable and functional. Blood samples were taken from the mice on Day 14 and analysed by flow cytometry for the presence of human PBMC, as indicated by CD45 expression, and T cell subsets. Results demonstrated that CD45+ cells were present in the untreated groups and soluporated groups at this timepoint, confirming that the cells were viable and functional (FIGS. 53A, B, C). Lower numbers of CD45+ cells were detected in nucleofected cells at this timepoint. These data demonstrate that soluporated human PBMC remain viable and functional in vivo such that they are capable of inducing GvHD in NSG mice. The results demonstrate successful engraftment of soluporated cells into the NSG mice indicating that their viability and functionality is retained following soluporation.

Filter Membrane Conditions for Delivery of Payload Composition to Cells

To facilitate and to enhance the exposure of cells (non-adherent cells or adherent cells) to permeableisation solution, the filter membrane is optionally vibrated before or after or during delivery or permutations of these. To assist in the formation of a monolayer of cells on a filter membrane, the membrane can vibrate before or after or during delivery or permutations of these. Vibration of a filter membrane can be carried out using a number of readily available devices, e.g., Piezoelectric Accelerometers such as a Miniature Triaxial DeltaTron® Accelerometers (available from Bruel and Kjaer, www.bksv.com). A number of other suitable vibrating motors are also available from Precision Microdrives; www.precisionmicrodrives.com.)

For example, the vibration may be brought about by an eccentric rotating mass (ERM) system or a linear resonant actuator (LRA) system. By preference, 1, 2 or 3 actuators (LRA) corresponding to the X, Y and Z axis may be attached to the membrane or membrane holder such that the membrane vibrates by mechanical coupling to the actuator.

The advantage of the LRA system is that each axis may be driven independently. Accordingly, complex but controllable vibration patterns may be developed on the membrane. Additionally, identification of mechanical resonance points due to the physical character of the membrane will improve the degree of control that may be exhibited over the membrane. A 3 axes accelerometer device will be mechanically coupled to the filter membrane or holder to feedback the excursions experienced by the membrane. The Accelerometer system may be used to monitor or as a control feedback signal to the vibrational system, generating an error signal between the desired vibrational pattern and the achieved vibrational pattern. The selection of driving vibrational frequencies is made based on the stiffness of the membrane and the size of cells on the membrane. An example vibrational pattern is brought about with sinusoidal signals at 3000 Hz on the x and y axes and no signal on the z axis. The excursions are 1 mm peak to peak and the x and y driving waveforms are coherent with no phase difference between them. Many other patterns are possible including ones that lead to swirling, shaking in the x, y and/or z axes.

Device for Delivering Cargo Molecule(s) to Mammalian Cells

The current subject matter generally relates the delivery biological payloads to cells. The delivery of biological payloads to cells can involve the atomization and delivery of a permeabilizing solution onto a monolayer of cells. Current techniques can fall short in a number of areas, which is discussed in more detail below.

Prior to receiving the payload, the cells can be submersed or suspended within a culture medium. To achieve effective payload uptake, it can be beneficial to remove the culture medium so that cells can be exposed to the permeabilizing solution, and to organize the cells in a monolayer conformation. With certain current techniques, the medium is removed by centrifugation. Although this technique can be effective at removing the medium, it typically does not result in the formation of a uniform monolayer of cells.

In order to ensure an appropriate distribution of the permeabilizing solution on the monolayer of cells, the cells can be aligned under a solution atomizer or nebulizer. With current techniques, cells are generally aligned under the atomizer using a manual system, which is subject to operator variability. The atomizer/nebulizer can be used to dispense the permeabilizing solution onto the monolayer of cells. However, certain atomizers are designed to dispense volumes of solution on the order of magnitude of milliliters, while dispensation volumes on the order of microliters can be preferable, or even required. Additionally, the transfection protocol for payload delivery can involve several time critical steps. Currently, handling of fluids is generally controlled manually, and it is therefore intrinsically variable.

Because of these shortcomings, the data generated can be inherently inconsistent. The lack of reproducibility of the data can hamper further development of the payload delivery process. In order to address the aforementioned issues, some aspects of the current subject matter provides a delivery system that enables greater consistency in the delivery process, and higher efficiency of delivery, while maintaining cell health.

Example Delivery System

Figure 65:
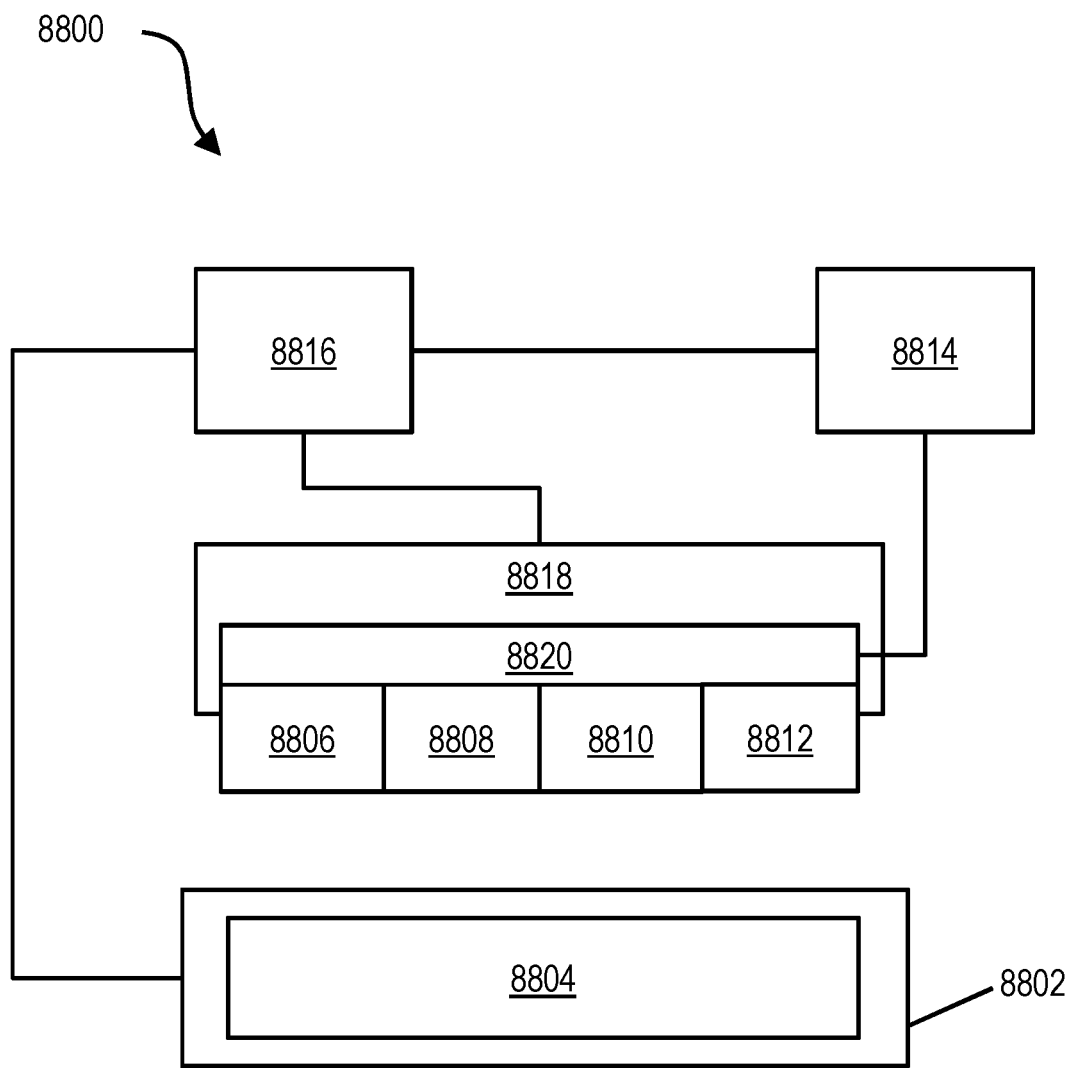
FIG. 65 is a diagram illustrating one embodiment of a delivery system

FIG. 65 shows an example of a delivery system 8800 configured to deliver a payload to cells. The delivery system 8800 can include a housing 8802 configured to receive a plate 8804 comprising a well. The delivery system 8800 can include a differential pressure applicator 8806 configured to apply a differential pressure to the well, a delivery solution applicator 8808 configured to deliver atomized delivery solution to the well, a stop solution applicator 8810 configured to deliver a stop solution to the well, and a culture medium applicator 8812 configured to deliver a culture medium to the well.

As an example, in some embodiments, the differential pressure applicator 8806 can be, or can include, a nozzle valve assembly, e.g., the nozzle valve assembly 9310, described below with regard to FIGS. 84, and 89-91. As another example, the differential pressure applicator 8806 can be, or can include, a vacuum manifold assembly, e.g. the vacuum manifold assembly 9008, described below with regard to FIGS. 93-107. In some embodiments, the delivery solution applicator 8808 can be, or can include a nebulizer such as, e.g., nebulizers 9304, 9804 described below with regard to FIGS. 85, 88, 93, and 115-118. In some embodiments, the stop solution applicator 8810 can be, or can include needle emitters such as, e.g., needle emitters 9303 described below with regard to FIGS. 85, 87. As another example, in some embodiments, the culture medium applicator 8812 can be, or can include, the needle emitters 9303.

The delivery system 8800 can also include a control system 8814, an actuation system 8816, a support frame 8818, and a sensing and management system 8820. In some embodiments, the differential pressure applicator 8806, delivery solution applicator 8808, stop solution applicator 8810, and/or the culture medium applicator 8812 can be coupled to the support frame 8818. The actuation system 8816 can coupled to the support frame 8818, the housing 8802, and/or the plate 8804, and can be configured to move the support frame 8818, the housing 8802, and/or the plate 8804. As another example, the actuation system 8816 can be coupled to, and configured to move, the differential pressure applicator 8806, delivery solution applicator 8808, stop solution applicator 8810, and/or the culture medium applicator 8812. For example, the support frame 8818 can be, or can include, the fluidic head module 9308, described below with regard to FIGS. 84-89. The actuation system can be, or can include, actuator 9319, described below with regard to FIGS. 84, 85. In some implementations, a vibration system can be included to vibrate a membrane (e.g., located within the well of the plate).

The sensing and management system 8820 can include sensors and/or thermal management systems. As an example, the sensors and/or thermal management system can be coupled to the differential pressure applicator 8806, delivery solution applicator 8808, stop solution applicator 8810, and/or the culture medium applicator 8812, and can be configured to measure and/or control pressures, temperatures, positions, and flow rates.

The control system 8814 can include at least one data processor and can be electrically coupled to the actuation system 8816 and the sensing and management system 8820. The control system can be configured to control the actuation system 8816, as well as the sensing and management system 8820. As an example, the control system 8814 can be, or can include, the control system 9306 described below with regard to FIG. 84.

Example Vacuum Pressure System

Figure 66:
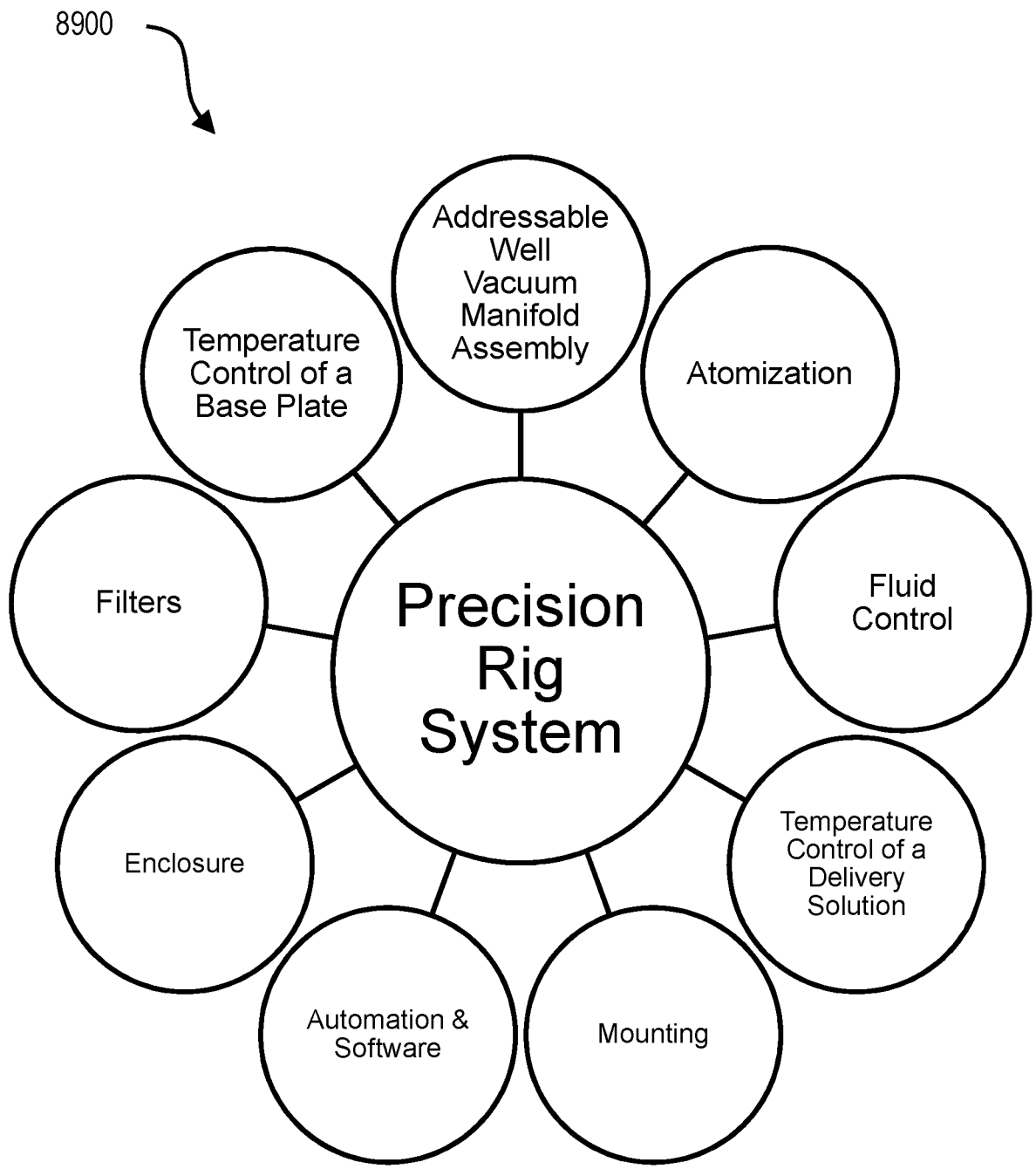
FIG. 66 is a diagram that illustrates 9 elements of a delivery system.

FIG. 66 shows a diagram 8900 that illustrates nine elements of a delivery system. The system includes: an addressable well vacuum manifold assembly; atomization; fluid control; temperature control of a delivery solution; mounting; automation and software; enclosure; filters; and temperature control of a base plate.

The delivery system can address the following areas of variability related delivering a payload to cells: monolayer formation; atomization; automation of the payload delivery; and temperature control of the solutions and the culture container.

In order to improve the consistency of the data and the delivery efficiency of payload delivery, the system removes certain known sources of variability from the process. The system can address: removal of media and creation of a monolayer of cells using a vacuum; atomization of the permeabilizing solution to produce monodispersed droplets;

fluidic control of the solutions to enable automation; temperature control of the solution; mounting of a spray head and a temperature reservoir; automation and software design; enclosure for the instrument; and temperature control of a base plate.

Figure 67:
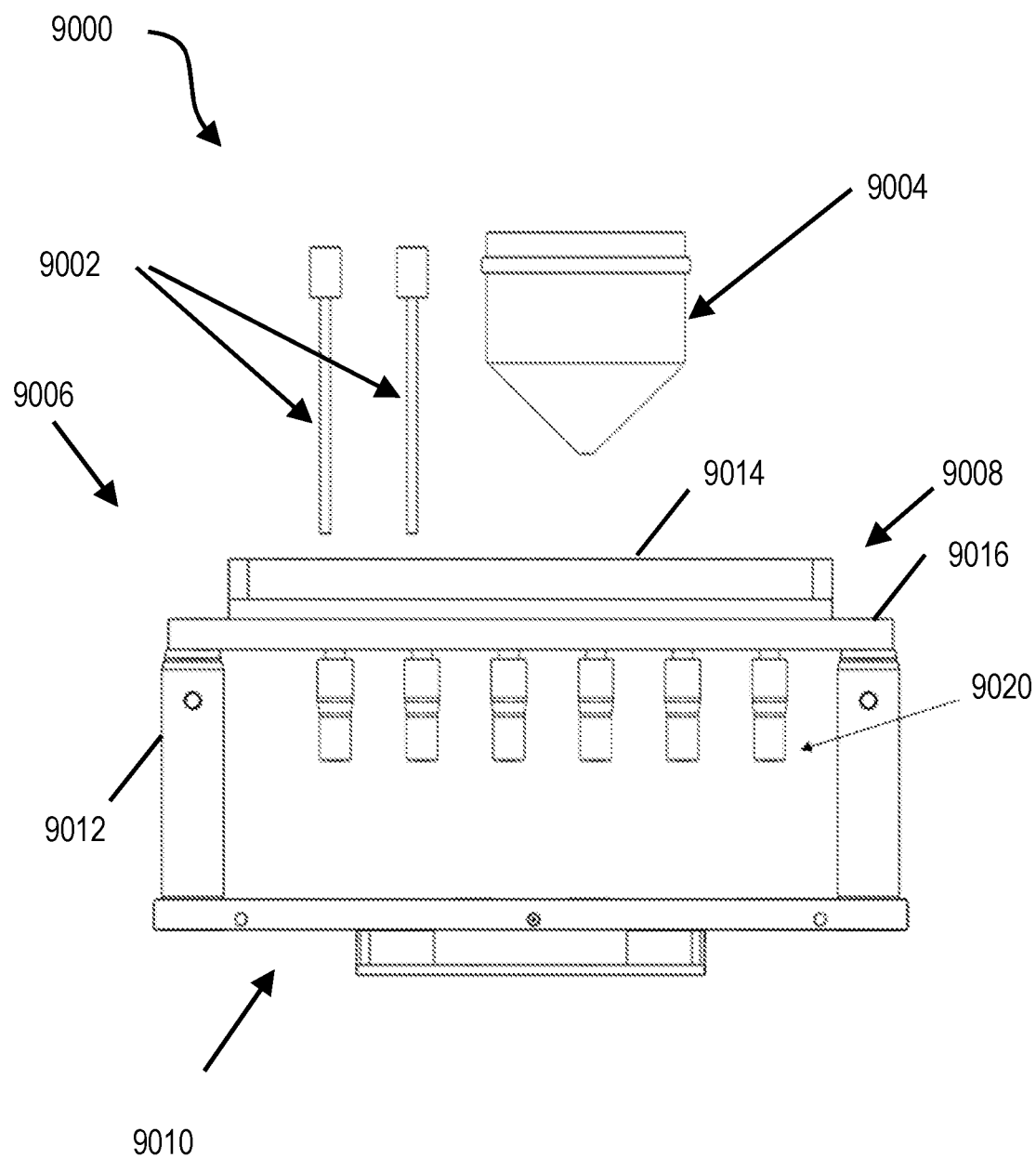
FIG. 67 is a side view of an embodiment of a delivery system.
Figure 68:
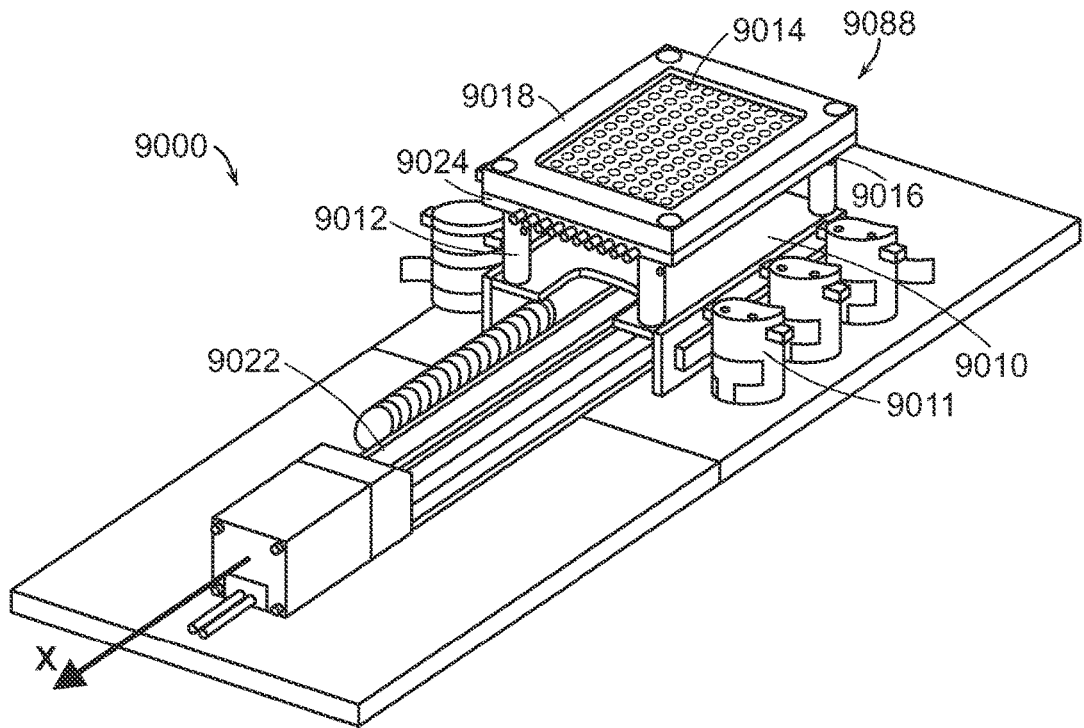
FIG. 68 is perspective of a portion of an embodiment of a delivery system.
Figure 69:
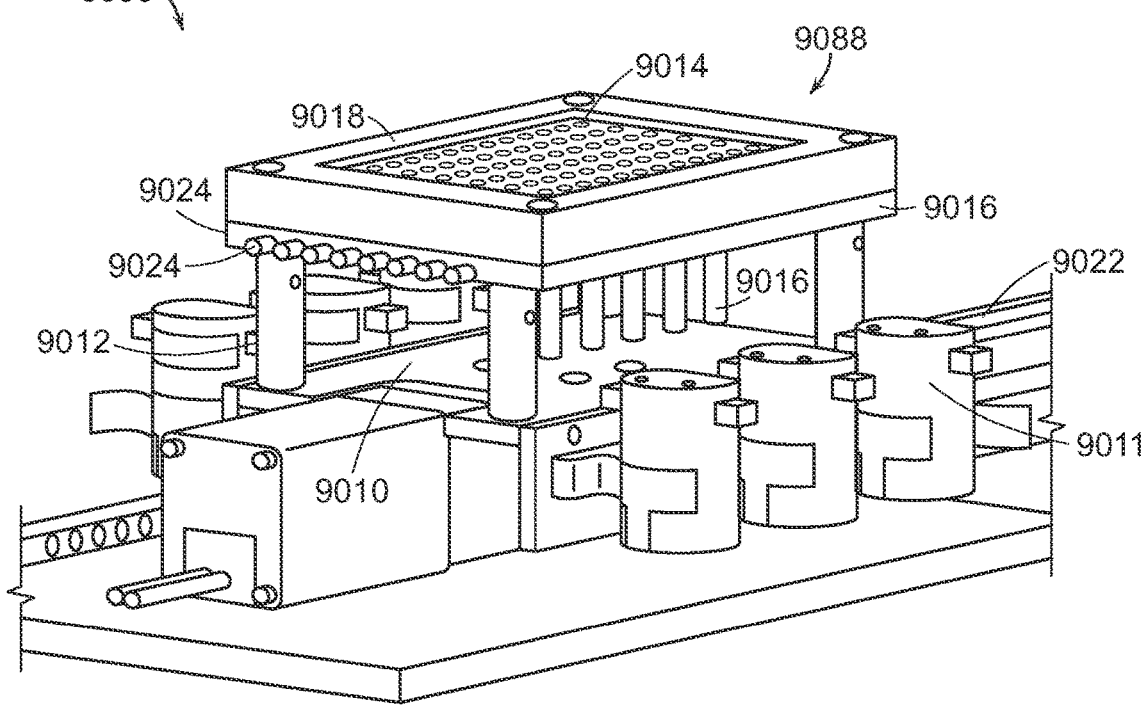
FIG. 69 is an enlarged perspective view of the delivery system shown in FIG. 68.

FIGS. 67-69 show an exemplary embodiment of a precision rig system 9000. The precision rig system 9000 can include needle emitters 9002, an atomizer 9004, and a vacuum manifold system 9006. The vacuum manifold system 9006 can include a vacuum manifold assembly 9008, a translational stage 9010, valves 9011 (shown in FIGS. 68-69), and a manifold 9024. In some embodiments, the vacuum manifold assembly 9008 can be coupled to a translational stage 9010 via coupling members 9012. In some embodiments, the valves 9011 can be pinch valves. The vacuum manifold assembly 9008 can include a filter plate 9014, a base plate 9016, and a top plate 9018 (shown in FIGS. 68-69). As shown in FIGS. 68-69 the filter plate can be a 96-well filter plate. The filter plate 9014 can seat within a recessed region of the base plate 9016, and the top plate can be positioned over the filter plate 9014 and coupled to the base plate 9016 to secure the filter plate 9014 in position.

The needle emitters 9002 can function to deliver a culture medium, which can contain cells, to wells of the filter plate 9014. The base plate 9016 can have vacuum couplings 9020 extending from a bottom surface thereof. The vacuum couplings 9020 can generally be in the form of cylindrical tubes, and can allow vacuum pressure to be applied to corresponding wells of the filter plate 9014. Vacuum pressure can be routed through ports 9024a of the manifold 9024 to each valve 9011, and to the vacuum couplings 9020. The atomizer 9004 can atomize a permeabilizing solution and deliver it to cells within a well of the filter plate 9014. Systems, devices, and methods related to the delivery a permeabilizing solution onto a monolayer of cells are discussed in more detail below.

As shown in FIGS. 68-69, the precision rig system 9000 can include guide rail 9022 that can extend along an X axis. In some embodiments, the translational stage 9010 can be coupled to a guide rail 9022, which can allow the vacuum manifold assembly 9008 to be translated along the X axis. This can allow the vacuum manifold assembly 9008 to be moved relative to other components such as, e.g., the needle emitters 9002 and/or the atomizer 9004.

Figure 70:
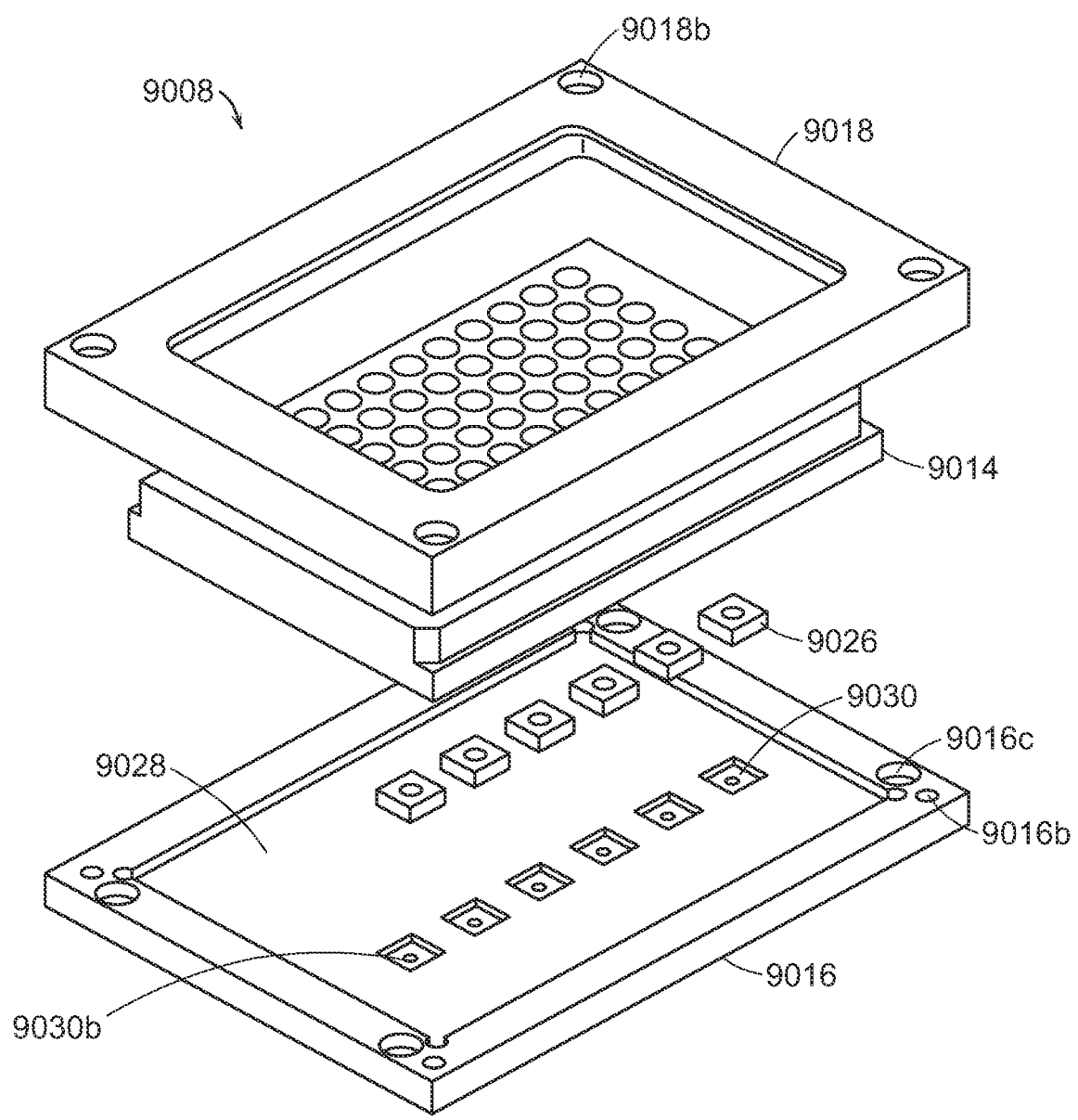
FIG. 70 is an exploded top perspective view of a vacuum manifold assembly of the delivery system shown in FIG. 68.
Figure 71:
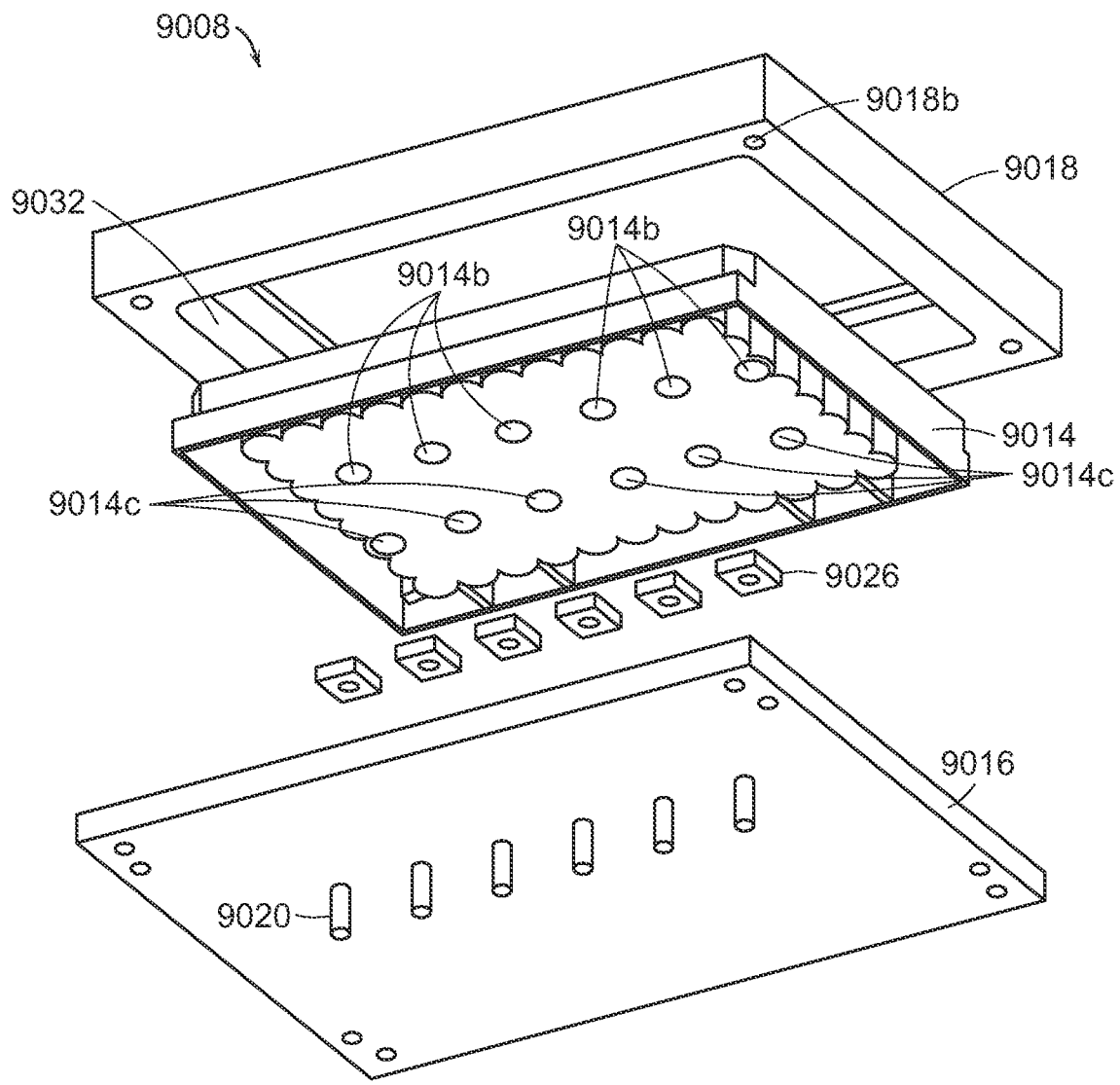
FIG. 71 is an exploded bottom perspective view of a vacuum manifold assembly of the delivery system shown in FIG. 68.
Figure 72:
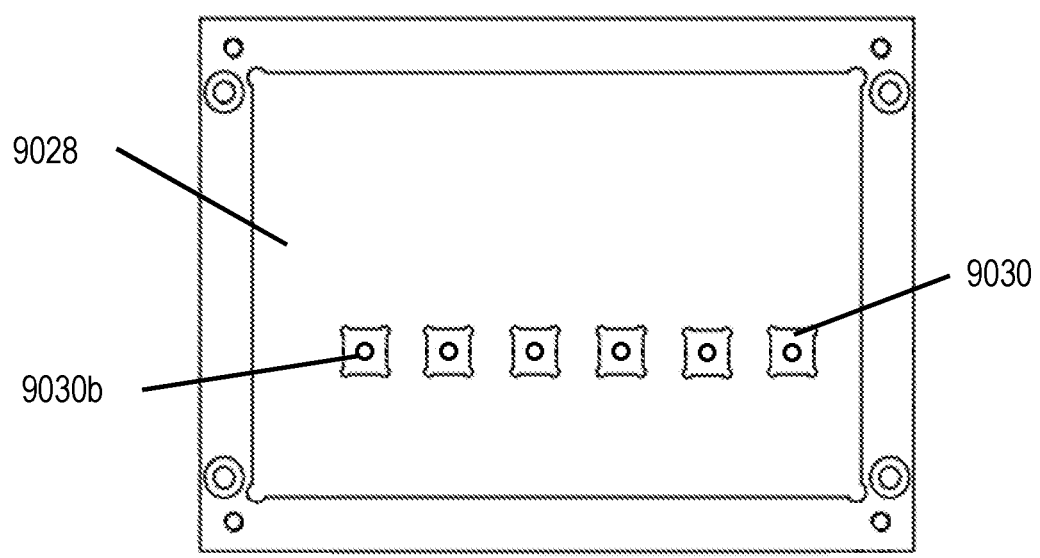
FIG. 72 show a top view of a base plate of the vacuum manifold assembly shown in FIG. 70.
Figure 73:
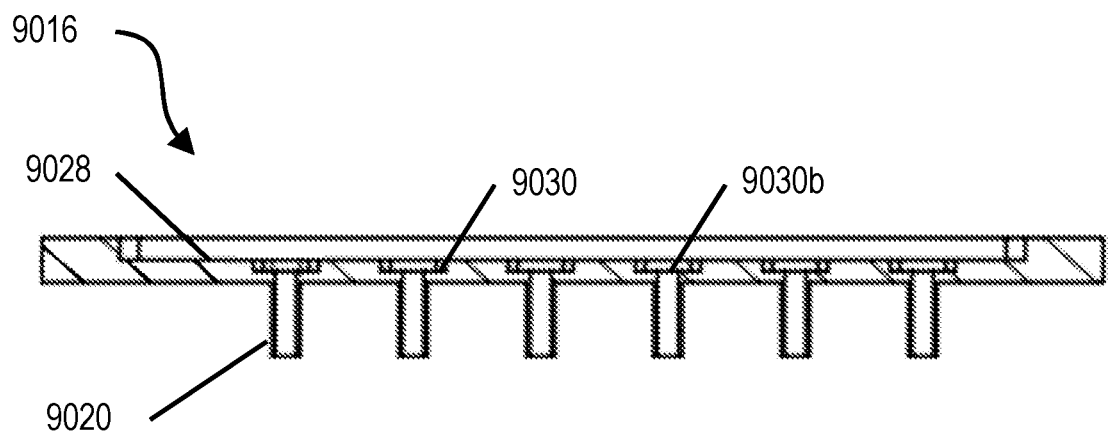
FIG. 73 is a side cross-sectional view of the base plate shown in FIG. 72.

FIGS. 70-71 show exploded views of the vacuum manifold assembly 9008. FIGS. 72-73 show a top view and a side cross-sectional view of the base plate 9016, respectively. As shown in FIGS. 70-71, the vacuum manifold assembly can include the filter plate 9014, the base plate 9016, gaskets 9026, and the top plate 9018 which can have coupling bores 9018b.

Referring to FIGS. 70-73, the base plate 9016 can include first and second sets coupling bores 9016b, 9016c. The first set of coupling bores 9016b can align with coupling bores 9018b in the top plate 9018 such that the base plate 9016 can be coupled to the top plate 9018 via a coupling element such as, e.g., a bolt or screw, that can extend through the coupling bores 9016b, 9018b. The coupling members 9012 can be coupled to the base plate 9016 via coupling elements that can extend into the second set of coupling 9016c.

The base plate 9016 can include a first recessed region 9028 where the filter plate 9014 can be received, or seated, as well as secondary recessed regions 9030 that can receive gaskets 9026. Each of the secondary recessed regions can have openings 9030b or passages that can couple with corresponding vacuum couplings 9020.

The filter plate 9014 can have wells that have active openings 9014b, in addition to having wells that have inactive openings 9014c. The active openings 9014b can be positioned over, and fluidly coupled to, openings 9030b in the base plate 9016. In other words, certain wells of the filter plate 9014 can be active, while other wells of the filter plate 9014 can be inactive.

The gaskets 9026 can have bores 9026b that can align with active openings 9014b of wells in the filter plate 9014 and with the openings 9030b in the base plate 9016. The gaskets 9026 can function to form seals between the base plate 9016 and the filter plate 9014, thereby isolating each active opening 9014b from other active openings 9014b, as well as from inactive openings 9014c, while allowing fluid communication between the active openings 9014b of the wells and corresponding vacuum couplings 9020.

Figure 74:
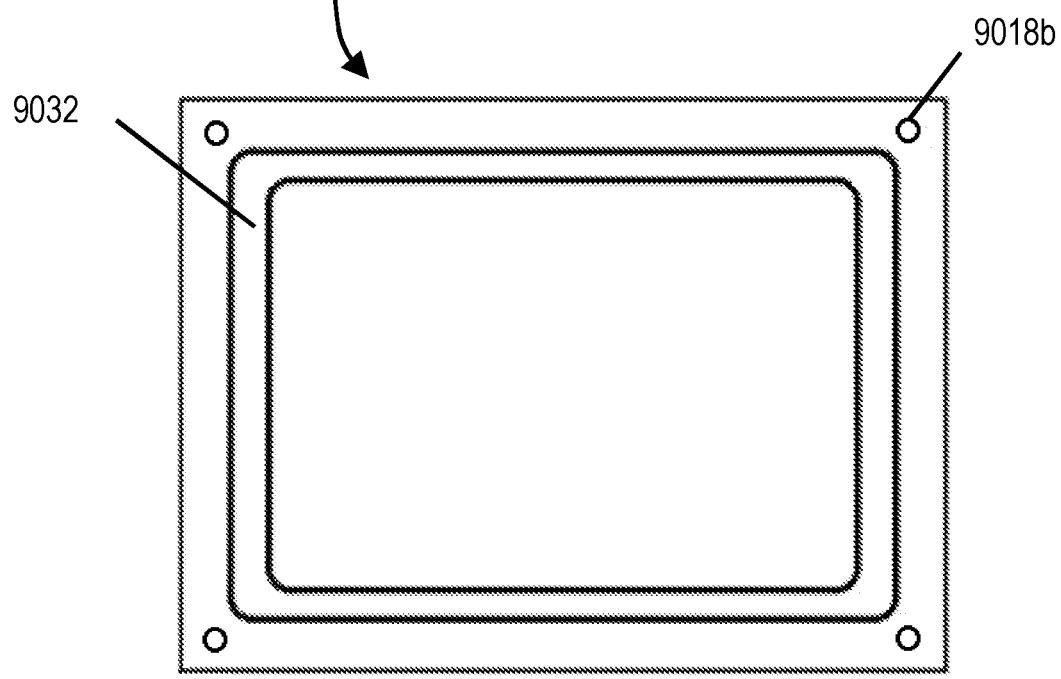
FIG. 74 is a bottom view of a top plate of the vacuum manifold assembly shown in FIG. 72.
Figure 75:
FIG. 75 is a side cross-sectional view of the top plate shown in FIG. 74.
Figure 76:
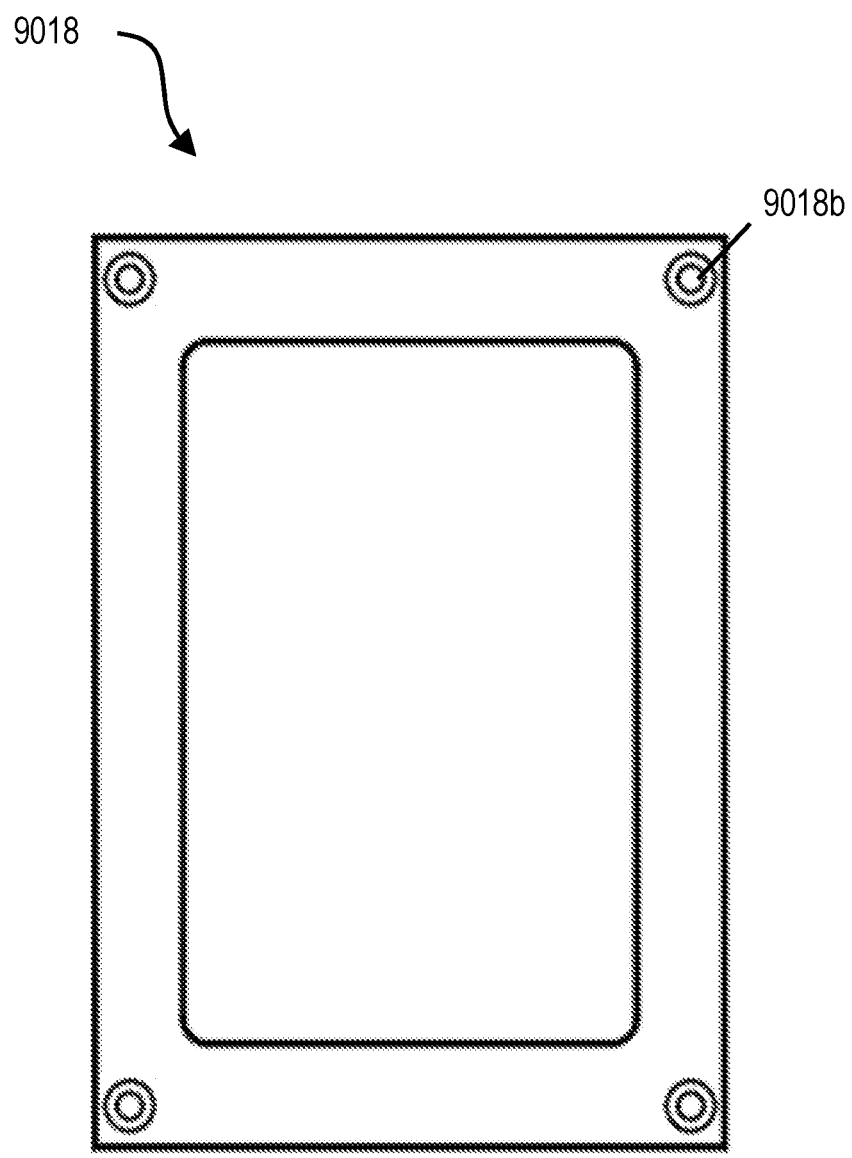
FIG. 76 is a top view of the top plate shown in FIG. 74.

FIGS. 74-76 show various view of the top plate 9018. As shown in FIGS. 70-71, and 9-11, the top plate 9018 can include a recessed region 9032 that can receive a portion of the filter plate 9014. When the vacuum manifold assembly 9008 is assembled, the gaskets 9026 can be seated in the secondary recessed regions 9030 of the base plate 9016, the filter plate 9014 can be received within the first recessed region 9028, and the top plate can be positioned over the filter plate 9014 and coupled to the base plate 9016 as described above.

In some embodiments, all of the wells of the filter plate 9014 can be coupled to different valves 9011, and to a manifold, such that all of the wells can be active.

Removal of Media and Creation of a Cell Monolayer Using a Vacuum

Figure 77:
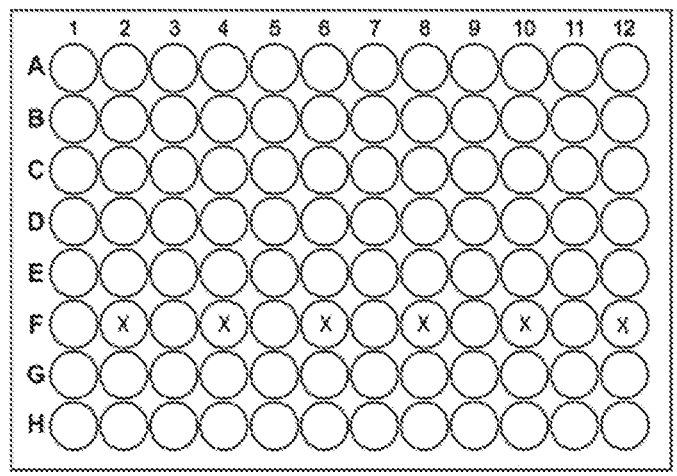
FIG. 77 is a top view of a well filter plate of the vacuum manifold assembly shown in FIG. 72.
Figure 78:
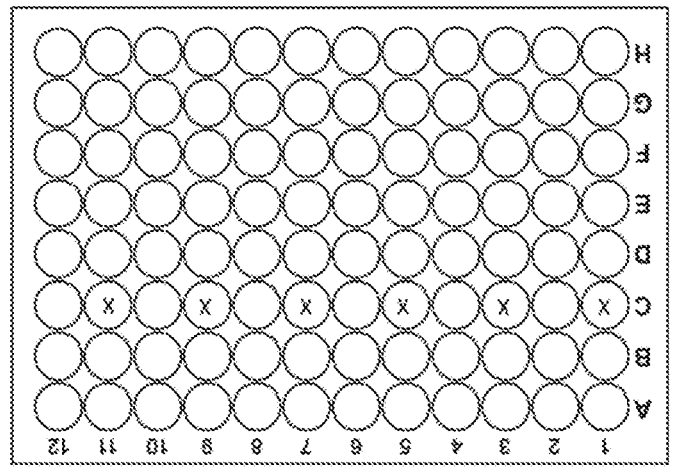
FIG. 78 is another top view of the well filter plate shown in FIG. 72, where the well filter plate has been rotated 180°.

The vacuum manifold system 9006 can remove a culture medium from between 1 and 12 wells of the filter plate 9014, with a total of 6 wells being addressable at a one time. FIGS. 77-78 show top views of the filter plate 9014. In FIG. 77 the filter plate 9014 is in a first position such that wells F2, F4, F6, F8, F10, and F12 can be active when the filter plate 9014 is received within the first recessed region 9028 of the base plate 9016. The filter plate 9014 can be rotated 180° such that wells C1, C3, C5, C7, C9, and C11 are active, as shown in FIG. 78.

Figure 79:
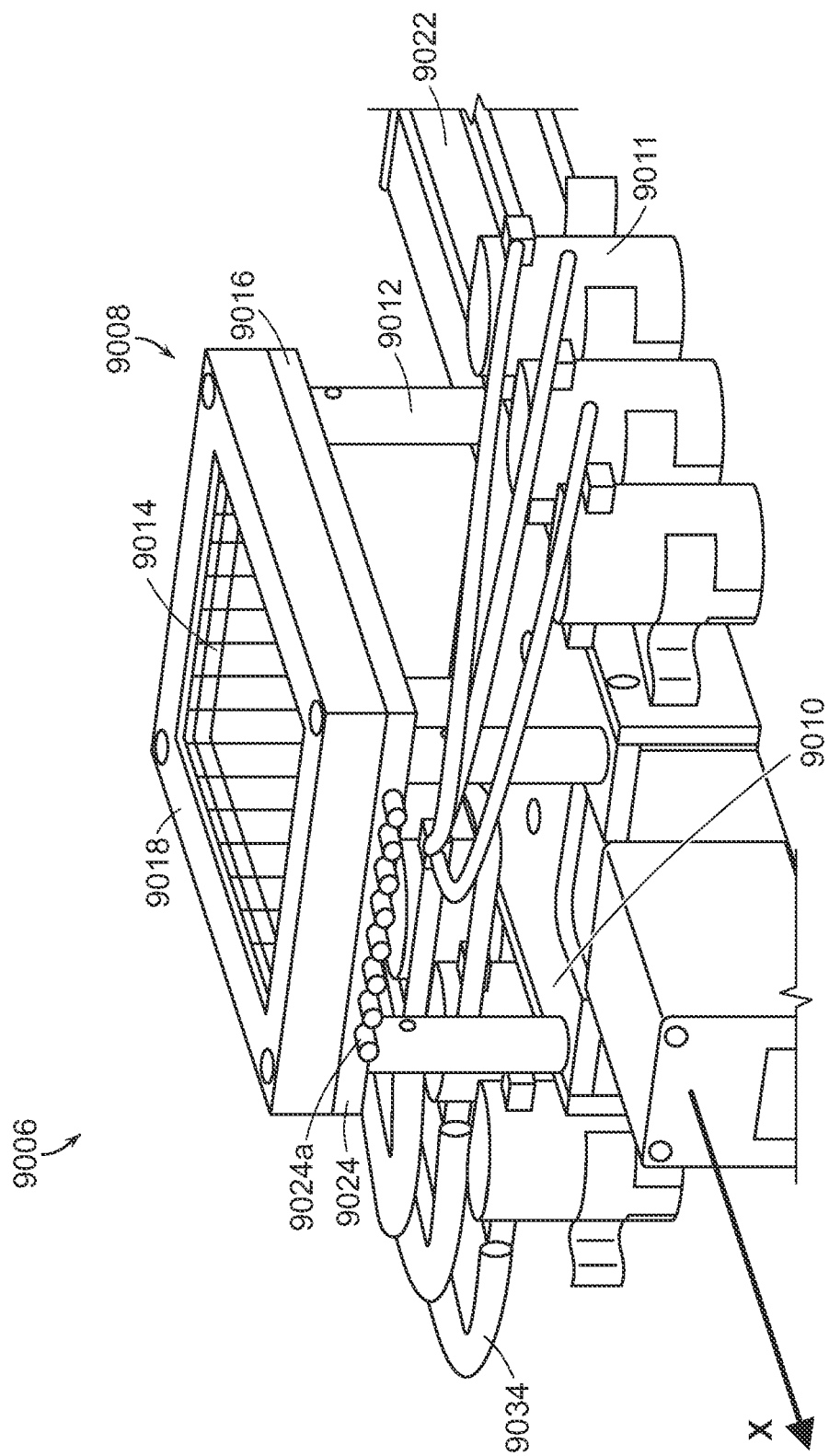
FIG. 79 is a front perspective view of a portion of the precision rig system shown in FIG. 67.
Figure 80:
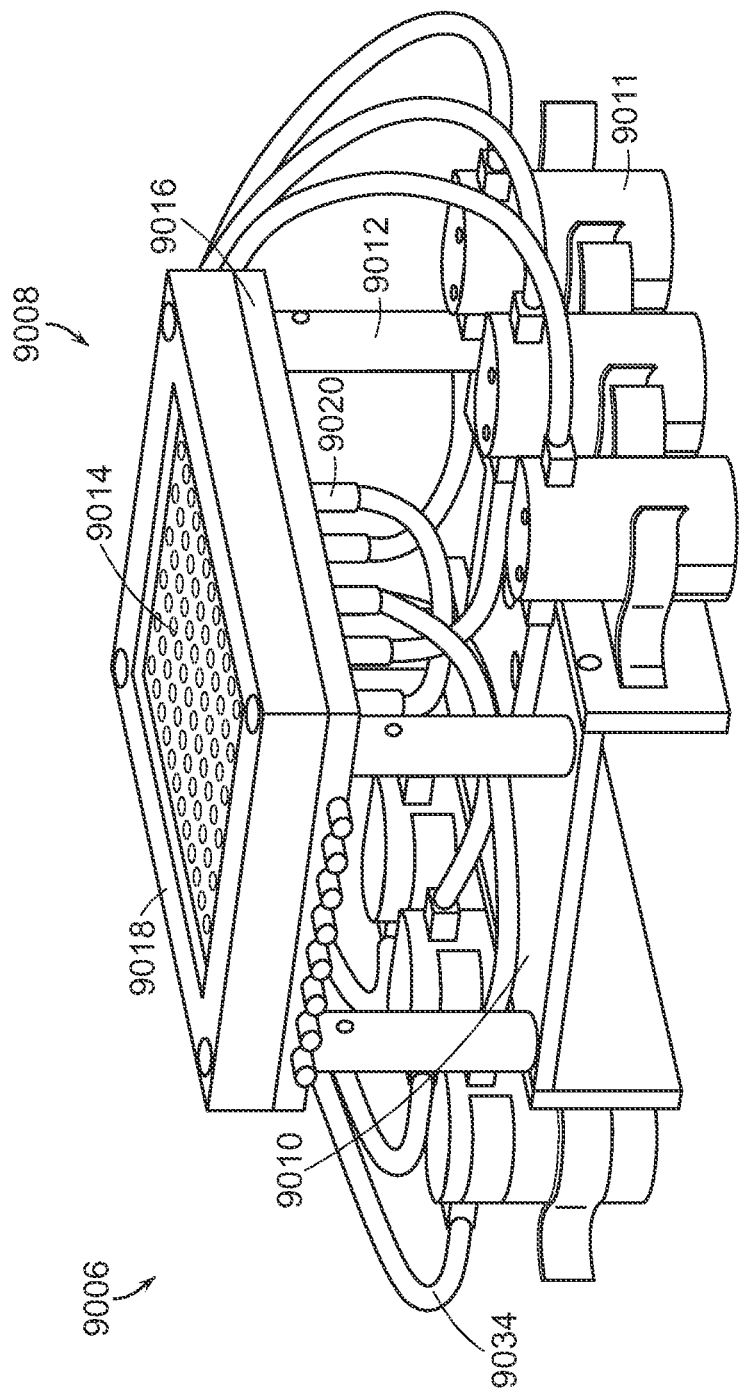
FIG. 80 is a back perspective view of a portion of the precision rig system shown in FIG. 67.
Figure 81:
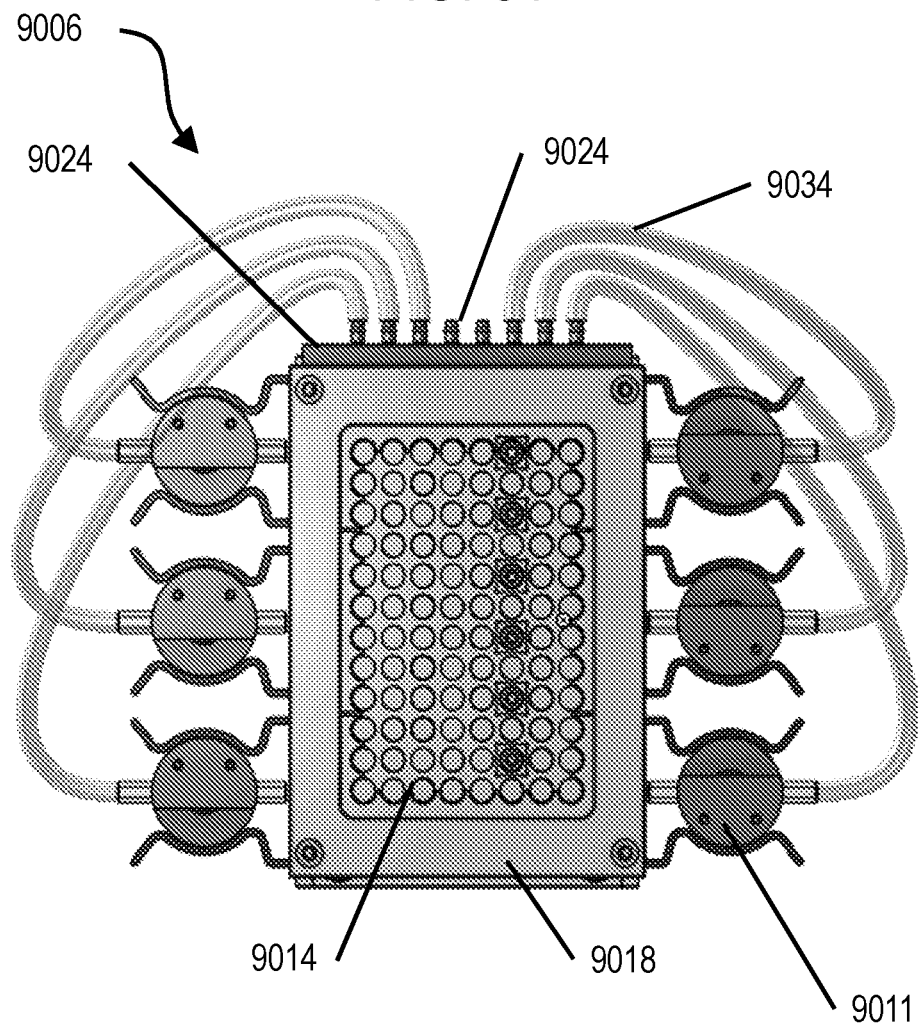
FIG. 81 is a top view of a portion of the precision rig system shown in FIG. 67.

As described above, vacuum pressure can be routed through a manifold 9024 to each valve 9011, and to the vacuum couplings 9020. FIGS. 79-81 show various views of a portion of the precision rig system 9000. As shown in FIGS. 79-81, the manifold can include 8 ports 9024a, and tubing 9034 can extend from 6 ports 9024a on the manifold to ports on the 6 valves 9011. The tubing can also connect a port on each valve 9011 to the vacuum couplings 9020 connected to the base plate 9016. A vacuum line (not shown) can be connected to 1 of the 2 remaining open ports 9024a on the manifold 9024, and the remaining port 9024a can be sealed.

The vacuum manifold system 9006 can be used to enable formation of a monolayer of suspension cells. As described above, needle emitters 9002 can deliver a culture medium, which can contain cells, to wells of the filter plate 9014. Vacuum pressure can be applied to the 8-channel manifold via the vacuum line. The valves 9011 can be opened or closed individually. Therefore, access to each active well can be controlled individually. When the valves 9011 are open, the applied vacuum pressure can be sufficient for effective removal of the culture medium in which the cells are suspended, without causing shear force that can lead to damage. The extracted medium can travel through the tubing 9034 and the valves 9011, through the manifold 9024, and out of the port 9024a where the vacuum line is attached. In this way, a cell monolayer can be formed and cell viability can be maintained. The formation of the cell monolayer can be achieved without damaging cells.

The vacuum manifold system 9006 has been built and tested. During testing a culture medium having cells was added to wells of a 96-well filter plate 9014. Vacuum pressure was applied via the manifold 9024. Vacuum pressure ranging from 10 bar to 100 mbar was applied to individual wells by opening the well's associated valve 9011.

At higher vacuum pressures, between −100 mBar and −75 mBar, the culture medium was removed far enough away from the well that when the filter plate 9014 was removed, the culture medium did not "wick" back into the well.

At lower pressures, between −50 to −10 mBar, the media stayed close enough to the well that when the filter plate 9014 was removed from the vacuum manifold assembly 9008, some of the medium "wicked" back in to the well. The amount of liquid that wicked back into the well was between approximately ~5-10 µl. This may not be a problem when the vacuum manifold assembly 9008 is part of the precision rig system 9000 as the well will be sprayed and have the culture medium replaced before the filter plate 9014 is removed from the manifold.

In some embodiments, filter paper, or other materials, can be used to prevent wicking. For example, filter paper can be placed between the gaskets 9026 and the base plate 9016 to prevent wicking of the media back into the well.

At pressures, as low as −10 mBar the culture medium was removed at a sedate, controlled rate which was gentler on the cells. This occurred both in presence and absence of cells. This can lead to better viability and recoverability of cells from the wells.

During testing, pulsing the valves 9011 on and off did not appear to aid in the removal of the culture medium.

Figure 82:
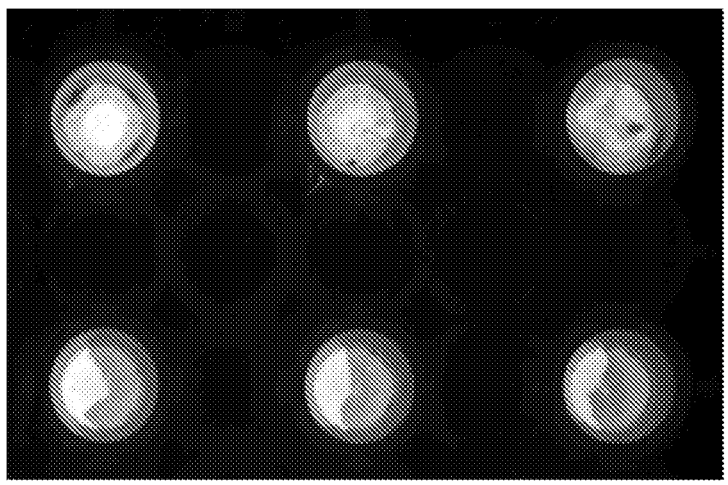
FIG. 82 is a distribution of GlowGerm particles that were observed following centrifugation and vacuum extraction.

Centrifugation was also investigated as a method of forming a cell monolayer. However, this was found to be ineffective as it formed an uneven layer of cells. FIG. 82 shows a distribution of GlowGerm particles that were observed following centrifugation and vacuum extraction. GlowGerm particles include. The top 3 images show the distribution of GlowGerm particles that resulted from using vacuum pressure to remove the culture medium, and the bottom 3 images show the distribution of GlowGerm particles that resulted from using centrifugation to remove the culture medium. The centrifuged samples were centrifuged at 350×g for 5 min, and the vacuum pressure samples were vacuumed for 15 sec at −800 mbar.

As shown in FIG. 82, the vacuum pressure samples show a more even distribution of GlowGerm particles, whereas an uneven, crescent shaped distribution of GlowGerm particles was observed following centrifugation.

Comparable results of mRNA uptake using vacuum and spin methods were achieved, even at −10 mBar. The GFP MFI was found to be greater in samples prepared by the vacuum vs spin (~300,000 vs 50,000 units). This indicates that more mRNA got into the positive cells.

The time needed to extract the culture medium from the wells is estimated to be between approximately 3 s and 20 s. However, the amount of time that it takes to remove the culture medium from the wells can be dependent on the amount of vacuum pressure that is applied. More work can be done to test the length of time required to remove the media at the lower vacuum pressures.

In some implementations, it is possible to be able to evacuate all wells at the same time at a lower pressure to remove residual media from the spouts (no plate on the manifold).]

The vacuum manifold system 9006 allows vacuum pressure to be applied to individual wells of a filter plate 9014. By applying a vacuum pressure to individual wells on a filter plate 9014, greater precision control of the vacuum pressure, and greater consistency of the vacuum pressure applied to each well, can be achieved. Existing vacuum manifolds apply a vacuum to an entire 96-well filter plate. During testing, lower vacuum pressures were effective in removal of the culture medium and creation of an even monolayer of cells within the well.

Example Positive Pressure System

Figure 83:
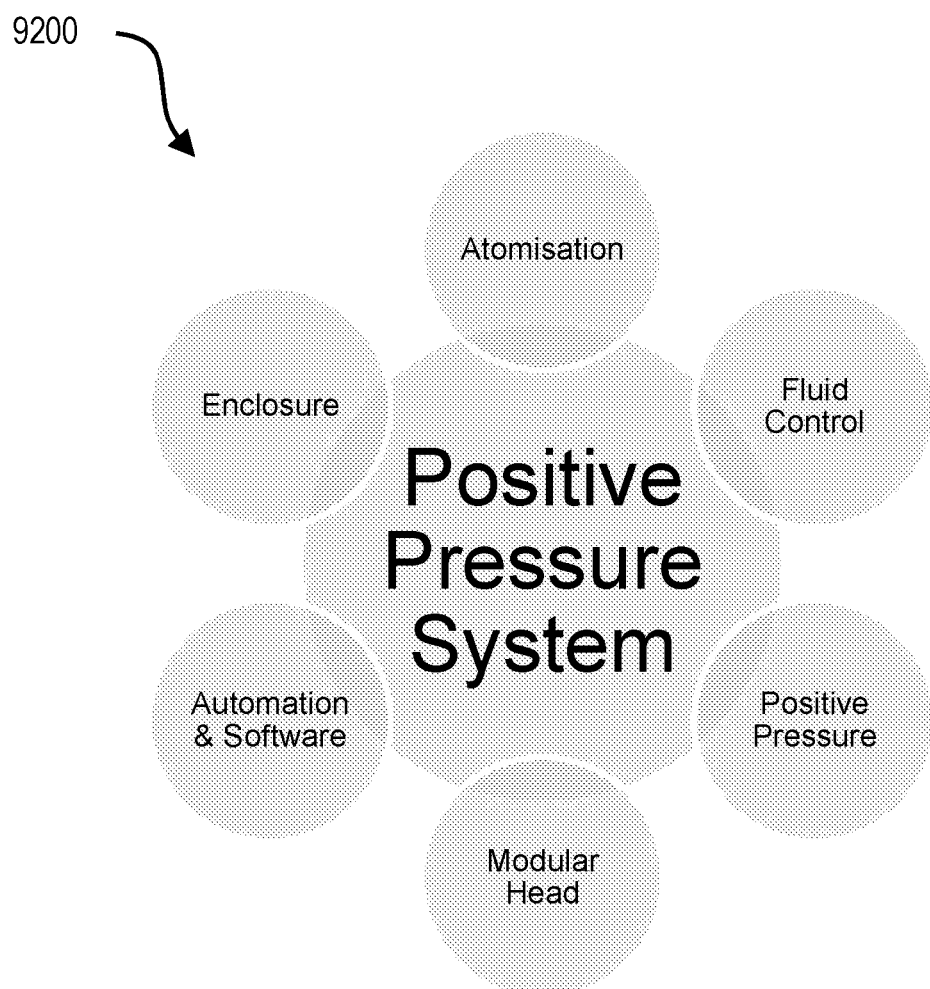
FIG. 83 is a diagram that illustrates six elements of a positive pressure delivery system.

FIG. 83 shows a diagram 9200 that illustrates six elements of an example positive pressure delivery system. The elements include: atomization; fluid control; positive pressure; a modular head; automation and software; and an enclosure.

The positive pressure delivery system can address the following areas of variability related delivering a payload to cells: monolayer formation; atomization; automation of the payload delivery; and temperature control of the solutions and the culture container.

In order to improve the consistency of the data and the delivery efficiency of payload delivery, the system removes certain known sources of variability from the process. The system can address: removal of culture medium and creation of a monolayer of cells using a positive pressure; atomization of the permeabilizing solution to produce monodispersed droplets; fluidic control of the solutions to enable automation; temperature control of the solution; mounting of a emitters, atomizers, nebulizers, and a temperature reservoir; automation and software design; enclosure for the instrument; and temperature control of a base plate configured to retain a well plate.

Figure 84:
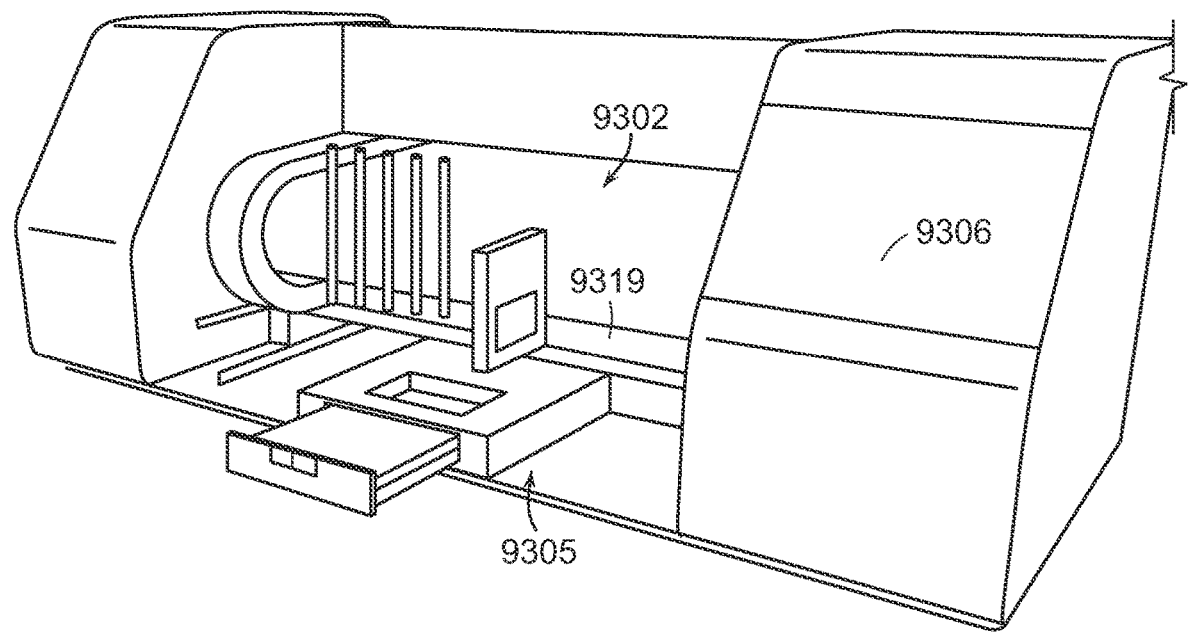
FIG. 84 is a perspective view of an embodiment of positive pressure delivery system that includes a manifold assembly, a mounting array having modular fluidic head modules, an X-Y actuator, and a control system.
Figure 85:
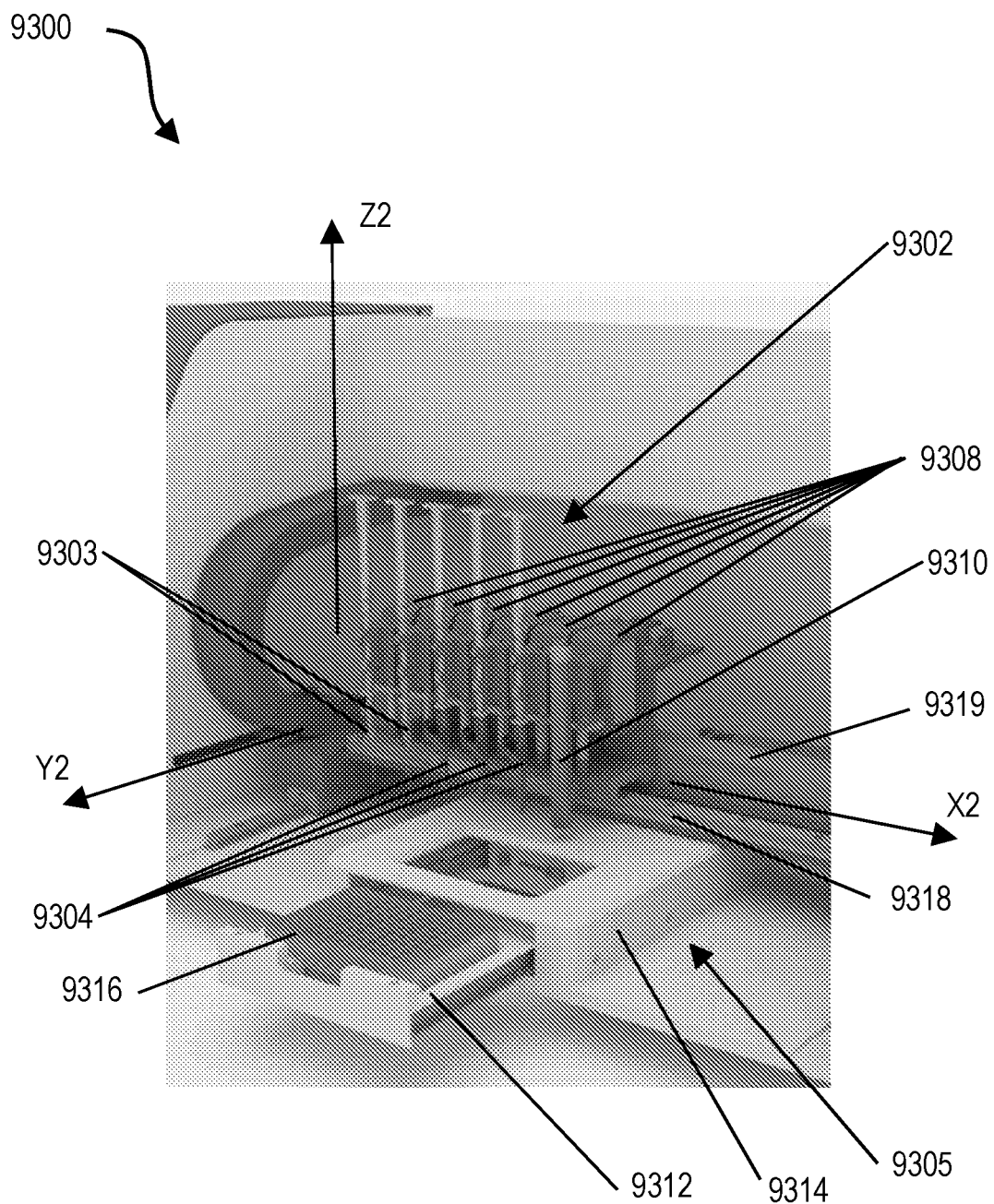
FIG. 85 is an enlarged view of a portion of the positive pressure delivery system shown in FIG. 84.

FIGS. 84-85 shows an exemplary embodiment of a positive pressure system 9300. This positive pressure system 9300 utilizes positive pressure as an alternative to vacuum for removal of the culture medium. Positive pressure provides greater accuracy and precision of delivery of low volumes (1 µl-100 µl) of fluid to force the culture medium from wells of a well plate. The positive pressure system 9300 can include a mounting array 9302, a manifold assembly 9305, and an actuation and control system 9306.

The manifold assembly 9305 can include a base 9312, also referred to as a plate holder, that can extend from a housing 9314 of the manifold assembly 9305. The base 9312 can be configured to receive filter plate 9316. As shown in the illustrated example, the filter plate 9316 can be a 96-well filter plate.

The mounting array 9302 can include fluidic head modules 9308 having needle emitters 9303, nebulizers 9304, and/or positive pressure nozzle assemblies 9310 attached thereto. The needle emitters 9303 can be configured to deliver a culture medium, which can contain cells, and a stop solution to wells of the filter plate 9316. The nebulizers 9304 can be configured to atomize a permeabilizing solution and deliver it to cells within wells of the filter plate 9316. The positive pressure nozzle assembly 9310 can be configured to apply a positive pressure to wells of the well filter plate 9316 to remove a liquid portion of the culture medium from the well, thereby creating a monolayer of cells. Systems, devices, and methods related to the delivery a permeabilizing solution onto a monolayer of cells are discussed in more detail below.

In some embodiments, the positive pressure system 9300 can include a guide rail 9318. In the illustrated example, the filter plate 9316 can be held stationary, and a position of the mounting array 9302 can be adjusted relative to the position of the filter plate 9316. For example, the mounting array 9302 can be coupled to a guide rail 9318, which can allow the mounting array 9302 to be translated along an axis X2 defined by the guide rail 9318. For example, an actuator 9319 can move the mounting array 9302 along the guide rail 9318. The guide rail 9318 can also be moved along an axis Y2, which can be perpendicular to the axis X2. The actuator 9319 can also move the mounting array 9302 along the axis Y2. Therefore, the mounting array 9302, including the needle emitters 9303, nebulizers 9304, and/or positive pressure nozzle assemblies 9310 can be selectively positioned above wells of the filter plate 9316 when the filter plate 9316 is positioned within the housing 9314.

As an example, a user can insert the filter plate 9316 into the base 9312, which can then be positioned within the housing 9314. The filter plate 9316 can be held stationary after it is received within the housing 9314. The filter plate 9316 can be selectively addressed by needle emitters 9303, nebulizers 9304, and/or positive pressure nozzle assemblies 9310 coupled to fluidic head modules 9308 of the mounting array 9302. In the illustrated example, the mounting array 9302 includes six fluidic head modules 9308. Two fluidic head modules 9308 include needle emitters 9303, three fluidic head modules 9308 include nebulizers 9304, and one fluidic head module 9308 includes a positive pressure nozzle assembly 9310. The mounting array 9302 can be moved along the axes X2, Y2, such that each of the fluidic head modules 9308, including the needle emitters 9303, nebulizers 9304, and/or positive pressure nozzle assemblies 9310, can address any location on the filter plate 9316.

In some embodiments, each of the individual fluidic head modules 9308 can have the capability to move up and down parallel to an axis Z2, which allows for independent actuation of the fluidic head modules 9308. In some embodiments, movement of the fluidic head modules 9308 and actuation of needle emitters 9303, nebulizers 9304, and/or positive pressure nozzle assemblies 9310, are controlled independently. The movement of one or more of the fluidic head modules 9308, and actuation of needle emitters 9303, nebulizers 9304, and/or positive pressure nozzle assemblies 9310 attached thereto, can occur contemporaneously. In some implementations, the fluidic head modules 9308 activate the needle emitters 9303, nebulizers 9304, and/or positive pressure nozzle assemblies 9310 when they move toward the filter plate 9316. The fluidic head modules 9308 can accommodate a variety of fluid dispensing assemblies, including but not limited to, needle assemblies, Ari Mist nebulizers, and positive pressure nozzle assemblies, as shown in FIGS. 84-85.

The actuation and control system (ACS) 9306 can include at least one data processor, and can control movement of the mounting array 9302 and/or the fluidic head modules 9308. The ACS 9306 can also control actuation of the needle emitters 9303, nebulizers 9304, and/or positive pressure nozzle assemblies 9310 attached to the fluidic head modules 9308. For example, the ACS 9306 can include software, having instructions that can be interpreted by the data processor of the ACS 9306. The data processor can receive the instructions, process the instructions, and execute the instructions. For example, the data processor can deliver control signals to actuators and/or motors of the ACS 9306 to adjust a position of the mounting array 9302, and/or to actuate needle emitters 9303, nebulizers 9304, and/or positive pressure nozzle assemblies 9310.

Example Fluidic Head Module

As described above, the fluidic head modules 9308 provide mounting points for various fluidic dispensing assemblies (e.g., the needle emitters 9303, nebulizers 9304, and/or positive pressure nozzle assemblies 9310) such that they can be coupled to the mounting array 9302. The fluidic head modules 9308 also provide actuation along the axis Z2 such that the dispensing assemblies can be selectively actuated.

FIG. 86 shows an enlarged view of a fluidic head module 9308. The fluidic head module 9308 can have a frame 9350 that is includes a series of machined aluminum pieces, which create the frame 9350. For example, the frame 9350 can include a base plate 9352, a back plate 9354, and upper and lower mounting elements 9356, 9358. The machined aluminum pieces can allow for high tolerance locating of the fluidic head module 9308.

The fluidic head module 9308 can include a shaft 9360 that extends between the base plate 9352 and the upper mounting element 9356. The shaft 9360 can extend through an opening in the lower mounting element 9358. A guide 9362 such as, e.g., a ball spline, can be mounted on the shaft 9360 and coupled to the lower mounting element 9358. The guide 9362 facilitates vertical motion of the fluidic dispensing assemblies (e.g. the needle emitters 9303, nebulizers 9304, and/or positive pressure nozzle assemblies 9310) along axis Z2. For example, a pneumatic actuator 9364 positioned between the upper and lower mounting elements 9356, 9358 can drive the lower mounting element 9358 up and down along the shaft 9360. The pneumatic actuator 9364 can drive associated pneumatic fittings as well as two proximity sensors. For example, the sensors can be embedded in a wall of the cylinders. FIGS. 87, 88, and 89 the fluidic head module 9308 with a needle emitter 9303, a nebulizer assembly 9301 including a nebulizer 9304, and a positive pressure nozzle assemblies 9310 mounted thereon, respectively.

Removal of Media and Creation of a Cell Monolayer Using Positive Pressure

Figure 91:
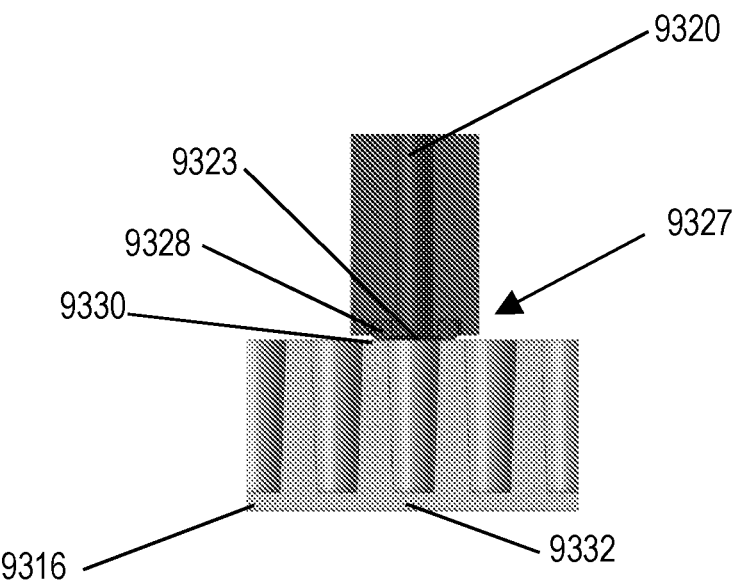
FIG. 91 is an enlarged view of a portion of the positive pressure nozzle shown in FIG. 90. The positive pressure nozzle is shown to form a seal with the well.

As described above, positive pressure nozzles can be configured to apply a positive pressure to wells of a well filter plate to remove a culture medium and create a monolayer of cells. FIGS. 90-91 show magnified views of the positive pressure nozzle assembly 9310 used with the positive pressure system 9300 shown in FIGS. 84-85. In the illustrated example, the nozzle assembly 9310 includes an internal lumen, which can be formed from a tube 9320, positioned within a housing 9322. The tube 9320 can have openings 9321, 9323 adjacent first and second ends 9326, 9327 of the positive pressure nozzle assembly 9310. In some embodiments, the housing 9322 can provide structural stability for the tube 9320.

As shown in FIG. 90, the nozzle assembly 9310 includes a coupling element 9324 coupled to a first end 9326 of the tube 9320. The coupling element 9324 can be configured to form a seal with the opening 9321 adjacent to the first end 9326 of the tube 9320 such that pressurized vapor (e.g., air) can be delivered to a well 9316a of the filter plate 9316. For example, compressed air can be delivered to an internal lumen 9325 of the coupling element 9324 from a compressor. The internal lumen 9325 of the coupling element 9324 can be in fluid communication with the lumen of the tube 9320 via the opening 9321, the lumen of the tube 9320 can be in fluid communication with the well 9316a via the opening 9323. The compressed air can increase a pressure within the tube 9320, thereby increasing pressure within the well 9316*a*. Accordingly, the positive pressure nozzle assembly 9310 controls the flow and pressure of compressed air.

As shown in FIG. 91, the second end 9327 of the tube 9320 includes a sealing element 9328 positioned adjacent to the opening 9323, outside of the tube 9320. The sealing element 9328 is configured to encompass the well 9316*a* and form a seal with an upper surface 9330 of the filter plate 9316, thereby isolating the well 9316*a*. The sealing element 9328 is configured to prevent air from leaking between the second end 9327 of the nozzle assembly 9310 and the upper surface 9330 of the filter plate 9316, thereby improving accuracy and precision of control of the pressure within the well 9316*a*. For example, when the nozzle assembly 9310 is engaged with the filter plate 9316, the application of compressed air will force liquid to flow through a filter base 9332 of the individual well.

Figure 92:
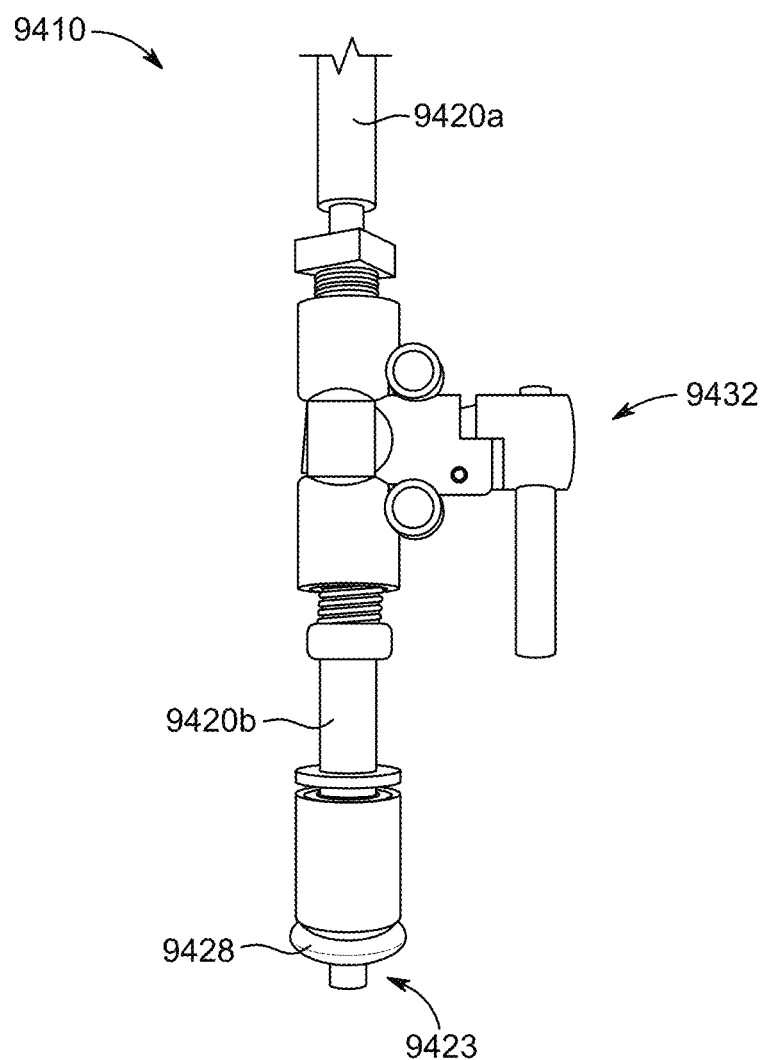
FIG. 92 is an exemplary embodiment of a portion of a nozzle assembly that includes a valve to control delivery of air to a well of a filter plate.

In some embodiments, a positive pressure nozzle assembly can include a valve positioned along its length. The valve can function as a manual control to control a pressure of air delivered to a well of a filter plate. FIG. 92 shows an example of a portion of a nozzle assembly 9410 that includes a valve 9432. In the illustrated example, the nozzle assembly 9410 includes a first tube portion 9420*a* and a second tube portion 9420*b* that are coupled to the valve 9432. The second tube portion 9420*b* can include a sealing element positioned adjacent to a distal opening 9423 of the second tube portion 9420*b*. The nozzle can generally function similarly to the nozzle assembly 9310, described above with regard to FIGS. 90-91. For example, the distal end of the second tube portion can be positioned adjacent to an upper surface of a filter plate such that the sealing element 9428 encompasses an opening of the well, and forms a seal with the upper surface of the filter plate. Compressed air can be delivered to an internal lumen of the first tube portion 9420*a*. When the valve is in an open position, the air can travel through the valve 9432, through the second tube portion 9420*b*, and into the well of the filter plate. Alternatively, the valve 9432 can be adjusted to an off position to prevent air flow to the well. The valve 9432 can be adjusted to control air pressure within the well.

Atomization of the Delivery Solution to Produce Monodispersed Droplets

Figure 93:
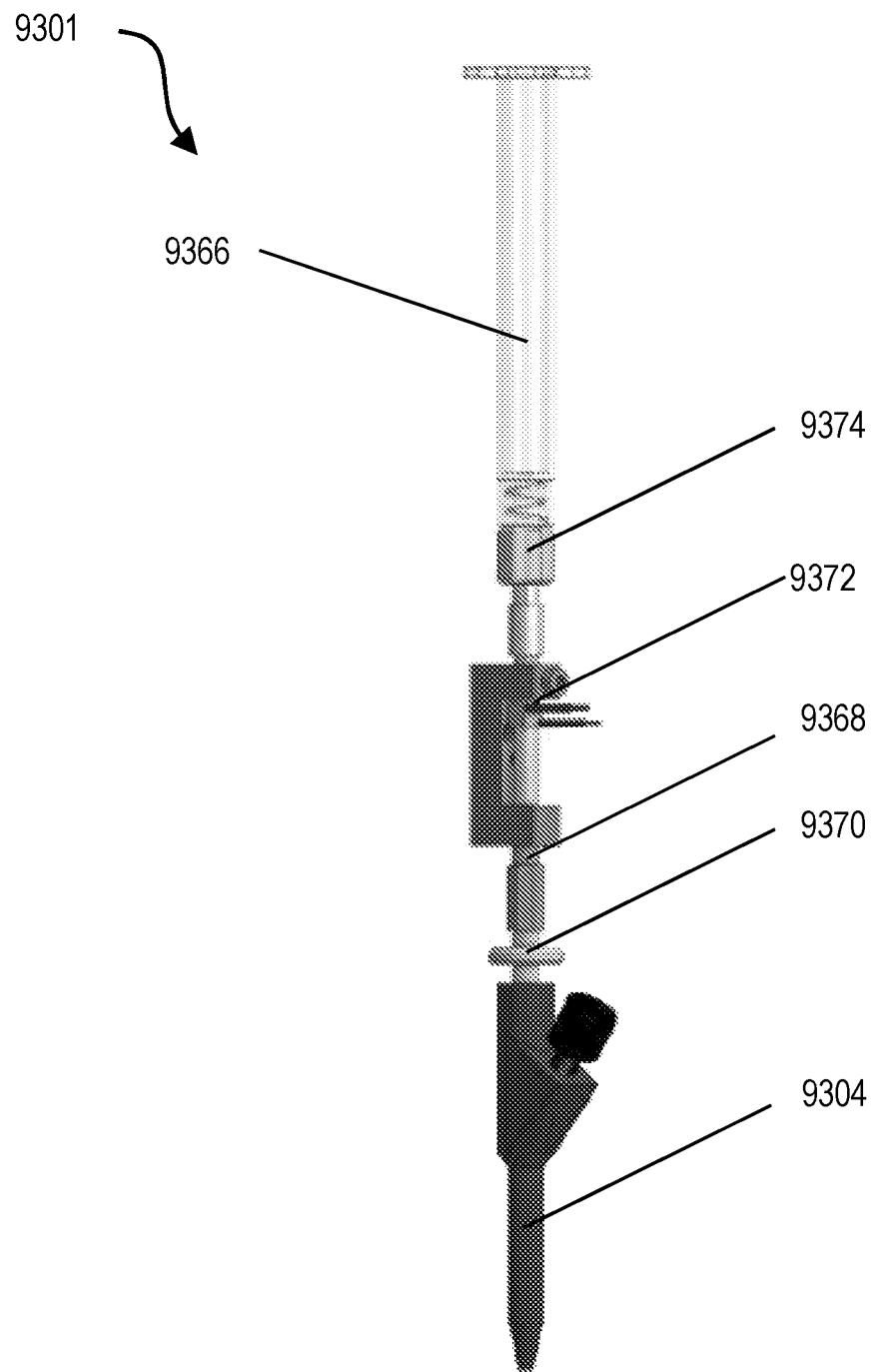
FIG. 93 is an embodiment of a nebulizer assembly used for optimization of atomization of a delivery solution. The nebulizer assembly includes a syringe, a micro valve, and a nebulizer. The nebulizer is be coupled to the micro valve via a coupling element (e.g., a precolumn coupler). The micro valve is retained within, and/or coupled to, a valve holder, which is be coupled to the syringe via an adapter. The nebulizer assembly enables high accuracy and precision of delivery of payload solutions to the nebulizer.

FIG. 93 shown an enlarged view of the nebulizer assembly 9301 that can be coupled to a fluidic head module 9308. In the illustrated example, the nebulizer assembly 9301 includes a syringe 9366, a micro valve 9368, and a nebulizer 9304. The nebulizer 9304 can be coupled to the micro valve 9368 via a coupling element 9370 (e.g., a precolumn coupler). The micro valve 9368 can be retained within, and/or coupled to, a valve holder 9372, which can be coupled to the syringe 9366 via an adapter 9374. The nebulizer assembly 9301 enables high accuracy and precision of delivery of payload solutions to the nebulizer 9304.

There are a number of different ways in which a permeabilizing solution can be delivered onto a monolayer of cells. For example, the permeabilizing solution can be atomized using ultrasonication or it can be nebulized using a nebulizer.

Both ultrasonication and nebulization were tested as delivery methods. A total of 4 different spray heads were tested.

The following parameters were assessed for each spray head: Air pressure, flow rate, distance, volume delivered, cell number, time of spray, frequency of ultrasonic probe, and power of ultrasonic probe.

The effect on the character of the spray was assessed using high-speed camera recording. The force experienced by the cells was determined by force sensor analysis. The volume delivered into the well was assessed using a colorimetric assay.

Ultrasonication tests were performed at 60 kHz, 130 kHz, and 180 kHz. Liquid can be driven to an ultrasonic nozzle by a pumping system, and it can be atomized into a fine mist spray using high frequency sound vibrations.

Piezoelectric transducers were used to electrical input into mechanical energy in the form of vibrations, which created capillary waves in the liquid when introduced into the nozzle, and resulted in atomization of the liquid. Each ultrasonic probe worked at a given resonant frequency. The operating frequency can determine the size of the liquid droplets generated. The size of the droplets can also be affected to a lesser extent by the power at which the ultrasonic probe is operated. An ancillary air stream can be used to help control and shape the spray.

Nebulization tests were performed using an Ari Mist nebulizer 9304 (FIG. 125). As shown in FIG. 125, the nebulizer 9304 includes a connection 9307 for liquid and a connection 9309 for air. The Ari Mist nebulizer operates on compressed gases and requires a pump to supply the sample solution. This atomizer has two channels, one for the gas (air) and the other one for the liquid to be nebulized, which run along parallel paths. Both paths end at the tip of the nebulizer with an orifice for the gas and an exit for the liquid. The gas flow can draw the liquid into the gas stream. The impact with the gas molecules can break the liquid into small droplets, resulting in nebulization.

Figure 94:
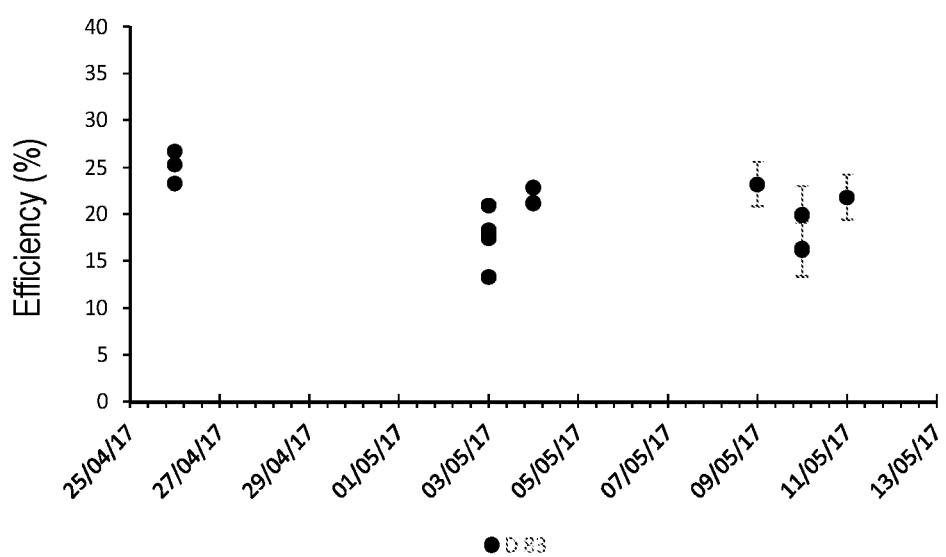
FIG. 94 is a plot showing efficiencies of payload delivery for and ultrasonic emitter operating at 180 kHz.

The ultrasonic emitter operating at 180 kHz proved to be more effective compared to the 130 kHz, 60 kHz ultrasonic heads and the Ari Mist nebuliser in delivering payloads to T-cells. FIG. 94 shows a series of results characterizing the efficiency of payload delivery for the ultrasonic emitter operating at 180 kHz. The test results indicated that payloads had been delivered to T-cells successfully, at an efficiency of approximately 15-25%, with high level of consistency between replicates (±1%). The health of the cells was maintained following delivery (85% viability).

The results indicate that the ultrasonic spray emitter generates a monodispersed spray which results in even deposition of the delivery solution and payload onto cells. Additionally reducing the volume delivered and reducing the ethanol concentration improved delivery efficiency with the ultrasonic spray head.

Figure 95:
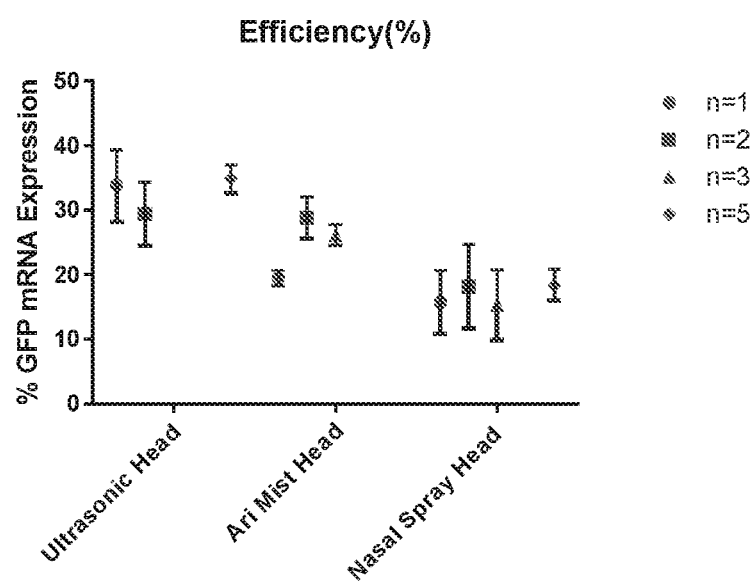
FIG. 95 is a plot showing a series of data characterizing GFP uptake for an ultrasonic emitter, an Ari Mist nebulizer, and a MAD nasal spray emitter. The data demonstrates GFP delivery efficiency of 32.7%, 24.8% and 16.9% with the ultrasonic emitter (180 Hz), Ari Mist nebulizer, and the MAD nasal spray emitter, respectively.

FIG. 95 shows another series of results characterizing GFP uptake for the ultrasonic emitter, the Ari Mist nebulizer, and a MAD nasal spray emitter. The MAD Nasal™ Intranasal Mucosal Atomization Device (Teleflex 3015 Carrington Mill Blvd, Morrisville, NC 27560) was used to atomize delivery solution containing payload. Briefly, 7 μl of delivery solution was pipetted directly into the nasal head. The spray head was directly connected to an air pressure source via a luer lock connection. 1.5 bar air pressure was supplied to the spray head over 330 ms to generate the spray. The ultrasonic spray emitter operating at 180 kHz is more efficient at delivering mRNA to T cells based on current data. A 32.7% GFP uptake was obtained with the ultrasonic spray emitter compared to 24.8% with the Ari Mist nebulizer (e.g., nebulizer 9304). Both ultrasonic emitter and Ari Mist nebulizer resulted in higher GFP mRNA delivery compared to the NAD nasal spray emitter which resulted in 16.9% delivery efficiency.

Figure 96:
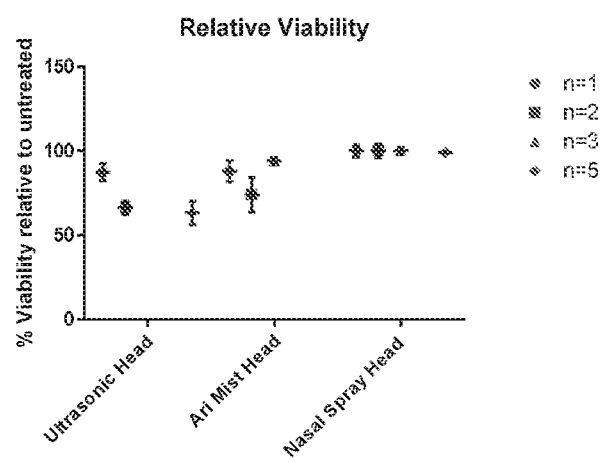
FIG. 96 is a plot showing a series of data characterizing cell viability for the ultrasonic emitter, the Ari Mist nebulizer, and the MAD nasal spray emitter. The data demonstrates relative cell viability of 72.3%, 85.3% and 99.7% with the ultrasonic (180 Hz) nebulizer, Ari Mist nebulizer and the MAD nasal nebulizer, respectively. The data represent a minimum of 3 technical repeats for each spray head tested.

FIG. 96 shows a results characterizing cell viability for the ultrasonic emitter, the Ari Mist nebulizer, and the MAD nasal spray emitter. The results represent a minimum of three technical repeats for each spray head (e.g., the ultrasonic emitter, the Ari Mist nebulizer, and the MAD nasal spray emitter) that was tested. The Ari Mist nebulizer resulted in better cell viability at 85.3% relative to untreated cells, compared to the ultrasonic head which had an average of 72.3% cell viability relative to untreated cells. The MAD nasal spray emitter resulted in the highest cell viability with 99.7% cell viability relative to untreated cells.

Enclosed Atomization

During delivery of a solution using e.g., an atomizer, nebulizer, and/or ultrasonic emitter, a fine aerosol is generated. In some cases, the fine aerosol may contaminate adjacent wells of a multi-well filter plate. In some embodiments, a distal end portion of an atomizer, nebulizer, and/or ultrasonic emitter can be enclosed, which may prevent contamination of adjacent wells of the filter plate.

Three rig platforms were built: rig 1 (R1), rig 3 (R3) and rig 4 (R4) (FIGS. 126-128). Table below shows several feature of the rigs.

As illustrated in FIG. 126, R1 11700 includes a solution reservoir 9810 (e.g., an Elveflow sample reservoir) configured to provide a permeabilizing solution to an Ari Mist nebulizer 9804, and a pinch valve 9808 (e.g., an Elveflow pinch valve) configured to control delivery of the permeabilizing solution to the nebulizer 9804. The nebulizer 9304 can be mounted on a spray head mount 11714 which can be configured to retain the nebulizer 9304 and facilitate alignment of the spray head. The pinch valve 9808 is configured to enable fluidic control of a payload solution to the nebulizer 9304. The spray head mount 11714 can be mounted on a guide 11717 configured to facilitate vertical motion of the spray head mount 11714 along a vertical axis Z3. The spray head mount 11714, including the nebulizer 9804, can be mounted above a plate holder 11718 that can be configured to receive a filter plate 11716.

As illustrated in FIG. 127, R3 11800 includes a nebulizer assembly 9301 having a sample reservoir syringe 9366 coupled to an Ari Mist nebulizer 9304 via a micro valve 9368 configured to control delivery of a permeabilizing solution to the nebulizer 9304. The nebulizer assembly 9301 can be mounted to a fluidic head module 9308. The fluidic head module 9308 can be mounted on a guide 11717 configured to facilitate vertical motion of the fluidic head module 9308 along a vertical axis.

As illustrated in FIG. 128, R4 9800 includes a LB-100 atomizer (not shown) coupled to a pinch valve 9808 (e.g., an Elveflow pinch valve) configured to control delivery of the permeabilizing solution from a sample reservoir (e.g., Elveflow sample reservoir, not shown) to the atomizer. The atomizer can be positioned within a collar 9816 of a spray head mount 9814 which can be configured to retain the atomizer and facilitate alignment of the spray head. The collar 9816, including the atomizer, can be positioned over an opening of a stirred cell system 11900 such that the atomizer can deliver a payload to cells within the stirred cell system 11900.

TABLE

Features of Rigs.

| | Spray Head | Spray head holder | Valve controlling payload delivery | Sample reservoir |
|---|---|---|---|---|
| Rig 1 | Ari Mist | Avectas holder | Pinch valve | Elveflow (1.5 ml Eppendorf) |

TABLE-continued

Features of Rigs.

| | Spray Head | Spray head holder | Valve controlling payload delivery | Sample reservoir |
|---|---|---|---|---|
| Rig 3 | Ari Mist | Spray head mounted on a fluidic head module | Micro valve | BD syringe |
| Rig 4 | LB-100 | Avectas holder | Pinch valve | Elveflow (50 ml tube) |

Below is a detailed description of the Rig features which enable fine control of the spray parameters.

In some embodiments (e.g., R1 and R4), fluidic control of the delivery solution containing the payload can be achieved using the Elveflow pinch valve. The fluidic control can be achieved by a fluid control system that can apply a constant pressure to an Elveflow fluidic reservoir to drive the fluid through a pinch valve 9808. A volume of fluid that can be dispensed can be controlled by at least: an amount of pressure applied; a length of time the valve 9808 is open, and/or a diameter of the tubing used. The valve 9808 can be activated by a metal-oxide-semiconductor field-effect transistor (MOS FET) which can be controlled by a microprocessor.

The Elveflow-Pinch valve 9808 described above had several limitations. For example, re-calibration of the R1 and R4 was required every time the system was re-loaded. There was poor accuracy and precision in dispensing volumes lower than 5 µl. For low volumes (<5 µl) the relative standard deviation was approximately 9% over repeated dispenses (10). To address the observed limitations, a R3 was developed. As described above, R4 includes the microvalve 9368 rather than the pinch valve 9808. Fluidic control of the delivery solution containing the payload can be achieved using the micro valve 9368. R3, which uses the micro valve 9368 had greater accuracy and precision when delivering volumes in the range of 1 µl to 100 µl.

Fluidic control of air delivered to the nebulizers/atomizers can be achieved using a solenoid valve. In some embodiments, electronics can be used to control actuation of the nebulizers/atomizers. To enable electronically controlled spray actuation, a system was designed using a microprocessor based development board to allow easy development of time controlled sequences. The development board used the microprocessor PIC16F1619. The spray actuation time and fluid delivery time can be manipulated through the development board's interface software. The microprocessor development board enables pulsing of the nebulizer/atomizer spray. This system was then upgraded to include the high speed and repeatable PLC (programmable logic controller) technology to better align with industry standards and to serve as proof of concept for the automated delivery technology (which is based on ultra-high-speed PLC technology). The Rig controller consisted of a PLC with a Gyger controller and a program which facilitates communication between the two pieces of hardware. There is operator interaction to the hardware via a momentary push button.

The Ari Mist nebulizer 9304 parallel path design inherently produces a spray which is off center from a tip of nebulizer 9304. Using a custom spray head holder equipped with a goniometer, the alignment of the spray head can be adjusted.

Several methods for delivering a solution using an enclosed emitter were tested. The results of GFP uptake using an enclosed emitter were compared to the results of GFP uptake using an unenclosed emitter.

Method 1: Using a Collar to Enclose the Emitter

Figure 97:
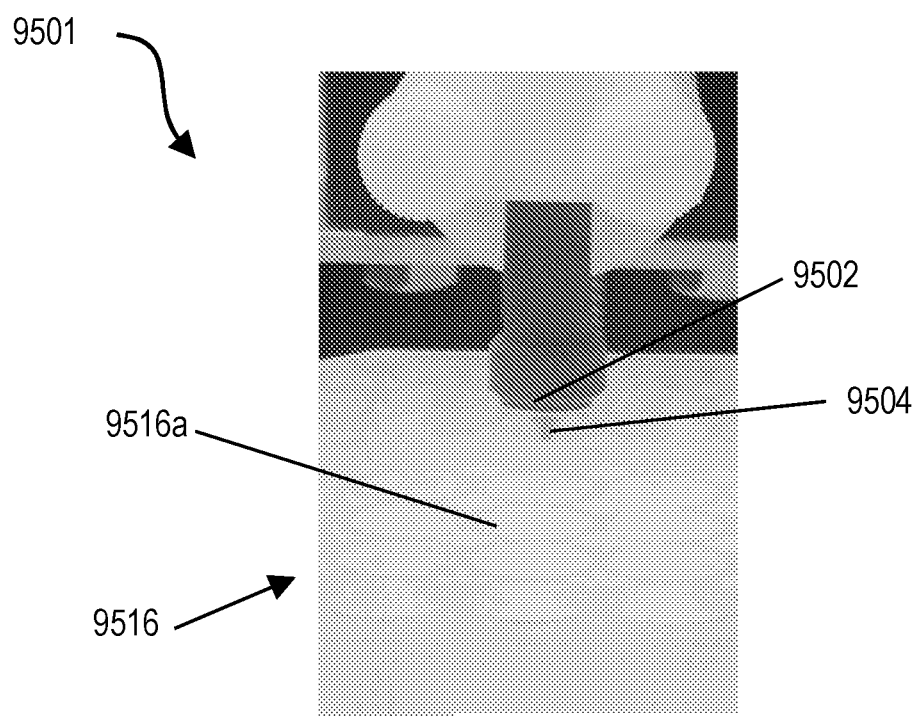
FIG. 97 is an exemplary embodiment of a nebulizer assembly that includes an enclosing collar positioned around a spray head of an Ari Mist nebulizer. The collar is inserted onto the Ari Mist Spray head, and the spray head is positioned 27 mm from the base of a well of a filter plate, thereby leaving a 1 mm gap between the collar and an upper surface of the filter plate.
Figure 98:
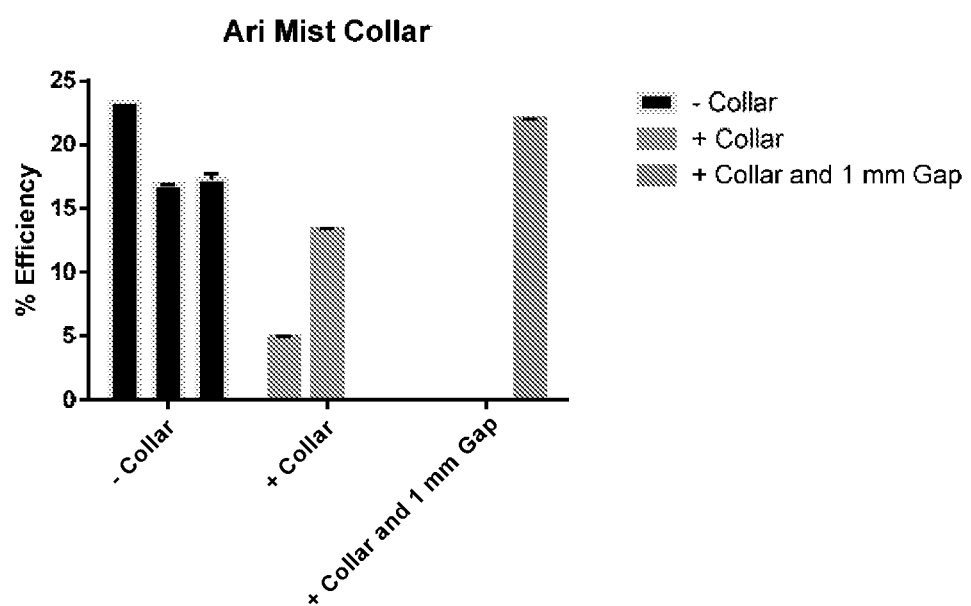
FIG. 98 is a plot showing data characterizing efficiency (GFP uptake) corresponding to a spray head without a collar, a spray head with a collar that forms a seal with a filter plate, and a spray head with the collar where a 1 mm gap exists between the collar and the filter plate. The data indicate that use of the collar that formed a seal with the filter plate had a negative impact on the spray. The collar that was positioned 1 mm above the filter plate did not impact the spray.
Figure 99:
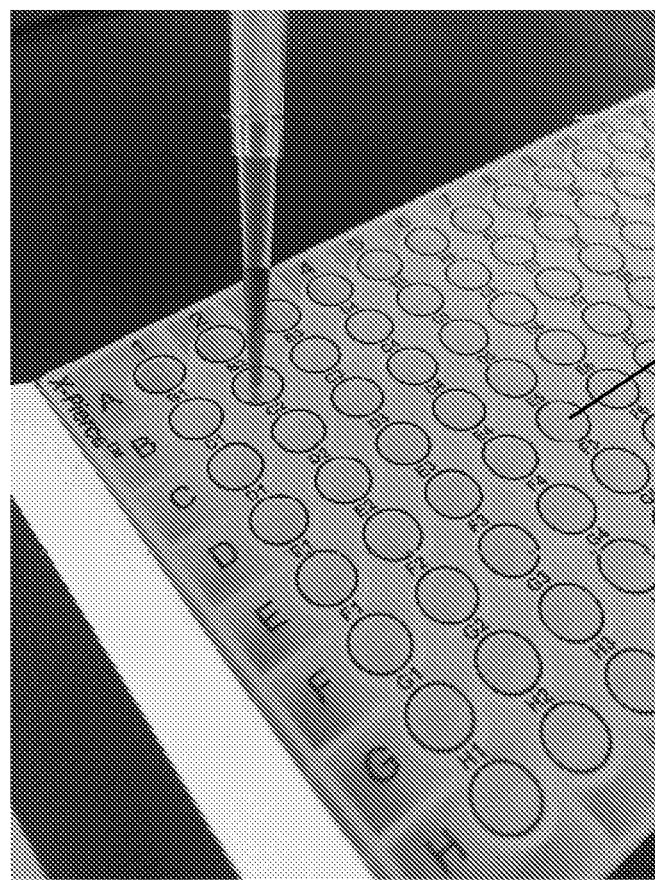
FIG. 99 is an exemplary embodiment of a 96-well PCTE filter plate with an X-pierce film adhered to an upper surface of the filter plate.
Figure 100:
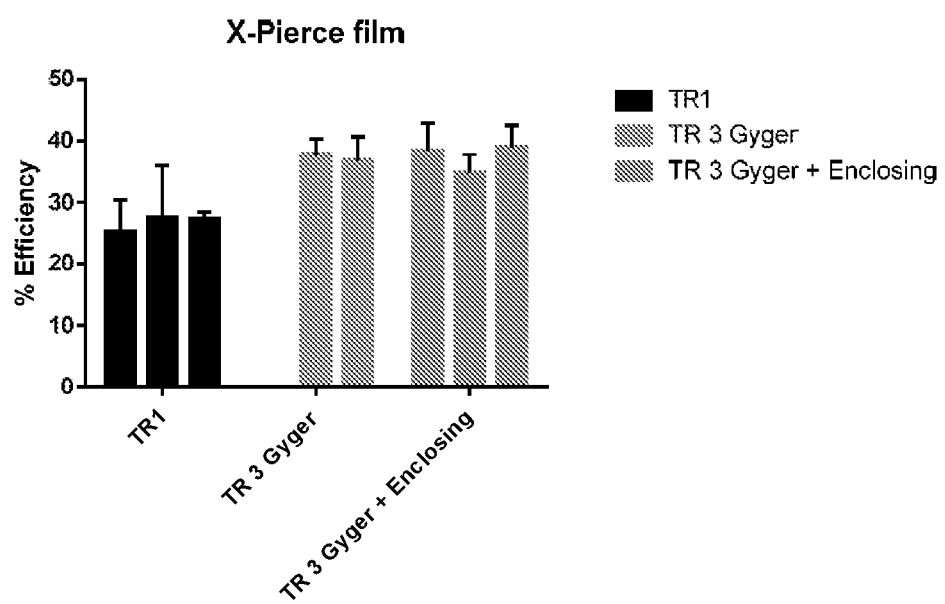
FIG. 100 is a plot showing data characterizing efficiency (GFP uptake) corresponding to tests performed with rig 1 (R1) with unenclosed filter plate, tests performed with rig 3 (R3) with an unenclosed filter plate, and tests performed with R3 with an filter plate that included X-pierce film enclosure over the wells of the filter plate. R1 utilizes a clippard pinch valve to control flow, and R3 utilizes a Gyger micro valve. The data indicates increased delivery efficiency when the Gyger micro valve (R3 Gyger) was used in place of the Clippard valve (R1). The addition of an X-Pierce film on the PCTE filter plate did not have any effect on the delivery efficiency. Each bar represents a single experiment with a minimum of 4 replicates.
Figure 101:
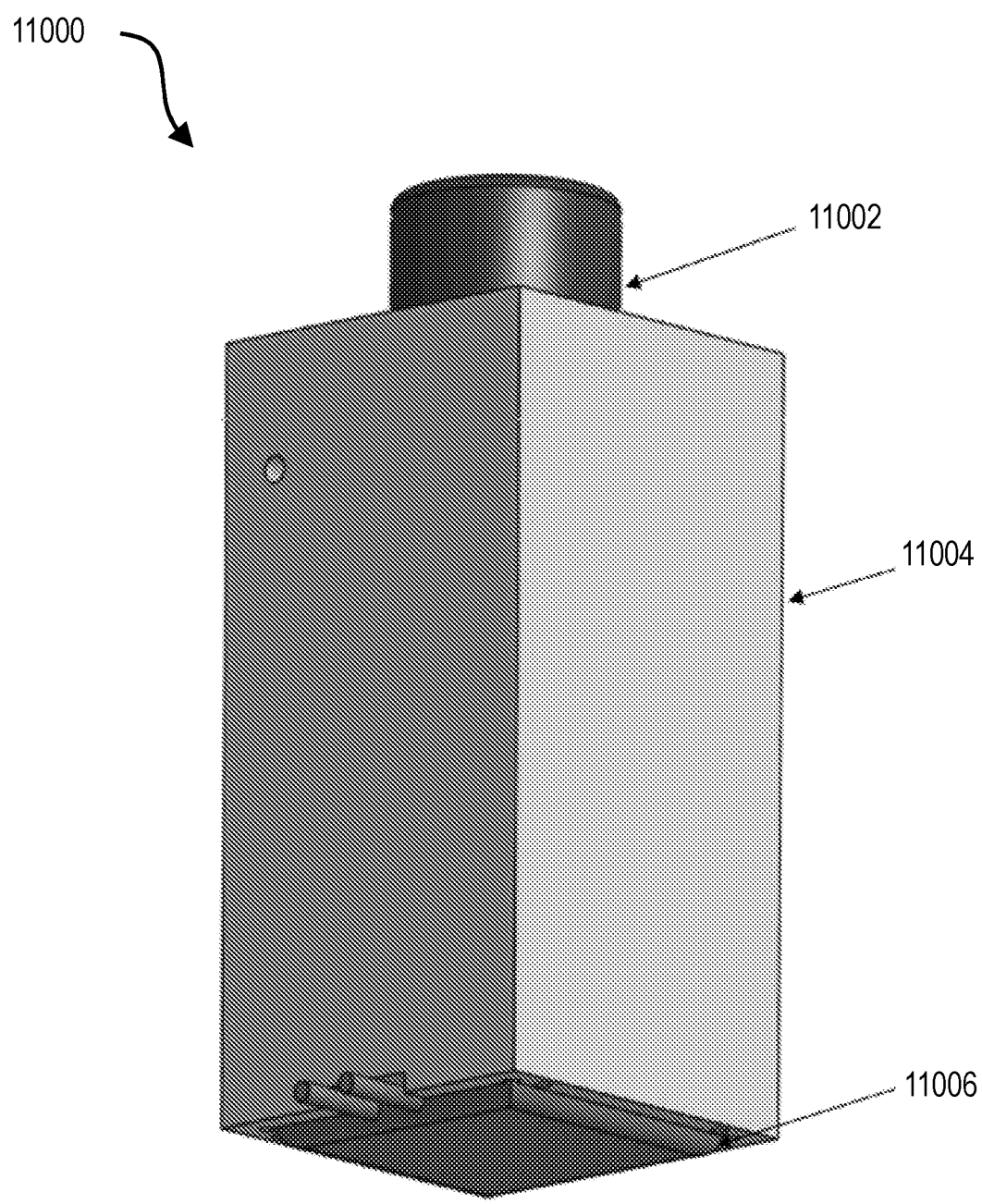
FIG. 101 is an embodiment of a heating system that can be used heat a delivery solution, stop solution, and culture medium.
Figure 102:
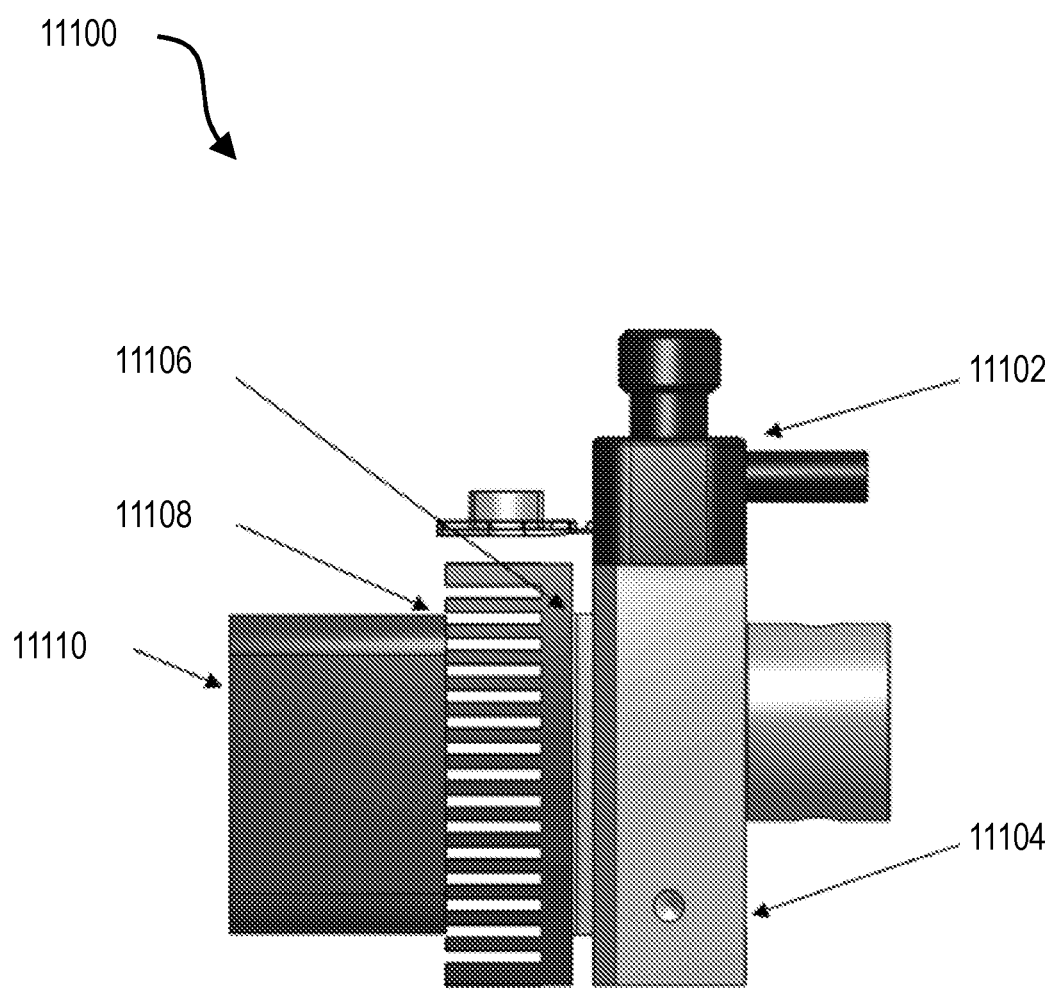
FIG. 102 is a side view of an embodiment of a cooling system that can be used cool the delivery solution, stop solution, and culture medium.
Figure 103:
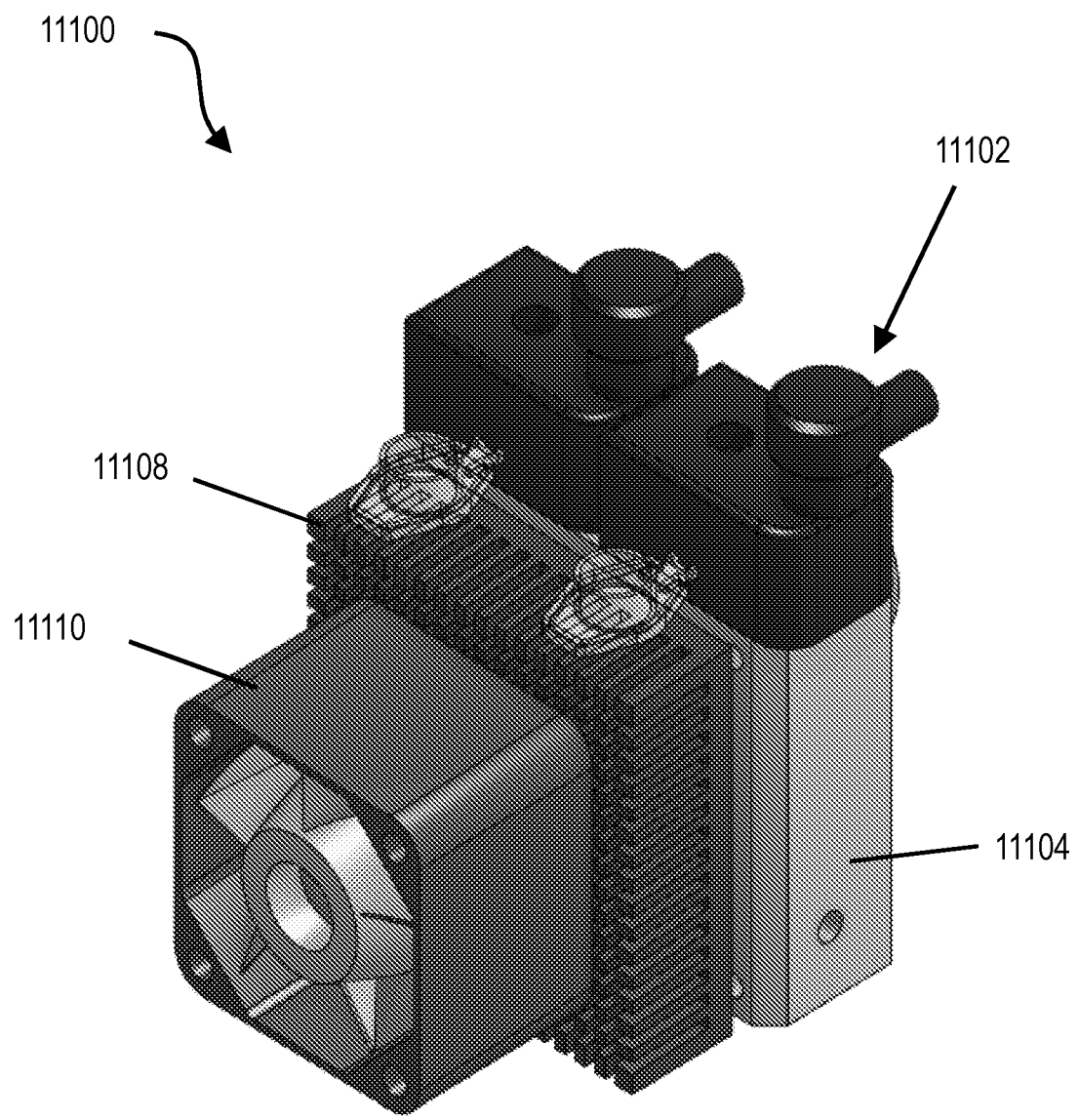
FIG. 103 is a perspective view of an embodiment of a cooling system that can be used cool the delivery solution, stop solution, and culture medium.

FIG. 97 shows an example of a nebulizer assembly 9501 that includes an enclosing collar 9502 positioned around a spray head 9504 of an Ari Mist nebulizer (e.g., nebulizer 9304). In the illustrated example, the spray head 9504 is positioned 27 mm above a well 9516*a* of a double height filter plate 9516. The collar 9502 was designed and manufactured for the Ari mist spray head 9504. This collar was installed onto the spray head 9504. A 96-well filter plate 9516 with a double height wall was used.

Method 1A: The Collar Forms a Seal with the Well Plate.

At a distance of 26 mm from a tip of the spray head 9504 to a base of the well 9516*a*, the collar 9502 mated with the top of the well 9516*a* of the filter plate 9516 and formed a seal. CD3+ T-cells, $1.5\times10^6$, were seeded in the filter plate 9516 and centrifuged for 5 min at 350×g to remove the culture medium. A delivery solution (4 μl) containing GFP mRNA was sprayed onto the cells and incubated for 2 min. Following the 2 min incubation 50 μl of a stop solution was added and incubated for 30 s. Finally, 100 μl culture medium was added.

Method 1B: Providing a 1 mm Gap Between the Collar and the Filter Plate

The collar 9502 was installed onto the spray head 9504, and the tip of the spray head 9504 was positioned a distance of 27 mm from the base of the well 9516*a*. Therefore, the collar was held 1 mm above the upper surface of the filter plate 9516. Note: a single hit protocol (e.g., single exposure to delivery solution and stop solution) was followed for the enclosing experiments.

Method 1: Results

FIG. 98 shows results characterizing efficiency (GFP uptake) corresponding to the spray head without the collar 9502, the spray head with the collar that forms a seal with the filter plate, and the spray head with the collar where a 1 mm gap exists between the collar 9502 and the filter plate.

The tests corresponding to method 1B, where there was a 1 mm gap between the collar 9502 and the upper surface of the filter plate 9516, shows that the collar 9502 had no impact on GFP uptake. The results highlighted comparable data between the wells with and without the collar 9502 in this set-up. Viability of the T-cells was unaffected using the enclosing collar in both set-ups.

Method 1: Conclusions

The result indicate that the collar 9502 does not affect the viability of T-cells. The collar 9502 does affect the spray, to varying degrees. This variance may be attributed to the degree to which the system is sealed. Sealing the system (e.g., method 1A) led to the formation of a local pressure maxima which inhibited the spray. Regarding method 1B, providing a gap between the collar 9502 and the upper surface of the filter plate 9516 provided an outlet for the pressure. The gap allowed for expansion of the air within the well, and permitted correct actuation of the spray. Therefore, a collar can be used to enclose the spray provided it permits expansion space for the air to expand during the spray process.

Method 2: Use of X-Pierce Film to Enclose the Spray.

Rather than enclosing a spray head using a collar, an X-pierce film (Sigma Aldrich, Catalog No. Z722529) was used to enclose the spray. The use of an X-pierce film to enclose the spray head may have benefits over the use of a collar (e.g., collar 9502) for enclosing the spray but avoiding the formation of a seal which can inhibit the spray.

FIG. 99 shows an example of a 96-well PCTE filter plate 9616 with an X-pierce film 9602 adhered to an upper surface of the filter plate 9616. A filter base of the wells of the filter plate 9616 have a 0.4 μm pore size. As shown in the illustrated example, the X-pierce film includes a precut "X" positioned over opening of each well of the filter plate 9616. During the experiment, CD3+ T-cells, $2.5\times10^5$, were seeded into each well. The filter plate 9616 was centrifuged for 1 min at 350×g to remove the culture medium, thereby creating a monolayer of cells. The air pressure delivered to the nebulizer was set to 1.65 bar and the tip of the spray head of the nebulizer was positioned 12 mm above an upper surface of a filter membrane positioned within the well, the filter membrane having the monolayer of cells formed thereon. A delivery solution (1 μl) containing GFP mRNA (2 μg) was sprayed onto the cell monolayer. The cells were then incubated 2 min. Following the 2-min incubation, 50 μl of stop solution was added to each well, and the wells were incubated for 30 s. 100 μl of culture medium was added to each cell thereafter, as shown in FIG. 99. The filter plate was incubated at 37° C. for 17-24 hours prior to analysis. The single hit protocol was followed for the enclosing experiments.

Method 2: Results

FIG. 100 shows results characterizing efficiency (GFP uptake) corresponding to tests performed with rig 1 (R1) with unenclosed filter plate, tests performed with rig 3 (R3) with an unenclosed filter plate, and tests performed with R3 with an filter plate that included X-pierce film enclosure over the wells of the filter plate. A description of the rigs is provided above. The results indicate that efficiency was comparable across wells with the film and without the film, thereby indicating the x-pierce film did not have a negative impact on the spray. The use of the X-pierce film did not affect cell viability.

The x-pierce film can be used to enclose the spray and avoid cross contamination between wells without reducing efficiency (GFP uptake) or cell viability.

Fluidic Control of the Solutions to Enable Automation

In some embodiments, the precision rig can provide an automated engineering solution for the payload delivery process. To enable this, fine fluidic control of the delivery solution, cold stop solution and culture medium can be used.

The fluidic control can be achieved by fluid control system that can apply a constant pressure to the system to drive the fluid through a pinch valve or micro valve. A volume of fluid that can be dispensed can be controlled by: an amount of pressure applied; a length of time the valve is open; and/or a diameter of the tubing used.

The valve can be activated by a metal-oxide-semiconductor field-effect transistor (MOS FET) which can be controlled by a microprocessor.

The fluid control system can allow fluid volumes in the range of 2-10 μl to be delivered using the fine fluidic control. Therefore, the precision rig system 9000 can control the delivery of metered units of volume in the range of 2-10 μl. In some implementations, other volumes are possible.

Temperature Control of the Solutions (Temperature Reservoirs).

In some embodiments, a fluid temperature control system can be implemented to control the temperature of the delivery solution, stop solution, and culture medium. The fluid temperature control system can include a heating system and a cooling system.

FIG. 101 shows an example of a heating system 11000 that can be used heat the delivery solution, stop solution, and culture medium. The heating system can include a fluid reservoir 11002, a housing 11004 and a heating element 11006. The fluid reservoir 11002 can generally be in the shape of a cylindrical tube that a fluid such as, e.g., the culture medium can be loaded into. The housing 11004 can be, e.g., an aluminum block having a passage for receiving the fluid reservoir 11002. The heating element 11006 can be positioned on a distal end of the housing 11004. The heating element 11006 can receive power from a power source and can heat the housing 11004, thereby heating the fluid within the fluid reservoir. The heating element 11006 can heat the housing 11004 via conduction.

FIGS. 76-77 show an example of a cooling system 11100 that can be used cool the delivery solution, stop solution, and culture medium. The cooling system 11100 can include one or more fluid reservoir 11102 such as, e.g., 1.5 ml Eppendorf tubes, a housing 11104, a cooling element 11106 such as, e.g., a thermoelectric cooler, a heat sink 11108, and a fan 11110. The delivery and/or stop solutions cab be loaded into the one or more fluid reservoirs 11102. Power can be delivered to the cooling element 11106, and the cooling element can generate a hot surface and a cold surface. The cold surface can be in contact with the housing 11104, and the hot surface can be in contact with the heat sink 11108. The fan 11110 can be coupled to, or positioned over, the heat sink 11108 to remove heat from the hot surface of the cooling element 11106.

In practice, the delivery solution and the stop solution can be held at approximately 4° C., and the culture medium can be held between approximately 20° C. and 37° C.

Mounting of the Spray Heads and Temperature Reservoirs.

Figure 104:
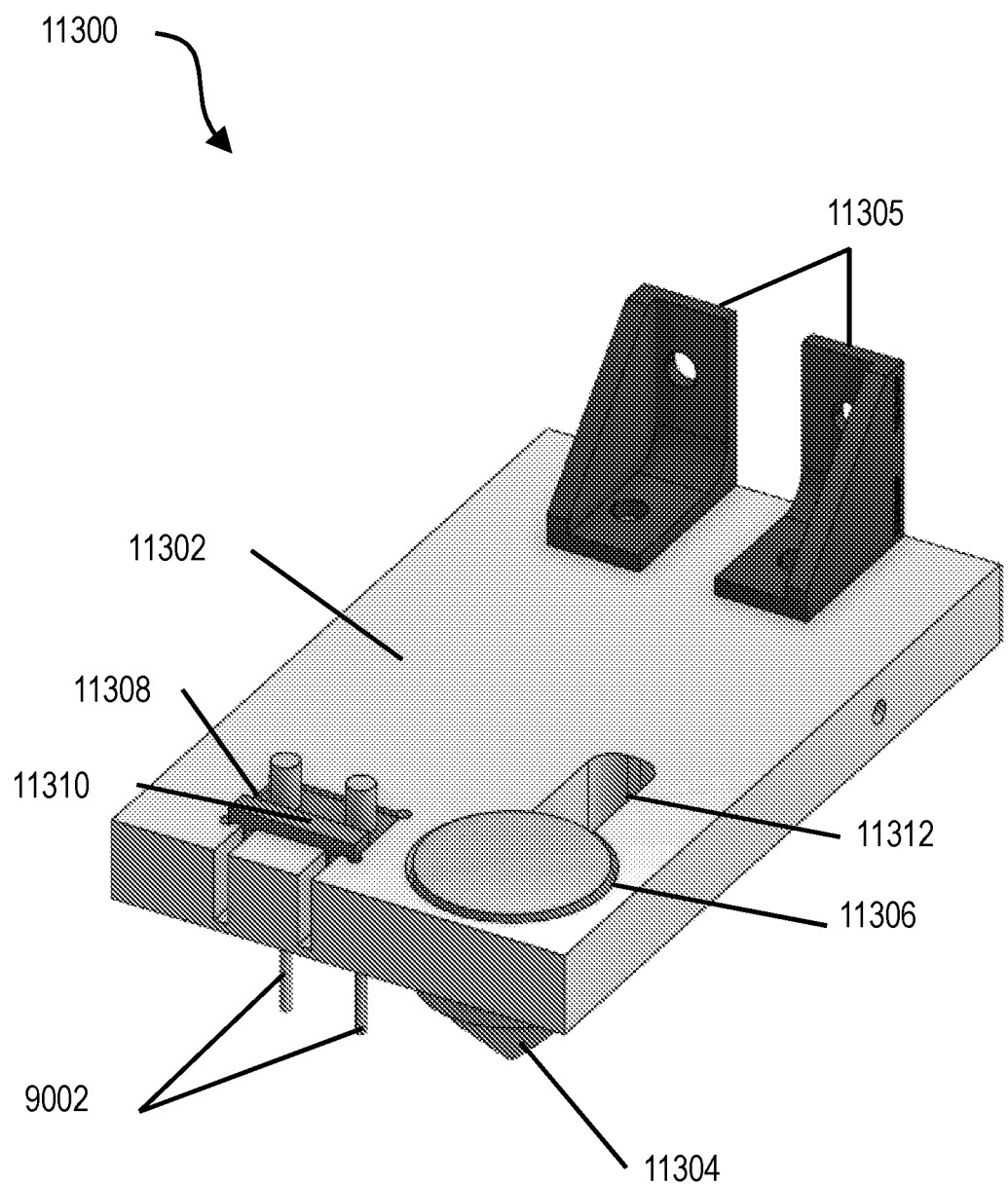
FIG. 104 is a perspective view of an embodiment of a mounting assembly that can releasably retain needle emitters and an ultrasonic atomizer.

The needle emitters 9002 and the atomizer 9004 can be mounted in a support. FIG. 104 shows an example of a mounting assembly 11300 that can releasably retain the needle emitters 9002 and an atomizer 11304. The atomizer 11304 can be an ultrasonic atomizer that can operate at frequencies between 60 kHz and 120 kHz. The mounting assembly 11300 can include a support plate 11302 having coupling members 11305 attached thereto. The support plate can include a bore 11306 that can receive the atomizer 11304, and an opening 11308 that can receive a retaining element 11310 that can have the needle emitters 9002 coupled thereto. The bore 11306 can have a slot 11312 extending therefrom. In some cases, ultrasonic atomizers that operate at 60 kHz can have the same design as those that operate at 120 kHz. Therefore, the mounting assembly 11300 can accommodate ultrasonic atomizers that can operate at either frequency.

FIG. 105 shows an exploded view of a portion of the mounting assembly 11300 with the retaining element 11310 and the needle emitters 9002. As shown in FIG. 105, the needle emitters 9002 can be inserted into bores 11310*a* of the retaining element 11310, and the retaining element can be inserted into the opening 11308. The design of the retaining element 11310 as a sliding insert can enable independent Z positioning, or vertical positioning, of the needle emitters 9002 relative to the spray head emitter. This can accommodate varied atomizer heights, in the range 15-31 mm from a tip of the emitter to a base of a well of a filter plate, while maintaining a consistent needle emitter height.

FIG. 106 shows an example of a mounting assembly 11500 that can releasably retain the needle emitters 9002 and an ultrasonic atomizer 11504. The mounting assembly 11500 can generally be similar to mounting assembly 11300, but can be designed to function with an ultrasonic atomizer 11504 that can operate at 180 kHz. The mounting assembly 11500 can include a support plate 11502 having coupling members 11505 attached thereto. The support plate can include a bore (not shown) that can receive the atomizer 11504, and an opening 11508 that can receive a retaining element 11510 that can have the needle emitters 9002 coupled thereto. The bore can have a slot 11512 extending therefrom.

In the illustrated embodiment, a collar 11514 can be attached to the atomizer 11504 and the collar slots in the same head holder at the same height and concentrically to the other two heads.

FIG. 107 shows an example of a mounting assembly 11600 that can releasably retain the needle emitters 9002 and a nebulizer 11604. The mounting assembly 11600 can generally be similar to mounting assembly 11300, and can include a support plate 11602 having coupling members 11505 attached thereto. The nebulizer 11604 can be coupled to the support plate 11602 via a bracket 11606. The support plate 11602 can include an opening 11608 that can receive a retaining element 11610 that can have the needle emitters 9002 coupled thereto.

Similar design templates to those shown in FIGS. 78-81 can be used to accommodate other emitter types.

The designs of the mounting assemblies 11300, 11500, and 11600 enables the precision rig system to perform as a platform for optimization of the delivery process. For example, 4 different spray heads can be accommodated.

Automation and Software Design

The precision rig system 9000, and/or the positive pressure system 9300 can include software program and user interface that can enable automation of the delivery process steps. For example, the software can be designed to control the translational stage 9010 and valves 9011. As another example, the software program can be configured to control movement of the mounting array 9302. A user interface can enable the critical parameters to be entered. A sequence of functional units can be selected by the user.

A system was designed which had the capability of ensuring repeatability of experiments but can also provide the flexibility to adjust experimental specific parameters. Such parameters can include the number of wells one wants to address or the volume which is dispensed into a well. In order to achieve this synchronization, a traverse mechanism (e.g., the actuator 9319) is included, which can be software controlled to position its carriage within a 200 mm location for a required period of time. The carriage includes 6 positions and each of these positions are coupled to an individually controlled high precision fluid escapement chamber. It is possible to move each position under a selection of dispensing locations (e.g., Payload, Culture Medium and Stop Solution stations). A device specific software platform can be included. The software platform can include: 1) a graphical user interface which enables the user to design an experiment; and 2) local control via a controller (e.g., programmable logic controller (PLC)), for example an Omron PLC. FIG. 129 shows a schematic 12000 of the software platform design. The software can include a user friendly experiment creation section and a background sequence generator. The user interface can include an experiment canvas which allows the user to change parameters in the experiment. The parameters, which can be varied by the user, include the location and number of wells to be addressed, the sequence of steps including vacuum and/or positive pressure, dispense of payload, stop solution and culture medium, and corresponding volumes to be delivered. The user can also modify the actuator speed and the incubation times (FIG. 130). FIG. 130 shows a portion of a graphical user interface (GUI) 12100 of the software platform. In the illustrated example, the GUI includes an experiment canvas which allows the user to vary parameters. For example, the parameters which can be varied by the user include the location and number of wells to be addressed, the sequence of steps including vacuum or positive pressure, dispensation of payload, stop solution, and/or culture medium, and the corresponding volumes to be delivered. The background sequence generator outputs a program for the PLC, which provides local control of the mechanical and electrical system. This software can be provided the operator (e.g., via an integrated display) with the ability to test various permutation of wells, media and time without having to manually calculate the dwell time between wells for optimum experimental success. These inputs can provide the end user with the capability of conducting multiple experiments.

In some implementations, a system can address ninety six positions within a filter plate substrate. This system can be faster, have multiple traverse mechanism and a user friendly HMI (human machine interface). The HMI can provide the operator with additional automated utilities such as automatic system purging or a touch screen driven calibration sequence. This system can operate as a standalone solution yet still maintained the link to the experimental designer for designing experiment. More aspects of the experiment can be adjusted from well to well, which means the potential permutations greatly increases. For example fluid can be dispense to a number of wells and then the applied pressure to the fluid delivery system for the next section of the experiment can be automatically adjusted. This example system has the capability of recording analytics from the experiments for further offline analysis.

Figure 64:
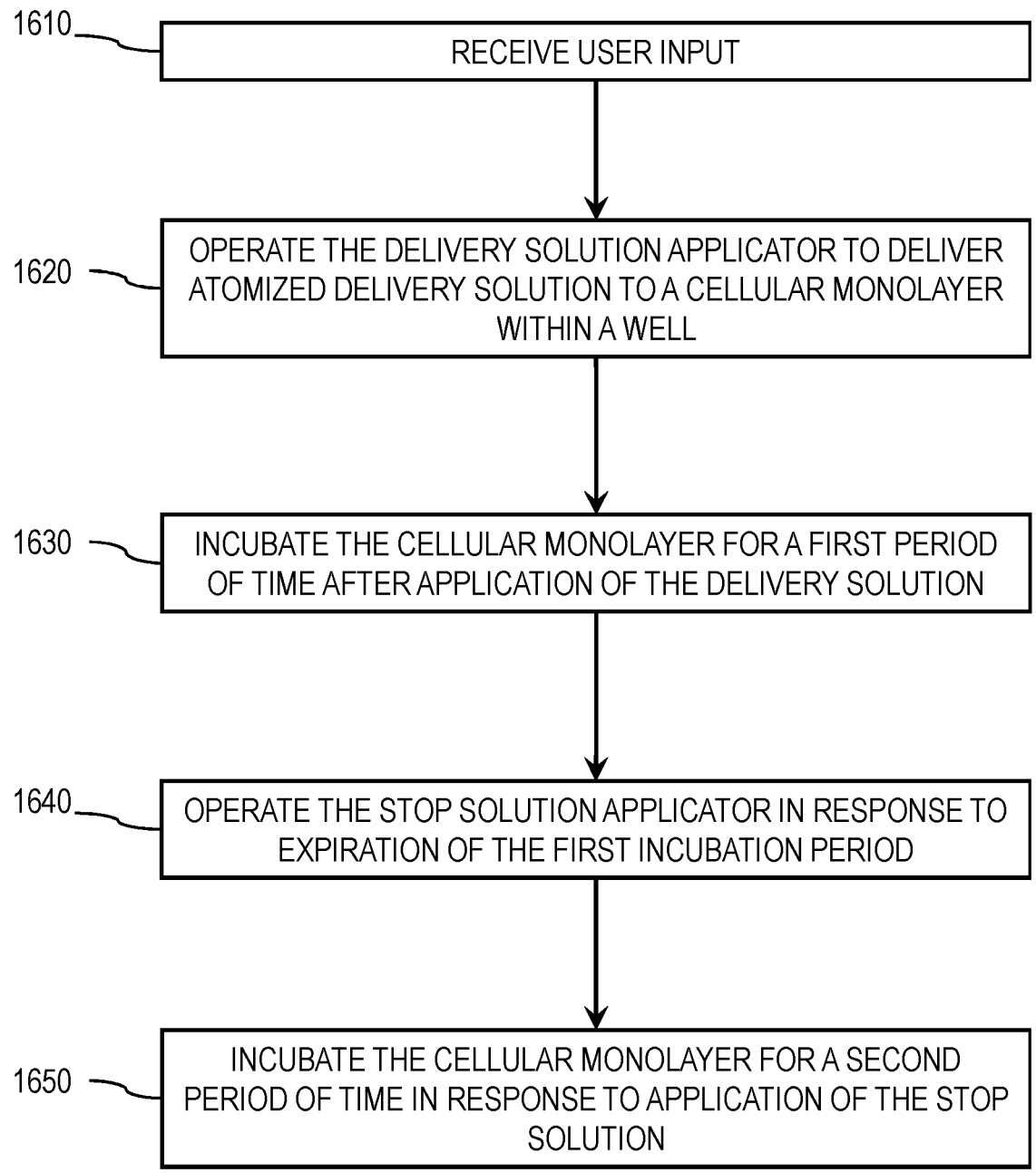
FIG. 64 is a process flow diagram illustrating an example process according to some aspects of the current subject matter.

FIG. 64 is a process flow diagram illustrating an example process according to some aspects of the current subject matter. The example process can be implemented, e.g., by a controller of a delivery system. At 1610, user input can be received, e.g., by a controller. At 1620, the delivery solution applicator can be operated to deliver atomized delivery solution to a cellular monolayer within a well. At 1630, the cellular monolayer can be incubated for a first period of time after application of the delivery solution. At 1640, the stop solution applicator can be operated in response to expiration of the first incubation period. The operation can be performed to deliver stop solution to the cellular monolayer. At 1650, in response to application of the stop solution, the cellular monolayer can be incubated for a second period of time.

In some implementation, the iteration of operation of the delivery solution applicator, incubation for the first incubation period, operation of the stop solution applicator, and incubation for the second incubation period for a predetermined number of iterations can be performed.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Enclosure for the Instrument

The precision rig system 9000, and/or the positive pressure system 9300 can be retained within an enclosure to maintain stable ambient conditions. The enclosure can be customized base on parameters to affect the design of the enclosure Temperature and Control of the Base Plate In some embodiments, a temperature control system can be implemented to control the temperature of the base plate 9016. For example, cartridge heaters can be installed at various locations on the base plate 9016 of the vacuum manifold assembly 9008. A thermodynamic analysis can be conducted to examine heat transfer from the cartridge heaters to the well filter plate 9014. Temperature ranging experiments can be performed to investigate the effect of temperature on payload delivery.

Although a few variations have been described above, other modifications are possible. For example, the filter plate can include any number of wells, and need not be a 96-well filter plate. Additionally, the system can include any number of valves that can control vacuum pressure to any number of active wells. As another example, the system can include one or more needle emitters, atomizers, and or nebulizers, each of which can be independently mounted and controlled.

The current subject matter provides many technical advantages. In general, the current subject matter provides a delivery system that enables greater consistency in the delivery process, and higher efficiency of delivery, while maintaining cell health.

The delivery system allows for vacuum pressure to be applied to individual wells of a filter plate to remove a culture medium, thereby creating a monolayer of cells. By applying a vacuum pressure to individual wells on a filter plate, greater precision, control of the vacuum pressure, and consistency of the vacuum pressure applied to each well, can be achieved.

The delivery system allows for dispensation of permeabilizing solution in volumes on the order of microliters. Microliter dispensation volumes allow for greater control over cell exposure to the solution, which can increase overall cell viability by reducing excessive exposure to the permeabilizing solution. Moreover, the system can be automated which minimizes error, and increases precision.

The system allows for control the temperature of the delivery solution, stop solution, and culture medium. Therefore, each solution can be maintained at an optimum temperature to increase efficiency of payload delivery as well as cell viability. The temperature of the base plate can also be controlled. This allows for temperature optimization to maximize efficiency of payload delivery.

The needle emitters and atomizer and/or nebulizer can be coupled to a mounting assembly that can accommodate various atomizer/nebulizer heights, in the range 15-31 mm from a tip of the emitter to a base of a well of a filter plate, while maintaining a consistent needle emitter height. This allows The system can include hardware, one or more software programs, and a user interface, that can enable automation of the delivery process steps. The software can be designed to control the translational stage and valves. A user interface can allow for critical parameters, such as to be entered. A sequence of functional units can be selected by the user. This is beneficial because The enclosure can function to maintain stable ambient conditions.

Additional Example Delivery System Aspects

Scaling the delivery process involved designing a system to enable optimization, determining a method for formation of a cell monolayer at a larger scale, and optimizing atomisation to enable intracellular delivery of mRNA to T-cells.

Figure 112:
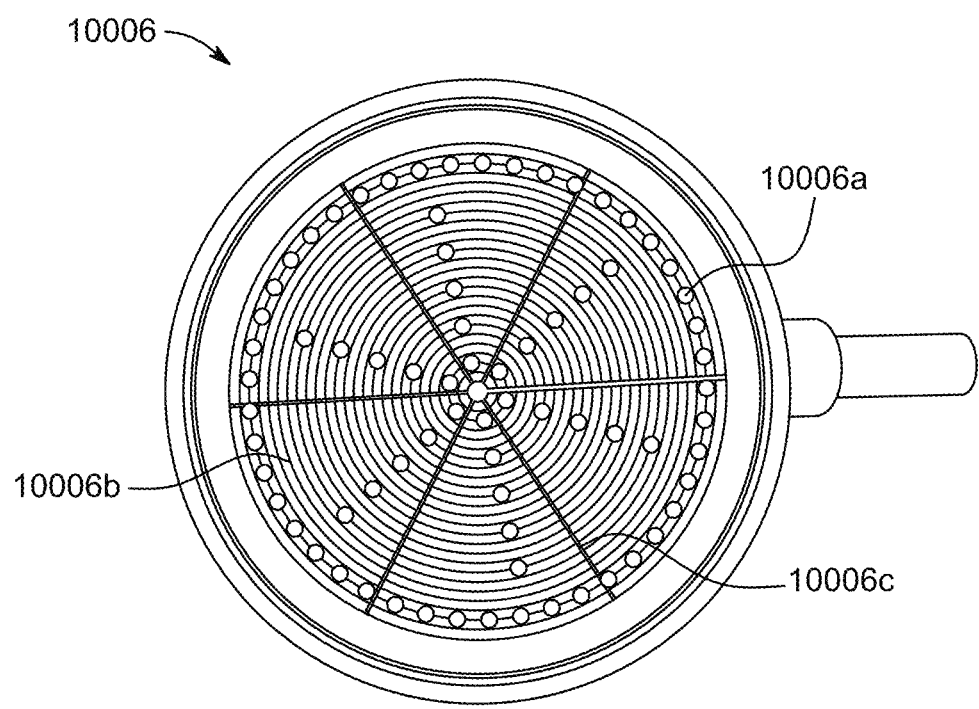
FIG. 112 is a top view of another embodiment of a membrane holder that includes holes, concentric channels, and straight channels.

Optimization work to date has achieved >50% efficiency of mRNA delivery to T-cells with >60% cell viability and cell recovery of up to 80%.

A system was designed and constructed to facilitate scaling of the delivery process. The system is based around the commercially available product, Amicon Stirred cell, pressure-based sample concentration unit (50 ml and 200 ml size; catalogue UFSC05001 and UFSC20001, respectively). FIG. 108 shows an example of a stirred cell system 9700 configured to facilitate forming a monolayer of cells.

The stirred cell system 9700 can include a cap 9702, a body 9704, a membrane holder 9706, and a base 9708. A stir bar 9710 can be positioned within the body 9704. The cap 9702 can be configured to couple to the body 9704 at a first end of the body 9704. A sealing element 9712 (e.g., a gasket) can be positioned between the cap 9702 and the first end of the body 9704 to form a seal between cap 9702 and the first end of the body 9704. The membrane holder 9706 can receive a membrane 9714, and can be positioned adjacent to a second end of the body 9704 such that a coupling element 9716 of the membrane holder 9706 extends through an opening 9718 in the second end of the body 9704. The second end of the body 9704 can be coupled to the base 9708, and a sealing element 9720 (e.g., an o-ring) can be positioned therebetween to form a seal. A pressure inlet tubing assembly 9722 can be coupled to cap 9702 such that a pressurized gas can be delivered to the body a chamber formed by the cap 9702, the body 9704 and the base 9708. A filtrate tubing assembly 9724 can be coupled to the coupling element 9716 of the membrane holder 9706 such that fluid can be drained from the chamber upon application of pressure.

In operation, a culture medium containing cells can be delivered to the chamber, and the cap 9702 can be coupled to the body 9704. The pressure inlet tubing assembly 9722 can be coupled to the cap 9702, and positive pressure can be applied to the chamber via the inlet tubing assembly 9722. In some embodiments, the pressure can be in the range of 50-1000 mbar, and the pressure can be applied for 10-60 seconds. Accordingly, upon application of positive pressure, the culture medium can be forced through the membrane 9714 and out of the chamber via the coupling element 9716 and the filtrate tubing assembly 9724. With the culture medium evacuated, a monolayer of cells can remain on the membrane 9714. Accordingly, the stirred cell system 9700 can be used to form the cell monolayer onto a filter membrane placed on the membrane holder of the stirred cell. With the monolayer formed, a nebulizer (e.g., the LB-100 from Burgener Research), can be used to atomize the delivery solution onto the cells sitting on the filter membrane.

The stirred cell system 9700, shown in FIG. 108, can have several limitations. For example, in some cases, the stirred cell system 9700 cannot filter culture mediums having cell suspensions above a certain concentration (e.g., concentrations above $10\times10^6$/mL when using when using a PCTE membrane). This may be, in part, due to the geometry of the membrane holder 9706. As shown in FIG. 109, the culture medium drains through a single channel **9706*a* of the membrane holder 9706. The channel 9706*a* can become clogged when filtering culture mediums having cell suspensions above a certain concentration. As another example, an even distribution of cells on the membrane 9714 was not achieved while using the membrane holder 9706**.

To address these limitations with of membrane holder 9706, a membrane holder 9906, shown in FIG. 110, was constructed. In this embodiment, the membrane holder 9906 is made of PTFE, and it includes a plurality of holes **9906*a* drilled through its bottom surface in a pattern forming concentric circles. When in use, a culture medium can drain through the holes 9906*a* when pressure is applied within a chamber of a stirred cell system. The membrane holder 9906 was assessed using dynabeads (microbeads used to mimic the cells). FIG. 111 shows a membrane 9914 that was used with the membrane holder 9906 during the dynabead assessment. As shown in FIG. 111, the results indicate that dynabeads accumulated in the proximity of the holes 9906*a***. Cells that were subjected to the delivery process using this holder resulted in poor uptake.

In order prevent accumulation of cells near the holes, and to generate a more even distribution of cells on a membrane, a membrane holder can include holes similar to holes 9906a, but can also include concentric channels that can facilitate radial flow between the holes. FIG. 112 shows another embodiment of a membrane holder 10006 that can be used with a stirred cell system (e.g. stirred cell system 9700). In the illustrated embodiment, the membrane holder 10006 includes holes 10006a, concentric channels 10006b, and straight, or linear, channels 10006c. The holes 10006a are formed along a pattern that includes a central circle, an outer circle, and linear spokes that extend from the central circle to the outer circle. The linear channels 10006c extend radially outward from a central point of the membrane holder 10006, and the concentric channels 10006b form concentric circles about the central point of the membrane holder 10006. The holes 10006a and channels 10006b, 10006c can promote an even distribution of the cells over the membrane, and can promote rapid removal of the culture medium. In some embodiments, the membrane holder 9706, illustrated in FIGS. 82-83, can be modified by drilling holes (e.g., the holes 10006a), to form the membrane holder 10006.

Figure 113:
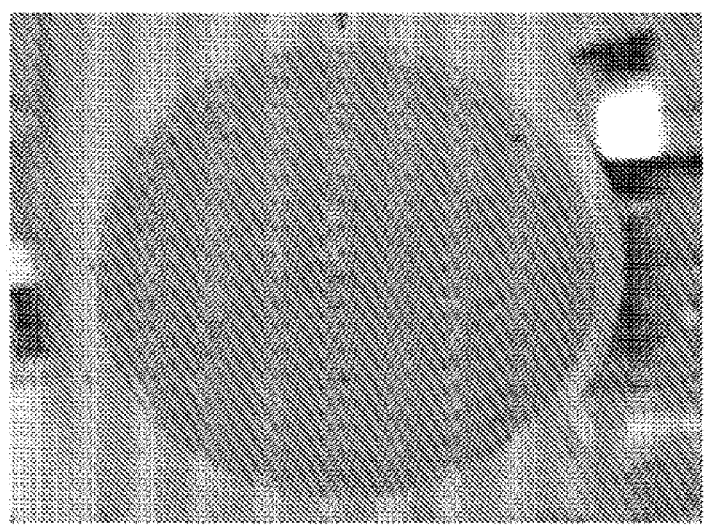
FIG. 113 is a top view of a membrane that was used with the membrane holder shown in FIG. 112 during tests to assess an impact of the design of the membrane holder on formation of a cell monolayer. Dynabeads were used in place of cells. The results indicate that the membrane holder generates an even distribution of Dynabeads.

The membrane holder 10006 was assessed using dynabeads. FIG. 113 shows a membrane 10014 that was used with the membrane holder 10006 during the dynabead assessment. As shown in FIG. 113, the results indicate that the dynabeads are more evenly distributed on the membrane 10014 that was used with the membrane holder 10006 than they are on the membrane 9914 that was used with the membrane holder 9906.

Figure 114:
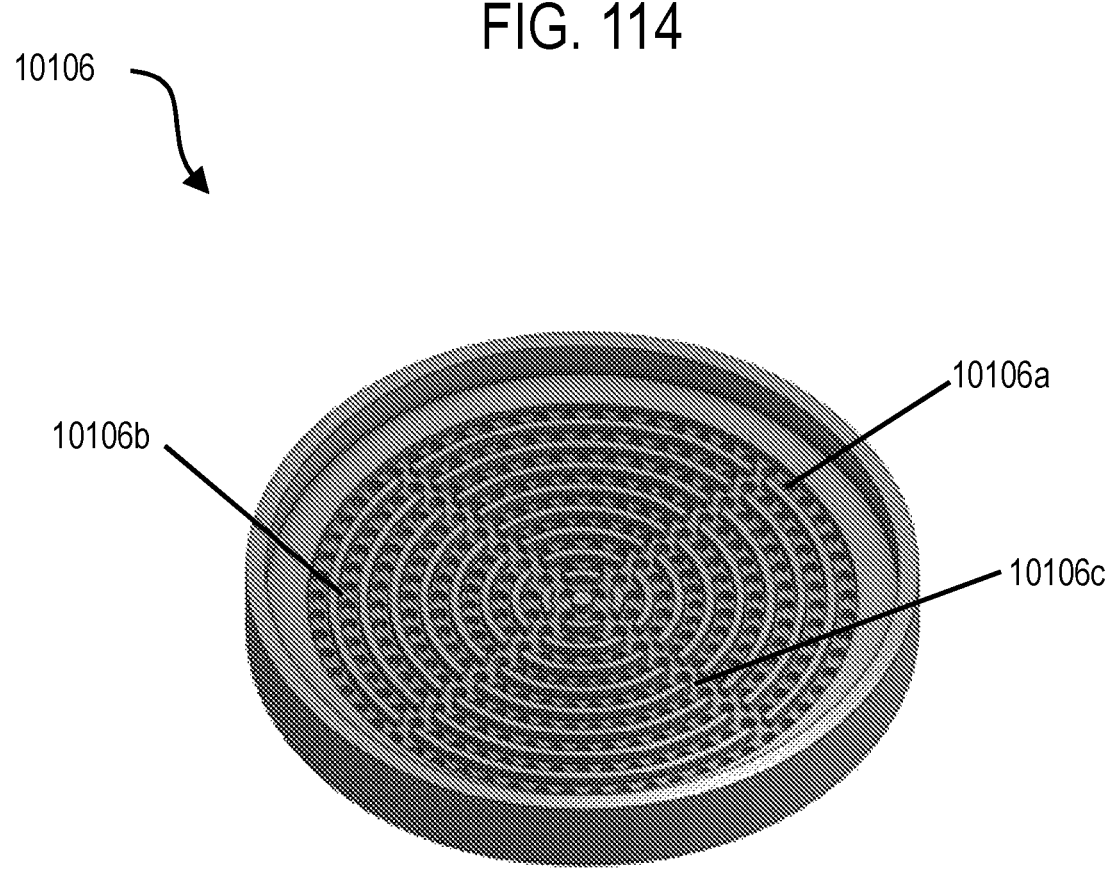
FIG. 114 is a perspective view of another embodiment of a membrane holder configured to facilitate effective removal of a culture medium and formation of a cell monolayer.
Figure 115:
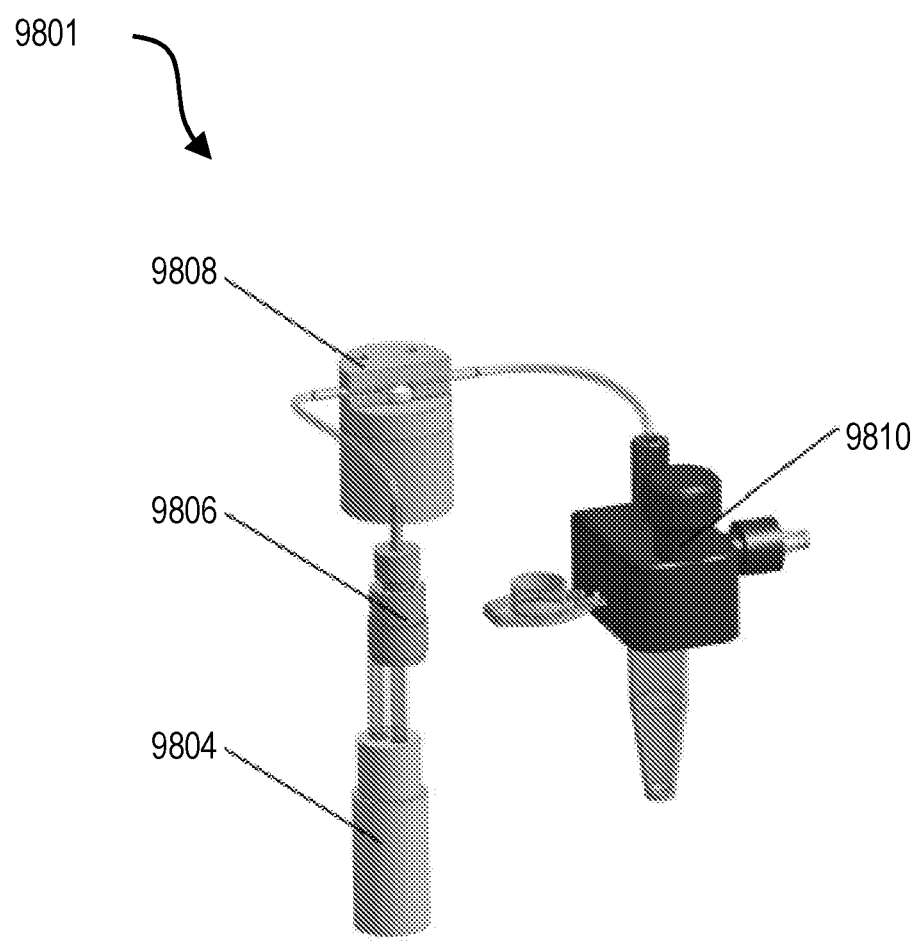
FIG. 115 is an exemplary embodiment of a nebulizer assembly of a solution delivery system, also referred to as rig 4 (R4). The nebulizer assembly includes a nebulizer (e.g., a LB-100 spray head), a coupling element (e.g., an IDEX connection) configured to facilitate delivering air and liquid (e.g., the permeabilizing solution) to the nebulizer, a solution reservoir (e.g., an Elveflow sample reservoir) configured to provide the permeabilizing solution to the nebulizer, and a pinch valve configured to control delivery of the permeabilizing solution to the nebulizer.
Figure 116:
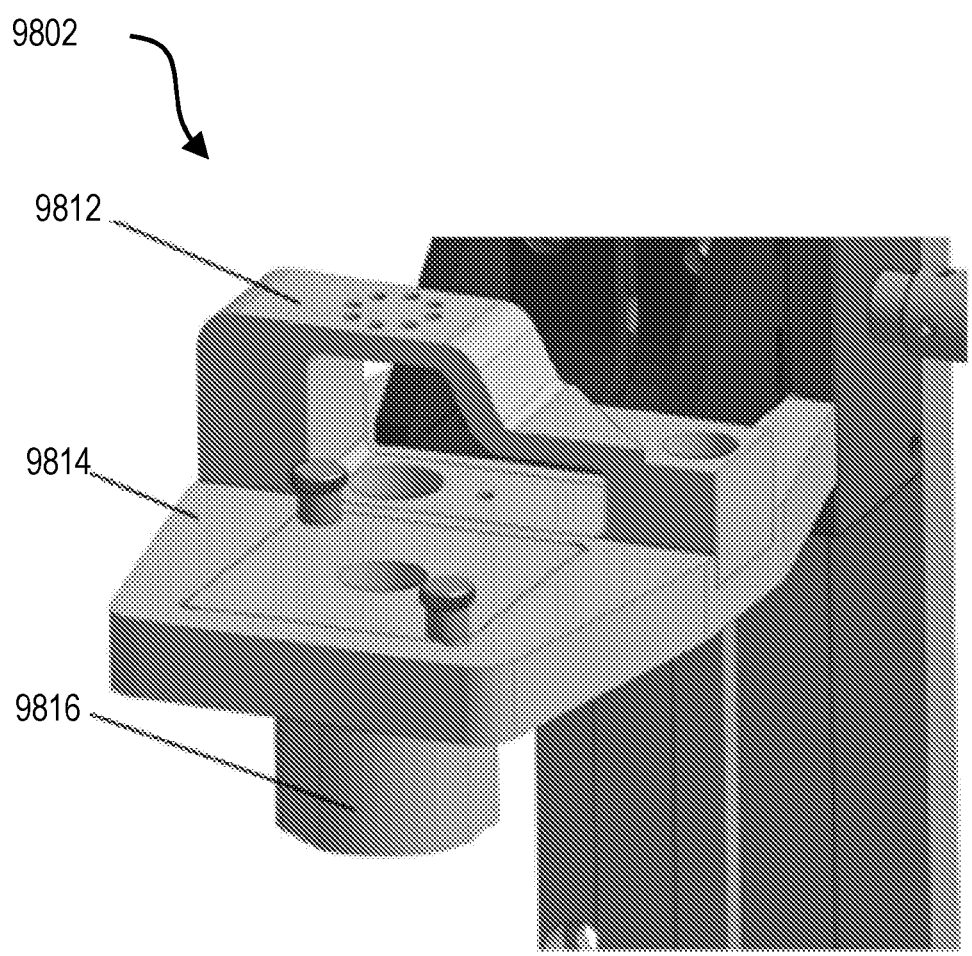
FIG. 116 is a perspective view of a mounting system of a solution delivery system. The nebulizer assembly shown in FIG. 115 can be mounted to the mounting system. The mounting system can include a valve and reservoir mount, a spray head mount, and a nebulizer retaining collar to accommodate the nebulizer.
Figure 117:
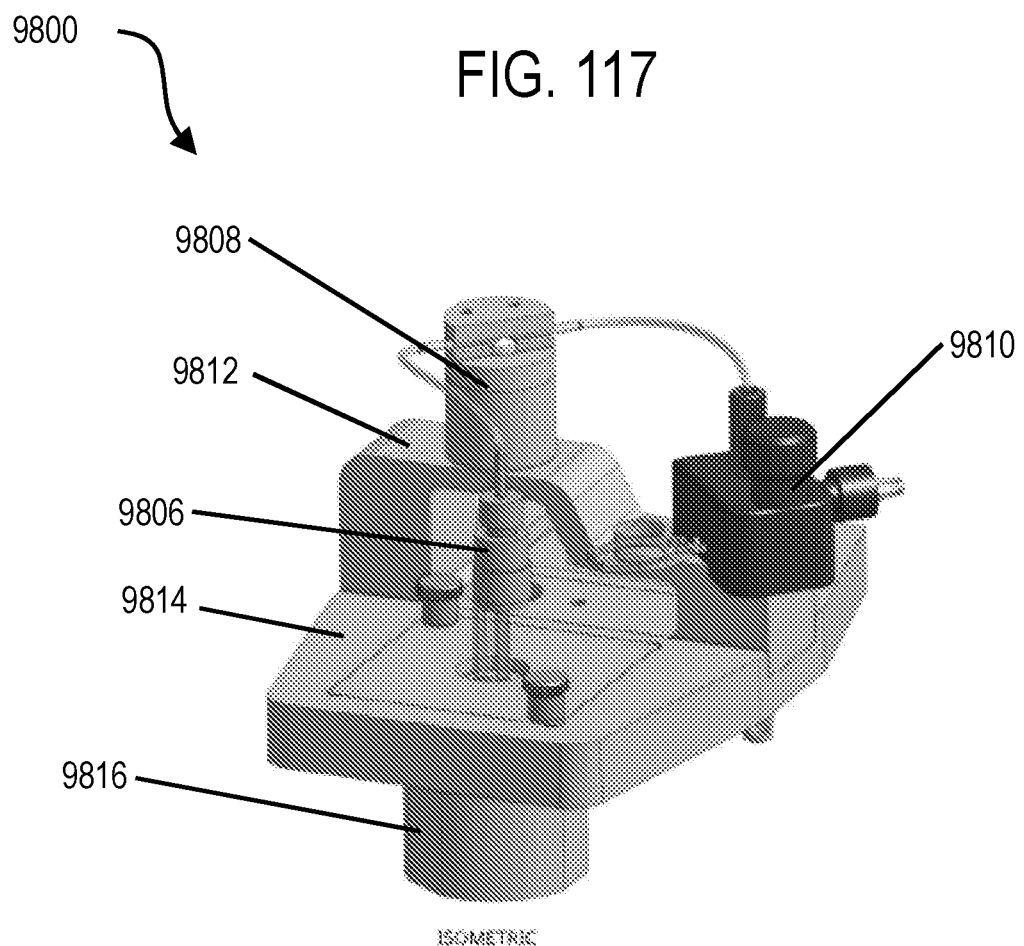
FIG. 117 is a perspective view of a solution delivery system illustrating the nebulizer assembly shown in FIG. 115 mounted to the mounting system shown in FIG. 116.
Figure 118:
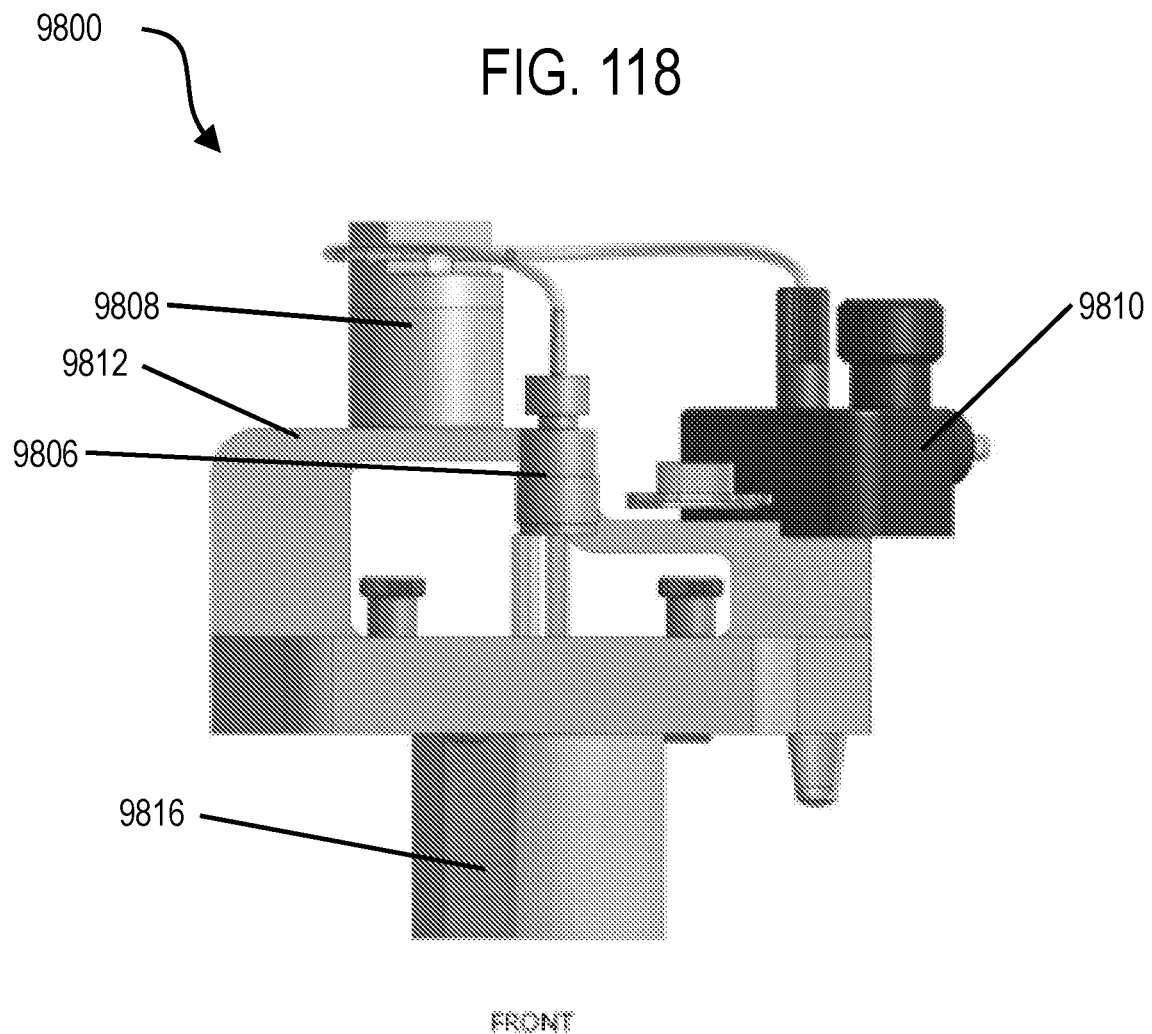
FIG. 118 is a side view of a solution delivery system illustrating the nebulizer assembly shown in FIG. 115 mounted to the mounting system shown in FIG. 116.
Figure 119:
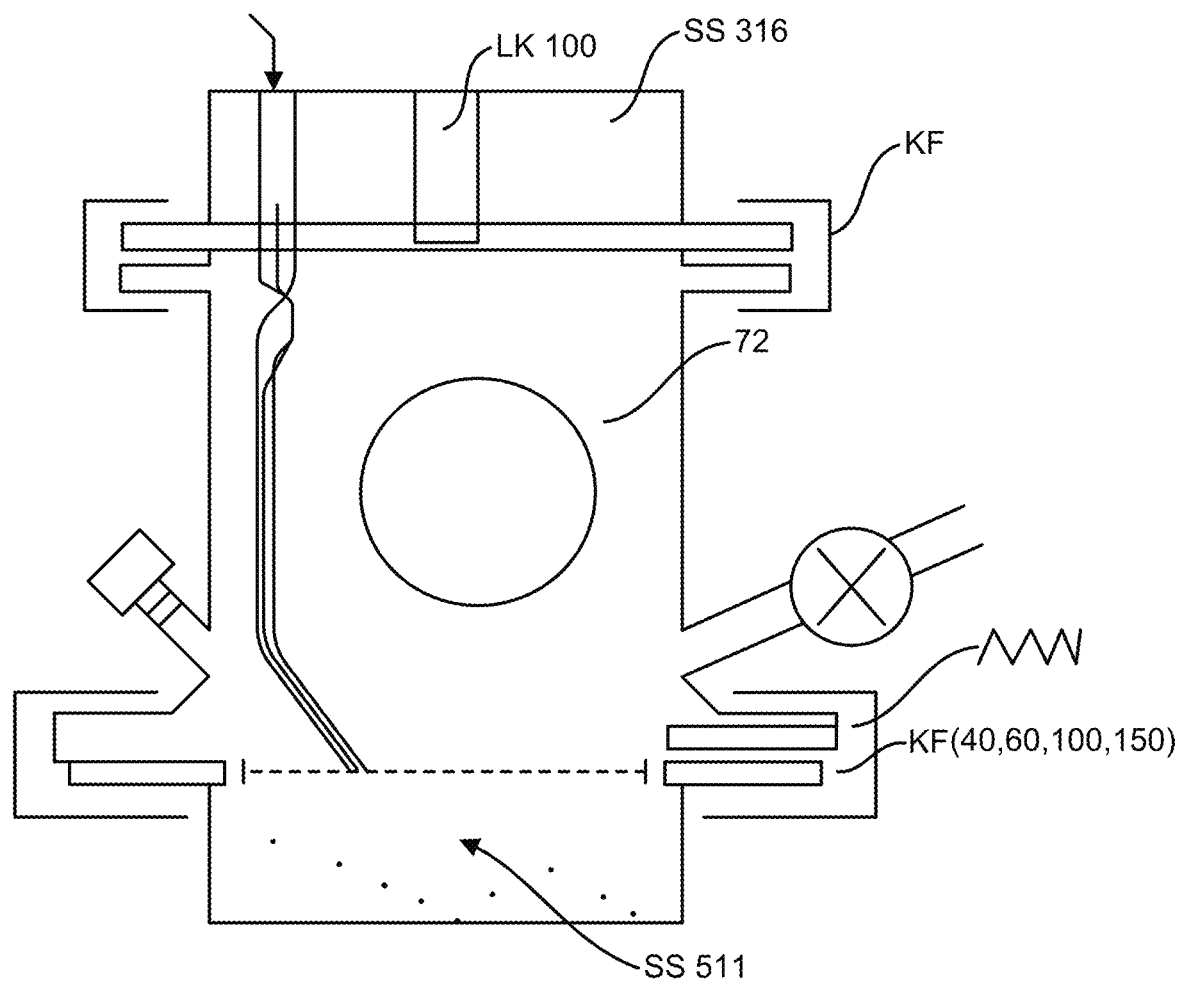
FIG. 119 is a side view of an exemplary closed stirred cell system. Shown are three component parts a) chamber lid, b) chamber wall and c) chamber base. Part a) the lid, is made from 316 stainless steel and accommodates the LB-100 spray head and inlets for addition of cell suspension, stop solution and culture medium. Part b) the wall, is manufactured from glass and includes inlets which can allow for introduction of a cell suspension through a cell introducer and includes ports which can permit entry of instrumentation to enable monitoring of humidity or gases. The wall is designed to allow for expansion of air through inclusion of an expansion port, which allows addition of an expansion chamber or through inclusion of expansion space by designing in an area of the wall with a wider diameter. Part c) the base, is manufactured from 316 stainless steel and will accommodate the custom membrane holder. To connect Part a to b and b to c are mating NW-KF flanges secured with a stainless steel clasp compliant with GMP manufacturing.
Figure 120:
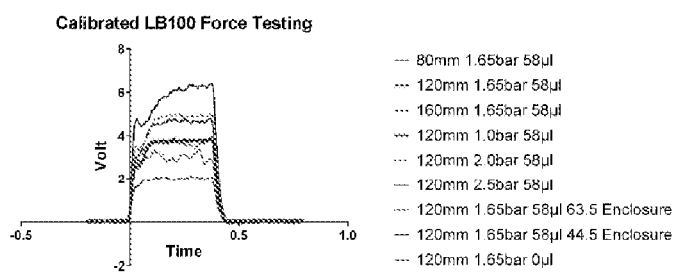

In some embodiments, a membrane holder can include holes formed within concentric channels. FIG. 114 shows an example of a membrane holder 10106 that includes holes 10106a, concentric channels 10106b, and linear channels 10106c. In the illustrated example, the holes 10106 are formed within the concentric channels 10106b and within the linear channels 10106c. This geometry can facilitate an even outflow of a culture medium such that a monolayer of cells can be formed on a membrane.

To enable atomisation of the delivery solution using a LB-100 spray head, R4 was built. FIGS. 115-118, and 128 show an example a solution delivery system, also referred to as R4 that can be used to deliver a permeabilizing solution to a monolayer of cells. The solution delivery system can include a nebulizer assembly 9801, shown in FIG. 115, and a mounting system 9802, shown in FIG. 116.

The nebulizer assembly 9801 can include a nebulizer 9804 (e.g., the LB-100 spray head), a coupling element 9806 (e.g., an IDEX connection) configured to facilitate delivering air and liquid (e.g., the permeabilizing solution) to the nebulizer 9804, a solution reservoir 9810 (e.g., an Elveflow sample reservoir) configured to provide the permeabilizing solution to the nebulizer 9804, and a pinch valve 9808 configured to control delivery of the permeabilizing solution to the nebulizer 9804. The mounting system 9802 can include a valve and reservoir mount 9812, a spray head mount 9814, and a nebulizer retaining collar 9816 to accommodate the nebulizer 9804. The nebulizer assembly 9801 can be coupled to the mounting system 9082, as illustrated in FIGS. 91-92, to be secured in place. The mounting system 9082 facilitates accurate alignment of the nebulizer 9804 with the target area.

Additional Example Approaches to Formation of a Cell Monolayer

Figure 108:
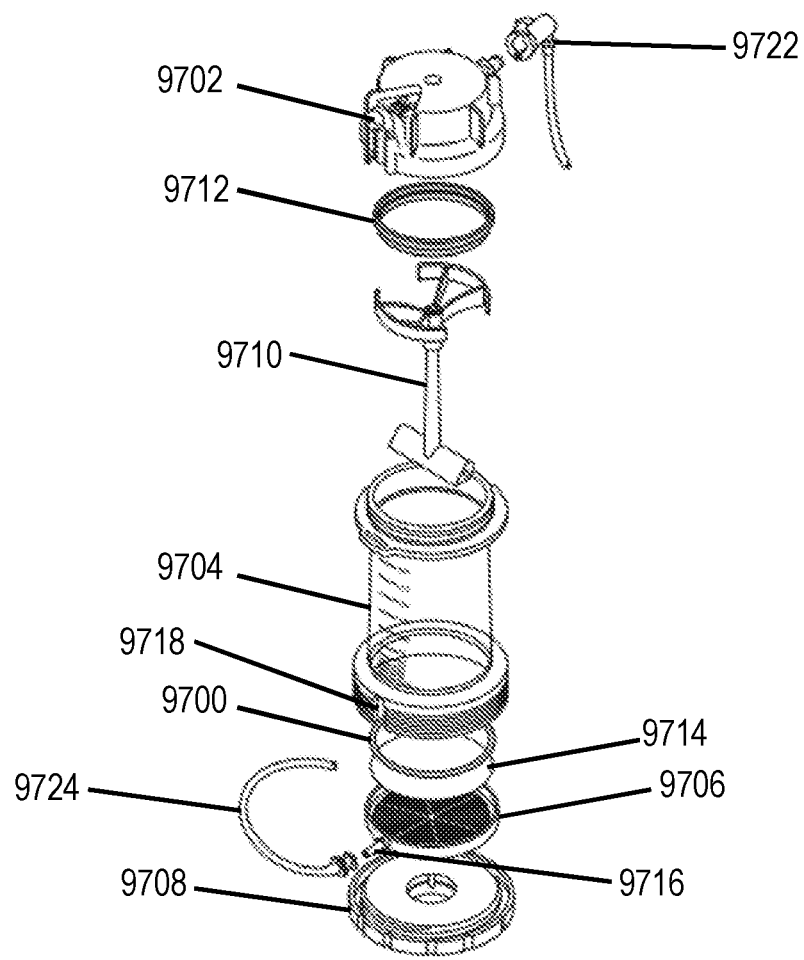
FIG. 108 is an exploded view of an exemplary embodiment of a stirred cell system configured to facilitate forming a monolayer of cells. The stirred cell system is assembled by inserting a membrane into a membrane holder, inserting the membrane holder into a base, and screwing a body of the system into the base. Cells (e.g., a culture medium containing cells) are delivered to a chamber formed by the base and the body, and a cap is screwed is screwed onto the body opposite the base to enclose the chamber. Positive pressure in the range of 50-100 mbar is delivered to the chamber via a pressure inlet tubing coupled to the cap. The pressure is applied for 10-60 seconds.

Two approaches to creating a cell monolayer are described. In both methods, the stirred cell unit was assembled as demonstrated in FIG. 108. A volume of 5-10 ml cell suspension containing 0.4-10×10$^6$ cells/ml was added to the stirred cell chamber and the lid of the chamber was then closed.

The monolayer can be created by applying vacuum pressure to the base of the stirred cell. In this method, −50 to −1000 mbar were applied to the chamber for 10-60 seconds or until the filter membrane appeared dry by eye.

Alternatively the monolayer was formed by applying a positive pressure through the tubing connection on the lid of the stirred cell. Pressure was applied for a set time (10-60 s) or until the filter membrane appeared dry by eye. In some case a lower pressure was used to drive >90% of the culture medium through the filter and then the pressure was gently increased for 10-15 seconds at the end to achieve complete removal of the culture medium. To form the monolayer and completely remove cell culture medium a pressure between 100-200 mbar was applied.

The actual specific pressure and time varied depending on cell concentration, membrane type, pore size and type of membrane holder. For example, with the original unmodified membrane holder, 50-100×10$^6$ T-cells were used to form a monolayer in the 63.5 mm stirred cell. With the PES (polyethylene sulfone) membrane, it was possible to remove the media applying 150 mbar for 20-30 s in the case of 50×10$^6$ cells while 30-60 seconds and 200 mbar were necessary to remove the media on 60×10$^6$ cells. With the PCTE (polycarbonate track etched) membrane it took 60 seconds at 250 mbar for the lower cell concentration. In the case of 100×10$^6$ cells after 2 min at 250 mbar the medium will still present on the filter membrane. To remove this the pressure was raised to 1 bar for 10 seconds and then decreased to normal levels (100 mbar). This was done several times to aid media removal.

Figure 109:
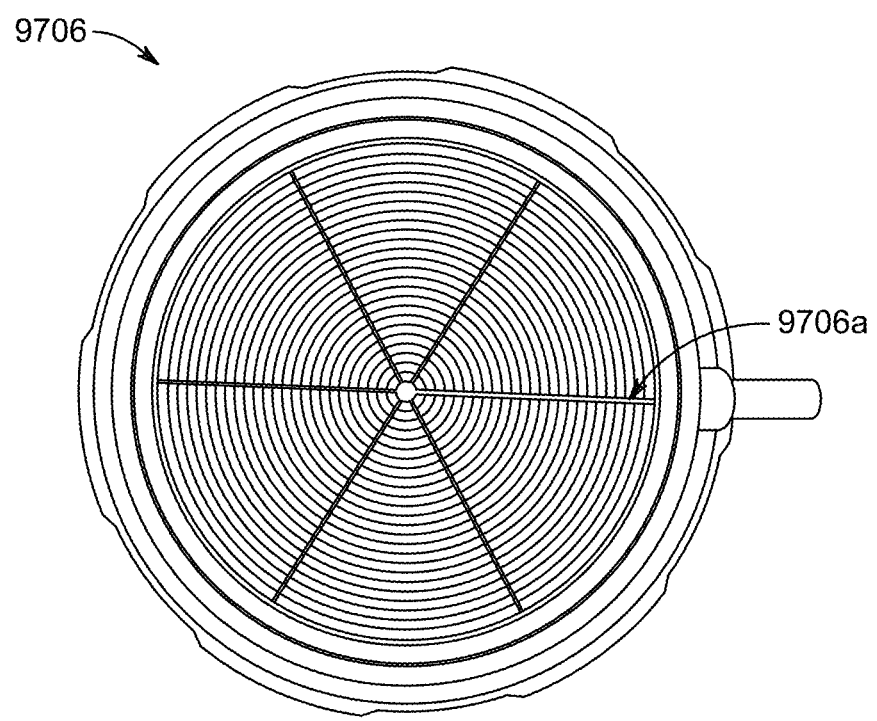
FIG. 109 is a top view the membrane holder of the stirred cell system shown in FIG. 108.
Figure 110:
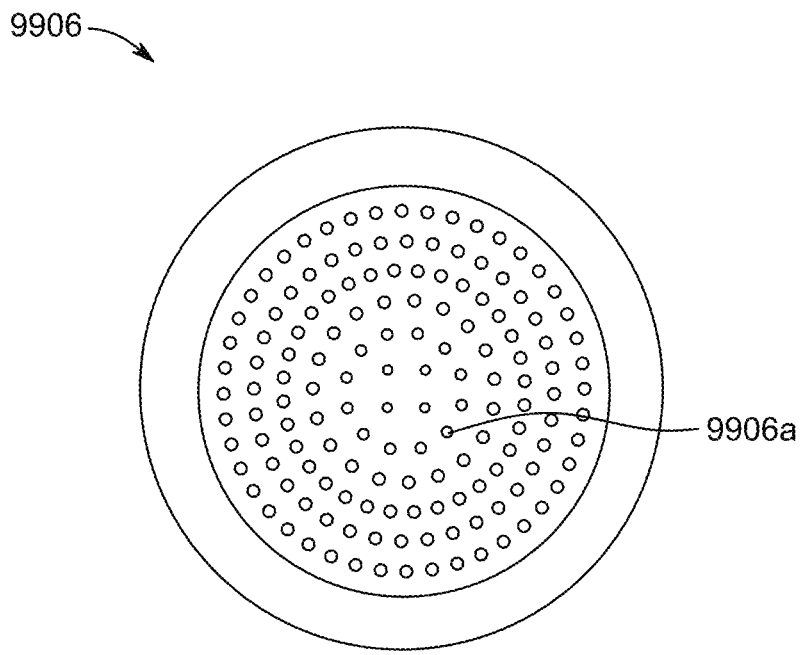
FIG. 110 is a top view of another embodiment of a membrane holder that includes holes, but no ridges.
Figure 111:
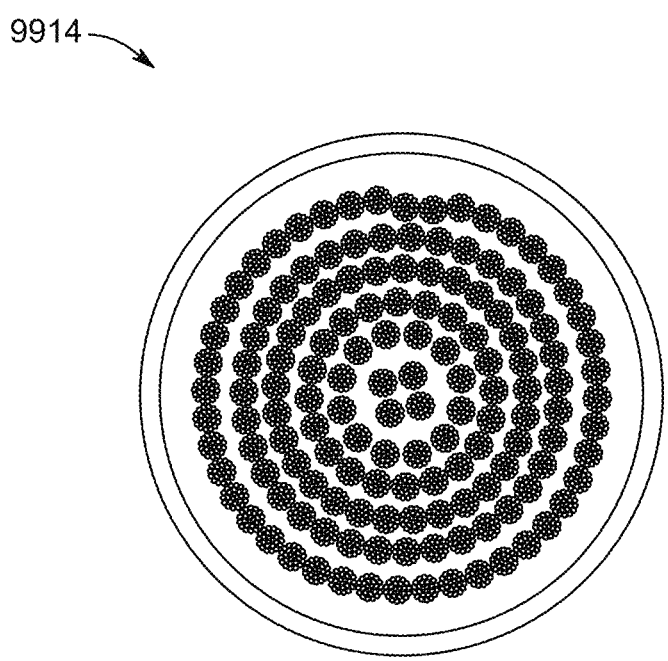
FIG. 111 is a top view of a membrane that was used with the membrane holder shown in FIG. 110 during tests to assess an impact of the design of the membrane holder on formation of a cell monolayer. Dynabeads were used in place of cells. The results indicate that the Dynabeads pooled at locations of the membrane corresponding to locations of holes in the membrane holder.

Positive pressure was tested with the unmodified filter holder (FIG. 109) in the 63.5 mm and 44.5 mm stirred cell with ~50×10^6 cells with the hydrophilic PCTE membrane with 2.0 µm pores. At no stage was all media removed with this setup (0-600 bar 0-6 mins).

With the modified filter holder (FIG. 113) in a 44.5 mm membrane a monolayer was achieved with as little as 100 mbar for 10 seconds in a 1 µm PCTE hydrophobic membrane with 20×10$^6$ cells but could be achieved with less time at higher pressures (500 mbar 5 secs).

The type of filter used to generate the monolayer was investigated. The filters differed in material, hydrophobicity and pore size. The materials tested included PES and Polycarbonate track etched filters, PCTE, hydrophobic and hydrophilic membrane coating, sizes included 13, 25 mm, 47 mm and 63 mm diameter and pore size ranged from 0.4 µm to 1.2 µm diameter. Also tested were PETE (Polyester), Silver and Gold membranes (See below Table).

TABLE

| Filter Type | Pore size |
| --- | --- |
| PES | 0.8, 1.2, 3, 5.0 |
| PCTE Hydrophobic | 0.4, 0.8, 1, 3 |
| PCTE Hydrophilic | 0.4, 0.8, 1, 2, 3 |
| PETE | 0.2, 1.0, 2.0 |

The filters were assessed for formation of an even monolayer, efficiency in removal of the culture medium and recovery of the cells from the filter membrane. Dynabeads were used as representative of cells to assess monolayer formation. In addition, expanded T-cells were used to assess monolayer formation, recovery and viability post monolayer formation.

The PES filters were investigated and it was found these filters enabled formation of an even monolayer and efficient removal of the culture medium. However, recovery of cells from the filter membrane was low (50%). The PCTE, track-edge filters, resulted in improved cell recovery (50-90%) from the filter membrane (FIG. 121). However, the efficiency of culture medium removal was slower compared to the PES filters (45 seconds to remove medium from PCTE filters compared to 10 seconds with the PES filter (at 150 mbar)). The best recovery that was achieved was ~87% with PCTE 0.4 Hydrophobic 20×10$^6$100 mbar for 60 seconds (FIG. 122).

Atomization to Enable Intracellular Delivery of mRNA to T-Cells

Investigation of the LB-100 spray head demonstrated a target area of 60 mm in diameter. Force analysis of the LB-100 was carried out (FIG. 120). Height, air pressure, volume delivered, number of hits, cell number and spray duration were adjusted to optimise delivery with the LB-100 spray onto a larger target area (25-65 mm filter membrane).

To optimise LB-100 spray delivery, the height of the spray head to the target area was adjusted. Distance in the range of 30 mm to 160 mm from spray head tip to the target area was investigated. The optimal range of distance was found to be within 60 to 100 mm from tip of the spray head to the target area. Uptake increased at the lower distance and decreased as you moved further away.

To optimise LB-100 spray delivery, the air pressure was varied in the range of 1 to 6 bar, with 2.5 to 3.0 bar found to be the optimal range for intracellular delivery. GFP mRNA delivery was reduced at pressures lower than 2.5 bar and cell viability was reduced at pressures higher than 3.0 bar. Increasing the air pressure did increase the effective target area.

To optimise LB-100 spray delivery, the volume delivered was varied in the range of 10 to 300 μl, with a volume between 80 to 100 μl found to be optimal for intracellular delivery. 5-10 ml cell suspension of human primary T cells in the range of $0.4\text{-}10\times10^6$/ml was added to the stirred cell unit (Merck Millipore; PCTE filter, 0.4 μm or 1 μm pore size). Positive pressure in the range of 100-150 mbar was applied for 20-50 s to form the cell monolayer. The cell monolayer was sprayed with 10-300 μl of delivery solution containing 0.1 μg/μl of GFP mRNA and incubated for 2 min. Stop solution (1 ml) was added and incubated for 30 s following this, culture medium (4 ml) was added to the filter membrane. Cells were incubated overnight at 37° C. and 5% $CO_2$ in a humidified incubator and assessed for GFP fluorescence by flow cytometry between 17-24 hours later.

To increase delivery efficiency, an assessment of the optimal number of hits comparing 1 and 2-hit strategies was performed. Data demonstrated an increase in delivery efficiency when cells received a second hit. 5-10 ml cell suspension of human primary T cells in the range of $0.4\text{-}10\times10^6$/ml was added to the stirred cell unit (Merck Millipore; PCTE filter, 0.4 μm or 1 μm pore size). Positive pressure in the range of 100-150 mbar was applied for 20-50 s to form the cell monolayer. The cell monolayer was sprayed with 80-100 μl of delivery solution containing 0.1 μg/μl of GFP mRNA and incubated for 2 min. Stop solution (1 ml) was added and incubated for 30 s following this, culture medium (4 ml) was added to the filter membrane. For the 2-hit strategy the cells were incubated for 2 hours before the spray process was repeated (as described above). Cells were incubated overnight at 37° C. and 5% $CO_2$ in a humidified incubator and assessed for GFP fluorescence by flow cytometry between 17-24 hours later. The double hit process resulted in increased delivery efficiency (FIG. 123).

FIG. 132 shows an exemplary embodiment of a Midi system 12300. As shown in the illustrated example, the Midi system 12300 includes a stirred cell system 11900 (e.g., a 63 mm stirred cell system) with membrane holder 10006 (e.g., a 44 mm membrane holder). An enclosing film 12303 is adhered to an opening of the stirred cell unit. A collar of a spray head holder 9814 has been inserted into stirred cell system 11900 through a 'slit' in the enclosing film 12303. In the illustrated example, a LB-100 atomizer is retained within the collar of the spray head holder 9814, and it is positioned such that a tip of the spray head is 82 mm from an upper surface of the membrane holder 10006.

FIG. 133 is a plot showing data characterizing efficiency (GFP uptake) and viability corresponding to tests performed with the Midi system 12300. The data demonstrates an average delivery efficiency of 59.63%±1.2 and average viability data of 74.6%±5.3 across 3 technical repeats.

To increase delivery efficiency, the number of cells seeded on the filter membrane was investigated. Cell density of $13\times10^3$ cells/$mm^2$ were seeded in the stirred cell unit (Merck Millipore; PCTE filter, 0.4 μm or 1 μm pore size). Positive pressure in the range of 100-200 mbar was applied for 10-50 s to form the cell monolayer. The cell monolayer was sprayed with 80-100 μl of delivery solution containing 0.1 μg/μl of GFP mRNA and incubated for 2 min Stop solution (1 ml) was added and incubated for 30 s, followed by addition of culture medium (4 ml) to the filter membrane. Cells were incubated overnight at 37° C. and 5% $CO_2$ in a humidified incubator and assessed for GFP fluorescence by flow cytometry between 17-24 hours later.

The duration of the spray was investigated. This was achieved by adjusting the opening time of the valves which control the flow of air and payload to the atomiser. Spray duration between 280-700 ms were tested.

FIG. 134 shows an exemplary embodiment of a delivery system configured to facilitate generating a monolayer of cells and delivering a payload to cells.

In some embodiments, to facilitate and to enhance the exposure of cells to permeabilizing solution a filter membrane can be vibrated before, after, and/or during, delivery of the permeabilizing solution. To assist in the formation of a monolayer of cells on a filter membrane, the membrane can be vibrated before, after, and/or during, formation of the monolayer.

The vibration may be brought about by an eccentric rotating mass (ERM) system or a linear resonant actuator (LRA) system. For example, in a preferred embodiment, 1, 2 or 3 actuators (LRA) corresponding to the X, Y and Z axis can be attached to the membrane or a corresponding membrane holder (e.g., membrane holders 10006, 10106) such that the membrane vibrates when the actuators are activated. An advantage of the LRAs is that each axis of vibration can be driven independently. Accordingly, controllable vibration patterns may be developed on the membrane. Additionally, identification of mechanical resonance points due to physical characteristics of the membrane can improve a degree of control that can be exhibited over the membrane. In some embodiments, a 3 axes accelerometer device can be mechanically coupled to the membrane and/or membrane holder to provide data characterizing motion and/or excursion of the membrane and/or membrane holder. Data from the accelerometer can be used within a feedback control system to control actuation of the LRAs. For example, the accelerometer can be used to monitor vibrations of the membrane and/or membrane holder. In some embodiments, data from the accelerometer can be used as a control feedback signal to adjust vibrations generated by the LRAs. For example, data from the accelerometer can be used to generate an error signal between a desired vibrational pattern and an achieved vibrational pattern. As an example, driving vibrational frequencies can be determined based on a stiffness of the membrane and/or sizes of cells on the membrane. An example vibrational pattern can brought about with sinusoidal signals at 3000 Hz on the x and y axes and no signal on the z axis. The excursions can be 1 mm peak to peak and the x and y driving waveforms can be coherent with no phase difference between them. Many other patterns are possible including ones that lead to swirling and/or shaking in the x, y, and/or z axes.

The current subject matter can include a non-viral, vector-free method that achieves intracellular delivery through gentle reversible permeabilization. The current subject matter can include 1) a permeabilising solution that contains a low dose of ethanol as the permeabilising agent and 2) a means of applying the delivery solution to the target cells in a dropletised form. The technology provides tight control over the volume, time and pressure at which the permeabilising solution is applied to the cells and this enables high levels of delivery efficiency as well as cell viability to be attained.

The steps of the process can include: a monolayer of target cells is generated; supernatant is removed from the cells; the cargo is mixed with the delivery solution and applied to the cells in a dropletised form and incubated for 2 min; during this period, the ethanol permeabilises the cell membrane and the cargo diffuses into the cell; cargo enters directly into the cytoplasm in an endocytosis-independent manner; a 'stop' solution is then applied to the cells and incubated for 30 sec—this acts to dilute the permeabilising delivery solution and allows the cell membrane to begin to reseal; culture medium is then added to complete the process.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention.

What is claimed:

1. A system comprising:
a housing configured to receive a plate comprising a well, wherein the plate comprises a population of cells;
a differential pressure applicator configured to apply a differential pressure to the well;
a delivery solution applicator configured to deliver atomized delivery solution to the well;
a reservoir fluidically coupled to the delivery solution applicator, the reservoir including a delivery solution that is vector-free, the delivery solution including an aqueous solution including a payload and an alcohol at greater than 5 percent (v/v) concentration, wherein the aqueous solution is isotonic wherein the population of cells is contacted with a volume of aqueous solution by gas propelling the aqueous solution to form a spray, wherein the payload comprises a gene editing composition;
a stop solution applicator configured to deliver a stop solution to the well; and
a culture medium applicator configured to deliver a culture medium to the well.

2. The system of claim 1, further comprising:
an addressable well assembly configured to:
align the differential pressure applicator adjacent the well for applying the differential pressure to the well;
align the delivery solution applicator adjacent the well for delivering the atomized delivery solution to the well;
align the stop solution applicator adjacent the well to deliver the stop solution to the well; and/or
align the culture medium applicator adjacent the well to deliver the culture medium to the well.

3. The system of claim 2, wherein the addressable well assembly includes a movable base-plate configured to receive the plate comprising the well and move the plate in at least one dimension.

4. The system of claim 2, wherein the addressable well assembly includes a mounting assembly configured to couple to the delivery solution applicator, the stop solution applicator and the culture medium applicator.

5. The system of claim 1, wherein the delivery solution applicator includes a nebulizer.

6. The system of claim 1, wherein the delivery solution applicator is configured to deliver 10-300 microliters of the delivery solution per actuation.

7. The system of claim 1, further comprising a temperature control system configured to control a temperature of the delivery solution and/or of the plate comprising the well.

8. The system of claim 1, further comprising an enclosure configured to control an environment of the plate comprising the well.

9. The system of claim 1, wherein the differential pressure applicator comprises a nozzle assembly configured to form a seal with an opening of the well and to deliver a vapor to the well to increase or decrease pressure within the well, thereby driving a liquid portion of the culture medium from the well such that a layer of cells remains within the well.

10. The system of claim 1, wherein the stop solution applicator comprises a needle emitter configured to couple to a stop solution reservoir.

11. The system of claim 1, wherein the culture medium applicator comprises a needle emitter configured to couple to a culture medium reservoir.

12. The system of claim 1, further comprising a controller configured to:
receive user input;
operate the delivery solution applicator to deliver the atomized delivery solution to a cellular monolayer within the well;
incubate, for a first incubation period, the cellular monolayer after application of the delivery solution;
operate, in response to expiration of the first incubation period, the stop solution applicator to deliver the stop solution to the cellular monolayer; and
incubate, for a second incubation period and in response to application of the stop solution, the cellular monolayer.

13. The system of claim 12, wherein the controller is further configured to:
iterate operation of the delivery solution applicator, incubation for the first incubation period, operation of the stop solution applicator, and incubation for the second incubation period for a predetermined number of iterations.

14. The system of claim 1, further comprising a controller configured to:
operate a positive pressure system to remove supernatant from the well to create a cellular monolayer within the well.

15. The system of claim 1, wherein the delivery solution applicator includes a spray head and a collar encircling a distal end of the spray head, wherein the collar is configured to prevent contamination between wells in a multi-well plate, wherein the collar is configured to provide a gap between the plate and the collar.

16. The system of claim 15, wherein the delivery solution applicator further includes a film encircling a distal end of the spray head.

17. The system of claim 1, further comprising a vibration system coupled to a membrane holder and configured to vibrate a membrane.

18. The system of claim 1, wherein the well contains a population of non-adherent cells.

19. The system of claim 1, wherein said alcohol comprises ethanol.

20. The system of claim 1, wherein said aqueous solution comprises greater than 10% ethanol.

21. The system of claim 1, wherein said aqueous solution comprises between 20-30% ethanol.

22. The system of claim 1, wherein said aqueous solution comprises 27% ethanol.

23. The system of claim 1, wherein said aqueous solution comprises between 12.5-500 mM KCl.

24. The system of claim 1, wherein said aqueous solution comprises 106 mM KCl.

25. The system of claim 18, wherein said non-adherent cell comprises a peripheral blood mononuclear cell.

26. The system of claim 18, wherein said non-adherent cell comprises an immune cell.

27. The system of claim 18, wherein said non-adherent cell comprises a T lymphocyte.

28. The system of claim 1, wherein said payload comprises a messenger ribonucleic acid (mRNA).

29. The system of claim 1, wherein said gene editing composition reduces the expression of PD-1.

30. The system of claim 28, wherein said mRNA encodes a chimeric antigen receptor.

31. The system of claim 18, wherein said population of non-adherent cells comprises a monolayer.

32. The system of claim 1, wherein the delivery solution is non-viral.

33. The system of claim 1, wherein said payload comprises a messenger ribonucleic acid (mRNA).

34. The system of claim 1, wherein said gene editing composition reduces the expression of PD-1.

35. The system of claim 33, wherein said mRNA encodes a chimeric antigen receptor.

36. The system of claim 1, wherein the gene editing composition comprises one or more of (a) gene editing protein; (b) RNA molecule; and/or (c) ribonucleoprotein (RNP).

37. The system of claim 1, wherein the gene editing composition includes a compound or complex that cleaves, nicks, splices, rearranges, translocates, recombines, or alters genomic DNA.

38. The system of claim 1, wherein the gene editing composition includes a compound that (i) can be included in a gene-editing complex that cleaves, nicks, splices, rearranges, translocates, recombines, or alters genomic DNA; or (ii) can be processed or altered to be a compound that is included in a gene-editing complex that cleaves, nicks, splices, rearranges, translocates, recombines, or alters genomic DNA.

* * * * *